(12) United States Patent
Almogy et al.

(10) Patent No.: US 12,319,959 B2
(45) Date of Patent: Jun. 3, 2025

(54) METHODS FOR NUCLEIC ACID ANALYSIS

(71) Applicant: Ultima Genomics, Inc., Newark, CA (US)

(72) Inventors: Gilad Almogy, Palo Alto, CA (US); Florian Oberstrass, Menlo Park, CA (US); Omer Barad, Mazkeret Batya (IL); Chandan Shee, Newark, CA (US)

(73) Assignee: Ultima Genomics, Inc., Fremont, CA (US)

( * ) Notice: Subject to any disclaimer, the term of this patent is extended or adjusted under 35 U.S.C. 154(b) by 0 days.

(21) Appl. No.: 17/394,692

(22) Filed: Aug. 5, 2021

(65) Prior Publication Data
US 2022/0042072 A1 Feb. 10, 2022

Related U.S. Application Data

(63) Continuation of application No. PCT/US2020/017491, filed on Feb. 10, 2020.

(60) Provisional application No. 62/916,683, filed on Oct. 17, 2019, provisional application No. 62/890,240, (Continued)

(51) Int. Cl.
*C12Q 1/686* (2018.01)

(52) U.S. Cl.
CPC ....... *C12Q 1/686* (2013.01); *C12Q 2563/107* (2013.01); *C12Q 2563/149* (2013.01); *C12Q 2563/159* (2013.01)

(58) Field of Classification Search
CPC .............. C12Q 1/686; C12Q 2563/149; C12Q 2563/159; C12Q 1/6844
See application file for complete search history.

(56) References Cited

U.S. PATENT DOCUMENTS

| 7,244,567 B2 | 7/2007 | Chen et al. |
| 8,048,627 B2 | 11/2011 | Dressman et al. |
| 9,309,557 B2 | 4/2016 | Li et al. |

(Continued)

FOREIGN PATENT DOCUMENTS

| EP | 2742151 A2 | 6/2014 |
| EP | 3095879 B1 | 9/2018 |

(Continued)

OTHER PUBLICATIONS

PCT International Search Report and Written Opinion, PCT Application No. PCT/US20/17491, dated May 4, 2020, 15 pages.
(Continued)

*Primary Examiner* — Aaron A Priest
*Assistant Examiner* — Tian N Yu
(74) *Attorney, Agent, or Firm* — Wilson Sonsini Goodrich & Rosati

(57) ABSTRACT

The present disclosure provides methods and processes for increasing the efficiency and accuracy of nucleic acid sequencing using techniques such as polymerase chain reaction (PCR). The methods described herein can be used to achieve clonal amplification even with a greater than Poisson distribution of beads and/or nucleic acid templates into an emulsion. A PCR method may comprise generating a partition (e.g., a droplet) comprising at least two beads and/or at least two nucleic acid molecules and generating clonal amplification products corresponding to the nucleic acid molecule, at least a subset of which may be attached to a bead.

22 Claims, 47 Drawing Sheets

Related U.S. Application Data filed on Aug. 22, 2019, provisional application No. 62/804,082, filed on Feb. 11, 2019.

(56) References Cited

U.S. PATENT DOCUMENTS

| | | | |
|---|---|---|---|
| 9,309,558 B2 | 4/2016 | Li et al. | |
| 9,334,531 B2 | 5/2016 | Li et al. | |
| 9,371,557 B2 | 6/2016 | Li et al. | |
| 9,694,361 B2 | 7/2017 | Bharadwaj et al. | |
| 10,011,872 B1* | 7/2018 | Belgrader | C12Q 1/6804 |
| 10,030,262 B2 | 7/2018 | Chen et al. | |
| 10,066,260 B2 | 9/2018 | Light et al. | |
| 10,113,195 B2 | 10/2018 | Li et al. | |
| 10,233,488 B2 | 3/2019 | Li et al. | |
| 10,240,192 B2 | 3/2019 | Berka et al. | |
| 10,329,544 B2 | 6/2019 | Li et al. | |
| 10,544,413 B2 | 1/2020 | Bharadwaj et al. | |
| 10,544,456 B2 | 1/2020 | Esfandyarpour et al. | |
| 10,738,353 B2 | 8/2020 | Light et al. | |
| 10,858,695 B2 | 12/2020 | Li et al. | |
| 11,001,815 B2 | 5/2021 | Li et al. | |
| 11,725,195 B2 | 8/2023 | Li et al. | |
| 11,773,426 B2 | 10/2023 | Joun et al. | |
| 2009/0203531 A1 | 8/2009 | Kurn | |
| 2012/0010087 A1 | 1/2012 | Shapero et al. | |
| 2013/0190191 A1 | 7/2013 | Froehlich et al. | |
| 2013/0338042 A1* | 12/2013 | Shen | C12Q 1/6874 506/26 |
| 2014/0148345 A1 | 5/2014 | Li et al. | |
| 2014/0335528 A1* | 11/2014 | Olejnik | C12Q 1/6806 435/6.12 |
| 2015/0361481 A1* | 12/2015 | Joun | C12Q 1/6846 506/26 |
| 2016/0001248 A1* | 1/2016 | Fan | C12Q 1/6874 506/4 |
| 2017/0292124 A1 | 10/2017 | Zhang et al. | |
| 2018/0327813 A1 | 11/2018 | Chen et al. | |
| 2018/0363042 A1 | 12/2018 | Solstad et al. | |
| 2019/0255505 A1 | 8/2019 | Rosenbaum et al. | |
| 2019/0352707 A1 | 11/2019 | Almogy et al. | |
| 2022/0220534 A1 | 7/2022 | Rosenbaum et al. | |

FOREIGN PATENT DOCUMENTS

| | | | |
|---|---|---|---|
| EP | 3488017 A1 | 5/2019 | |
| JP | 2015528283 A | 9/2015 | |
| JP | 2018183097 A | 11/2018 | |
| JP | 2019500009 A | 1/2019 | |
| WO | WO-2005082098 A2 | 9/2005 | |
| WO | WO-2010003132 A1 | 1/2010 | |
| WO | WO-2012047889 A2 | 4/2012 | |
| WO | WO-2013023176 A2 | 2/2013 | |
| WO | WO-2013158313 A1 | 10/2013 | |
| WO | WO-2013158982 A1 | 10/2013 | |
| WO | WO-2014151961 A1 | 9/2014 | |
| WO | WO-2014186152 A1 | 11/2014 | |
| WO | WO-2014210353 A2 | 12/2014 | |
| WO | WO-2015191815 A1 | 12/2015 | |
| WO | WO-2016187466 A1 | 11/2016 | |
| WO | WO-2017079593 A1 * | 5/2017 | C12N 15/1065 |
| WO | WO-2017120531 A1 * | 7/2017 | B01J 19/0046 |
| WO | WO-2018017884 A1 | 1/2018 | |
| WO | WO-2019079653 A1 | 4/2019 | |
| WO | WO-2019094524 A1 | 5/2019 | |
| WO | WO-2019157529 A1 | 8/2019 | |
| WO | WO-2020167656 A1 | 8/2020 | |
| WO | WO-2020172197 A1 | 8/2020 | |
| WO | WO-2022040557 A2 | 2/2022 | |
| WO | WO-2022217112 A1 | 10/2022 | |

OTHER PUBLICATIONS

PCT/US2021/046951 International Search Report and Written Opinion dated Feb. 4, 2022.

SG11202108563Q Search Report dated Jul. 25, 2023.

Co-pending U.S. Appl. No. 18/176,418, inventors Oberstrass; Florian et al., filed Feb. 28, 2023.

Dumousseau, et al. Melting, a flexible platform to predict the melting temperatures of nucleic acids. BMC Bioinformatics 13, 101 (2012). https://doi.org/10.1186/1471-2105-13-101.

EP20755711.7 European Search Report dated Jul. 25, 2022.

Karakas, et al., Noninvasive Digital Detection of Fetal DNA in Plasma of 4-Week-Pregnant Women following in Vitro Fertilization and Embryo Transfer. PloS one 10(5): 1-10 (2015).

Graham, H. et al., The genesis and evolution of based multiplexing. Methods 158: 2-11 (2019).

* cited by examiner

METHODS FOR NUCLEIC ACID ANALYSIS

CROSS-REFERENCE

This application is a continuation of International Application No. PCT/US20/17491, filed Feb. 10, 2020, which claims the benefit of U.S. Provisional Patent App. No. 62/804,082, filed Feb. 11, 2019, U.S. Provisional Patent App. No. 62/890,240, filed Aug. 22, 2019, and U.S. Provisional Patent App. No. 62/916,683, filed Oct. 17, 2019, each of which is entirely incorporated herein by reference for all purposes.

BACKGROUND

Advances in the study of biological molecules have been led, in part, by improvements in technologies used to characterize molecules and/or their biological reactions. In particular, the study of nucleic acids has benefited from developing technologies used for sequence analysis. Sequencing of nucleic acids has various applications in the fields of molecular biology and medicine (e.g., diagnosis and treatment monitoring). Nucleic acid sequencing may provide information that may be used to diagnose a certain condition in a subject and/or tailor a treatment plan. Sequencing is widely used for molecular biology applications, including vector designs, gene therapy, vaccine design, industrial strain design and verification. The way in which an eventual sequence analysis is performed may play a role in the type and quality of information that may be obtained in such analysis.

SUMMARY

Recognized herein is the need for methods, processes, and compositions for increasing the efficiency, sensitivity, and accuracy of methods (e.g., emulsion PCR) for analyzing and/or processing nucleic acid sample. The present disclosure provides methods and compositions for analyzing and/or processing nucleic acid molecules (e.g., those found in biological samples) with high accuracy and sensitivity and efficient reagent usage. Using a higher number of beads (e.g., using a higher ratio of beads to nucleic acid molecules) in emulsion droplets (or other types of partitions, such as wells) for nucleic acid amplification or sequencing (e.g., polymerase chain reaction or PCR) may result in higher clonal copy numbers and reduced template loss, which may in turn result in an increased accuracy and sensitivity while maintaining an efficient workflow. The present disclosure also provides methods and systems for achieving clonal amplification even in cases where more than one nucleic acid template is present in a partition (e.g., emulsion partition). The systems and methods described here can allow for loading of a plurality of beads and/or nucleic acid templates in a partition (e.g., at a density greater than a Poisson distribution) such that, e.g., reagents (e.g., PCR reagents) can be used efficiently.

In an aspect, provided is a method for nucleic acid processing, comprising: (a) providing a plurality of partitions, wherein a partition of the plurality of partitions comprises (i) at least two beads of a plurality of beads, (ii) a nucleic acid molecule, and (iii) one or more reagents; (b) in the partition, using the nucleic acid molecule and the one or more reagents to generate one or more amplification products of the nucleic acid molecule, wherein at least a subset of the one or more amplification products are attached to a bead of the at least two beads; (c) recovering the bead from the partition; and (d) assaying an amplification product of the one or more amplification products or derivatives thereof attached to the bead to identify a sequence of the nucleic acid molecule.

In some embodiments, (a) comprises bringing (i) a first solution comprising a plurality of nucleic acid molecules comprising the nucleic acid molecule and (ii) a second solution comprising the plurality of beads comprising the at least two beads in contact with a fluid that is immiscible with the first solution and the second solution, to generate the plurality of partitions. In some embodiments, the first solution and the second solution are the same solution. In some embodiments, the first solution and the second solution are different solutions.

In some embodiments, the bead has attached thereto a plurality of primer molecules for performing one or more amplification reactions using the nucleic acid molecule, and (b) comprises using primer molecules of the plurality of primer molecules to conduct the one or more amplification reactions to generate the amplification product of the one or more amplification products. In some embodiments, the bead has attached thereto a plurality of additional primer molecules for performing one or more additional amplification reactions using the nucleic acid molecule, which plurality of additional primer molecules are different than the plurality of primer molecules.

In some embodiments, (b) further comprises using additional primer molecules of the plurality of additional primer molecules to conduct the one or more additional amplification reactions to generate additional amplification products of the one or more amplification products, wherein at least a subset of the additional amplification products are attached to the bead, and wherein (d) further comprises assaying the additional amplification products attached to the bead, or derivatives thereof, to identify a sequence of the nucleic acid molecule. In some embodiments, the nucleic acid molecule is a double-stranded nucleic acid molecule. In some embodiments, amplification products corresponding to a first strand of the nucleic acid molecule are generated using the plurality of primer molecules, and amplification products corresponding to a second strand of the nucleic acid molecule are generated using the plurality of additional primer molecules. In some embodiments, (d) comprises generating paired-end sequencing reads associated with sequences of the one or more amplification products or derivatives thereof.

In some embodiments, an additional bead of the at least two beads has attached thereto a plurality of additional primer molecules for performing one or more additional amplification reactions using the nucleic acid molecule, which plurality of additional primer molecules are different than the plurality of primer molecules. In some embodiments, the method further comprises: (e) using additional primer molecules of the plurality of additional primer molecules to conduct the one or more additional amplification reactions to generate additional amplification products of the one or more amplification products, wherein at least a subset of the additional amplification products are attached to the additional bead of the at least two beads; (f) recovering the additional bead from the partition; and (g) assaying the additional amplification products attached to the additional bead, or derivatives thereof, to identify a sequence of the nucleic acid molecule. In some embodiments, the nucleic acid molecule is a double-stranded nucleic acid molecule. In some embodiments, amplification products corresponding to a first strand of the nucleic acid molecule are generated using the plurality of primer molecules coupled to the bead, and wherein amplification products corresponding to a second strand of the nucleic acid molecule are generated using the plurality of additional primer molecules coupled to the additional bead. In some embodiments, (d) further comprises generating paired-end sequencing read associated with sequences of the plurality of amplification products or derivatives thereof.

In some embodiments, each of at least 80% of the plurality of partitions comprises two or more beads of the plurality of beads. In some embodiments, each of at least 85% of the plurality of partitions comprises two or more beads of the plurality of beads. In some embodiments, each of at least 90% of the plurality of partitions comprises two or more beads of the plurality of beads.

In some embodiments, each of at least 80% of the plurality of partitions comprises three or more beads of the plurality of beads. In some embodiments, each of at least 85% of the plurality of partitions comprises three or more beads of the plurality of beads. In some embodiments, each of at least 90% of the plurality of partitions comprises three or more beads of the plurality of beads.

In some embodiments, the at least two beads are attached to one another. In some embodiments, the at least two beads are attached to one another via at least one chemical linker. In some embodiments, the at least two beads are attached to one another via a splint oligonucleotide.

In some embodiments, the method further comprises separating partitions of the plurality of partitions that each comprise at least two beads from other partitions of the plurality of partitions that each comprise at most one bead. In some embodiments, the separating comprises optically detecting the partitions that each comprise at least two beads and/or the other partitions that each comprise at most one bead and, based at least in the part on the optically detecting, adjusting a direction of flow of a fluid in a fluidic device to provide the partitions that each comprise at least two beads in a first channel of the fluidic device and the other partitions that each comprise at most one bead in a second channel of the fluidic device.

In some embodiments, the one or more reagents comprise nucleic acid molecules comprising priming sequences. In some embodiments, the nucleic acid molecules comprising the priming sequences further comprise unique molecular identifier sequences. In some embodiments, the nucleic acid molecules comprising the priming sequences further comprise barcode sequences. In some embodiments, the priming sequences are target-specific priming sequences. In some embodiments, the priming sequences are non-target specific priming sequences.

In some embodiments, the one or more reagents comprise one or more polymerizing enzymes.

In some embodiments, the nucleic acid molecule is derived from a cell or constituent of the cell.

In some embodiments, the plurality of partitions is a plurality of droplets.

In some embodiments, (d) comprises sequencing the amplification products or derivatives thereof.

In some embodiments, in (a), the nucleic acid molecule is attached to the bead.

In another aspect, provided is a method for nucleic acid processing, comprising: (a) providing a plurality of partitions, wherein a partition of the plurality of partitions comprises (i) at least two beads of a plurality of beads, wherein the at least two beads are attached to one another, (ii) a nucleic acid molecule, and (iii) one or more reagents; and (b) in the partition, using the nucleic acid molecule and the one or more reagents to generate one or more amplification products of the nucleic acid molecule, wherein at least a subset of the one or more amplification products are attached to a bead of the at least two beads.

In some embodiments, the method further comprises (c) recovering the bead from the partition; and (d) assaying an amplification product of the one or more amplification products attached to the bead, or derivatives thereof, to identify a sequence of the nucleic acid molecule. In some embodiment, (a) comprises bringing (i) a first solution comprising a plurality of nucleic acid molecules comprising the nucleic acid molecule and (ii) a second solution comprising the plurality of beads comprising the at least two beads in contact with a fluid that is immiscible with the first solution and the second solution, to generate the plurality of partitions.

In some embodiments, the bead has attached thereto a plurality of primer molecules for performing one or more amplification reactions using the nucleic acid molecule, and wherein (b) comprises using primer molecules of the plurality of primer molecules to conduct the one or more amplification reactions to generate the amplification product of the one or more amplification products.

In some embodiments, the bead has attached thereto a plurality of additional primer molecules for performing one or more additional amplification reactions using the nucleic acid molecule, which plurality of additional primer molecules are different than the plurality of primer molecules. In some embodiments, (b) further comprises using additional primer molecules of the plurality of additional primer molecules to conduct the one or more additional amplification reactions to generate additional amplification products of the one or more amplification products, wherein at least a subset of the additional amplification products are attached to the bead, and wherein (d) further comprises assaying the additional amplification products attached to the bead, or derivatives thereof, to identify a sequence of the nucleic acid molecule.

In some embodiments, an additional bead of the at least two beads has attached thereto a plurality of additional primer molecules for performing one or more additional amplification reactions using the nucleic acid molecule, which plurality of additional primer molecules are different than the plurality of primer molecules. In some embodiments, the method further comprises: (e) using additional primer molecules of the plurality of additional primer molecules to conduct the one or more additional amplification reactions to generate additional amplification products of the one or more amplification products, wherein at least a subset of the additional amplification products are attached to the additional bead of the at least two beads; (0 recovering the additional bead from the partition; and (g) assaying the additional amplification products attached to the additional bead, or derivatives thereof, to identify a sequence of the nucleic acid molecule.

In another aspect, provided is a method for clonally amplifying a nucleic acid molecule, the method comprising: (a) providing a reaction mixture comprising (i) a surface comprising a plurality of first primers immobilized thereto, wherein the plurality of first primers have sequence identity (or homology) to a first sequence, (ii) the nucleic acid molecule, wherein the nucleic acid molecule comprises end sequences different from a complement of the first sequence and (iii) a second primer comprising a first portion and a second portion, wherein the first portion is configured to anneal to the nucleic acid molecule and wherein the second portion comprises an extension sequence, and wherein the extension sequence, or complement thereof, is configured to hybridize with the first sequence; (b) generating an extension product using the nucleic acid molecule and the second primer, which extension product comprises the extension sequence, or complement thereof; and (c) amplifying the extension product using the plurality of first primers immobilized to the surface.

In some embodiments, the second primer is immobilized to the surface.

In some embodiments, the nucleic acid molecule does not hybridize with the plurality of first primer prior to (b).

In some embodiments, the surface comprises an array of amplification sites, wherein the array of amplification sites comprise a plurality of sets of first primers immobilized thereto, wherein the plurality of sets of first primers have sequence homology to the first sequence. In some embodiments, the nucleic acid molecule has fluidic access to the array of amplification sites in the reaction mixture. In some embodiments, each amplification site of the array of amplification sites comprise a set of first primers of the plurality of sets of first primers immobilized thereto the surface.

In some embodiments, the surface is a bead.

In some embodiments, the reaction mixture is provided in a volume of dispersed phase of an emulsion. In some embodiments, the emulsion comprises a second volume of dispersed phase comprising a second reaction mixture comprising a second surface.

In some embodiments, (b) and (c) are performed in the reaction mixture.

In some embodiments, the reaction mixture comprises a plurality of nucleic acid molecules, wherein the plurality of nucleic acid molecules comprises nucleic acid molecules comprising different nucleic acid sequences. In some embodiments, each of the plurality of nucleic acid molecules is configured to couple to the second primer to generate an extension product comprising the extension sequence or complement thereof.

In some embodiments, the method further comprises providing a plurality of partitions comprising a plurality of reaction mixtures, wherein the plurality of partitions comprises (i) a plurality of nucleic acid molecules including the nucleic acid molecule and (ii) a plurality of surfaces including the surface, wherein a first partition of the plurality of partitions comprises the reaction mixture, and wherein a second partition of the plurality of partitions comprises a second nucleic acid molecule of the plurality of nucleic acid molecules and a second surface of the plurality of surfaces. In some embodiments, the plurality of nucleic acid molecules are distributed amongst the plurality of partitions at a density which is greater than an average of 1 nucleic acid molecule per partition in the plurality of partitions.

In some embodiments, the reaction mixture comprises a third nucleic acid molecule and an additional second primer, and wherein the nucleic acid molecule, or a derivative thereof, is coupled to at least 99% of the plurality of first primers prior to the second nucleic acid molecule coupling to the additional second primer.

In some embodiments, (c) occurs at a rate that is at least 10-fold faster than a rate of (b).

In some embodiments, the nucleic acid molecule is single stranded.

In some embodiments, the second primer has a predetermined concentration in the reaction mixture that limits the rate of (b) with respect to a rate of (c).

In some embodiments, the reaction mixture further comprises an additional first primer that is not immobilized to the surface, wherein the additional first primer has sequence identity to the first sequence.

In some embodiments, the reaction mixture further comprises a plurality of third primers that is configured to exponentially amplify the nucleic acid molecule when used in a polymerase chain reaction (PCR) reaction with the first primer or the second primer. In some embodiments, the reaction mixture further comprises a fourth primer, wherein the fourth primer has a third portion and a fourth portion, wherein the third portion is configured to anneal to the nucleic acid molecule and wherein the second portion comprises a second extension sequence.

In some embodiments, the method further comprises: (d) generating a second extension product using the nucleic acid molecule and the fourth primer, which second extension comprises the second extension sequence, or complement thereof, configured to hybridize with the third primer; and (e) amplifying the second extension product using the plurality of third primers. In some embodiments, the nucleic acid molecule does not hybridize with a third primer of the plurality of third primers prior to (d). In some embodiments, a concentration of the plurality of third primers is at least 10-fold greater than a concentration of the fourth primer in the reaction mixture.

In some embodiments, the reaction mixture further comprises a nucleic acid polymerase.

In some embodiments, (b) is performed under isothermal conditions.

In some embodiments, (c) is performed under isothermal conditions.

In some embodiments, the method further comprises recovering the surface.

In some embodiments, the method further comprises assaying an amplification product of the nucleic acid molecule or derivative thereof to identify a sequence of the nucleic acid molecule.

In some embodiments, the nucleic acid molecule comprises a first adapter attached to a 5' end of the nucleic acid molecule and a second adapter attached to a 3' end of the nucleic acid molecule. In some embodiments, the first adapter and the second adapter have an identical sequence.

In some embodiments, the method further comprises subjecting the reaction mixture to a condition that makes (b) a slower and/or rarer event with respect to (c). In some embodiments, the condition comprises a temperature. In some embodiments, the temperature is approximately equal to an annealing temperature between the nucleic acid molecule and the second primer.

In another aspect, provided is a system for clonally amplifying a nucleic acid molecule, the system comprising: a reaction mixture comprising (i) a surface comprising a plurality of first primers immobilized thereto, wherein the plurality of first primers have sequence identity (or homology) to a first sequence; (ii) the nucleic acid molecule, wherein the nucleic acid molecule comprises end sequences different from a complement of the first sequence; (iii) a second primer comprising a first portion and a second portion, wherein the first portion is configured to anneal to the nucleic acid molecule and wherein the second portion comprises an extension sequence, wherein the extension sequence, or complement thereof, is configured to hybridize with the first sequence; and (iv) reagents configured to perform a nucleic acid extension reaction using the nucleic acid molecule.

In some embodiments, the nucleic acid molecule is single stranded.

In some embodiments, the second primer is configured to couple to the nucleic acid molecule to generate an extension product comprising the extension sequence, or complement, configured to hybridize with the first sequence.

In some embodiments, wherein the extension product is capable of being generated in the reaction mixture. In some embodiments, the extension product is capable of being generated under isothermal conditions. In some embodiments, the extension product, or amplification products thereof, are configured to couple to the plurality of first primers immobilized to the surface. In some embodiments, the extension product, or amplification products thereof, are configured to couple to the plurality of first primers immobilized to the surface within the reaction mixture. In some embodiments, the amplification products of the extension product are configured for generation under isothermal conditions. In some embodiments, the reaction mixture comprises a second nucleic acid molecule and an additional second primer, and wherein the nucleic acid molecule, or a derivative thereof, is configured to couple to at least 99% of the plurality of first primers prior to the second nucleic acid molecule coupling to the additional second primer.

In some embodiments, the second primer has a predetermined concentration in the reaction mixture that limits a rate at which the nucleic acid molecule couples to the second primer to generate an extension product with respect to a rate at which the extension product is amplified on the surface.

In some embodiments, the second primer is immobilized to the surface.

In some embodiments, the surface comprises an array of amplification sites, wherein the array of amplification sites comprise a plurality of sets of first primers immobilized thereto, wherein the plurality of sets of first primers have sequence identity to the first sequence. In some embodiments, the nucleic acid molecule has fluidic access to the array of amplification sites in the reaction mixture. In some embodiments, each amplification site of the array of amplification sites comprise a set of first primers of the plurality of sets of first primers immobilized thereto the surface.

In some embodiments, the surface is a bead.

In some embodiments, the system further comprises an emulsion, wherein the reaction mixture is provided in a volume of dispersed phase of the emulsion. In some embodiments, the emulsion comprises a second volume of dispersed phase comprising a second reaction mixture comprising a second surface.

In some embodiments, the reaction mixture comprises a plurality of nucleic acid molecules, wherein the plurality of nucleic acid molecules comprises nucleic acid molecules comprising different nucleic acid sequences. In some embodiments, each of the plurality of nucleic acid molecules is configured to couple to the second primer to generate an extension product comprising the extension sequence or complement thereof.

In some embodiments, the system further comprises a plurality of partitions comprising a plurality of reaction mixtures, wherein the plurality of partitions comprises (i) a plurality of nucleic acid molecules including the nucleic acid molecule and (ii) a plurality of surfaces including the surface, wherein a first partition of the plurality of partitions comprises the reaction mixture, and wherein a second partition of the plurality of partitions comprises a second nucleic acid molecule of the plurality of nucleic acid molecules and a second surface of the plurality of surfaces. In some embodiments, the plurality of nucleic acid molecules are distributed amongst the plurality of partitions at a density which is greater than an average of 1 nucleic acid molecule per partition in the plurality of partitions.

In some embodiments, wherein the reaction mixture further comprises an additional first primer that is not immobilized to the surface.

In some embodiments, the reaction mixture further comprises a plurality of third primers that is configured to exponentially amplify the nucleic acid molecule when used in a polymerase chain reaction (PCR) reaction with the first primer or the second primer. In some embodiments, the reaction mixture further comprises a fourth primer, which fourth primer has a third portion and a fourth portion, wherein the third portion is configured to anneal to the nucleic acid molecule and wherein the fourth portion comprises a second extension sequence.

In some embodiments, the system further comprises one or more processors, individually or collectively, configured to assay an amplification product of the nucleic acid molecule or derivative thereof to identify a sequence of the nucleic acid molecule.

In some embodiments, the surface comprises a plurality of amplification sites and each of the amplification sites has multiple copies of a different first primer attached to the surface.

In some embodiments, the nucleic acid molecule comprises a first adapter attached to a 5' end of the nucleic acid molecule and a second adapter attached to a 3' end of the nucleic acid molecule. In some embodiments, the first adapter and the second adapter have an identical sequence.

In another aspect, provided is a method for clonally amplifying a nucleic acid sample, the method comprising: (a) forming an emulsion comprising a plurality of partitions, wherein a partition of the plurality of partitions comprises (i) a nucleic acid molecule, (ii) a bead comprising a plurality of first primers immobilized thereto, wherein the plurality of first primers have sequence identity (or homology) to a first sequence, and (iii) a reagent mixture configured to perform an attachment reaction that permits the nucleic acid molecule or a derivative thereof to attach to the bead and an amplification reaction that uses the plurality of first primers; and (b) incubating the emulsion, thereby (i) performing the attachment reaction to attach the nucleic acid molecule, or derivative thereof, to the bead and (ii) performing the amplification reaction to generate copies of the nucleic acid molecule, or derivative thereof, attached to the bead, wherein a first period of time is greater than a second period of time, wherein the first period of time begins with the incubating in (b) and concludes when the nucleic acid molecule, or derivative thereof, attaches to the bead, and wherein the second period of time begins when the nucleic acid molecule, or derivative thereof, attaches to the bead and concludes when amplification reaction concludes.

In some embodiments, the first period of time is at least about 5 times, at least about 10 times, at least about 20 times, at least about 50 times, or at least about 100 times greater than the second period of time.

In some embodiments, the incubating in (b) comprising subjecting the emulsion to at least two different conditions. In some embodiments, the emulsion is subject to (i) a first condition of the at least two different conditions for the first period of time and (ii) a second condition of the at least two different conditions for the second period of time.

In some embodiments, the incubating in (b) begins when the emulsion is subject to conditions sufficient to initiate the attachment reaction. In some embodiments, the condition is selected from the group consisting of a temperature, a pressure, a concentration of a reagent, an electric field, a magnetic field, and exposure to radiation.

In some embodiments, the nucleic acid molecule is dissolved in the reagent mixture and the reagent mixture is in contact with the bead.

In some embodiments, the nucleic acid molecule is not capable of attaching to the bead prior to incubation of the emulsion.

In some embodiments, the nucleic acid molecule does not hybridize with the first primer prior to incubation of the emulsion.

In some embodiments, the attachment reaction is a ligation reaction.

In some embodiments, the attachment reaction is a primer extension reaction.

In some embodiments, the reagent mixture a second primer comprising a first portion and a second portion, which first portion anneals to the nucleic acid molecule and which second portion comprises an extension sequence.

In some embodiments, the second primer is attached to the bead. In some embodiments, the attachment reaction uses the second primer and the nucleic acid molecule to generate an extension product, product comprises the extension sequence, or complement thereof, configured to hybridize with the first sequence. In some embodiments, the amplification reaction uses the plurality of first primers immobilized to the bead to amplify the extension product. In some embodiments, the second primer has a predetermined concentration such that the first period of time is greater than the second period of time. In some embodiments, the emulsion further comprises a plurality of third primers that is capable of exponentially amplifying the nucleic acid molecule when used in a polymerase chain reaction (PCR) reaction with the first primer or the second primer.

In some embodiments, the amplification reaction concludes when at least 99% of the plurality of first primers attached to the bead are coupled to the extension product, or derivative thereof.

In some embodiments, the emulsion comprises a library of nucleic acid molecules, including the nucleic acid molecule, that are distributed amongst the plurality of partitions at a density which is greater than an average of 1 nucleic acid molecule per partition in the plurality of partitions. In some embodiments, each nucleic acid molecule of the library of nucleic acid molecules is capable of coupling to the second primer.

In some embodiments, the partition of the plurality of partitions comprises a plurality of nucleic acid molecules, wherein the plurality of nucleic acid molecules comprises the nucleic acid molecule. In some embodiments, the nucleic acid molecule completes the attachment reaction and the amplification reaction before a second nucleic acid molecule attaches to the bead.

In some embodiments, the nucleic acid molecule is single stranded.

In some embodiments, the emulsion further comprises an additional first primer that is not attached to the bead.

In some embodiments, the emulsion further comprises a nucleic acid polymerase.

In some embodiments, the extension reaction is performed under isothermal conditions.

In some embodiments, the amplification reaction is performed under isothermal conditions.

In some embodiments, the method further comprises recovering the bead from the emulsion.

In some embodiments, the method further comprises assaying an amplification product of the nucleic acid molecule or derivative thereof to identify a sequence of the nucleic acid molecule.

In some embodiments, the reagent mixture is further configured to perform an extension reaction prior to the attachment reaction to allow the amplification reaction to proceed. In some embodiments, the extension reaction takes place in a third period of time, which third period of time begins when the emulsion begins incubation and concludes when the amplification reaction initiates. In some embodiments, the third period of time occurs concurrently with the first period of time. In some embodiments, the third period of time occurs prior to the second period of time.

Another aspect of the present disclosure provides a method for preparing a support configured to attach to a nucleic acid molecule, comprising: (a) providing a mixture comprising a plurality of supports and a plurality of extension groups, wherein a support of the plurality of supports comprises a first primer, wherein an extension group of the plurality of extension groups comprises an extension primer molecule; (b) subjecting the mixture to conditions sufficient to attach the first primer of the support to the extension primer of the extension group, to generate a resulting mixture comprising (i) an un-extended support not associated with the plurality of extension groups and (ii) an extended support associated with the extension group and a capture entity configured for capture by a capturing entity, wherein the extended support comprises a second primer comprising a sequence complementary to a sequence of the extension primer molecule; and (c) isolating the extended support from the resulting mixture by capturing the capture entity using the capturing entity.

In some embodiments, the method further comprises dissociating the extension group from the extended support. In some embodiments, dissociating comprises melting. In some embodiments the method further comprises annealing the nucleic acid molecule to the second primer to generate a template-attached support. In some embodiments the method further comprises partitioning the template-attached support in a partition. In some embodiments the method further comprises performing an amplification reaction to immobilize a plurality of amplification products of the nucleic acid molecule to the extended support.

In some embodiments, the support comprises a bead. In some embodiments, the support comprises a plurality of first primers, wherein the plurality of first primers comprises the first primer. In some embodiments, the capture entity comprises biotin and the capturing entity comprises streptavidin. In some embodiments, the capture entity comprises a capture sequence and the capturing entity comprises a complementary capture sequence to the capture sequence.

In some embodiments, the capture entity comprises a magnetic particle and the capturing entity comprises a magnetic field system. In some embodiments, the capture entity comprises a charged particle and the capturing entity comprises an electric field system.

In some embodiments, in (a) the extension group comprises the capture entity.

In some embodiments, (b) comprises performing an extension reaction using the first primer to incorporate a nucleotide comprising the capture entity.

In some embodiments, isolating the extended support from the resulting mixture by capturing the capture entity using the capturing entity comprises: providing a capturing group comprising (i) the capturing entity and (ii) a secondary capture entity configured for capture by a secondary capturing entity; associating the capturing group with the extended support by capturing the capture entity using the capturing entity; and isolating the extended support from the resulting mixture by capturing the secondary capture entity using the secondary capturing entity.

In some embodiments, the secondary capture entity comprises biotin and the secondary capturing entity comprises streptavidin. In some embodiments, the secondary capture entity comprises a capture sequence and the secondary capturing entity comprises a complementary capture sequence to the capture sequence. In some embodiments, the secondary capture entity comprises a magnetic particle and the secondary capturing entity comprises a magnetic field system. In some embodiments, the secondary capture entity comprises a charged particle and the secondary capturing entity comprises an electric field system. In some embodiments, the secondary capturing entity captures a plurality of extended supports, and the plurality of extended supports comprise the extended support. In some embodiments, the method further comprises dissociating the capture group from the extended support.

In another aspect, the present disclosure provides a method for preparing a support configured to attach to a nucleic acid molecule, comprising: (a) providing a mixture comprising a plurality of un-extended supports and a plurality of extended supports, wherein an un-extended support of the plurality of un-extended support does not comprise a primer sequence and an extended support of the plurality of extended supports comprises the primer sequence, wherein the primer sequence is configured to attach to the nucleic acid molecule; (b) providing a capture group comprising (i) a capture entity configured for capture by a capturing entity and (ii) a sequence configured to attach to the primer sequence to the mixture to associate the extended support with the capture group using the primer sequence of the extended support and the sequence of the capture group; and (c) isolating the extended support from the resulting mixture by capturing the capture entity using the capturing entity.

In some embodiments, the method further comprises dissociating the capture group from the extended support. In some embodiments, the disassociating comprises melting.

In some embodiments, the method further comprises, subsequent to isolating the extended support from the resulting mixture by capturing the capture entity, using the capturing entity attaching the nucleic acid molecule to the primer sequence. In some embodiments, the extended support comprises a bead. In some embodiments, the capture entity comprises biotin and the capturing entity comprises streptavidin.

In some embodiments, the capture entity comprises a capture sequence and the capturing entity comprises a complementary capture sequence to the capture sequence. In some embodiments, the capture entity comprises a magnetic particle and the capturing entity comprises a magnetic field system. In some embodiments, the capture entity comprises a charged particle and the capturing entity comprises an electric field system In another aspect, the present disclosure provides a method for preparing a support, comprising: (a) providing a mixture comprising a plurality of supports and a plurality of template nucleic acid molecules, wherein a support of the plurality of support comprises a plurality of primers, wherein a template nucleic acid molecule of the plurality of template nucleic acid molecules comprises (i) an adapter configured to attach to a primer of the plurality of primers and (ii) a capture entity configured for capture by a capturing entity coupled thereto; (b) subjecting the mixture to conditions sufficient to attach the primer of the support to the adapter of the template nucleic acid molecule, to generate a resulting mixture comprising (i) an un-extended support not associated with the plurality of template nucleic acid molecules and (ii) an extended support associated with the capture entity coupled to the template nucleic acid molecule, wherein the extended support comprises a nucleic acid molecule comprising a sequence complementary to a sequence of the template nucleic acid molecules, wherein at least 50% of the plurality of primers on the extended support is not associated with the plurality of template nucleic acid molecules; and (c) isolating the extended support from the resulting mixture by capturing the capture entity using the capturing entity.

In another aspect, the present disclosure provides a method for preparing a support, comprising: (a) providing a mixture comprising a plurality of supports and a plurality of template nucleic acid molecules, wherein a support of the plurality of support comprises a plurality of primers, wherein a template nucleic acid molecule of the plurality of template nucleic acid molecules comprises an adapter configured to attach to a primer of the plurality of primers; (b) subjecting the mixture to conditions sufficient to attach the primer of the support to the adapter of the template nucleic acid molecule, to generate a resulting mixture comprising (i) an un-extended support not associated with the plurality of template nucleic acid molecules and (ii) an extended support associated with a capture entity coupled to the template nucleic acid molecule, wherein the capture entity is configured for capture by a capturing entity, wherein the extended support comprises a nucleic acid molecule comprising a sequence complementary to a sequence of the template nucleic acid molecules, wherein at least 50% of the plurality of primers on the extended support is not associated with the plurality of template nucleic acid molecules; (c) isolating the extended support from the resulting mixture by capturing the capture entity using the capturing entity; and (d) partitioning a plurality of extended supports into a plurality of droplets, wherein the plurality of extended supports comprises the extended support, wherein a droplet of the plurality of droplets comprises the extended support.

In some embodiments, at least 80% of the plurality of primers on the extended supports is not associated with the plurality of template nucleic acid molecules. In some embodiments, at least 90% of the plurality of primers on the extended support is not associated with the plurality of template nucleic acid molecules. In some embodiments, at least 95% of the plurality of primers on the extended support is not associated with the plurality of template nucleic acid molecules. In some embodiments, at least 99% of the plurality of primers on the extended support is not associated with the plurality of template nucleic acid molecules.

In some embodiments, the method further comprises disassociating the template nucleic acid molecule from the extended support. In some embodiments, the disassociating comprises melting. In some embodiments, the support comprises a bead. In some embodiments, the capture entity comprises biotin and the capturing entity comprises streptavidin. In some embodiments, the capture entity comprises a capture sequence and the capturing entity comprises a complementary capture sequence to the capture sequence. In some embodiments, the capture entity comprises a magnetic particle and wherein the capturing entity comprises a magnetic field system. In some embodiments, the capture entity comprises a charged particle and wherein the capturing entity comprises an electric field system.

In some embodiments, isolating the extended support from the resulting mixture by capturing the capture entity using the capturing entity comprises: providing a capturing group comprising (i) the capturing entity and (ii) a secondary capture entity configured for capture by a secondary capturing entity; associating the capturing group with the extended support by capturing the capture entity using the capturing entity; and isolating the extended support from the resulting mixture by capturing the secondary capture entity using the secondary capturing entity.

In some embodiments, the secondary capture entity comprises biotin and the secondary capturing entity comprises streptavidin. In some embodiments, the secondary capture entity comprises a capture sequence and the secondary capturing entity comprises a complementary capture sequence to the capture sequence. In some embodiments, the secondary capture entity comprises a magnetic particle and the secondary capturing entity comprises a magnetic field system.

In some embodiments, the capture entity comprises a charged particle and the secondary capturing entity comprises an electric field system. In some embodiments, the secondary capturing entity captures a plurality of extended supports, wherein the plurality of extended supports comprise the extended support. In some embodiments, the method further comprises disassociating the capture group from the extended support.

In some embodiments, in (a) the template nucleic acid molecule comprises the capture entity.

In some embodiments, (b) comprises performing an extension reaction using the primer to incorporate a nucleotide comprising the capture entity.

In some embodiments, wherein the droplet comprises a single extended support of the plurality of extended supports, wherein the single extended support is the extended support. In some embodiments, a majority of occupied droplets of the plurality of droplets comprises a single extended support of the plurality of extended supports. In some embodiments, the plurality of droplets comprises an unoccupied droplet, wherein the unoccupied droplet does not include any extended support of the plurality of extended supports.

In some embodiments, (d) comprises partitioning a mixture, wherein the mixture comprises the plurality of extended supports, wherein the mixture comprises more extended supports than un-extended supports. In some embodiments, substantially all supports in the mixture are extended supports.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

DETAILED DESCRIPTION

Figure 1:
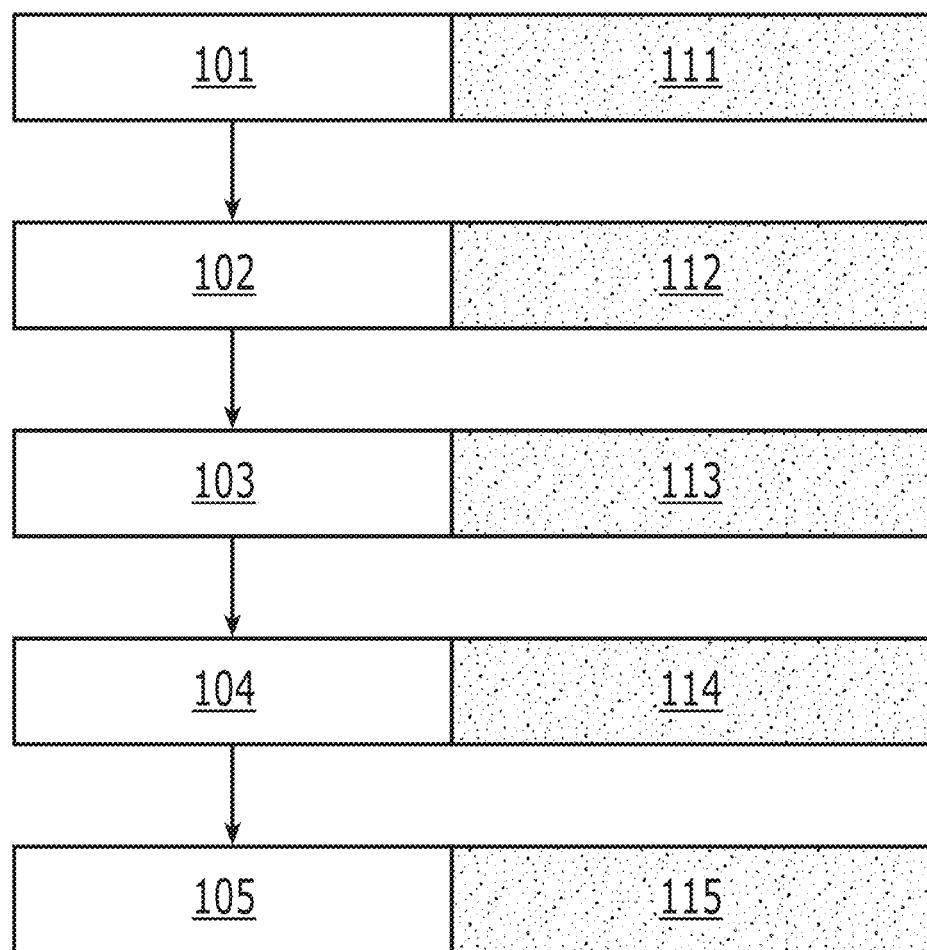
FIG. 1 depicts a schematic of a generic next-generation sequencing (NGS) approach and shows situations where genetic material may escape analysis and/or indicates potential noise sources and mutations that may be present in the work flow.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

Ranges may be expressed herein as from "about" one particular value, and/or to "about" another particular value. The terms "about" and "approximately" shall generally mean an acceptable degree of error or variation for a given value or range of values, such as, for example, a degree of error or variation that is within 20 percent (%), within 15%, within 10%, or within 5% of a given value or range of values.

The term "amplification," as used herein, generally refers to the production of one or more copies of a nucleic acid molecule or an extension product (e.g., a product of a primer extension reaction on the nucleic acid molecule). Amplification of a nucleic acid molecule may yield a single strand hybridized to the nucleic acid molecule, or multiple copies of the nucleic acid molecule or complement thereof. An amplicon may be a single-stranded or double-stranded nucleic acid molecule that is generated by an amplification procedure from a starting template nucleic acid molecule. The amplicon may comprise a nucleic acid strand, of which at least a portion may be substantially identical or substantially complementary to at least a portion of the starting template. Where the starting template is a double-stranded nucleic acid molecule, an amplicon may comprise a nucleic acid strand that is substantially identical to at least a portion of one strand and is substantially complementary to at least a portion of either strand. The amplicon can be single-stranded or double-stranded irrespective of whether the initial template is single-stranded or double-stranded. An amplification reaction may be, for example, a polymerase chain reaction (PCR), such as an emulsion polymerase chain reaction (ePCR; e.g., PCR carried out within a microreactor such as a well or droplet).

The term "denaturation," as used herein, generally refers to separation of a double-stranded molecule (e.g., DNA) into single-stranded molecules. Denaturation may be complete or partial denaturation. In partial denaturation, a single-stranded region may form in a double-stranded molecule by denaturation of the two deoxyribonucleic acid (DNA) strands flanked by double-stranded regions in DNA.

The term "clonal," as used herein, generally refers to a population of nucleic acids for which a substantial portion (e.g., greater than 50%, 60%, 70%, 80%, 90%, 95%, or 99%) of its members have substantially identical sequences. Members of a clonal population of nucleic acid molecules may have sequence homology to one another. In some instances, such members may have sequence homology to a template nucleic acid molecule. In some instances, such members may have sequence homology to a complement of the template nucleic acid molecule (if single stranded). The members of the clonal population may be double stranded or single stranded. Members of a population may not be 100% identical or complementary because, e.g., "errors" may occur during the course of synthesis such that a minority of a given population may not have sequence homology with a majority of the population. For example, at least 50% of the members of a population may be substantially identical to each other or to a reference nucleic acid molecule (i.e., a molecule of defined sequence used as a basis for a sequence comparison). At least 60%, at least 70%, at least 80%, at least 90%, at least 95%, at least 99%, or more of the members of a population may be substantially identical to the reference nucleic acid molecule. Two molecules may be considered substantially identical (or homologous) if the percent identity between the two molecules is at least 60%, 70%, 75%, 80%, 85%, 90%, 95%, 98%, 99%, 99.9% or greater. Two molecules may be considered substantially complementary if the percent complementarity between the two molecules is at least 60%, 70%, 75%, 80%, 85%, 90%, 95%, 98%, 99%, 99.9% or greater. A low or insubstantial level of mixing of non-homologous nucleic acids may occur, and thus a clonal population may contain a minority of diverse nucleic acids (e.g., less than 30%, e.g., less than 10%).

The term "complementary sequence," as used herein, generally refers to a sequence that hybridizes to another sequence or has sequence complementarity with such other sequence. Hybridization between two single-stranded nucleic acid molecules may involve the formation of a double-stranded structure that is stable under certain conditions. Two single-stranded polynucleotides may be considered to be hybridized if they are bonded to each other by two or more sequentially adjacent base pairings. A substantial proportion of nucleotides in one strand of a double-stranded structure may undergo Watson-Crick base-pairing with a nucleoside on the other strand. Hybridization may also include the pairing of nucleoside analogs, such as deoxyinosine, nucleosides with 2-aminopurine bases, and the like, that may be employed to reduce the degeneracy of probes, whether or not such pairing involves formation of hydrogen bonds.

The term "polymerizing enzyme," as used herein, generally refers to a substance catalyzing a polymerization reaction. A polymerizing enzyme may be used to extend a nucleic acid primer paired with a template strand by incorporation of nucleotides or nucleotide analogs. A polymerizing enzyme may add a new strand of DNA by extending the 3' end of an existing nucleotide chain, adding new nucleotides matched to the template strand one at a time via the creation of phosphodiester bonds. A polymerizing enzyme may be a polymerase such as a nucleic acid polymerase. A polymerase may be naturally occurring or synthesized. A polymerase may have relatively high processivity, namely the capability of the polymerase to consecutively incorporate nucleotides into a nucleic acid template without releasing the nucleic acid template. A polymerizing enzyme may be a transcriptase. Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase, 029 (phi29) DNA polymerase, Taq polymerase, Tth polymerase, Tli polymerase, Pfu polymerase, Pwo polymerase, VENT polymerase, DEEPVENT polymerase, EXTaq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. A polymerase may be a single subunit polymerase.

The term "melting temperature" or "melting point," as used herein, generally refers to the temperature at which at least a portion of a strand of a nucleic acid molecule in a sample has separated from at least a portion of a complementary strand. The melting temperature may be the temperature at which a double-stranded nucleic acid molecule has partially or completely denatured. The melting temperature may refer to a temperature of a sequence among a plurality of sequences of a given nucleic acid molecule, or a temperature of the plurality of sequences. Different regions of a double-stranded nucleic acid molecule may have different melting temperatures. For example, a double-stranded nucleic acid molecule may include a first region having a first melting point and a second region having a second melting point that is higher than the first melting point. Accordingly, different regions of a double-stranded nucleic acid molecule may melt (e.g., partially denature) at different temperatures. The melting point of a nucleic acid molecule or a region thereof (e.g., a nucleic acid sequence) may be determined experimentally (e.g., via a melt analysis or other procedure) or may be estimated based upon the sequence and length of the nucleic acid molecule. For example, a software program such as MELTING may be used to estimate a melting temperature for a nucleic acid sequence (Dumousseau M, Rodriguez N, July N, Le Novère N, MELTING, a flexible platform to predict the melting temperatures of nucleic acids. BMC Bioinformatics. 2012 May 16; 13:101. doi: 10.1186/1471-2105-13-101). Accordingly, a melting point as described herein may be an estimated melting point. A true melting point of a nucleic acid sequence may vary based upon the sequences or lack thereof adjacent to the nucleic acid sequence of interest as well as other factors.

The term "nucleotide," as used herein, generally refers to a substance including a base (e.g., a nucleobase), sugar moiety, and phosphate moiety. A nucleotide may comprise a free base with attached phosphate groups. A substance including a base with three attached phosphate groups may be referred to as a nucleoside triphosphate. When a nucleotide is being added to a growing nucleic acid molecule strand, the formation of a phosphodiester bond between the proximal phosphate of the nucleotide to the growing chain may be accompanied by hydrolysis of a high-energy phosphate bond with release of the two distal phosphates as a pyrophosphate. The nucleotide may be naturally occurring or non-naturally occurring (e.g., a modified or engineered nucleotide).

The term "nucleotide analog," as used herein, may include, but is not limited to, a nucleotide that may or may not be a naturally occurring nucleotide. For example, a nucleotide analog may be derived from and/or include structural similarities to a canonical nucleotide such as adenine- (A), thymine- (T), cytosine- (C), uracil- (U), or guanine- (G) including nucleotide. A nucleotide analog may comprise one or more differences or modifications relative to a natural nucleotide. Examples of nucleotide analogs include inosine, diaminopurine, 5-fluorouracil, 5-bromouracil, 5-chlorouracil, 5-iodouracil, hypoxanthine, xanthine, deazaxanthine, deazaguanine, isocytosine, isoguanine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids, and modified versions thereof (e.g., by oxidation, reduction, and/or addition of a substituent such as an alkyl, hydroxyalkyl, hydroxyl, or halogen moiety). Nucleic acid molecules (e.g., polynucleotides, double-stranded nucleic acid molecules, single-stranded nucleic acid molecules, primers, adapters, etc.) may be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety, or phosphate backbone. In some cases, a nucleotide may include a modification in its phosphate moiety, including a modification to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates), and modifications with selenium moieties (e.g., phosphoroselenoate nucleic acids). A nucleotide or nucleotide analog may comprise a sugar selected from the group consisting of ribose, deoxyribose, and modified versions thereof (e.g., by oxidation, reduction, and/or addition of a substituent such as an alkyl, hydroxyalkyl, hydroxyl, or halogen moiety). A nucleotide analog may also comprise a modified linker moiety (e.g., in lieu of a phosphate moiety). Nucleotide analogs may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure may provide, for example, higher density in bits per cubic mm, higher safety (resistant to accidental or purposeful synthesis of natural toxins), easier discrimination in photo-programmed polymerases, and/or lower secondary structure. Nucleotide analogs may be capable of reacting or bonding with detectable moieties for nucleotide detection.

The term "support" or "substrate," as used herein, generally refers to any solid or semi-solid article on which reagents such as nucleic acid molecules may be immobilized. Nucleic acid molecules may be synthesized, attached, ligated, or otherwise immobilized. Nucleic acid molecules may be immobilized on a substrate by any method including, but not limited to, physical adsorption, by ionic or covalent bond formation, or combinations thereof. A substrate may be 2-dimensional (e.g., a planar 2D substrate) or 3-dimensional. In some cases, a substrate may be a component of a flow cell and/or may be included within or adapted to be received by a sequencing instrument. A substrate may include a polymer, a glass, or a metallic material. Examples of substrates include a membrane, a planar substrate, a microtiter plate, a bead (e.g., a magnetic bead), a filter, a test strip, a slide, a cover slip, and a test tube. A substrate may comprise organic polymers such as polystyrene, polyethylene, polypropylene, polyfluoroethylene, polyethyleneoxy, and polyacrylamide (e.g., polyacrylamide gel), as well as co-polymers and grafts thereof. A substrate may comprise latex or dextran. A substrate may also be inorganic, such as glass, silica, gold, controlled-pore-glass (CPG), or reverse-phase silica. The configuration of a support may be, for example, in the form of beads, spheres, particles, granules, a gel, a porous matrix, or a substrate. In some cases, a substrate may be a single solid or semi-solid article (e.g., a single particle), while in other cases a substrate may comprise a plurality of solid or semi-solid articles (e.g., a collection of particles). Substrates may be planar, substantially planar, or non-planar. Substrates may be porous or non-porous, and may have swelling or non-swelling characteristics. A substrate may be shaped to comprise one or more wells, depressions, or other containers, vessels, features, or locations. A plurality of substrates may be configured in an array at various locations. A substrate may be addressable (e.g., for robotic delivery of reagents), or by detection approaches, such as scanning by laser illumination and confocal or deflective light gathering. For example, a substrate may be in optical and/or physical communication with a detector. Alternatively, a substrate may be physically separated from a detector by a distance. An amplification substrate (e.g., a bead) can be placed within or on another substrate (e.g., within a well of a second support).

The term "label," as used herein, generally refers to a moiety that is capable of coupling with a species, such as, for example a nucleotide analog. A label may include an affinity moiety. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after a primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP), tris(hydroxypropyl)phosphine (THP) or enzymatically cleavable (e.g., via an esterase, lipase, peptidase or protease). In some cases, the label may be luminescent; that is, fluorescent or phosphorescent. Labels may be quencher molecules. The term "quencher," as used herein refers to a molecule that can reduce an emitted signal. For example, a template nucleic acid molecule may be designed to emit a detectable signal. Incorporation of a nucleotide or nucleotide analog comprising a quencher can reduce or eliminate the signal, which reduction or elimination is then detected. In some cases, as described elsewhere herein, labelling with a quencher can occur after nucleotide or nucleotide analog incorporation. Dyes and labels may be incorporated into nucleic acid sequences. Dyes and labels may also be incorporated into linkers, such as linkers for linking one or more beads to one another. Non-limiting examples of dyes include SYBR green, SYBR blue, DAPI, propidium iodine, Hoechst, SYBR gold, ethidium bromide, acridine, proflavine, acridine orange, acriflavine, fluorocoumarin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methylcoumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be a type that does not self-quench or exhibit proximity quenching. Non-limiting examples of a label type that does not self-quench or exhibit proximity quenching include Bimane derivatives such as Monobromobimane. The term "proximity quenching," as used herein, generally refers to a phenomenon where one or more dyes near each other may exhibit lower fluorescence as compared to the fluorescence they exhibit individually. In some cases, the dye may be subject to proximity quenching wherein the donor dye and acceptor dye are within 1 nm to 50 nm of each other.

The term "detector," as used herein, generally refers to a device that is capable of detecting a signal, such as a signal indicative of the presence or absence of an incorporated nucleotide or nucleotide analog. A detector may include optical and/or electronic components that may detect signals. Non-limiting examples of detection methods involving a detector include optical detection, spectroscopic detection, electrostatic detection, and electrochemical detection. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The term "sequencing," as used herein, generally refers to a process for generating or identifying a sequence of a biological molecule, such as a nucleic acid molecule. Such sequence may be a nucleic acid sequence, which may include a sequence of nucleic acid bases (e.g., nucleobases). Sequencing may be, for example, single molecule sequencing, sequencing by synthesis, sequencing by hybridization, or sequencing by ligation. Sequencing may be performed using template nucleic acid molecules immobilized on a support, such as a flow cell or one or more beads. A sequencing assay may yield one or more sequencing reads corresponding to one or more template nucleic acid molecules.

The term "read," as used herein, generally refers to a nucleic acid sequence, such as a sequencing read. A sequencing read may be an inferred sequence of nucleic acid bases (e.g., nucleotides) or base pairs obtained via a nucleic acid sequencing assay. A sequencing read may be generated by a nucleic acid sequencer, such as a massively parallel array sequencer (e.g., Illumina or Pacific Biosciences of California). A sequencing read may correspond to a portion, or in some cases all, of a genome of a subject. A sequencing read may be part of a collection of sequencing reads, which may be combined through, for example, alignment (e.g., to a reference genome), to yield a sequence of a genome of a subject.

The term "subject," as used herein, generally refers to an individual or entity from which a biological sample (e.g., a biological sample that is undergoing or will undergo processing or analysis) may be derived. A subject may be an animal (e.g., mammal or non-mammal) or plant. The subject may be a human, dog, cat, horse, pig, bird, non-human primate, simian, farm animal, companion animal, sport animal, or rodent. A subject may be a patient. The subject may have or be suspected of having a disease or disorder, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. Alternatively or in addition, a subject may be known to have previously had a disease or disorder. The subject may have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease. A subject may be undergoing treatment for a disease or disorder. A subject may be symptomatic or asymptomatic of a given disease or disorder. A subject may be healthy (e.g., not suspected of having disease or disorder). A subject may have one or more risk factors for a given disease. A subject may have a given weight, height, body mass index or other physical characteristic. A subject may have a given ethnic or racial heritage, place of birth or residence, nationality, disease or remission state, family medical history, or other characteristic.

As used herein, the term "biological sample" generally refers to a sample obtained from a subject. The biological sample may be obtained directly or indirectly from the subject. A sample may be obtained from a subject via any suitable method, including, but not limited to, spitting, swabbing, blood draw, biopsy, obtaining excretions (e.g., urine, stool, sputum, vomit, or saliva), excision, scraping, and puncture. A sample may be obtained from a subject by, for example, intravenously or intraarterially accessing the circulatory system, collecting a secreted biological sample (e.g., stool, urine, saliva, sputum, etc.), breathing, or surgically extracting a tissue (e.g., biopsy). The sample may be obtained by non-invasive methods including but not limited to: scraping of the skin or cervix, swabbing of the cheek, or collection of saliva, urine, feces, menses, tears, or semen. Alternatively, the sample may be obtained by an invasive procedure such as biopsy, needle aspiration, or phlebotomy. A sample may comprise a bodily fluid such as, but not limited to, blood (e.g., whole blood, red blood cells, leukocytes or white blood cells, platelets), plasma, serum, sweat, tears, saliva, sputum, urine, semen, mucus, synovial fluid, breast milk, colostrum, amniotic fluid, bile, bone marrow, interstitial or extracellular fluid, or cerebrospinal fluid. For example, a sample may be obtained by a puncture method to obtain a bodily fluid comprising blood and/or plasma. Such a sample may comprise both cells and cell-free nucleic acid material. Alternatively, the sample may be obtained from any other source including but not limited to blood, sweat, hair follicle, buccal tissue, tears, menses, feces, or saliva. The biological sample may be a tissue sample, such as a tumor biopsy. The sample may be obtained from any of the tissues provided herein including, but not limited to, skin, heart, lung, kidney, breast, pancreas, liver, intestine, brain, prostate, esophagus, muscle, smooth muscle, bladder, gall bladder, colon, or thyroid. The methods of obtaining provided herein include methods of biopsy including fine needle aspiration, core needle biopsy, vacuum assisted biopsy, large core biopsy, incisional biopsy, excisional biopsy, punch biopsy, shave biopsy or skin biopsy. The biological sample may comprise one or more cells. A biological sample may comprise one or more nucleic acid molecules such as one or more deoxyribonucleic acid (DNA) and/or ribonucleic acid (RNA) molecules (e.g., included within cells or not included within cells). Nucleic acid molecules may be included within cells. Alternatively or in addition, nucleic acid molecules may not be included within cells (e.g., cell-free nucleic acid molecules). The biological sample may be a cell-free sample.

The term "cell-free sample," as used herein, generally refers to a sample that is substantially free of cells (e.g., less than 10% cells on a volume basis). A cell-free sample may be derived from any source (e.g., as described herein). For example, a cell-free sample may be derived from blood, sweat, urine, or saliva. For example, a cell-free sample may be derived from a tissue or bodily fluid. A cell-free sample may be derived from a plurality of tissues or bodily fluids. For example, a sample from a first tissue or fluid may be combined with a sample from a second tissue or fluid (e.g., while the samples are obtained or after the samples are obtained). In an example, a first fluid and a second fluid may be collected from a subject (e.g., at the same or different times) and the first and second fluids may be combined to provide a sample. A cell-free sample may comprise one or more nucleic acid molecules such as one or more DNA or RNA molecules.

A sample that is not a cell-free sample (e.g., a sample comprising one or more cells) may be processed to provide a cell-free sample. For example, a sample that includes one or more cells as well as one or more nucleic acid molecules (e.g., DNA and/or RNA molecules) not included within cells (e.g., cell-free nucleic acid molecules) may be obtained from a subject. The sample may be subjected to processing (e.g., as described herein) to separate cells and other materials from the nucleic acid molecules not included within cells, thereby providing a cell-free sample (e.g., comprising nucleic acid molecules not included within cells). The cell-free sample may then be subjected to further analysis and processing (e.g., as provided herein). Nucleic acid molecules not included within cells (e.g., cell-free nucleic acid molecules) may be derived from cells and tissues. For example, cell-free nucleic acid molecules may derive from a tumor tissue or a degraded cell (e.g., of a tissue of a body). Cell-free nucleic acid molecules may comprise any type of nucleic acid molecules (e.g., as described herein). Cell-free nucleic acid molecules may be double-stranded, single-stranded, or a combination thereof. Cell-free nucleic acid molecules may be released into a bodily fluid through secretion or cell death processes, e.g., cellular necrosis, apoptosis, or the like. Cell-free nucleic acid molecules may be released into bodily fluids from cancer cells (e.g., circulating tumor DNA (ctDNA)). Cell free nucleic acid molecules may also be fetal DNA circulating freely in a maternal blood stream (e.g., cell-free fetal nucleic acid molecules such as cffDNA). Alternatively or in addition, cell-free nucleic acid molecules may be released into bodily fluids from healthy cells.

A biological sample obtained directly from a subject may not have been further processed following being obtained from the subject. For example, a blood sample may be obtained directly from a subject by accessing the subject's circulatory system, removing the blood from the subject (e.g., via a needle), and transferring the removed blood into a receptacle. The receptacle may comprise reagents (e.g., anti-coagulants) such that the blood sample is useful for further analysis. In another example, a swab may be used to access epithelial cells on an oropharyngeal surface of the subject. Following obtaining the biological sample from the subject, the swab containing the biological sample may be contacted with a fluid (e.g., a buffer) to collect the biological fluid from the swab.

Any suitable biological sample that comprises one or more nucleic acid molecules may be obtained from a subject. A sample (e.g., a biological sample or cell-free biological sample) suitable for use according to the methods provided herein may be any material comprising tissues, cells, degraded cells, nucleic acids, genes, gene fragments, expression products, gene expression products, and/or gene expression product fragments of an individual to be tested. A biological sample may be solid matter (e.g., biological tissue) or may be a fluid (e.g., a biological fluid). In general, a biological fluid may include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, microbiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. Methods for determining sample suitability and/or adequacy are provided. A sample may include, but is not limited to, blood, plasma, tissue, cells, degraded cells, cell-free nucleic acid molecules, and/or biological material from cells or derived from cells of an individual such as cell-free nucleic acid molecules. The sample may be a heterogeneous or homogeneous population of cells, tissues, or cell-free biological material. The biological sample may be obtained using any method that can provide a sample suitable for the analytical methods described herein.

A sample (e.g., a biological sample or cell-free biological sample) may undergo one or more processes in preparation for analysis, including, but not limited to, filtration, centrifugation, selective precipitation, permeabilization, isolation, agitation, heating, purification, and/or other processes. For example, a sample may be filtered to remove contaminants or other materials. In an example, a sample comprising cells may be processed to separate the cells from other material in the sample. Such a process may be used to prepare a sample comprising only cell-free nucleic acid molecules. Such a process may consist of a multi-step centrifugation process. Multiple samples, such as multiple samples from the same subject (e.g., obtained in the same or different manners from the same or different bodily locations, and/or obtained at the same or different times (e.g., seconds, minutes, hours, days, weeks, months, or years apart)) or multiple samples from different subjects may be obtained for analysis as described herein. In an example, the first sample is obtained from a subject before the subject undergoes a treatment regimen or procedure and the second sample is obtained from the subject after the subject undergoes the treatment regimen or procedure. Alternatively or in addition, multiple samples may be obtained from the same subject at the same or approximately the same time. Different samples obtained from the same subject may be obtained in the same or different manner. For example, a first sample may be obtained via a biopsy and a second sample may be obtained via a blood draw. Samples obtained in different manners may be obtained by different medical professionals, using different techniques, at different times, and/or at different locations. Different samples obtained from the same subject may be obtained from different areas of a body. For example, a first sample may be obtained from a first area of a body (e.g., a first tissue) and a second sample may be obtained from a second area of the body (e.g., a second tissue).

A biological sample as used herein (e.g., a biological sample comprising one or more nucleic acid molecules) may not be purified when provided in a reaction vessel. Furthermore, for a biological sample comprising one or more nucleic acid molecules, the one or more nucleic acid molecules may not be extracted when the biological sample is provided to a reaction vessel. For example, ribonucleic acid (RNA) and/or deoxyribonucleic acid (DNA) molecules of a biological sample may not be extracted from the biological sample when providing the biological sample to a reaction vessel. Moreover, a target nucleic acid (e.g., a target RNA or target DNA molecules) present in a biological sample may not be concentrated when providing the biological sample to a reaction vessel. Alternatively, a biological sample may be purified and/or nucleic acid molecules may be isolated from other materials in the biological sample.

A biological sample as described herein may contain a target nucleic acid. As used herein, the terms "template nucleic acid", "target nucleic acid", "nucleic acid molecule," "nucleic acid sequence," "nucleic acid fragment," "oligonucleotide," "polynucleotide," and "nucleic acid" generally refer to polymeric forms of nucleotides of any length, such as deoxyribonucleotides (dNTPs) or ribonucleotides (rNTPs), or analogs thereof, and may be used interchangeably. Nucleic acids may have any three-dimensional structure, and may perform any function, known or unknown. A nucleic acid molecule may have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotides. Non-limiting examples of nucleic acids include DNA, RNA, genomic DNA (e.g., gDNA such as sheared gDNA), cell-free DNA (e.g., cfDNA), synthetic DNA/RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or following assembly of the nucleic acid. The sequence of nucleotides of a nucleic acid may be interrupted by non-nucleotide components. A nucleic acid may be further modified following polymerization, such as by conjugation or binding with a reporter agent.

A target nucleic acid or sample nucleic acid as described herein may be amplified to generate an amplified product. A target nucleic acid may be a target RNA or a target DNA. When the target nucleic acid is a target RNA, the target RNA may be any type of RNA, including types of RNA described elsewhere herein. The target RNA may be viral RNA and/or tumor RNA. A viral RNA may be pathogenic to a subject. Non-limiting examples of pathogenic viral RNA include human immunodeficiency virus I (HIV I), human immunodeficiency virus n (HIV 11), orthomyxoviruses, Ebola virus. Dengue virus, influenza viruses (e.g., H1N1, H3N2, H7N9, or H5N1), herpes virus, hepatitis A virus, hepatitis B virus, hepatitis C (e.g., armored RNA-HCV virus) virus, hepatitis D virus, hepatitis E virus, hepatitis G virus, Epstein-Barr virus, mononucleosis virus, cytomegalovirus, SARS virus, West Nile Fever virus, polio virus, and measles virus.

A biological sample may comprise a plurality of target nucleic acid molecules. For example, a biological sample may comprise a plurality of target nucleic acid molecules from a single subject. In another example, a biological sample may comprise a first target nucleic acid molecule from a first subject and a second target nucleic acid molecule from a second subject.

The methods described herein may be conducted in a reaction vessel (e.g., a droplet in an emulsion, or a well among a plurality of wells). Any suitable reaction vessel may be used. A reaction vessel comprises a body that may include an interior surface, an exterior surface, and, in some cases, an open end and an opposing closed end. In some cases, a reaction vessel may not comprise an open or closed end. For example, a reaction vessel may be a droplet. In other cases, a reaction vessel may comprise a cap, which cap may be configured to contact the body at an open end, such that when contact is made the open end of the reaction vessel is closed. The cap may be permanently associated with the reaction vessel such that it remains attached to the reaction vessel in open and closed configurations. The cap may be removable, such that when the reaction vessel is open, the cap is separated from the reaction vessel. A reaction vessel such as a flow cell chamber (e.g., a flow cell chamber comprising a water-in-oil emulsion or a plurality of wells) may comprise one or more inlets or outlets, which inlets or outlets may be used to provide and remove reagents for use in a reaction. Reagents may be moved in and out of the chamber via pressure and vacuum controls. A reaction vessel as used herein may be sealed, optionally hermetically sealed (e.g., a sealed microwell plate).

A reaction vessel may be of varied size, shape, weight, and configuration. Some reaction vessels may be substantially round or oval tubular shaped. Some reaction vessels may be rectangular, square, diamond, circular, elliptical, or triangular shaped. A reaction vessel may be regularly shaped or irregularly shaped. For example, a reaction vessel that is a droplet (e.g., a droplet in an emulsion, such as an aqueous droplet) may be substantially spherical. A closed end of a reaction vessel (e.g., a well of a microwell plate or flow cell) may have a tapered, rounded, or flat surface. Non-limiting examples of types of a reaction vessel include a tube, a well, a capillary tube, a cartridge, a cuvette, a centrifuge tube, a droplet, or a pipette tip. Reaction vessels may be comprised of any suitable material with non-limiting examples of such materials that include glasses, metals, plastics, immiscible fluids, and combinations thereof. In an example, a reaction vessel may be a droplet, such as an aqueous droplet in an immiscible fluid such as an oil. A reaction vessel may be of any suitable size. For example, a reaction vessel may be an approximately spherical droplet having a diameter of at least about 1 nanometer (nm), 10 nm, 50 nm, 100 nm, 1 micron (μm), 10 μm, 50 μm, 100 μm, 1 millimeter (mm), 10 mm, 50 mm, 100 mm, or 1 centimeter (cm). Alternatively, a reaction vessel may be a well having a diameter of at least about 100 μm, 1 mm, 5 mm, or 10 mm. The depth of a well may be the same as or different than the diameter of the well. For example, the well may have a diameter of about 5 mm and a depth of about 10 mm.

A reaction vessel may be part of a collection or an array of reaction vessels. A collection or an array of reaction vessels may be particularly useful for automating methods and/or simultaneously processing multiple samples. A reaction vessel may be a well of a microwell plate comprised of a number of wells. A reaction vessel may be held in a well of a thermal block of a thermocycler, wherein the block of the thermal cycle comprises multiple wells each capable of receiving a sample vessel. A collection or an array comprised of reaction vessels (e.g., droplets or microwells) may comprise any appropriate number of reaction vessels. A collection or an array of reaction vessels may include at least 1, 2, 3, 4, 5, 6, 7, 8, 9, 10, 20, 30, 40, 50, 100, 200, 300, 400, 500, 1,000, 10,000 or more vessels. For example, a collection or an array of reaction vessels may comprise at least 2, 4, 6, 8, 10, 12, 14, 16, 18, 20, 25, 35, 48, 96, 144, 384, or more reaction vessels. A reaction vessel part of a collection or an array of reaction vessels (e.g., microwells) may also be individually addressable by a fluid handling device, such that the fluid handling device may correctly identify a reaction vessel and dispense appropriate fluid materials into the reaction vessel. Fluid handling devices may be useful in automating the addition of fluid materials to reaction vessels.

In some cases, one or more reaction vessels may be included within another reaction vessel. For example, a plurality of droplets may be included in a container such as a beaker, test tube, flow cell chamber, or other container, or a plurality of wells (e.g., of a microwell plate or flow cell) may be included in a container, such as a flow cell chamber. In an example, a plurality of wells may be provided on a surface of a flow cell chamber, such that a nucleic acid reaction may take place directly on a flow cell. In another example, one or more droplets may be physically constrained to a given area, such as a surface of a container. Droplets may be physically constrained via, for example, an electromagnetic force, such as via a magnetic attraction between a material (e.g., surface) of the container and a material included within the droplet (e.g., a paramagnetic bead or a magnetic label coupled to a bead) or via the use of optical tweezers. In an example, droplets may be constrained within wells (e.g., of a microwell plate or flow cell).

A reaction vessel (e.g., droplet or well) as used herein may comprise multiple thermal zones. Thermal zones may be created within a reaction vessel with the aid of thermal sensitive layering materials within the reaction vessels. In such cases, heating of the thermal sensitive layering materials may be used to release reaction mixtures from one thermal zone to the next. A reaction vessel may comprise 2, 3, 4, 5, 6, 7, 8, 9, 10, 11, 12, 13, 14, 15, 20 or more thermal zones. Thermal zones within a reaction vessel may be achieved by exposing different regions of the reaction vessel to different temperature cycling conditions. For example, different regions of a flow cell chamber (e.g., comprising a plurality of wells and/or droplets) may be subjected to different temperature cycling conditions. Alternatively, one or more reaction vessels of an array or a collection of reaction vessels may be subjected to one or more different thermal zones. For example, a first set of reaction vessels may be placed within a first thermal zone and a second set of reaction vessels may be placed within a second thermal zone (e.g., by physically separating the various reaction vessels). Alternatively or in addition, one or more reaction vessels of an array or a collection of reaction vessels may be subjected to multiple different temperatures (e.g., at different times throughout a process). Temperatures applied to a reaction vessel may be suitable for, for example, initialization of a nucleic acid reaction, annealing of nucleic acid molecules, extension of an annealed nucleic acid molecule (e.g., primer extension), partial or complete denaturation of a double-stranded nucleic acid sequence or portion thereof, or any other useful process. For example, temperatures may be controlled according to a thermocycling protocol. In an example, all or a portion of a reaction vessel may be subjected to a first temperature at a first time for a first duration, and the reaction vessel or portion thereof may subsequently be subjected to a second temperature at a second time for a second duration. The first temperature may be, for example, a temperature suitable for initialization of a nucleic acid reaction (e.g., PCR) or annealing (e.g., hybridization) of a first nucleic acid molecule to a second nucleic acid molecule. The second temperature may be, for example, a temperature suitable for extension of an annealed nucleic acid molecule (e.g., a primer molecule) and/or denaturation of annealed nucleic acid molecules. Additional different temperatures may also be applied. Temperatures may be repeated any suitable number of times (e.g., for any number of thermocycles).

The term "bead," as described herein, generally refers to a solid support, resin, gel (e.g., hydrogel), colloid, or particle of any shape and dimensions. A bead may comprise any suitable material such as glass or ceramic, one or more polymers, and/or metals. Examples of suitable polymers include, but are not limited to, nylon, polytetrafluoroethylene, polystyrene, polyacrylamide, agarose, cellulose, cellulose derivatives, or dextran. Examples of suitable metals include paramagnetic metals, such as iron. A bead may be magnetic or non-magnetic. For example, a bead may comprise one or more polymers bearing one or more magnetic labels. A magnetic bead may be manipulated (e.g., moved between locations or physically constrained to a given location, e.g., of a reaction vessel such as a flow cell chamber) using electromagnetic forces. A bead may have one or more different dimensions including a diameter. A dimension of the bead (e.g., the diameter of the bead) may be less than about 1 mm, less than about 0.1 mm, less than about 0.01 mm, less than about 0.005 mm, from about 1 nm to about 100 nm, from about 1 µm to about 100 µm, or from about 1 mm to about 100 mm. A collection of beads may comprise one or more beads having the same or different characteristics. For example, a first bead of a collection of beads may have a first diameter and a second bead of the collection of beads may have a second diameter. The first diameter may be the same or approximately the same as or different from the second diameter. Similarly, the first bead may have the same or a different shape and composition than a second bead. In an example, the first bead may comprise a first polymeric material and the second bead may comprise a second polymeric material. The first polymeric material may be the same or different as the second polymeric material. The first bead may comprise a first material, such as a first oligonucleotide (e.g., primer) coupled thereto, and a second bead may comprise a second material, such as a second oligonucleotide (e.g., primer) coupled thereto. The first and second oligonucleotides may be the same or different. For example, the first oligonucleotide (e.g., first primer) may have the same nucleic acid sequence as the second oligonucleotide (e.g., second primer) or a different nucleic acid sequence. In some cases, the first oligonucleotide (e.g., first primer) may comprise a first nucleic acid sequence and a second nucleic acid sequence, and the second oligonucleotide (e.g., second primer) may comprise a third nucleic acid sequence and a fourth nucleic acid sequence. The first and third nucleic acid sequences may be the same. For example, the first and third nucleic acid sequences may be barcode sequences. The second and fourth nucleic acid sequences may be different. For example, the second and fourth nucleic acid sequences may be functional sequences configured to perform different functions. The second and fourth nucleic acid sequences may be primer (e.g., capture) sequences configured to capture different nucleic acid molecules, as described herein. In an example, the first bead may have a plurality of first oligonucleotides (e.g., first primers) coupled thereto and the second bead may have a plurality of second oligonucleotides (e.g., second primers) coupled thereto, where a given first oligonucleotide of the plurality of first oligonucleotides comprises a first nucleic acid sequence and a second nucleic acid sequence and a given second oligonucleotide of the plurality of second oligonucleotides comprises a third nucleic acid sequence and a fourth nucleic acid sequence. The first and third nucleic acid sequences may be the same (e.g., barcode sequences). The second and fourth nucleic acid sequences may be different (e.g., different functional sequences). In some cases, the second nucleic acid sequences of the plurality of first oligonucleotides coupled to the first bead may vary, and/or the fourth nucleic acid sequences of the plurality of first oligonucleotides coupled to the second bead may vary. For example, the second nucleic acid sequences and/or the fourth nucleic acid sequences may be random N-mers that may be suitable for capturing various template nucleic acid molecules. Nucleic acid sequences of oligonucleotides coupled to a bead may have any useful sequence of any useful base composition and length. In some cases, a nucleic acid sequence of an oligonucleotide coupled to a bead may comprise only canonical nucleotides, while in other cases, a nucleic acid sequence of an oligonucleotide coupled to a bead may comprise one or more nucleotide analogs. A nucleic acid sequence may comprise one or more labels or dyes, such as one or more fluorescent labels, dyes, magnetic labels, radiofrequency labels, or other tags. A nucleic acid sequence of an oligonucleotide coupled to a bead may comprise one or more additional features such as a replication block, cleavable base, or reversible terminator.

As used herein, the term "primer" or "primer molecule" generally refers to a polynucleotide which is complementary to a portion of a template nucleic acid molecule. For example, a primer may be complementary to a portion of a strand of a template nucleic acid molecule. The primer may be a strand of nucleic acid that serves as a starting point for nucleic acid synthesis, such as a primer extension reaction which may be a component of a nucleic acid reaction (e.g., nucleic acid amplification reaction such as PCR). A primer may hybridize to a template strand and nucleotides (e.g., canonical nucleotides or nucleotide analogs) may then be added to the end(s) of a primer, sometimes with the aid of a polymerizing enzyme such as a polymerase. Thus, during replication of a DNA sample, an enzyme that catalyzes replication may start replication at the 3'-end of a primer attached to the DNA sample and copy the opposite strand. A primer (e.g., oligonucleotide) may have one or more functional groups that may be used to couple the primer to a support or carrier, such as a bead or particle.

A primer may be completely or partially complementary to a template nucleic acid. A primer may exhibit sequence identity or homology or complementarity to the template nucleic acid. The homology or sequence identity or complementarity between the primer and a template nucleic acid may be based on the length of the primer. For example, if the primer length is about 20 nucleic acids, it may contain 10 or more contiguous nucleic acid bases complementary to the template nucleic acid.

The complementarity or homology or sequence identity between the primer and the template nucleic acid may be limited. The length of the primer may be between 8 nucleotide bases to 50 nucleotide bases. The length of the primer may be more than 2 nucleotide bases, more than 3 nucleotide bases, 4 nucleotide bases, 5 nucleotide bases, 6 nucleotide bases, 7 nucleotide bases, 8 nucleotide bases, 9 nucleotide bases, 10 nucleotide bases, 11 nucleotide bases, 12 nucleotide bases, 13 nucleotide bases, 14 nucleotide bases, 15 nucleotide bases, 16 nucleotide bases, 17 nucleotide bases, 18 nucleotide bases, 19 nucleotide bases, 20 nucleotide bases, 21 nucleotide bases, 22 nucleotide bases, 23 nucleotide bases, 24 nucleotide bases, 25 nucleotide bases, 26 nucleotide bases, 27 nucleotide bases, 28 nucleotide bases, 29 nucleotide bases, 30 nucleotide bases, 31 nucleotide bases, 32 nucleotide bases, 33 nucleotide bases, 34 nucleotide bases, 35 nucleotide bases, 37 nucleotide bases, 40 nucleotide bases, 42 nucleotide bases, 45 nucleotide bases, 47 nucleotide bases or 50 nucleotide bases. The length of the primer may be less than 50 nucleotide bases, 47 nucleotide bases, 45 nucleotide bases, 42 nucleotide bases, 40 nucleotide bases, 37 nucleotide bases, 35 nucleotide bases, 34 nucleotide bases, 33 nucleotide bases, 32 nucleotide bases, 31 nucleotide bases, 30 nucleotide bases, 29 nucleotide bases, 28 nucleotide bases, 27 nucleotide bases, 26 nucleotide bases, 25 nucleotide bases, 24 nucleotide bases, 23 nucleotide bases, 22 nucleotide bases, 21 nucleotide bases, 20 nucleotide bases, 19 nucleotide bases, 18 nucleotide bases, 17 nucleotide bases, 16 nucleotide bases, 15 nucleotide bases, 14 nucleotide bases, 13 nucleotide bases, 12 nucleotide bases, 11 nucleotide bases, 10 nucleotide bases, 9 nucleotide bases, 8 nucleotide bases, 7 nucleotide bases, 6 nucleotide bases, 5 nucleotide bases, 4 nucleotide bases, 3 nucleotide bases or 2 nucleotide bases.

The term "% sequence identity" may be used interchangeably herein with the term "% identity" and may refer to the level of nucleotide sequence identity between two or more nucleotide sequences, when aligned using a sequence alignment program. As used herein, 80% identity may be the same thing as 80% sequence identity determined by a defined algorithm, and means that a given sequence is at least 80% identical to another length of another sequence. The % identity may be selected from, e.g., at least 60%, at least 65%, at least 70%, at least 75%, at least 80%, at least 85%, at least 90%, at least 95%, or at least 99% or more sequence identity to a given sequence. The % identity may be in the range of, e.g., about 60% to about 70%, about 70% to about 80%, about 80% to about 85%, about 85% to about 90%, about 90% to about 95%, or about 95% to about 99%.

The terms "% sequence homology" or "percent sequence homology" or "percent sequence identity" may be used interchangeably herein with the terms "% homology," "% sequence identity," or "% identity" and may refer to the level of nucleotide sequence homology between two or more nucleotide sequences, when aligned using a sequence alignment program. For example, as used herein, 80% homology may be the same thing as 80% sequence homology determined by a defined algorithm, and accordingly a homologue of a given sequence has greater than 80% sequence homology over a length of the given sequence. The % homology may be selected from, e.g., at least 60%, at least 65%, at least 70%, at least 75%, at least 80%, at least 85%, at least 90%, at least 95%, or at least 99% or more sequence homology to a given sequence. The % homology may be in the range of, e.g., about 60% to about 70%, about 70% to about 80%, about 80% to about 85%, about 85% to about 90%, about 90% to about 95%, or about 95% to about 99%.

As used herein, the term "primer extension reaction" generally refers to the binding of a primer to a strand of the template nucleic acid, followed by elongation of the primer(s). It may also include, denaturing of a double-stranded nucleic acid and the binding of a primer strand to either one or both of the denatured template nucleic acid strands, followed by elongation of the primer(s). Primer extension reactions may be used to incorporate nucleotides or nucleotide analogs to a primer in template-directed fashion by using enzymes (e.g., polymerizing enzymes such as polymerases). A primer extension reaction may be a process of a nucleic acid amplification reaction.

The term "adapter" as used herein, generally refers to a molecule (e.g., polynucleotide) that is adapted to permit a sequencing instrument to sequence a target polynucleotide, such as by interacting with a target nucleic acid molecule to facilitate sequencing (e.g., next generation sequencing (NGS)). The sequencing adapter may permit the target nucleic acid molecule to be sequenced by the sequencing instrument. For instance, the sequencing adapter may comprise a nucleotide sequence that hybridizes or binds to a capture polynucleotide attached to a solid support of a sequencing system, such as a bead or a flow cell. The sequencing adapter may comprise a nucleotide sequence that hybridizes or binds to a polynucleotide to generate a hairpin loop, which permits the target polynucleotide to be sequenced by a sequencing system. The sequencing adapter may include a sequencer motif, which may be a nucleotide sequence that is complementary to a flow cell sequence of another molecule (e.g., a polynucleotide) and usable by the sequencing system to sequence the target polynucleotide. The sequencer motif may also include a primer sequence for use in sequencing, such as sequencing by synthesis. The sequencer motif may include the sequence(s) for coupling a library adapter to a sequencing system and sequence the target polynucleotide (e.g., a sample nucleic acid).

As described herein, an adapter may have a first sub-part and a second sub-part. The first sub-part and the second sub-part may have sequence complementarity. An adapter as described herein may be a paired-end adapter useful for generating paired-end sequence reads.

The terms "polymerase," "polymerizing enzyme, or "polymerization enzyme," as used herein, generally refer to any enzyme capable of catalyzing a polymerization reaction and may be used interchangeably. A polymerizing enzyme may be used to extend primers with the incorporation of nucleotides or nucleotide analogs. Examples of polymerases include, without limitation, a nucleic acid polymerase. The polymerase may be naturally occurring or synthesized. An example polymerase is a D29 polymerase or derivative thereof. A polymerase may be a polymerization enzyme. A transcriptase or a ligase may also be used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase D29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. The polymerase may be a single subunit polymerase. The polymerase may have high processivity, namely the capability of the polymerase to consecutively incorporate nucleotides in a nucleic acid template without releasing the nucleic acid template.

The term "at least partially" as used herein, generally refers to any fraction of a whole amount. For example, "at least partially" may refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99.9% of a whole amount.

The term "barcode" or "barcode sequence," as used herein, generally refers to one or more nucleotide sequences that may be used to identify one or more particular nucleic acids. A barcode may comprise at least 1, 2, 3, 4, 5, 6, 7, 8, 9, 10, 11, 12, 13, 14, 15, 16, 17, 18, 19, 20 or more nucleotides (e.g., consecutive nucleotides). A barcode may comprise at least about 10, about 20, about 30, about 40, about 50, about 60, about 70, about 80, about 90, about 100 or more consecutive nucleotides. All of the barcodes used for an amplification and/or sequencing process (e.g., NGS) may be different. The diversity of different barcodes in a population of nucleic acids comprising barcodes may be randomly generated or non-randomly generated.

A barcode may be comprised of one or more segments. For example, a barcode may comprise a first segment that has a first nucleic acid sequence and a second segment that has a second nucleic acid sequence. The first nucleic acid sequence may be the same or different than the second nucleic acid sequence. Barcode sequences comprising multiple segments may be assembled in a combinatorial fashion according to a split-pool scheme, in which a plurality of different first segments are distributed amongst a plurality of first partitions, the contents which are then pooled and distributed amongst a plurality of second partitions. A plurality of different second segments are then distributed amongst the plurality of second partitions and linked to the plurality of different first segments within the plurality of second partitions, and then the contents of the plurality of second partitions are pooled. The process may be repeated any number of times using any number of different segments and partitions to provide any level of barcode diversity. In some cases, the first segment of a barcode sequence may be coupled to a bead.

As described herein, the use of barcodes may permit high-throughput analysis of multiple samples using next generation sequencing techniques. A sample comprising a plurality of nucleic acid molecules may be distributed throughout a plurality of partitions (e.g., droplets in an emulsion), where each partition comprises a nucleic acid barcode molecule comprising a unique barcode sequence. The sample may be partitioned such that all or a majority of the partitions of the plurality of partitions include at least one nucleic acid molecule of the plurality of nucleic acid molecules. A nucleic acid molecule and nucleic acid barcode molecule of a given partition may then be used to generate one or more copies and/or complements of at least a sequence of the nucleic acid molecule (e.g., via nucleic acid amplification reactions), which copies and/or complements comprise the barcode sequence of the nucleic acid barcode molecule or a complement thereof. The contents of the various partitions (e.g., amplification products or derivatives thereof) may then be pooled and subjected to sequencing. In some cases, nucleic acid barcode molecules may be coupled to beads. In such cases, the copies and/or complements may also be coupled to the beads. Nucleic acid barcode molecules, and copies and/or complements may be released from the beads within the partitions or after pooling to facilitate nucleic acid sequencing using a sequencing instrument. Because copies and/or complements of the nucleic acid molecules of the plurality of nucleic acid molecules each include a unique barcode sequence or complement thereof, sequencing reads obtained using a nucleic acid sequencing assay may be associated with the nucleic acid molecule of the plurality of nucleic acid molecules to which they correspond. This method may be applied to nucleic acid molecules included within cells divided amongst a plurality of partitions, and/or nucleic acid molecules deriving from a plurality of different samples.

In some aspects, provided herein are systems, methods, and compositions wherein a partition comprises more than a single bead. In some aspects, provided herein are systems, methods, and compositions wherein a partition comprises more than a single analyte (e.g., nucleic acid molecule, e.g., template nucleic acid molecule). Beneficially, the systems, methods, and compositions of the present disclosure need not depend on singular loading of content (e.g., with single bead, with single analyte) for successful downstream processing. Beneficially, the systems, methods, and compositions of the present disclosure need not depend on forming partitions that are at most singularly loaded (e.g., with single bead, with single analyte) according to the Poisson distribution, which can often lead to a waste of resources where a substantial number of partitions consume certain resources (e.g., bead, analyte, reagent, etc.) but are not useful because of a lack of (or otherwise wrong number or wrong composition of) one or more of certain other resources (e.g., bead, analyte). In some instances, beneficially, the systems, methods, and compositions of the present disclosure may achieve higher efficiency and/or higher output than systems, methods, and compositions that depend on singular loading.

Methods

The present disclosure provides methods for analyzing and/or processing a biological sample. In particular, the present disclosure provides a method for analyzing and/or processing a nucleic acid sample comprising one or more nucleic acid molecules (e.g., a plurality of nucleic acid molecules). The nucleic acid sample (e.g., biological sample or cell-free biological sample) may comprise a plurality of nucleic acid molecules, such as a plurality of deoxyribonucleic acid (DNA) and/or ribonucleic acid (RNA) molecules. The methods for analyzing and/or processing a biological sample as disclosed herein may comprise generating a plurality of partitions (e.g., a plurality of wells or droplets, such as by generating an emulsion comprising a plurality of droplets), wherein each partition (e.g., a droplet or a well) may comprise (i) a plurality of beads and (ii) at least one nucleic acid molecule (e.g., a target nucleic acid molecule of a biological sample). A given partition of the plurality of partitions may also comprise one or more reagents.

In some cases, a partition (e.g., a given partition) of the plurality of partitions may comprise at least two beads. Thus, the methods of the present disclosure may provide an increased ratio of beads to nucleic acid molecules (e.g., a ratio of equal to or greater than 2, or equal to or greater than 4, etc.) inside a partition such as a droplet in an emulsion. The at least one nucleic acid molecule of a first partition of the plurality of partitions may be different (e.g., having a different nucleotide sequence) than the at least one nucleic acid molecule of a second partition of the plurality of partitions. For example, the at least one nucleic acid molecule of the first partition may derive from a first biological sample (e.g., from a first subject) and the at least one nucleic acid molecule of the second partition may derive from a second biological sample (e.g., from a second subject or from the first subject but taken at a different time or via a different method). In another example, the at least one nucleic acid molecule of the first partition may derive from a first cell from a biological sample and the at least one nucleic acid molecule of the second partition may derive from a second cell from the same biological sample. Alternatively, the at least one nucleic acid molecule of a first partition of the plurality of partitions may be identical (e.g., having an identical nucleotide sequence) or approximately identical (e.g., having a high sequence complementarity) to the at least one nucleic acid molecule of a second partition of the plurality of partitions.

The at least one nucleic acid molecule disposed in a partition of a plurality of partitions may be amplified inside the partition (e.g., inside a droplet in an emulsion) by generating one or more amplification products of the at least one nucleic acid molecule. The amplification process and/or sequencing process may be performed via a polymerase chain reaction (PCR). The amplification process may be performed while the at least one nucleic acid molecule is attached (e.g., covalently or non-covalently linked) to a bead or while the at least one nucleic acid molecule is not attached to a bead. For example, one or more amplification products of the at least one nucleic acid molecule may be generated within a partition of a plurality of partitions while the at least one nucleic acid molecule is attached to a bead of at least two beads included within the partition. The contents of the plurality of partitions may be pooled (e.g., nucleic acid molecules and corresponding amplification products and beads may be released from droplets of a plurality of droplets in an emulsion). Upon release of a bead-nucleic acid molecule complex (or complexes) from the partition of the plurality of partitions, the bead-nucleic acid molecule complex (or complexes) may be separated (e.g., magnetically separated) from other materials (e.g., from the pooled contents of droplets of a plurality of droplets of an emulsion). Subsequently, the at least one nucleic acid molecule or any amplification products corresponding thereto or derivatives thereof of a partition of the plurality of partitions that may have formed may be assayed or analyzed (e.g., by determining the nucleotide sequence in a sequencer).

Figure 2:
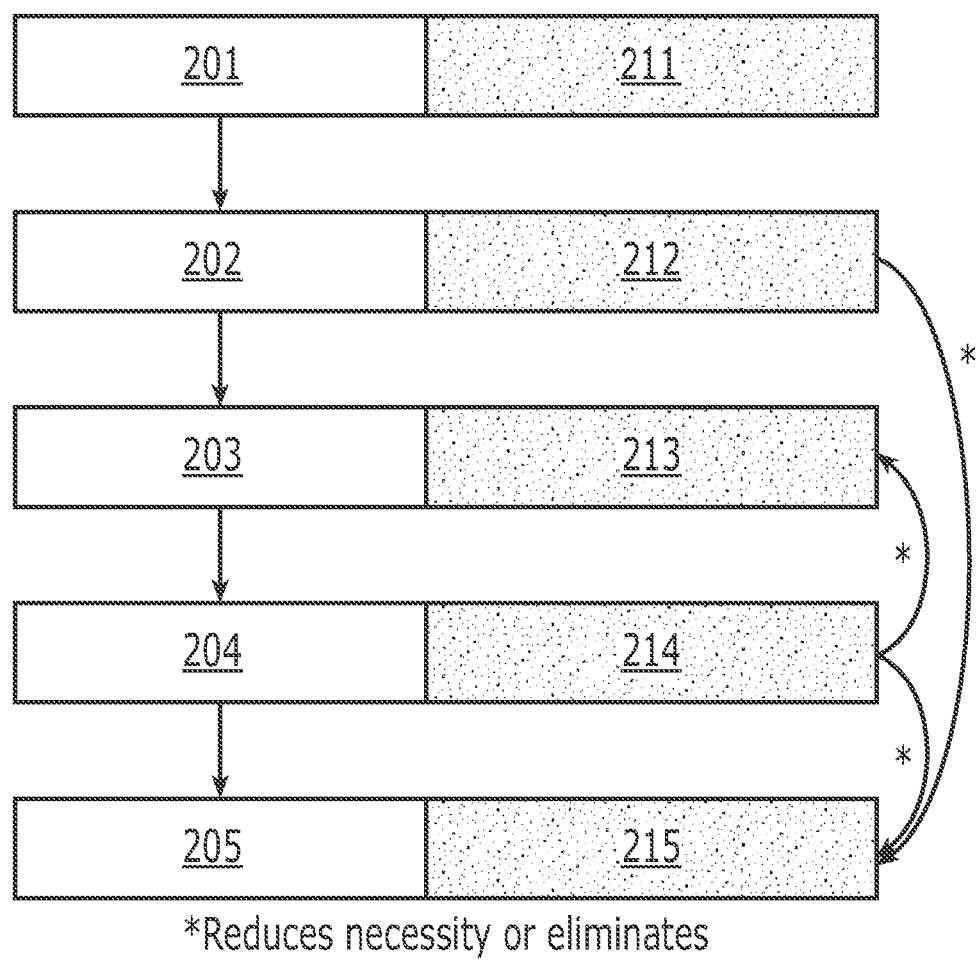
FIG. 2 depicts a schematic of a generic NGS approach and shows situations where modification to the analysis workflow may increase yield (e.g., the amount of information gained from an analyzed biological sample) and reduce the probability of noise and mutations during nucleic acid analysis.

FIG. 1 depicts a schematic of a generic next-generation sequencing (NGS) approach and indicates portions of a workflow in which genetic material may escape analysis and/or potential noise sources and mutations may be introduced. A biological sample may be provided (101). For example, the biological sample may comprise appropriately sized DNA, such as cfDNA and sheared gDNA. The biological sample may be a limited input (111) that is representative of the total material including rare variants. The biological sample may be subjected to adapter ligation (102). During this process, genomic material may be lost (112), such as due to incomplete ligation and non-productive adapter combinations. The adapter-ligated sample may be subjected to PCT amplification (103), which may result in the increase of copy number and mutations (113). The products may be subjected to clonal amplification, such as by emulsion PCR (104). During this process, more material may be lost and mutation numbers may increase (114), such as due to double Poisson loading schemes, optimization schemes to minimize clonal copies of mixed templates. The clonally amplified products may be subjected to sequencing (105). During this process, errors may result from general noise and signal decay (115). FIG. 2 depicts a modified version of the schematic of FIG. 1 in which modifications to the workflow may increase yield (e.g., the amount of information gained from an analyzed biological sample) and reduce the probability of noise and mutations during nucleic acid analysis. A biological sample may be provided (201). During this provision, performing PCR enrichment may reduce sample loss (211). In some cases, mutation rate may increase. The biological sample may be subjected to adapter ligation (202). During this process, an adapter with a randomized identifier may be employed. In some cases, paired-end adapters may be used (212). During sequencing (e.g., 205), such adapters may reduce or eliminate the need for multiple reads. The adapter-ligated sample may be subjected to PCT amplification (203), during which mutations can be correctable by the randomized identifier (213). The products may be subjected to clonal amplification, such as by emulsion PCR (204). During this process, multiple beads per library template may be employed (214), which can minimize template loss. The clonally amplified products may be subjected to sequencing (205). During this process, multiple reads and/or paired-end reads may be processed (215). In some cases, using multiple beads (e.g., 214) per library template may reduce or eliminate the need for generating multiple reads and/or having to correct PCR amplification-derived mutations using randomized identifiers. The methods provided herein introduce modifications to a generic NGS approach to provide enhanced nucleic acid amplification and sequencing. An advantage of the methods of the present disclosure may be an increased ratio (e.g., >2) of beads to nucleic acid molecules inside a partition (e.g., a droplet), which may result in increased accuracy and sensitivity during sample analysis due to e.g., higher clonal copy numbers of a given nucleic acid molecule and reduced sample or template loss.

The term 'double Poisson,' as used herein, generally refers to the statistical difficulty of distributing single discrete items from two different species of items into partitions through random sampling. Generally, the loading of each species is governed by Poisson statistics. For a given case of N items randomly distributed among M equal partitions, the relative population found in the partitions is dependent on the ratio of items to partitions, $\lambda$:

$$\lambda = \frac{N}{M}.$$

When two species of items are distributed into partitions separately each will follow its own Poisson distribution, leading to double Poisson distribution, resulting in, at best, a small fraction of partitions having a single instance of each of the species. The probability of a partition containing n number of items given an item to partition ratio, $\lambda$, may be calculated as:

$$P(n|\lambda) = \frac{\lambda^n e^{-\lambda}}{n!}.$$

For a single Poisson process, the fraction of partitions having only one item at a loading of one per partition is calculated as:

$$P(n=1|\lambda=1)=1/e\approx36.8\%.$$

This can be derived by setting the derivative $$\frac{dP}{d\lambda} = \frac{(n-\lambda)\lambda^{n-1}e^{-\lambda}}{n!} = 0$$

and noting that the extrema occur when $n=\lambda$ for any n. This also represents 36.8% of items. If two species, a and b, are loaded into partitions, the distribution is:

$$P(n_a, b|\lambda_a, \lambda_b) = P(n_a|\lambda_a)P(n_b|\lambda_b) = \frac{\lambda_a^{n_a}\lambda_b^{n_b}e^{-\lambda_a-\lambda_b}}{n_a!n_b!}.$$

This is tabulated below in Table 1 for $\lambda=1$ for each species. In this case, only $1/e^2\approx13.5\%$ of partitions have a single item each of species a and b.

TABLE 1

Distribution of Partition Populations

| Number of b | Number of a | | | | |
|---|---|---|---|---|---|
| | 0 | 1 | 2 | 3 | 4 |
| 0 | 13.5% | 13.5% | 6.8% | 2.3% | 0.6% |
| 1 | 13.5% | 13.5% | 6.8% | 2.3% | 0.6% |
| 2 | 6.8% | 6.8% | 3.4% | 1.1% | 0.3% |

TABLE 1-continued

Distribution of Partition Populations

| Number of b | Number of a | | | | |
|---|---|---|---|---|---|
| | 0 | 1 | 2 | 3 | 4 |
| 3 | 2.3% | 2.3% | 1.1% | 0.4% | 0.1% |
| 4 | 0.6% | 0.6% | 0.3% | 0.1% | 0.0% |

If a species of nucleic acid templates (e.g., a) and a species of beads (e.g., b) are partitioned into droplets (e.g., partitions), as contemplated in the present disclosure, because the relative costs of templates, beads, partitions and positive beads (beads in partitions with at least one template) can vary substantially, the optimum value for $\lambda_{template}$ and $\lambda_{bead}$ may be optimized to minimize cost and increase efficiency. For example, partitions and beads may be weighted at lower cost and templates and positive beads may be weighted at higher cost. Such optimization may account for the cost of different failure events, such as the failure to load a droplet with a template which will cost a droplet and a bead. However, in this case, because the bead is a negative bead (bead in partition without any template), no further costs are assessed after an enrichment step that washes away the negative bead. In another failure event, a partition is loaded with two or more templates and one or more beads, which will cost the templates and the beads, as well as create one or more positive beads that are polyclonal (with mixed templates) which can incur further downstream processing cost.

A biological sample for use according to the methods provided herein may be a solid biological sample (e.g., a tissue sample such as a biopsy sample) or a liquid biological sample (e.g., from a body fluid such as blood). A biological sample may comprise a plurality of nucleic acid molecules. In some cases, a biological sample may comprise a plurality of cells comprising a plurality of nucleic acid molecules. In other cases, a biological sample may be a cell-free biological sample (e.g., as described herein). A biological sample may be processed to remove cellular matter and/or other debris, to isolate and/or lyse cells, add or remove reagents, or otherwise prepare the biological sample for subsequent processing. For example, a biological sample may be processed to provide a cell-free biological sample. A nucleic acid molecule that may be analyzed using the herein disclosed methods may be a cell-free nucleic acid molecule (e.g., cfDNA or ctDNA). A cell-free nucleic acid molecule may have originated from a certain tissue or organ of an organism or subject, e.g., from a cancerous tissue, and may be present in a sample in low to very low concentrations (e.g., <10 ng/mL).

The methods for analyzing a biological sample as disclosed herein may comprise contacting (e.g., mixing or combining) two or more solvents, liquids, or fluids with the same or different physicochemical properties such as polarity and viscosity. Contacting two or more materials may result in generation of an emulsion comprising a plurality of droplets (e.g., a water-in-oil or an oil-in-water emulsion). The two or more materials (e.g., liquids) may be immiscible. The methods disclosed herein may comprise contacting a first material (e.g., solvent or solution) having a first polarity (e.g., having a certain first hydrophilicity or lipophilicity) with a second material (e.g., solvent or solution) having a second polarity (e.g., having a certain second hydrophilicity or lipophilicity). The polarity of a first material (e.g., an aqueous solution) may be identical, similar, or different than the polarity of the second material (e.g., a non-polar fluid such as oil). As disclosed herein, the first material may be an aqueous solution and the second material may be oil. Upon contact of the aqueous solution with the oil, an emulsion may be formed (e.g., at a droplet generation junction). The emulsion may have a dispersed phase and a continuous phase.

Generally, the methods of the present disclosure comprise emulsions comprising an aqueous dispersed phase and a continuous oil phase. Thus, the methods disclosed herein may comprise contacting an aqueous solution comprising a plurality of nucleic acid molecules, a plurality of beads, and a plurality of reagents and an oil to generate a plurality of aqueous droplets comprising nucleic acid molecules of the plurality of nucleic acid molecules (e.g., target nucleic acid molecules), beads of the plurality of beads, and reagents of the plurality of reagents. In some cases, the plurality of nucleic acid molecules may be included within a plurality of cells, such that the plurality of aqueous droplets may comprise a plurality of cells. In some instances, a droplet may comprise no more than one cell. In some cases, one or more droplets of the same phase may be combined. For example, a plurality of first droplets (e.g., aqueous droplets) comprising a plurality of nucleic acid molecules (e.g., target nucleic acid molecules) may be combined (e.g., merged or coalesced) with a plurality of second droplets (e.g., aqueous droplets) comprising a plurality of beads and/or reagents to provide a plurality of third droplets (e.g., aqueous droplets) comprising the plurality of nucleic acid molecules and the plurality of beads and/or reagents. The first and the second pluralities of droplets may comprise the same material (e.g., having the same properties such as polarity) or may be different materials (e.g., having the different properties such as different polarities). In other cases, a first material (e.g., aqueous solution) comprising a plurality of nucleic acid molecules (e.g., target nucleic acid molecules) may be combined with a second material (e.g., aqueous solution) comprising a plurality of beads and/or reagents to provide a third material comprising a plurality of nucleic acid molecules and a plurality of beads and/or reagents. The third material may then be contacted with (or brought in contact with) a liquid or fluid that may be immiscible with the first and/or the second solution (e.g., an oil) to generate a plurality of droplets (e.g., aqueous droplets). Thus, the first and the second solution may be an aqueous solution and the third liquid or fluid that may be immiscible with the first and second solution may be oil (or any derivative thereof).

Droplets may be generated by any useful method. For example, aerosol or air knife droplet generators may be used to generate droplets by dispensing droplets of precursor fluids (e.g., a first material such as an aqueous solution) into another solution. Microfluidic droplet generation methods may also be employed. For example, a first material (e.g., aqueous solution) may be flowed in a first channel toward a droplet generation junction where it is contacted with a second material (e.g., oil) flowed in a second channel toward the droplet generation junction, where droplets may form. In some cases, droplets of the first material may be formed by forcing the first material through a nozzle into a region comprising the second material. The first material may be an aqueous solution and may comprise one or more elements, such as a plurality of nucleic acid molecules, a plurality of beads, and/or a plurality of reagents, such that the droplets formed may comprise nucleic acid molecules, beads, and/or reagents. A variety of other configurations may be used to generate droplets. Examples of such configurations and details of droplet generation methods can be found in, for example, U.S. Pat. No. 9,694,361 and U.S. Patent Publication No. 2018/0334670, which are herein incorporated by reference in their entireties.

In some cases, generating a plurality of partitions (e.g., droplets) may comprise the use of a first aqueous solution comprising a plurality of nucleic acid molecules and a second aqueous solution comprising a plurality of particles such as beads (e.g., meads having primer sequences attached to their surface). The first aqueous solution and the second aqueous solution may then be contacted (e.g., at a droplet generation junction) with a third liquid or fluid (e.g., an oil) that may be immiscible with the first and/or the second solution. This immiscibility or difference in polarity may result in the formation of an emulsion (e.g., an aqueous in oil emulsion). An emulsion as described herein may comprise a plurality of partitions such as droplets (e.g., aqueous droplets). These droplets may comprise beads, nucleic acid molecules, and additional components such as reagents. In some cases, droplets of a plurality of droplets generated according to the methods provided herein may each comprise one or more nucleic acid molecules (e.g., target nucleic acid molecules), two or more beads, and one or more reagents. Such reagents may serve as reaction vessels in which amplification products corresponding to the one or more nucleic acid molecules may be generated within the droplets. Where droplets include one or more cells each comprising one or more nucleic acid molecules, the reagents may include reagents for lysing and/or permeabilizing the cells to provide access to the one or more nucleic acid molecules therein.

The plurality of nucleic acid molecules (e.g., target nucleic acid molecules) may be provided in a first solution (e.g., aqueous solution), and the plurality of beads may be provided in a second solution (e.g., aqueous solution). The first and the second solutions may be the same solution (e.g., both aqueous solutions) or may be different solutions. The first solution comprising the plurality of nucleic acid molecules and the second solution comprising the plurality of beads may be contacted with a third liquid or fluid (e.g., oil). The third liquid or fluid may be immiscible with both the first and the second solution and may form an emulsion when contacted with the first and the second solution (e.g., as described herein). The emulsion resulting from contacting one or more solutions with one or more immiscible fluids may form or generate a plurality of partitions (e.g., a plurality of droplets).

A partition, as disclosed herein, may be a droplet that forms from an aqueous dispersed phase and may be enclosed by the continuous phase (e.g., the oil). An emulsion may be a micro-emulsion or a nano-emulsion depending on the size (e.g., approximate diameter) of the dispersed phase particles (e.g., a partition such as a droplet) within the continuous phase. In some instances, a partition may refer to any unit configured to separate a first partition from a second partition or to separate an inner volume of a partition from the volumes outside the partition. For example, a partition may be a well, microwell, container, tube, repository, receptacle or other vessel.

Thus, partitioning may be described herein as the provision of a plurality of droplets (e.g., aqueous droplets in an emulsion) or wells. A partition of a plurality of partitions such as a droplet of a plurality of droplets may contain an aqueous solution comprising one or more nucleic acid molecules and/or one or more (e.g., two or more) beads. A partition may also comprise one or more reagents, such as one or more reagents for lysing or permeabilizing a cell or one or more reagents for carrying out an amplification reaction (e.g., nucleotides, polymerizing enzyme, etc.). Partitions of a plurality of partitions may comprise different components or amounts thereof. For example, a first partition of a plurality of partitions may comprise one or more nucleic acid molecules and not include a bead, while a second partition of the plurality of partitions may comprise one or more nucleic acid molecules and two or more beads. Further, a third partition of the plurality of partitions may comprise one or more nucleic acid molecules and one bead, while a fourth partition of the plurality of partitions may comprise one or more beads and may not comprise any nucleic acid molecules. In some cases, one or more partitions of a plurality of partitions may be unoccupied (e.g., contain no nucleic acid molecules, beads, or reagents). The distribution of materials within the partitions may be controlled at least in part by a Poissonian distribution. In some cases, the amounts of materials (e.g., nucleic acid molecules, beads, and reagents) provided within droplets may be tuned by optimizing the amounts of materials provided in the various solutions and the flow rates of solutions and fluids through microfluidic channels. For example, the flow rate of a fluid or solution through a microfluidic channel may be controlled at least in part by application of a particular pressure or vacuum, and/or careful selection of the length and width of a channel. Elements such as filtration structures, tapered regions, flow regulators, and air traps may also be used to control the occupancy of droplets generated using a droplet generation system. In an example, an excess of beads may be used to attempt to defeat Poisson statistics and generate more partitions comprising at least two beads than may otherwise be generated. For example, a droplet generation system may be overloaded with beads to promote generation of a greater proportion of partitions of a plurality of partitions that comprise at least two beads.

In some cases, at most about 90%, 80%, 70%, 60%, 50%, 40%, 30%, 20%, 10%, 5%, or fewer generated partitions may be unoccupied. In some cases, at most about 90%, 80%, 70%, 60%, 50%, 40%, 30%, 20%, 10%, 5%, or fewer generated partitions do not include a bead. In some cases, at most about 90%, 80%, 70%, 60%, 50%, 40%, 30%, 20%, 10%, 5%, or fewer generated partitions do not include a nucleic acid molecule (e.g., target nucleic acid molecule). In some cases, at most about 90%, 80%, 70%, 60%, 50%, 40%, 30%, 20%, 10%, 5%, or fewer generated partitions do not include a reagent. At least a subset of generated partitions may comprise one or more nucleic acid molecules (e.g., target nucleic acid molecules), one or more beads, and one or more reagents (e.g., as described herein). At least a subset of generated partitions may comprise one or more nucleic acid molecules (e.g., target nucleic acid molecules), two or more beads (e.g., at least two beads), and one or more reagents (e.g., as described herein). A partition such as a droplet may comprise at least one, at least two, or at least five nucleic acid molecules and at least one, at least two, at least three, at least five, or at least ten beads.

A partition such as a droplet may comprise at least two nucleic acid molecules that are either identical or different, such as identical or different in terms of their nucleotide sequence and/or in terms of the one or more adapter sequences that those nucleic acid molecules are linked to. Generally, a partition of the present disclosure may comprise an excess of beads compared the number of nucleic acid molecules present in said partition. A partition may comprise at least twice as many beads as nucleic acid molecules. The at least two, at least three, at least four, at least five, or more beads of a partition such as a droplet may be the same (e.g., identical) beads or may be different beads. Different beads may comprise different properties such as size, diameter, fluidity, rigidity, porosity, or compressibility. Different beads may be formed of different materials (e.g., different hydrogels). In some cases, a partition may comprise at least one bead that is a hydrogel bead and at least one bead that is paramagnetic. Moreover, the at least one, at least two, at least three, at least five, or at least ten beads of a first partition such as a first droplet may be the same or different as the at least one, at least two, at least three, at least five, or at least ten beads of a second partition such as a second droplet. A bead may comprise a plurality of materials (e.g., nucleic acid barcode molecules or primer molecules) coupled thereto (e.g., bound or linked to a surface of component of a bead).

Each partition (e.g., each droplet) of a plurality of partitions (e.g., a plurality of droplets) may comprise either identical or different nucleic acid molecules and/or identical or different beads compared to any other partition (e.g., another droplet) of the plurality of partitions (e.g., a plurality of droplets), or any combination thereof. Thus, a first partition (e.g., a first droplet) of a plurality of partitions (e.g., a plurality of droplets) may comprise either an identical or different nucleic acid molecule (e.g., having different nucleotide sequences) compared to a second partition (e.g., a first droplet) of a plurality of partitions (e.g., a plurality of droplets). Similarly, a first partition (e.g., a first droplet) may comprise either an identical or different bead (e.g., having different primers) compared to a second partition (e.g., a first droplet).

A particle (e.g., a bead) as described herein (e.g., a bead located inside a partition such as an emulsion droplet) may comprise a plurality of primer molecules (e.g., nucleic acid barcode molecules). The plurality of primer molecules may be attached (e.g., chemically linked) to the bead, and may be comprised of one or more primer molecules. The one or more primer molecules that may be attached to the bead may comprise identical or different nucleotide sequences. The plurality of primer molecules may be attached (e.g., chemically linked) to the bead such that a nucleic acid molecule (e.g., target nucleic acid molecule) may bind (e.g., covalently or non-covalently) or hybridize to at least one primer molecule of the plurality of primer molecules coupled to the bead, thereby linking (e.g., immobilizing) the nucleic acid molecule to the bead. The plurality of primer molecules may be used to conduct one or more amplification reactions (e.g., PCRs) to generate the plurality of amplification products inside the partition such as a droplet. The one or more amplification reactions may comprise one or more primer extension reactions, which reactions may comprise hybridization of a primer to a target nucleic acid molecule and subsequent extension of the primer molecule (e.g., via a polymerizing enzyme) to generate a complement of a sequence of the target nucleic acid molecule. The amplification products generated in each partition (e.g., droplet) may be identical copies of the nucleic acid molecule (e.g., target nucleic acid molecule) included within the partition (e.g., having an identical nucleotide sequence) or derivatives or fragments thereof (e.g., having a different nucleotide sequences). Such derivatives and fragments may vary in length and/or sequence of their nucleotide sequences and may be generated during the amplification reactions (e.g., PCR). In some cases, an amplification reaction may be used to incorporate one or more sequences into an amplification product. For example, one or more barcode sequences, unique molecular identifiers, adapter sequences, flow cell adapters, or other sequences may be incorporated into an amplification product. Such sequences may facilitate subsequent processing (e.g., via a nucleic acid sequencing assay).

For example, a first bead may comprise a first set of nucleic acid barcode molecules coupled thereto, and a second bead may comprise a second set of nucleic acid barcode molecules coupled thereto. Nucleic acid barcode molecules of the first set of nucleic acid barcode molecules may each comprise a first barcode sequence and a first primer sequence, while nucleic acid barcode molecules of the second set of nucleic acid barcode molecules may each comprise a second barcode sequence and a second primer sequence. The first barcode sequence may be different from the second barcode sequence. The first primer sequence may be the same or different than the second primer sequence. A first and second bead of a given partition may be linked (e.g., tethered) together. The barcode sequences may be unique such that no bead comprises the same barcode sequence. Alternatively, the barcode sequences may be significantly diluted (e.g., present in such a large number, such as at least 1 million, at least 10 million, or more different barcode sequences are used) that a barcode sequence is not expected to be repeated between different partitions. In an example, a first partition of a plurality of partitions may comprise (i) a first bead comprising a first set of nucleic acid barcode molecules coupled thereto, which nucleic acid barcode molecules each comprise a first barcode sequence and a first primer sequence, and (ii) second bead comprising a second set of nucleic acid barcode molecules coupled thereto, which nucleic acid barcode molecules each comprise a second barcode sequence and a second primer sequence. A second partition of the plurality of partitions may comprise (i) a third bead comprising a third set of nucleic acid barcode molecules coupled thereto, which nucleic acid barcode molecules each comprise a third barcode sequence and a third primer sequence, and (ii) fourth bead comprising a fourth set of nucleic acid barcode molecules coupled thereto, which nucleic acid barcode molecules each comprise a fourth barcode sequence and a fourth primer sequence. The first, second, third, and fourth barcode sequences may all differ from one another. The first, second, third, and fourth primer sequences may all the same. For example, the various primer sequences may be targeted primer sequences configured to hybridize to and/or capture a given target nucleic acid molecule, or an adapter coupled to one or more target nucleic acid molecules. In an example, the various primer sequences may comprise a poly(T) sequence and be configured to hybridize to a poly(A) sequence of a ribonucleic acid (RNA) molecule such as a messenger RNA (mRNA) molecule.

Figure 4:
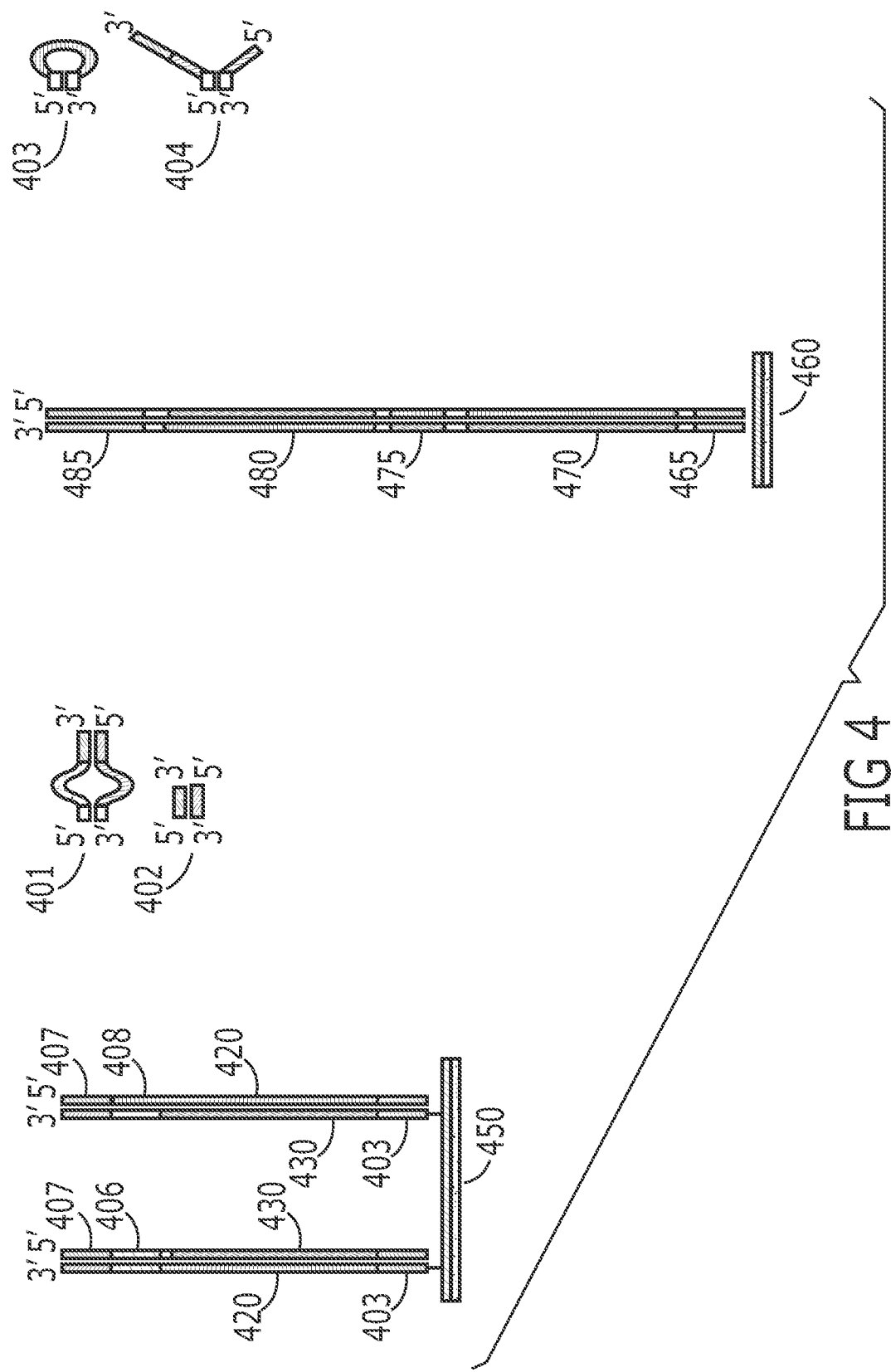
FIG. 4 shows that noise in sequence analysis may be further decreased by incorporating additional measures into the nucleic acid analysis workflow such as reading of coding and reverse complement strands (e.g., generating paired-end sequence reads).

FIG. 4 depicts examples of functional sequences that may be coupled to template nucleic acid molecules. For example, a functional sequence is an amplification primer sequence, a sequencing primer sequence, a complement thereof and/or combination thereof. An amplification primer sequence may be a solution amplification primer sequence. An amplification primer sequence may be a substrate immobilization primer sequence. A sequencing primer sequence may be configured for facilitating sequencing of a coding strand. A sequencing primer sequence may be configured for facilitating sequencing of a reverse complement of a template strand. The left portion of the left panel shows a template nucleic acid molecule immobilized to a surface 450 via a substrate immobilization primer molecule 403 coupled to a first strand 420 of the template nucleic acid molecule. The second strand 430 of the template nucleic acid molecule comprises an adapter 406 for sequencing of a coding strand as well as a solution amplification primer molecule 407. The right portion of the left panel shows an identical copy of the template nucleic acid molecule immobilized to the surface 450 via a substrate immobilization primer molecule 403 coupled to the second strand 430 of the template nucleic acid molecule. The first strand 420 of the nucleic acid molecule comprises a solution amplification primer molecule 407 and an adapter 408 for sequencing of the reverse complement strand. The substrate immobilization primer (e.g., 403) may be considered a second adapter 402 ("Adapter 2") while the amplification and sequencing primers (e.g., 406 and 407, 408 and 407) coupled to a given strand of a template nucleic acid molecule may together make up the first adapter 401 ("Adapter 1"). As shown in FIG. 4, the first adapter 401 may be configured such that various sequences may have different melting temperatures and may therefore be partially denatured, e.g., by heating the molecule comprising the adapter to a given temperature range. The right panel of FIG. 4 shows a first template nucleic acid molecule 470 linked to a second template nucleic acid molecule 480 via a sequencing adapter 475 (e.g., sequencing primer), where the complex is immobilized to a substrate 460 via a substrate immobilization primer molecule 465. The sequencing adapter 475 may be provided in a stem loop configuration 403 ("Adapter 1") while an adapter 485 appended to a free end of the complex may be provided in a Y-shaped configuration 404 ("Adapter 2"). The adapter 485 may comprise a sequencing primer and a solution amplification primer.

In as much as one or more different primer molecules may be linked (e.g., chemically linked) to one bead, a partition or droplet as described herein may comprise a plurality of beads, wherein each bead is linked to one or more primer molecules, wherein the one or more primer molecules may be identical or different (e.g., comprise an identical or different nucleotide sequence). In other words, a plurality of beads within a single partition or droplet may comprise a plurality of identical or different primer molecules that are capable of binding to a plurality of identical or different nucleic acid molecules (e.g., target nucleic acid molecules). Thus, a plurality of nucleic acid molecules may be amplified in a partition to generate a plurality of amplification products using the plurality of primer molecules (e.g., nucleic acid barcode molecules). The methods of the present disclosure may also comprise the use of bead pairs that may be formed by linking a first bead to a second bead (e.g., via one or more chemical linkers or one or more splint oligonucleotides), wherein the first bead and the second bead of the bead pair comprise different primer molecules (e.g., nucleic acid barcode molecules).

Beads may be linked via one or more linkers. A linker may be an oligonucleotide. A linker may comprise one or more carbohydrate molecules. A linker may comprise an affinity binding protein. A linker may be hydrophilic. A linker may be hydrophobic. A linker may be electrostatic. A linker may be labeled. A linker may be a cleavable linker or a non-cleavable linker. One or more nucleotides and/or one or more linker moieties may be labeled with a dye, fluorophore, or quantum dot (e.g., as described herein).

Each partition (e.g., droplet) of a plurality of partitions (e.g., plurality of droplets) may, in addition to one or more target nucleic acid molecules and one or more beads, further comprise one or more reagents. Reagents that may be present inside each partition may include buffers (e.g., various ions in certain concentrations), proteins (e.g., enzymes such as polymerizing enzymes), monomeric molecules (e.g., nucleotides such dNTPs), oligomeric molecules (e.g., oligonucleotides), and polymeric molecules (e.g., nucleic acids such as synthetic nucleic acid molecules). A reagent may be useful for lysing or permeabilizing a cell to provide access to nucleic acid molecules therein. A reagent may be useful in an amplification and/or primer extension reaction. A "reagent" nucleic acid molecules (as opposed to "sample" or "target" nucleic acid molecules of a biological sample) may comprise priming sequences and/or unique molecular identifiers (e.g., randomized identifiers or barcodes). A priming sequence as described and used herein may be target-specific or non-target-specific (e.g., a random N-mer). Moreover, the reagent nucleic acid molecules may comprise functional sequences such as sequencing adapters and flow cell sequences. Such "reagent" nucleic acid molecules may be coupled to beads (e.g., as described herein). A polymerizing enzyme as disclosed herein may be a polymerase enzyme (e.g., as described herein). The polymerase enzyme may be an endogenous polymerase enzyme or a modified (e.g., engineered) polymerase enzyme. The polymerase enzymes may be used to perform amplification reactions (e.g., PCR such as ePCR) to generate a plurality of amplification products.

An additional component of a partition may be a synthetic nucleic acid molecule. The synthetic nucleic acid molecule may be double stranded. The synthetic nucleic acid molecule may comprise a cleavable element. The cleavable element may allow separation of components of the synthetic nucleic acid molecule. The separation may be accomplished by chemical, light, heat or other approaches. The synthetic nucleic acid molecule may also be subjected to ligation and/or circularization. Upon ligation and/or circularization, the synthetic nucleic acid molecule may be cleaved to provide a cleaved synthetic nucleic acid molecule. The cleaved synthetic nucleic acid molecule may then be subjected to gap filling through an amplification reaction (e.g., as described herein).

Nucleic acid molecules (e.g., DNA or RNA molecules) of a biological sample may be processed prior to being partitioned between a plurality of partitions. Alternatively, nucleic acid molecules of a biological sample may be processed after partitioning between a plurality of partitions. For example, nucleic acid molecules may be functionalized with one or more adapters (e.g., via a hybridization or ligation process). An adapter may comprise a randomized identifier sequence (e.g., barcode or a unique molecular identifier (UMI) sequence) that may allow identification of original sample nucleic acid molecules and corresponding amplification products during data analysis (e.g., sequencing and sequence analysis) (e.g., as described herein). The ligation reaction of a nucleic acid molecule to an adapter (or multiple adapters) may occur in a solution (e.g., prior to partitioning between a plurality of partitions) or in an emulsion (e.g., subsequent to partitioning between a plurality of partitions). Thus, the ligation reaction may occur when both the nucleic acid molecule and the adapter are in an aqueous solution, wherein the aqueous solution may be an aqueous solution inside a partition such as an emulsion droplet. A sequence of an adapter attached to (e.g., covalently or non-covalently linked to) a nucleic acid molecule (e.g., a single nucleic acid strand) may facilitate binding of the nucleic acid molecule to a primer molecule or sequence thereof. Such a primer molecule may be attached to a bead, such that the interaction (e.g., binding such as covalently or non-covalently) of the nucleic acid molecule via its adapter sequence with the primer may attach the nucleic acid molecule to the bead within a partition such as an emulsion droplet or well. Upon linking a nucleic acid molecule to a bead, one or more amplification reactions (e.g., PCR such as ePCR) may be performed to generate a plurality of amplification products of said nucleic acid molecule (e.g., as described herein). An adapter that may be used in combination with the described methods and compositions herein may enable production of paired-end sequence reads. Thus, the combination of using higher quantity ratios of beads to nucleic acid molecules and paired-end adapters may provide methods with increased accuracy and sensitivity for analyzing biological samples (e.g., target nucleic acid molecules).

The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises one or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises two or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises three or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises four or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises five or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises six or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises seven or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises eight or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises nine or more beads. The methods of the present disclosure may provide a plurality of partitions (e.g., droplets), wherein at least 50%, at least 60%, at least 70%, at least 75%, at least 80%, at least 85%, at least 90%, at least 95%, at least 97%, at least 99%, or 100% of the plurality of partitions comprises ten or more beads.

The methods of the present disclosure may provide a plurality of partitions (e.g., droplets), wherein at least 75% of the plurality of partitions comprises between about one and three beads. A method may provide a plurality of partitions (e.g., droplets), wherein at least 80% of the plurality of partitions comprises between about one and three beads. A method may provide a plurality of partitions (e.g., droplets), wherein at least 85% of the plurality of partitions comprises between about one and three beads. A method may provide a plurality of partitions (e.g., droplets), wherein at least 90% of the plurality of partitions comprises between about one and three beads. A method may provide a plurality of partitions (e.g., droplets), wherein at least 95% of the plurality of partitions comprises between about one and three beads. A method may provide a plurality of partitions (e.g., droplets), wherein at least 97% of the plurality of partitions comprises between about one and three beads. A method may provide a plurality of partitions (e.g., droplets), wherein at least 99% of the plurality of partitions comprises between about one and three beads. A method may provide a plurality of partitions (e.g., droplets), wherein about 100% of the plurality of partitions comprises between about one and three beads.

The methods of the present disclosure may provide a plurality of partitions (e.g., droplets), wherein at least 75% of the plurality of partitions comprises between about two and five beads. A method may provide a plurality of partitions (e.g., droplets), wherein at least 80% of the plurality of partitions comprises between about two and five beads. A method may provide a plurality of partitions (e.g., droplets), wherein at least 85% of the plurality of partitions comprises between about two and five beads. A method may provide a plurality of partitions (e.g., droplets), wherein at least 90% of the plurality of partitions comprises between about two and five beads. A method may provide a plurality of partitions (e.g., droplets), wherein at least 95% of the plurality of partitions comprises between about two and five beads. A method may provide a plurality of partitions (e.g., droplets), wherein at least 97% of the plurality of partitions comprises between about two and five beads. A method may provide a plurality of partitions (e.g., droplets), wherein at least 99% of the plurality of partitions comprises between about two and five beads. A method may provide a plurality of partitions (e.g., droplets), wherein 100% of the plurality of partitions comprises between about two and five beads.

The methods of the present disclosure may provide a plurality of partitions (e.g., droplets), wherein at least 75% of the plurality of partitions comprises between about three and seven beads. A method may provide a plurality of partitions (e.g., droplets), wherein at least 80% of the plurality of partitions comprises between about three and seven beads. A method may provide a plurality of partitions (e.g., droplets), wherein at least 85% of the plurality of partitions comprises between about three and seven beads. A method may provide a plurality of partitions (e.g., droplets), wherein at least 90% of the plurality of partitions comprises between about three and seven beads. A method may provide a plurality of partitions (e.g., droplets), wherein at least 95% of the plurality of partitions comprises between about three and seven beads. A method may provide a plurality of partitions (e.g., droplets), wherein at least 97% of the plurality of partitions comprises between about three and seven beads. A method may provide a plurality of partitions (e.g., droplets), wherein at least 99% of the plurality of partitions comprises between about three and seven beads. A method may provide a plurality of partitions (e.g., droplets), wherein 100% of the plurality of partitions comprises between about three and seven beads.

The methods of the present disclosure may provide a plurality of partitions (e.g., droplets), wherein at least 75% of the plurality of partitions comprises between about five and ten beads. A method may provide a plurality of partitions (e.g., droplets), wherein at least 80% of the plurality of partitions comprises between about five and ten beads. A method may provide a plurality of partitions (e.g., droplets), wherein at least 85% of the plurality of partitions comprises between about five and ten beads. A method may provide a plurality of partitions (e.g., droplets), wherein at least 90% of the plurality of partitions comprises between about five and ten beads. A method may provide a plurality of partitions (e.g., droplets), wherein at least 95% of the plurality of partitions comprises between about five and ten beads. A method may provide a plurality of partitions (e.g., droplets), wherein at least 97% of the plurality of partitions comprises between about five and ten beads. A method may provide a plurality of partitions (e.g., droplets), wherein at least 99% of the plurality of partitions comprises between about five and ten beads. A method may provide a plurality of partitions (e.g., droplets), wherein 100% of the plurality of partitions comprises between about five and ten beads.

The methods of the present disclosure may provide a plurality of partitions (e.g., droplets), wherein at least 75% of the plurality of partitions comprises a bead-to-nucleic acid molecule ratio of equal to or greater than 2, equal to or greater than 3, equal to or greater than 4, equal to or greater than 5, or equal to or greater than 10. A method may provide a plurality of partitions (e.g., droplets), wherein at least 85% of the plurality of partitions comprises a bead-to-nucleic acid molecule ratio of equal to or greater than 2, equal to or greater than 3, equal to or greater than 4, equal to or greater than 5, or equal to or greater than 10. A method may provide a plurality of partitions (e.g., droplets), wherein at least 95% of the plurality of partitions comprises a bead-to-nucleic acid molecule ratio of equal to or greater than 2, equal to or greater than 3, equal to or greater than 4, equal to or greater than 5, or equal to or greater than 10. A method may provide a plurality of partitions (e.g., droplets), wherein at least 99% of the plurality of partitions comprises a bead-to-nucleic acid molecule ratio of equal to or greater than 2, equal to or greater than 3, equal to or greater than 4, equal to or greater than 5, or equal to or greater than 10.

A method of the present disclosure may comprise the use of multiple different sets of beads. For example, a method may comprise the use of a first set of beads and a second set of beads. A first bead of a first set (or plurality) of beads may comprise a first primer having at least partial sequence complementarity with a first adapter (e.g., a first paired-end adapter sequence) coupled (e.g., covalently or non-covalently linked) to a first nucleic acid strand of the biological sample (e.g., one or more nucleic acid molecules, such as one or more DNA or RNA molecules). A second bead of a second set of beads may comprise a second primer having sequence complementarity with a second adapter (e.g., a second paired-end adapter sequence) coupled to a second nucleic acid strand of the biological sample. The first primer may be different from the second primer. A method as described herein may comprise partitioning (e.g., co-partitioning) (i) a first bead of the first set of beads, (ii) a second bead of the second set of beads, and (iii) a nucleic acid molecule comprising a first or second adapter coupled thereto, in a partition. The partitioning may be achieved using, for example, one or more droplets (e.g., in an emulsion) or wells. Bead pairs comprising beads of the first and second sets may be used such that a given bead pair comprises a bead of the first set and a bead of the second set. Such a method may facilitate delivery of both first and second primers to a given partition comprising a bead pair.

In an example, a partition (e.g., a droplet) of a plurality of partitions (e.g., a plurality of droplets) comprising at least two beads (a first bead of a first set of beads and a second bead of a second set of beads, optionally configured as a bead pair, which first bead comprises a first primer molecule and which second bead comprises a second primer molecule) and a nucleic acid molecule comprising one or more adapter sequences (a first adapter configured to interact with a primer sequence of the first bead and/or a second adapter configured to interact with a primer sequence of second bead) may be subjected to conditions enabling the generation of one or more copies of the nucleic acid molecule or a strand thereof (e.g., single-stranded (ss) DNA or RNA) coupled to the first and/or second adapter, or complements (or fragments) thereof. Where the nucleic acid molecule is a double-stranded nucleic acid molecule (e.g., double-stranded (ds) DNA), one or more copies of both strands of the nucleic acid molecule, or complements or fragments thereof, may be generated. Generating the one or more copies of the first strand and/or the second strand, or complements thereof, may involve subjecting the first and second beads and the nucleic acid molecule to conditions sufficient to perform a primer extension reaction and/or nucleic acid amplification reaction (e.g., PCR such as ePCR). The first primer molecule of the first bead and/or the second primer molecule of the second bead may be used to generate the one or more copies of a nucleic acid molecule comprising the first and/or second adapter sequence, and/or complements thereof. The one or more copies of the nucleic acid molecule, and/or complements thereof, may be coupled to the first or second bead and thus may be used for additional amplification reactions. In a particular example, the nucleic acid molecule may comprise a first strand coupled to the first adapter and a second strand coupled to the second adapter, where the first adapter is configured to interact with the first primer molecule of the first bead and the second adapter is configured to interact with the second primer molecule of the second bead. The first primer molecule may be used to generate one or more copies of the first strand of the nucleic acid molecule, and/or complements thereof, and the second primer molecule may be used to generate one or more copies of the second strand of the nucleic acid molecule, and/or complements thereof. The one or more copies of the first strand of the nucleic acid molecule, and/or complements thereof, may be coupled to the first bead. The one or more copies of the second strand, and/or complements thereof, may be coupled to the second bead. These coupled copies and/or complements may be used for additional amplification reactions. The sequences of the one or more copies of the first strand, or complements thereof, may at least partially overlap the sequences of the one or more copies of the second strand, or complements thereof.

It will be understood by a skilled artisan that examples describing a double strand template molecule will also apply to single strand template molecules. In a particular example, a template single strand may be coupled to the first adapter and may comprise a region that is complementary to a second adapter, wherein the first adapter is configured to interact with the first primer molecule of the first bead and the second adapter is configured to interact with the second primer molecule of the second bead. Though the second adapter is not present in the template, after synthesis of a complementary strand, the new strand comprises the second adapter. The first primer molecule may be used to generate one or more complements of the template and the second primer molecule may be used to generate one or more complements or copies of the complement of the template. The one or more copies of the template single strand molecule, and/or complements thereof, may be coupled to the first bead. The one or more copies of the complement to the template single strand molecule, and/or complements thereof, may be coupled to the second bead. Generally, throughout the forgoing examples a double strand template is described; however, it will be understood that a single strand template may also be used comprising a region complementary to a region described in a second strand.

Upon completion of an amplification process, the plurality of beads (e.g., the plurality of bead-nucleic acid molecule complexes) distributed amongst a plurality of partitions may be recovered from the plurality of partitions (e.g., droplets or wells), and the beads (e.g., the plurality of bead-nucleic acid molecule complexes) may be separated (e.g., magnetically separated) from the emulsion or mixture. Subsequently, the nucleic acid molecules or any derivatives thereof that may have formed during any of the previous amplification and/or processing steps may be assayed or analyzed (e.g., by determining the nucleotide sequence in a sequencer).

In some cases, partitions (e.g., droplets) comprising different numbers of beads may be separated from one another. For example, a first partition (e.g., droplet) comprising a first number of beads may be separated from a second partition (e.g., droplet) comprising a second number of beads. The first number of beads and the second number of beads may be the same or different. For example, the first partition may comprise a single bead and the second partition may comprise two beads. In some cases, all or a majority of partitions comprising a given number of beads may be separated from all or a majority of partitions comprising a different number of beads. For example, all or a majority of partitions comprising a single bead may be separated from partitions comprising zero beads and/or partitions comprising two or more beads. In another example, all or a majority of partitions comprising two beads may be separated from partitions comprising other numbers of beads. Separation of partitions comprising different number of beads may be accomplished by, for example, optically detecting partitions comprising different numbers of beads and, based at least in part on such optical detection, adjusting a direction of flow (e.g., within a microfluidic channel system) to send partitions (e.g., droplets) comprising a first number of beads in a first direction (e.g., along a first channel) and partitions (e.g., droplets) comprising a second number of beads in a second direction (e.g., along a second channel). Alternatively or in addition, other separation strategies can be used, including optical and non-optical strategies. For example, physical properties, such as mass or density, of the partitions may be used to separate the partitions. In some instances, a plurality of partitions may be subject to one or more forces or fields to facilitate such separation.

In some cases, nucleic acid molecules (e.g., amplification products or derivatives thereof) attached to beads are sequenced. In other cases, nucleic acid molecules (e.g., amplification products or derivatives thereof) not attached to beads are sequenced. For example, nucleic acid molecules (e.g., amplification products or derivatives thereof) attached to beads may be removed from beads (e.g., by decoupling the nucleic acid molecules and the beads) and provided to a sequencing system for sequencing (e.g., as described herein). Nucleic acid molecules may be removed from a bead by, for example, applying a stimulus to the bead or the partition comprising the same. Such a stimulus may be, for example, a thermal stimulus, photo stimulus, or chemical stimulus (e.g., a reducing agent). Nucleic acid molecules removed from a bead may subsequently attach to a surface of a flow cell (e.g., to one or more wells within a flow cell), where they may undergo one or more sequencing reactions and/or one or more additional amplification reactions.

In some cases, multiple different sets of beads may be used to prepare a nucleic acid sample for sequencing. For example, a first bead of a first set of beads may be used to perform a first function and a second bead of a second set of beads may be used to perform a second function. Different sets of beads may comprise the same or different materials and have any number of shared or different properties (e.g., shape, size, paramagnetic state, etc.). For example, a first bead of a first set of beads may be smaller than a second bead of a second set of beads. First beads of the first set of beads may be nanobeads having diameters between about 1-100 nanometers (nm), such as about 50 nm, while second beads of the second set of beds may have diameters larger than about 100 nm. For example, second beads of the second set of beads may be microbeads having diameters between about 1-100 micrometers (µm). The first bead may also be magnetic, while the second bead may not be magnetic. Different functions performed by different sets of beads may include, for example, template loading, amplification, and sequencing. In an example, first beads of a first set of beads may be used to prepare a sample comprising a plurality of nucleic acid molecules for subsequent processing. First beads may comprise a plurality of primer molecules coupled thereto, which primer molecules may be complementary to sequences of nucleic acid molecules of the plurality of nucleic acid molecules. For instance, a first subset of the first set of beads may comprise first primer molecules complementary to a first sequence of nucleic acid molecules of the plurality of nucleic acid molecules and a second subset of the first set of beads may comprise second primer molecules complementary to a second sequence of nucleic acid molecules of the plurality of nucleic acid molecules. The first sequence may be a sequence of a first adapter coupled to nucleic acid molecules of the plurality of nucleic acid molecules and the second sequence may be a sequence of a second adapter coupled to nucleic acid molecules (e.g., the same or different nucleic acid molecules) of the plurality of nucleic acid molecules. The first sequence may be coupled to first strands of nucleic acid molecules of the plurality of nucleic acid molecules and the second sequence may be coupled to second strands of nucleic acid molecules of the plurality of nucleic acid molecules. The first set of beads and the plurality of nucleic acid molecules may be combined in a bulk solution and subjected to conditions sufficient to hybridize primer molecules coupled to first beads of the first set of beads to sequences of nucleic acid molecules of the plurality of nucleic acid molecules. The primer molecules may then be extended to generate strands complementary to strands of the plurality of nucleic acid molecules. The resultant double-stranded nucleic acid molecules may be coupled to first beads of the first set of beads. The double-stranded nucleic acid molecules coupled to beads may be end-blocked using, e.g., a terminal transferase. In some cases, a single double-stranded nucleic acid molecule may be coupled to a given first bead. In other cases, multiple double-stranded nucleic acid molecules may be coupled to a given bead. The bulk solution may then be washed and the first set of beads may be separated from other materials in the solution (e.g., via magnetic separation) including free nucleic acid molecules of the plurality of nucleic acid molecules.

The first set of beads may then be partitioned among a plurality of partitions (e.g., droplets; as described herein). Partitions of the plurality of partitions may comprise one or more first beads of the first set of beads that are coupled to one or more double-stranded nucleic acid molecules (e.g., template nucleic acid molecules). Other partitions of the plurality of partitions may comprise one or more first beads of the first set of beads that are not coupled to a double-stranded nucleic acid molecule. Still other partitions of the plurality of partitions may not include a first bead of the first set of beads.

Figure 9:
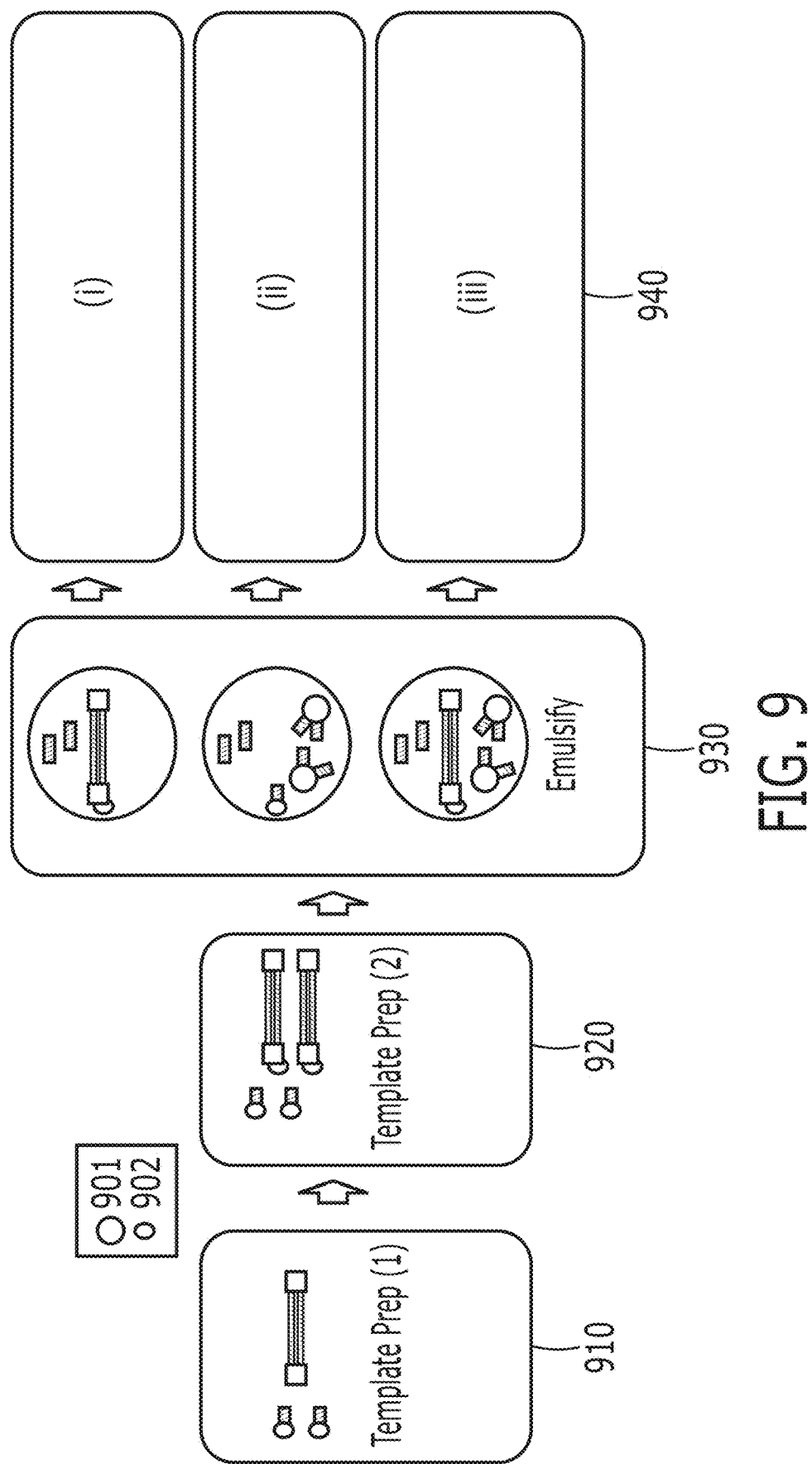
FIG. 9 illustrates a workflow involving first and second sets of beads for template loading and sequencing, respectively.

The first set of beads may be co-partitioned with one or more reagents (e.g., as described herein) and a second set of beads. The second set of beads may comprise primer molecules suitable for capturing and amplifying template nucleic acid molecules in preparation for sequencing (e.g., as described herein). The second set of beads may be referred to herein as "sequencing beads." Accordingly, the plurality of partitions may comprise one or more of (i) a first subset of partitions including one or more first beads of the first set of beads that are coupled to one or more double-stranded nucleic acid molecules and at least two second beads of the second set of beads; (ii) a second subset of partitions including one or more first beads of the first set of beads that are coupled to one or more double-stranded nucleic acid molecules and only one second beads of the second set of beads; (iii) a third subset of partitions including one or more first beads of the first set of beads that are coupled to one or more double-stranded nucleic acid molecules and no second beads of the second set of beads; (iv) a fourth subset of partitions including one or more first beads of the first set of beads that are not coupled to a double-stranded nucleic acid molecule and at least two second beads of the second set of beads; (v) a fifth subset of partitions including one or more first beads of the first set of beads that are not coupled to a double-stranded nucleic acid molecule and only one second bead of the second set of beads; (vi) a sixth subset of partitions including one or more first beads of the first set of beads that are not coupled to a double-stranded nucleic acid molecule and no second bead of the second set of beads; (vii) a seventh subset of partitions that do not include a first bead of the first set of beads and do include at least two second beads of the second set of beads; (viii) a eighth subset of partitions that do not include a first bead of the first set of beads and do include only one second beads of the second set of beads; and (ix) a ninth subset of partitions that do not include a first bead of the first set of beads or a second bead of the second set of beads. Accordingly, only certain subsets of the plurality of partitions may include both a template nucleic acid molecule and at least one second bead of the second set of beads. Partitions of the third subset of partitions described above include at least one template nucleic acid molecule coupled to a first bead of the first set of beads but do not include a second bead of the second set of beads (e.g., a sequencing beads). Because these partitions do not include sequencing beads, no material will be prepared for sequencing. Upon recovery of the contents of partitions of the third set of partitions, magnetic capture can be used to eliminate the first bead. Accordingly, no sequencing products will be detected corresponding to partitions of the third set of partitions. Partitions of the seventh subset of partitions described above do not include a first bead bearing a template nucleic acid molecule but do include at least two second beads of the second set of beads. Because these partitions do not include template nucleic acid molecules, no amplification products will be generated that correspond to template nucleic acid molecules and no sequencing reads will be obtained. Magnetic separation can be used to remove any first beads that are not linked to a template nucleic acid molecule. Partitions of the first subset of partitions described above include at least one first bead coupled to a template nucleic acid molecule and at least two second beads of the second set of beads (e.g., as described herein). Accordingly, amplification and sequencing may take place on the at least two second beads, as described herein. Post-amplification magnetic capture may eliminate template loaded nanobeads (e.g., first beads) such that these beads will not be detected via a sequencing assay. FIG. 9 illustrates this method involving first and second set of beads. A set of sequencing beads 901 and a set of template loading nanobeads 902 are provided. In an example, a template loading nanobead is about 50 nanometers in diameter. The template loading nanobeads may be magnetic and/or comprise another capture mechanism. The template loading nanobeads may be coated in primers. In a first template preparation operation 910, the template loading nanobeads (primer-coated) and template nucleic acid molecules may be combined in a bulk mixture. The nanobeads may be provided in excess. In a second template preparation operation 920, the templates may be subjected to conditions sufficient to (i) anneal the templates to the nanobeads and (ii) extension. Unbound templates may be washed away, such as by immobilizing or otherwise capturing the nanobeads and applying a washing solution. Optionally, ends are blocked using terminal transferase. Such template preparation operations may generate nanobead-bound templates. In an emulsion operation 930, the nanobead-bound templates may be partitioned into droplets along with sequencing beads and other reagents (e.g., solution primer molecules), to generate (940) variously occupied droplets and in some cases unoccupied droplets. Some droplets (i) may comprise a nanobead-bound template without a sequencing bead. Some droplets (ii) may comprise a sequencing bead without a nanobead-bound template. Some droplets (iii) may comprise both a nanobead-bound template and a sequencing bead. To achieve template positive sequencing beads, a nanobead must be present. The droplets may be subjected to amplification 940. The emulsion may be broken and contents of the droplets pooled. Where no sequencing beads are present as in case (i), post-amplification nanobead capture (e.g., using a magnet) can eliminate nanobead-bound templates, and due to the capture and small size of the nanobeads, a sequencer may not detect the nanobeads (or templates bound to such nanobeads), resulting in no sequencing reads from these droplets. Where no templates are present as in case (ii), amplification may not proceed as there are no templates. Post-amplification nanobead capture may eliminate empty nanobeads (that do not have templates bound to them). No sequencing reads are generated from these droplets. Where a sequencing bead and a nanobead-bound template are present as in case (iii), amplification products may be immobilized to sequencing beads. Post-amplification nanobead capture may eliminate nanobead-bound templates and other nanobeads. Due to the capture and small size of the nanobeads, a sequencer may not detect the nanobeads (or templates bound to such nanobeads), and sequencing reads will be generated from sequencing of nucleic acid molecules on the sequencing beads in these droplets.

Amplification Reactions

The methods for analyzing and/or processing a biological sample as disclosed herein may comprise any useful type of reaction (e.g., any nucleic acid amplification reaction) to analyze and/or process a target nucleic acid molecule to generate one or more copies or complements of the target nucleic acid molecule (e.g., an amplified nucleic acid molecule or an amplified product). The amplification products (e.g., the copies or complements) of a nucleic acid molecule may have at least partial sequence complementarity (e.g., >90%) to the nucleic acid molecule. Amplification reactions as described herein may comprise single primer extension reactions, for example, when nucleic acid amplification is performed. Amplification of a nucleic acid may be linear, exponential, or a combination thereof. Amplification may be emulsion based or may be non-emulsion based. Non-limiting examples of nucleic acid amplification reactions that may be used in combination with the herein disclosed methods include reverse transcription, primer extension, polymerase chain reaction (e.g., PCR), ligase chain reaction, helicase-dependent amplification, asymmetric amplification, rolling circle amplification, and multiple displacement amplification (MDA). An amplified product that may be generated using the herein described methods may be DNA. In cases where a target RNA is amplified, DNA (e.g., complementary DNA (cDNA)) may be obtained by reverse transcription of the RNA and subsequent amplification of the DNA may be used to generate an amplified DNA product. The amplified DNA product may be indicative of the presence of the target RNA in the biological sample. In cases where DNA is amplified, any DNA amplification method may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR (e.g., ePCR), dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). The methods described herein may comprise linear DNA amplification. The methods described herein may comprise exponential DNA amplification. DNA amplification may be achieved with nested PCR, which may improve sensitivity of detecting amplified DNA products. Moreover, paired-end adapters may be used for PCR amplification to increase accuracy and/or sensitivity (e.g., by increasing the signal-to-noise ratio) for analyzing a biological sample.

The methods described herein may employ amplification reactions for various time periods (e.g., several minutes or several hours). The time period over which amplification yields a detectable amount of amplified product indicative of the presence of a target nucleic acid molecule in a biological sample may vary depending upon the biological sample from which the target nucleic acid molecule may be obtained, the particular nucleic acid amplification reactions that may be conducted, the particular number of cycles of amplification reaction that may be performed, and the partitioning process conducted such as the generation of a plurality of droplets. Various detection and sequencing schemes may also permit varying detection limits. Amplification of a target nucleic acid molecule may yield a detectable amount of amplified product indicative of the presence of the target nucleic acid over a time period of 240 minutes or less; 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less. In some cases, a single copy or complement of a nucleic acid molecule may be detectable (e.g., using a nucleic acid sequencing assay). Such a low detection limit may be made possible by paired end sequencing.

In any of the methods provided herein, nucleic acid sequencing may be used to identify sequences of copies and/or complements of nucleic acid molecules (e.g., target nucleic acid molecules). The sequences of the copies and/or complements of the nucleic acid molecules, obtained in a nucleic acid sequencing assay as sequencing reads, may be associated with the nucleic acid molecules from which they originate using barcode sequences or other sample indices or labels. For example, sequencing reads corresponding to nucleic acid molecules of a given cell or a given sample may be identified with the given cell or sample using barcode sequences and the like. In some cases, one or more copies of a first strand of a nucleic acid molecule of the sample (e.g., target nucleic acid molecule) and one or more copies of a second strand of the nucleic acid molecule, or complements thereof, may undergo nucleic acid sequencing (e.g., as described herein). As described above, nucleic acid sequencing is a type of nucleic acid processing reaction which may include sequencing by synthesis or a polymerase chain reaction (PCR). In some methods, nucleic acid sequencing may comprise an emulsion polymerase chain reaction (ePCR).

At least one partition of a plurality of partitions may comprise materials or components in addition to at least a first bead, a second bead, and a first and second sample nucleic acid molecule. An additional component of a partition may be a synthetic nucleic acid molecule. The synthetic nucleic acid molecule may be double stranded. The synthetic nucleic acid molecule may comprise a cleavable element. The cleavable element may allow separation of components of the synthetic nucleic acid molecule. The separation may be accomplished by chemical, light, heat or other approaches. The synthetic nucleic acid molecule may also be subjected to ligation and/or circularization. Upon ligation and/or circularization, the synthetic nucleic acid molecule may be cleaved to provide a cleaved synthetic nucleic acid molecule. The cleaved synthetic nucleic acid molecule may then be subjected to gap filling through an amplification reaction (e.g., as described herein).

Upon completion of an amplification process (e.g., after a certain duration of time and/or number of amplification cycles), the plurality of beads (e.g., the plurality of bead-nucleic acid molecule complexes) distributed amongst a plurality of partitions may be recovered from the plurality of partitions (e.g., droplets or wells), and the beads (e.g., the plurality of bead-nucleic acid molecule complexes) may be separated (e.g., magnetically separated) from the emulsion or mixture. Subsequently, the nucleic acid molecules or any derivatives thereof that may have formed during any of the previous amplification and/or processing steps may be assayed or analyzed (e.g., by determining the nucleotide sequence in a sequencer). In some cases, only nucleic acid molecules (e.g., amplification products or derivatives thereof) coupled to beads are sequenced. In other cases, only nucleic acid molecules (e.g., amplification products or derivatives thereof) that are not coupled to beads are sequenced. In some cases, both nucleic acid molecules coupled to beads and nucleic acid molecules not coupled to beads (e.g., amplification products or derivatives thereof) are sequenced (e.g., simultaneously or separately).

An advantage of the methods of the present disclosure may be an increased ratio (e.g., >2) of beads to nucleic acid molecules inside a partition (e.g., a droplet), which may result in increased accuracy and sensitivity during sample analysis, at least in part, due to higher clonal copy numbers of a given nucleic acid molecule and reduced sample or template loss. The percentage of partitions with template but without a bead can be greatly reduced by adding sufficiently high numbers of beads. This reduces a double Poisson distribution scheme to a single Poisson distribution scheme. This may be of high significance in areas where biological samples may contain only trace amounts of nucleic acids such as cfDNA in tumor diagnosis and staging. Moreover, the combination of using higher quantity ratios of beads to nucleic acid molecules and paired-end adapters may provide methods with increased accuracy and sensitivity for analyzing biological samples (e.g., sample nucleic acid molecules).

Bead Compositions

The herein disclosed methods for analyzing a biological sample may comprise amplification of one or more (e.g., a plurality of) nucleic acid molecules (e.g., target nucleic acid molecule). Nucleic acid amplification as described herein may be performed using one or more beads or bead particles (e.g., one or more sets of beads) to which the one or more nucleic acid molecules (e.g., single stranded nucleic acid molecules) may bind. A first set of beads and/or a second set of beads may be prepared using a variety of methods. The first set of beads and/or the second set of beads may be comprised of one or more materials and/or components. The first set of beads and/or the second set of beads may be, for example, polymer beads (e.g., as described herein). The first and/or second set of beads may have a coating such as a PEG layer or hydrogel (e.g., as described herein). The first and/or second set of beads may contain the same core bead or different core beads (e.g., comprise the same or different material). Thus, the beads of the first set of beads may be prepared from a first material and the beads of the second set of beads may be prepared from a second material, wherein the first material may be the same as or different from the second material. Beads of the first set of beads may comprise first primer molecules coupled thereto, while beads of the second set of beads may comprise second primer molecules coupled thereto. The first and second primer molecules may be provided to the first set of beads and the second set of beads, respectively, during the preparation (e.g., synthesis) of the first and second sets of beads. Alternatively, the first and second primer molecules may be provided to the first set of beads and the second set of beads, respectively, following preparation of the first and second sets of beads (e.g., to "core beads" and/or pre-functionalized beads that do not yet comprise primer molecules). Where primer molecules are immobilized to beads in a subsequent process, the beads of the first and second sets of beads may be further processed separately. The primer molecule for each bead set may be immobilized to the beads using a variety of chemistries. Coupling may occur through, for example, amide, ester, or disulfide functional groups. Click chemistry (e.g., Staudinger ligation or Diels-Alder chemistry) may be used for the immobilization of the primer molecules on beads. Immobilized primer molecules may be further modified using additional downstream chemistry.

The herein disclosed methods for analyzing and/or processing a biological sample may comprise preparation (e.g., synthesis) of a first set of beads and a second set of beads such that a set of releasably (e.g., thermally or chemically releasable) coupled first beads and second beads is produced. For example, a first bead may be releasably coupled to a second bead, such that the beads may be releasable from one another upon application of a stimulus (e.g., a thermal, chemical, or photo stimulus). Similarly, primer molecules coupled to beads of the first and/or second set of beads may be releasable from the beads upon application of a stimulus, such as a thermal, chemical, or photo stimulus.

Releasably coupled first beads and second beads may be coupled through non-covalent interactions or bonds (e.g., protein interactions) or covalent bonds. A first bead may be linked to a second bead via one or more chemical linker and/or via one or more splint oligonucleotides. Non-covalent interactions such as protein interactions may be hydrogen bonding, Van der Waal's forces, dipole-dipole interaction, or any combination thereof. The covalent bonds may be formed (e.g., synthetically formed) between the beads using various chemistries such as coupling reaction (e.g., amide bond formations) or click chemistry (e.g., Staudinger ligation or Diels-Alder reactions).

A releasably coupled bead pair comprising a first bead releasably coupled to a second bead may be subjected to a stimulus (e.g., a thermal or chemical) that stimulates the release of the first bead from the second bead. The stimulus may comprise a temperature change and/or a chemical stimulus (e.g., a change in pH and/or ion concentration).

Alternatively, the first set of beads and the second set of beads may also be prepared (e.g., synthesized) such that a set of irreversibly coupled first beads and second beads (e.g., a set of bead pairs each comprising a first bead irreversibly coupled to a second bead) may be produced. The first bead of the first set of beads may also be irremovably coupled to the second bead of the second set of beads. This irremovable coupling may comprise cross-linking between the first bead and the second bead via covalent chemical bonds.

Following initial preparation (e.g., synthesis) of beads of the first and second sets of beads, a size selection process may be performed that may discriminate between various combinations of first beads and/or second beads. For example, a size selection process may discriminate between a bead pair comprising a first bead coupled to a second bead and a bead pair comprising two first beads or a bead pair comprising two second beads. A size selection process such as a filtration process may also be used to separate clumps or aggregates of beads and/or to remove debris from a solution comprising a plurality of beads.

Methods for Generating Paired-End Sequence Reads

As described herein, the methods of the present disclosure may utilize an increased ratio (e.g., >2) of beads to nucleic acid molecules (e.g., target nucleic acid molecules) inside a partition (e.g., a droplet) when performing an amplification and/or sequencing process. This results in increased accuracy and sensitivity during sample analysis due at least in part to the ability to generate higher clonal copy numbers of a given nucleic acid molecule with reduced sample or template loss. Combining the use of higher bead-to-nucleic acid molecule ratios with the use of paired-end adapters may provide methods with even higher accuracy and sensitivity for analyzing nucleic acid molecules (e.g., target nucleic acid molecules) of a biological sample.

In some cases, a method provided herein may comprise generating paired-end sequencing reads that may be associated with a sequence of a nucleic acid molecule (e.g., target nucleic acid molecule) of a biological sample. The generation of paired-end sequencing reads may increase sensitivity and accuracy of the methods provided herein.

Methods described herein that comprise one or more steps for generating paired-end sequencing reads may comprise providing a first set of particles (e.g., beads) and a second set of particles (e.g., beads) (e.g., as described herein). A first bead of the first set of beads may comprise a first primer molecule (e.g., coupled to the first bead) having at least partial sequence complementarity to a first adapter coupled to a first nucleic acid strand of a nucleic acid molecule of a biological sample (e.g., a target nucleic acid molecule, such as a DNA or RNA molecule). A second bead of the second set of beads may comprise a second primer molecule (e.g., coupled to the second bead) having sequence complementarity to a second adapter coupled to a second nucleic acid strand of the target nucleic acid molecule. The first primer molecule may be different from the second primer molecule. Alternatively, the first and second primer molecules may be the same (e.g., comprise the same nucleic acid sequence) or complementary to one another.

A method comprising generating paired-end sequencing reads may comprise partitioning (e.g., co-partitioning) (i) a first bead of a first set of beads, (ii) a second bead of a second set of beads, and (iii) a nucleic acid molecule of a biological sample (e.g., target nucleic acid molecule), wherein the nucleic acid molecule comprises a first adapter coupled to a first strand of the nucleic acid molecule and a second adapter coupled to a second strand of the nucleic acid molecule, in a partition (e.g., a droplet, such as an aqueous droplet in an emulsion). Partitioning may be achieved according to the methods provided herein and may provide a plurality of partitions (e.g., a plurality of droplets or wells), at least a subset of which may each comprise at least a first bead of a first set of beads and a second bead of a second set of beads and a nucleic acid molecule of a plurality of nucleic acid molecules, which nucleic acid molecule may comprise a first strand comprising a first adapter sequence and a second strand comprising a second adapter sequence. The first and second adapter sequences may be paired-end adapter sequences. Each strand of a given nucleic acid molecule of the plurality of nucleic acid molecules may also comprise a template nucleic acid sequence.

A method comprising generating paired-end sequencing reads may comprise partitioning (e.g., co-partitioning) (i) a first bead of a first set of beads, (ii) a second bead of a second set of beads, and (iii) a nucleic acid molecule of a biological sample (e.g., target single-stranded nucleic acid molecule), wherein the nucleic acid molecule comprises a first adapter coupled thereto and a region (e.g. sequence) complementary to a second adapter, in a partition (e.g., a droplet, such as an aqueous droplet in an emulsion). Partitioning may be achieved according to the methods provided herein and may provide a plurality of partitions (e.g., a plurality of droplets or wells), at least a subset of which may each comprise at least a first bead of a first set of beads and a second bead of a second set of beads and a nucleic acid molecule of a plurality of nucleic acid molecules, which nucleic acid molecule may comprise a first adapter sequence coupled thereto and a region (e.g. sequence) complementary to a second adapter sequence. The first and second adapter sequences may be paired-end adapter sequences.

A partition comprising at least a first bead of a first set of beads, a second bead of a second set of beads, and a nucleic acid molecule of a plurality of nucleic acid molecules that comprises a first adapter coupled to a first strand of the nucleic acid molecule and a second adapter coupled to a second strand of the nucleic acid molecule may be subjected to conditions sufficient to generate one or more copies of the first strand of the first nucleic acid molecule, or complements thereof, and/or one or more copies of the second strand of the second nucleic acid molecule coupled to the second adapter, or complements thereof. Generating the one or more copies of the first strand and/or the second strand, or complements thereof, may involve subjecting the partition comprising the first and second beads and the nucleic acid molecule to conditions sufficient to perform a primer extension reaction and/or nucleic acid amplification reaction (e.g., PCR such as ePCR). The reaction may comprise the use of one or more reagents, which one or more reagents may be included within the partition. The first primer molecule of the first bead may be used to generate the one or more copies of the first strand, and/or complements thereof. The one or more copies of the first strand, and/or complements thereof, may be coupled to the first bead and thus may be used as templates for additional amplification reactions (e.g., exponential amplification). The second primer molecule of the second bead may be used to generate the one or more copies of the second strand, and/or complements thereof. The one or more copies of the second strand, and/or complements thereof, may be coupled to the second bead and thus may be used as templates for additional amplification reactions (e.g., exponential amplification). The sequences of the one or more copies of the first strand, or complements thereof, may at least partially overlap the sequences of the one or more copies of the second strand, or complements thereof.

In order to analyze a biological sample as described herein, any useful type of reaction (e.g., any nucleic acid amplification reaction) may be used to process a target nucleic acid molecule to generate one or more copies or complements thereof of the target nucleic acid molecule (e.g., an amplified product). Amplification may be emulsion based or may be non-emulsion based. Non-limiting examples of nucleic acid amplification reactions that may be used in combination with the herein disclosed methods include reverse transcription, primer extension, polymerase chain reaction (e.g., PCR), ligase chain reaction, helicase-dependent amplification, asymmetric amplification, rolling circle amplification, and multiple displacement amplification (MDA). An amplified product that may be generated using the herein described methods may be DNA. In cases where a target RNA is amplified, DNA (e.g., complementary DNA (cDNA)) may be obtained by reverse transcription of the RNA and subsequent amplification of the DNA may be used to generate an amplified DNA product. The amplified DNA product may be indicative of the presence of the target RNA in the biological sample. In cases where DNA is amplified, any DNA amplification method may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR (e.g., ePCR), dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). The methods described herein may comprise linear DNA amplification. The methods described herein may comprise exponential DNA amplification. DNA amplification may be achieved with nested PCR, which may improve sensitivity of detecting amplified DNA products. Moreover, paired-end adapters may be used for PCR amplification to increase accuracy and/or sensitivity (e.g., by increasing the signal-to-noise ratio) for analyzing a biological sample.

The time period over which amplification yields a detectable amount of amplified product indicative of the presence of a target nucleic acid amplified may vary depending upon the biological sample from which the target nucleic acid was obtained, the particular nucleic acid amplification reactions to be conducted, the particular number of cycles of amplification reaction (e.g., up to 120 minutes), and the partitioning process conducted such as the generation of a plurality of droplets. Amplification of a target nucleic acid molecule may yield a detectable amount of amplified product indicative of the presence of the target nucleic acid over a time period of 240 minutes or less; 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less.

The first bead from the first set (e.g., plurality) of beads may be releasably coupled (e.g., thermally and/or chemically releasable) to the second bead from the second set (e.g., plurality) of beads. Similarly, additional beads of the first set of beads may be releasably coupled to additional beads of the second set of beads, such that there may be a set of releasably coupled first beads and second beads. For example, a first bead may be releasably coupled to a second bead, such that the beads may be releasable from one another upon application of a stimulus (e.g., a thermal, chemical, or photo stimulus). Similarly, primer molecules coupled to beads of the first and/or second set of beads may be releasable from the beads upon application of a stimulus, such as a thermal, chemical, or photo stimulus.

Releasably coupled first beads and second beads may be coupled through non-covalent interactions or bonds (e.g., protein interactions) or covalent bonds. A first bead may be linked to a second bead via one or more chemical linker and/or via one or more splint oligonucleotides. Non-covalent interactions such as protein interactions may be hydrogen bonding, Van der Waal's forces, dipole-dipole interaction, or any combination thereof. The covalent bonds may be formed (e.g., synthetically formed) between the beads using various chemistries such as coupling reaction (e.g., amide bond formations) or click chemistry (e.g., Staudinger ligation or Diels-Alder reactions).

A releasably coupled bead pair comprising a first bead releasably coupled to a second bead may be subjected to a stimulus (e.g., a thermal or chemical) that stimulates the release of the first bead from the second bead. The stimulus may comprise a temperature change and/or a chemical stimulus (e.g., a change in pH and/or ion concentration).

Alternatively, the first set of beads and the second set of beads may also be prepared (e.g., synthesized) such that a set of irreversibly coupled first beads and second beads (e.g., a set of bead pairs each comprising a first bead irreversibly coupled to a second bead) may be produced. The first bead of the first set of beads may also be irremovably coupled to the second bead of the second set of beads. This irremovable coupling may comprise cross-linking between the first bead and the second bead via covalent chemical bonds.

Following initial preparation (e.g., synthesis) of beads of the first and second sets of beads, a size selection process may be performed that may discriminate between various combinations of first beads and/or second beads. For example, a size selection process may discriminate between a bead pair comprising a first bead coupled to a second bead and a bead pair comprising two first beads or a bead pair comprising two second beads. A size selection process such as a filtration process may also be used to separate clumps or aggregates of beads and/or to remove debris from a solution comprising a plurality of beads.

As described herein, a first strand (e.g., a first nucleic acid molecule of a biological sample) may be coupled to a first adapter (e.g., a first paired-end adapter) and a second strand (e.g., a second nucleic acid molecule of a biological sample) may be coupled to a second adapter (e.g., a first paired-end adapter). The first and/or second adapters may participate in a nucleic acid sequencing process (e.g., PCR such as ePCR). The first adapter may comprise a first sub-part and a second sub-part, which first sub-part may have sequence complementarity to the second sub-part. Sequence complementarity generally refers to sequences which are complementary to the sequence to which it is paired with. Similarly, the second adapter may comprise a first sub-part and a second sub-part, which first sub-part may have sequence complementarity to the second sub-part. One or more portions of an adapter may have different melting temperatures. For example, an adapter may comprise a first portion having a first melting temperature and a second portion having a second melting temperature, wherein the first melting temperature is higher than the second melting temperature. Different melting temperatures may be conferred by using adapters comprising, for example, sequences enriched with adenine, thymine, and inosine. Such adapters may facilitate partial denaturation of the adapters to provide access for subsequent processing of the nucleic acid molecules to which they are coupled.

As described herein, nucleic acid sequencing (e.g., NGS) may occur in a partition or a plurality of partitions (e.g., a plurality of droplets or wells). Such a partition (e.g., of a plurality of partitions) may comprise at least (i) one first bead from the first set of beads, (ii) at least one second bead from the second set of beads, and (iii) the biological sample (or a certain fraction of volume thereof) (e.g., a nucleic acid molecule) comprising the first adapter coupled to the first strand (e.g., the first nucleic acid molecule) and the second adapter coupled to the second strand (e.g., the second nucleic acid molecule). The partition may be a droplet, or the partition may be a well.

Figure 7:
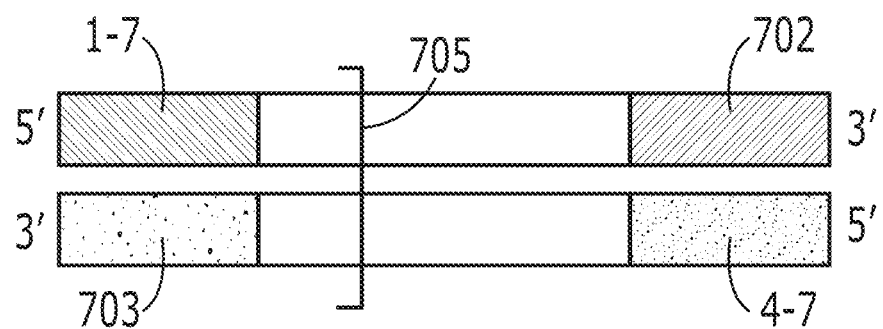
FIG. 7 depicts a schematic of the biological sample (nucleic acid molecule 5) flanked by distinct adapter sequences. Adapter A comprises Primer A (1-7) and Primer A' (703) and Adapter B comprises Primer B (4-7) and Primer B' (702).
Figure 8:
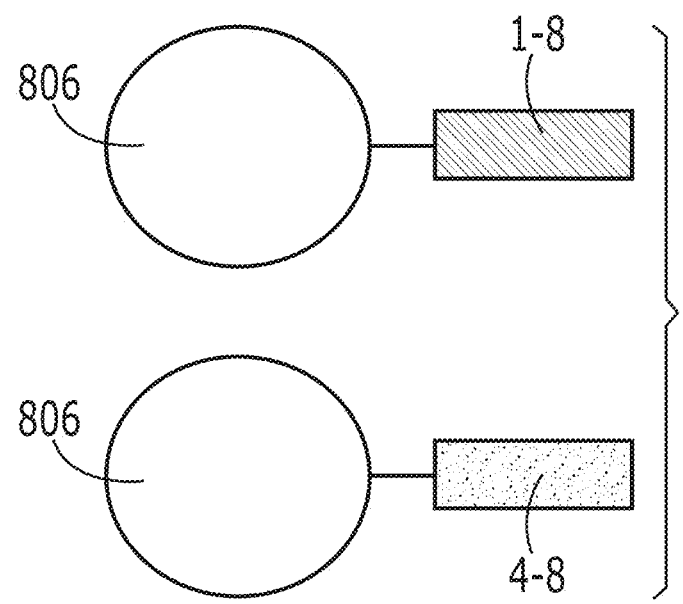
FIG. 8 depicts a schematic of two types of beads (806). One type of bead comprises immobilized Primer A (1-8) or a fragment or portion thereof. One type of bead comprises immobilized Primer B (4-8) or a fragment or portion thereof.

The methods including paired-end sequence reads as described herein may comprise providing a first bead from a first set of beads with a first primer molecule (e.g., part 1-8 of FIG. 8) having sequence complementarity with a first adapter and a second bead from a second set of beads with a second primer molecule (e.g., part 4-8 of FIG. 8) having sequence complementarity with a second adapter (see e.g., FIG. 8). The first set of beads and the second set of beads may then be distributed (e.g., randomly distributed) (e.g., as described herein) among a plurality of partitions such that a given partition of the plurality of partitions comprises a first bead of the first set of beads and a second bead of the second set of beads. As shown in FIG. 7, a nucleic acid molecule 705 may comprise a first strand and a second strand, where the first strand has sequence complementarity to the second strand. Adapters 1-7 and 4-7 may be selected so that nucleic acid amplification from both ends creates a region of overlap. Adapter 1-7 corresponds to complementary sequence 703, and adapter 4-7 corresponds to complementary sequence 702. The overlap may allow for the matching of a copy of a first strand of a biological sample, or a complement thereof, with the copy of a second strand of the biological sample, or a complement thereof. The overlap may comprise, for example, 10, 20, 30, 40, 50, 60, 70, 80, 90, 100, 110, 120, 130, 140, 150, 160, 170, 180, 190, 200, 250, 300, 350, or more base pairs (e.g., 10, 20, 30, 40, 50, 60, 70, 80, 90, 100, 110, 120, 130, 140, 150, 160, 170, 180, 190, 200, 250, 300, 350, or more nucleotides of a copy of each strand, or a complement thereof). Nucleic acid sequencing (e.g., PCR such as ePCR) of the first and second strands, or copies or complements thereof, may provide sequence reads including all or a portion of the overlap. The region of overlap may be positioned between two adapters. For example, the first strand may comprise a first adapter and a third adapter which first and third adapters flank a first template sequence, and the second strand may comprise a second adapter and a fourth adapter which second and fourth adapters flank a second template sequence, where the first template sequence may have sequence complementarity to the second template sequence. These adapters may be single-stranded adapters. The third and fourth adapters may be complements of the second and first adapters, respectively. Alternatively, double-stranded adapters may be used. Such a system is depicted in FIG. 7, in which the first adapter comprises a first sub-part (e.g., part 1-7 of FIG. 7) and a second sub-part (e.g., sequence 703 of FIG. 7), which first sub-part may have sequence complementarity to the second sub-part. The second adapter has a first sub-part (e.g., part 4-7 of FIG. 7) and a second sub-part (e.g., sequence 702 of FIG. 7), which first sub-part may have sequence complementarity to the second sub-part. The biological sample (e.g., a nucleic acid molecule) comprising the first and second strand may be partitioned with a first bead from a first set of beads and a second bead from a second set of beads (e.g., as described herein), in a partition (e.g., one or more droplets or wells). The materials included in the partition may subsequently be subjected to a nucleic acid amplification reaction and/or nucleic acid sequencing. A biological sample may be a nucleic acid molecule such as that depicted in FIG. 7. The nucleic acid molecule comprises a region of overlap (e.g., nucleic acid molecule 705 of FIG. 7, depicted in white) comprising a plurality of base pairs. Following partitioning in a partition with first and second beads, the materials in the partition may be subjected to nucleic acid sequencing to provide sequence reads corresponding to the first and second strands of the nucleic acid molecule. As an example, if the system read length is about 1000 nucleotides and the length of the biological sample is about 1800 nucleotides, a sequence read of about 1000 nucleotides corresponding to the first strand and a sequence read of about 1000 nucleotides corresponding to the second strand may be generated, where the first and second sequence reads will have an overlap of about 200 nucleotides.

The methods for analyzing and/or processing a biological sample as described herein may comprise a first bead of a first set of beads with a first primer molecule (e.g., part 1-8 of FIG. 8) having sequence complementarity with a first adapter and a second bead of a second set of beads with a second primer molecule (e.g., part 4-8 of FIG. 8) having sequence complementarity with a second adapter (see e.g., FIG. 8). The first bead of the first set of beads and the second bead of the second set of beads may be releasably coupled. Thus, a releasably coupled bead pair comprising a first bead of the first set of beads and a second bead of the second set of beads may be formed. The coupling of the first bead and the second bead may be accomplished through protein interactions or covalent bonds as described herein. A set of such releasably coupled bead pairs may be prepared, in which each bead pair includes a bead of the first set of beads releasably coupled to a bead of the second set of beads. During the preparation of the set of releasably coupled first beads and second beads, a size selection process may be performed to discriminate between or select for pairs of releasably coupled first beads and second beads separate from other combinations of first beads and/or second beads (e.g., a pair including two beads of the first set of beads or two beads of the second set of beads). As described herein, a releasably coupled bead pair comprising a first bead releasably coupled to a second bead may be subjected to a stimulus (e.g., a thermal or chemical stimulus). Application of the stimulus may release the first bead from the second bead.

The first and second strands of the biological sample may be flanked by two distinct adapters, a first adapter and a second adapter, each of which may be a double stranded adapter. The first adapter is comprised of a first sub-part (e.g., part 1-7 of FIG. 7) and a second sub-part (e.g., sequence 703 of FIG. 7), which first sub-part may have sequence complementarity to the second sub-part (see e.g., FIG. 7). The second adapter has a first sub-part (e.g., part 4-7 of FIG. 7) and a second sub-part (e.g., sequence 702 of FIG. 7), which first sub-part may have sequence complementarity to the second sub-part (see e.g., FIG. 7). The biological sample is then partitioned with the first bead of the first set of beads and the second bead of the second set of beads into a partition (e.g., one or more droplets in an emulsion or wells). The materials and/or components located or present in the partitions (e.g., droplets) may be then subjected to subsequent processing such as nucleic acid amplification and nucleic acid sequencing (e.g., PCR such as ePCR).

The presently disclosed methods may comprise a first bead of a first set of beads comprising a first primer molecule (e.g., as depicted by part 1-8 of FIG. 8) having sequence complementarity with a first adapter and a second bead of a second set of beads comprising a second primer molecule (e.g., as depicted by part 4-8 of FIG. 8) having sequence complementarity with a second adapter are provided (see e.g., FIG. 8). The first bead of the first set of beads and the second bead of the second set of beads may be irreleasably (e.g., irreversibly) coupled to form a bead pair including the first bead of the first set of beads and the second bead of the second set of beads. The coupling of the first bead and the second bead may be accomplished through protein interactions, covalent bonds, via one or more chemical linker, and/or via one or more splint oligonucleotides. A set of such irreleasably coupled bead pairs may be prepared, in which each bead pair includes a bead of the first set of beads irreleasably coupled to a bead of the second set of beads. During the preparation of the set of irreleasably coupled first beads and second beads, a size selection process may be performed to discriminate between and/or select for pairs of first beads and second beads separate from other combinations of first beads and/or second beads (e.g., a pair including two beads of the first set of beads or two beads of the second set of beads).

A biological sample (e.g., as depicted by nucleic acid molecule 705 of FIG. 7 comprising a first strand and a second strand) may be selected so that nucleic acid amplification from both ends creates an overlap (see e.g., FIG. 7). The overlap allows for the matching of a copy of a first strand of a biological sample with the copy of a second strand of a biological sample. The biological sample may be flanked by two distinct adapters, a first adapter and a second adapter, each of which may be a double stranded adapter. The first adapter may be comprised of a first sub-part (e.g., as depicted by part 1-7 of FIG. 7) and a second sub-part (e.g., as depicted by sequence 703 of FIG. 7), which first sub-part may have sequence complementarity to the second sub-part (see e.g., FIG. 7). The second adapter comprises a first sub-part (e.g., as depicted by part 4-7 of FIG. 7) and a second sub-part (e.g., as depicted by sequence 702 of FIG. 7), which first sub-part may have sequence complementarity to the second sub-part (see e.g., FIG. 7). The biological sample may then be partitioned (e.g., into one or more droplets) with the first bead of the first set of beads and the second bead of the second set of beads into a partition (e.g., one or more droplets or wells). The materials in the partitions are then subjected to subsequent processing such as nucleic acid amplification and/or nucleic acid sequencing.

The present disclosure further provides methods for processing a biological sample (e.g., a nucleic acid molecule comprising a first strand and a second strand) comprising providing a first set of beads and a second set of beads. A first bead of the first set of beads may comprise a first primer molecule having sequence complementarity to a first adapter coupled to a first strand of the biological sample. A second bead of the second set of beads may comprise a second primer molecule having sequence complementarity to a second adapter coupled to a second strand of the biological sample. The first primer molecule may be different than the second primer molecule.

The method may comprise partitioning (e.g., generating one or more droplets) (i) the first bead of the first set of beads, (ii) the second bead of the second set of beads, and (iii) the biological sample comprising the first adapter coupled to the first strand and the second adapter coupled to the second strand, in a partition. The partitioning may be achieved using, for example, droplets in an emulsion or wells.

The partition comprising the first and second beads and the biological sample may be subjected to conditions sufficient to generate one or more copies of the first strand coupled to the first adapter, or complements thereof, and/or one or more copies of the second strand coupled to the second adapter or complements thereof. Generating the one or more copies of the first strand and/or the second strand, or complements thereof, may involve subjecting the first and second beads and the biological sample to conditions sufficient to perform a primer extension reaction and/or nucleic acid amplification reaction (e.g., PCR such as ePCR). The first primer of the first bead may be used to generate the one or more copies of the first strand, and/or complements thereof. The one or more copies of the first strand, and/or complements thereof, may be coupled to the first bead and may be used for amplification reactions (e.g., linear or exponential amplification). The second primer of the second bead may be used to generate the one or more copies of the second strand, and/or complements thereof. The one or more copies of the second strand, and/or complements thereof, may be coupled to the second bead and may be used for amplification reactions (e.g., linear or exponential amplification). The sequences of the one or more copies of the first strand, or complements thereof, may at least partially overlap the sequences of the one or more copies of the second strand, or complements thereof. As described herein, any type of nucleic acid amplification reaction may be used to generate an amplified product (e.g., one or more copies of the first and/or second strand or complements thereof). The one or more copies of the first strand may have no overlap with the one or more copies of the second strand.

At least one partition of a plurality of partitions may comprise materials or components in addition to at least a first bead, a second bead, and a first and second sample nucleic acid molecule. An additional component of a partition may be a synthetic nucleic acid molecule. The synthetic nucleic acid molecule may be double stranded. The synthetic nucleic acid molecule may comprise a cleavable element. The cleavable element may allow separation of components of the synthetic nucleic acid molecule. The separation may be accomplished by chemical, light, heat or other approaches. The synthetic nucleic acid molecule may also be subjected to ligation and/or circularization. Upon ligation and/or circularization, the synthetic nucleic acid molecule may be cleaved to provide a cleaved synthetic nucleic acid molecule. The cleaved synthetic nucleic acid molecule may then be subjected to gap filling through an amplification reaction (e.g., as described herein). Alternatively or in addition, a partition may comprise one or more reagents, such as one or more reagents for lysing or permeabilizing cells or for use in a primer extension or amplification reaction (e.g., nucleotides and polymerizing enzyme).

As disclosed herein, a method for analyzing and/or processing a biological sample may comprise a first bead of a first set of beads may be releasably coupled to a second bead of a second set of beads. The first bead of the first set of beads and the second bead of the second set of beads may be releasably coupled through protein interactions or covalent bonds. The protein interactions may refer to hydrogen bonding, Van der Waal's forces, dipole-dipole interactions, or any combination thereof. The covalent bonds may be formed (e.g., synthetically formed) between the beads using a variety of chemical reaction such as coupling reactions and/or click chemistry.

The first bead releasably coupled to the second bead may be subjected to a stimulus. The stimulus causes the release of the first bead from the second bead. The stimulus may be a temperature change or a chemical stimulus. Alternatively, the first bead of the first set of beads may be irremovably coupled to the second bead of the second set of beads. This irremovable coupling may comprise cross-linking (e.g., covalent linkage) between the first bead and the second bead.

In the presently disclosed methods for analyzing and/or processing a biological sample, the method may comprise preparing (e.g., synthesizing) a plurality of beads comprising a first set of beads and/or a second set of beads. The first set of beads or the second set of beads may be, for example, polymer beads. The beads may be hydrogel beads. The beads may have a coating such as a PEG layer or hydrogel. Where multiple sets of beads are used, the multiple sets of beads may contain the same core bead or different core beads (e.g., comprise the same or different material). For example, the beads of a first set of beads may be prepared from a first material and beads of a second set of beads may be prepared from a second material, where the first material may be the same as or different from the second material. First and second primer molecules may be provided to the first set of beads and the second set of beads, respectively, during the preparation (e.g., synthesis) of the first and second sets of beads. Alternatively, the first and second primer molecules may be provided to the first set of beads and the second set of beads, respectively, following preparation of the first and second sets of beads (e.g., to "core beads" that do not yet comprise primer molecules). Where primer molecules are immobilized to beads in a subsequent process, the beads of the first and second sets of beads may be further processed separately. The primer molecule for each bead set may be immobilized to the beads using a variety of chemistries. Coupling may occur through, for example, amide, ester, or disulfide functional groups. Click chemistry (e.g., Staudinger ligation or Diels-Alder chemistries) may be used for the immobilization of the primer on beads. Immobilized primer molecules may be further modified using additional downstream chemistry.

As described herein, beads may be provided in bead pairs. Beads of a bead pair may be releasably or unreleasably (e.g., irreversibly) coupled to one another (e.g., as described herein). A bead pair may comprise a first bead of a first set of beads and a second bead of a second set of beads (e.g., as described herein).

The herein disclosed methods for analyzing and/or processing a biological sample may comprise one or more copies of the first strand and one or more copies of the second strand that may undergo nucleic acid sequencing (e.g., NGS). As described herein, nucleic acid sequencing is a type of nucleic acid amplification reaction which may include sequencing by synthesis or a polymerase chain reaction (PCR). Nucleic acid amplification and/or sequencing may comprise an emulsion polymerase chain reaction (ePCR). As disclosed herein, PCR such as ePCR may be performed in partitions such as emulsion droplets, at least a subset of which may each comprise at least a first bead comprising a first primer molecule, a second bead comprising a second primer molecule, and first and second nucleic acid strands comprising first and second adapters, respectively, wherein the first and second adapters (e.g., paired-end adapters) may have at least partial sequence complementarity to the first and second primer molecules, respectively.

The first adapter may comprise a first sub-part and a second sub-part, which first sub-part has sequence complementarity to the second sub-part (e.g., as shown in FIG. 7). Sequence complementarity generally refers to a sequence which is complementary to the sequence to which it is paired with.

Each partition (e.g., each droplet or well) of a plurality of partitions may comprise at least one first bead of the first set of beads, at least one second bead of the second set of beads, and the biological sample comprising the first adapter coupled to the first strand and the second adapter coupled to the second strand. The partition may be a droplet or a well.

The herein described methods for analyzing a biological sample may comprise two types of beads (e.g., a first bead and a second bead) comprising primer sequences each corresponding to a specific adapter, wherein the adapter may be coupled to a nucleic acid molecule of the biological sample that comprise one or more template sequences. The template sequences of the nucleic acid molecule may be identifiable by one or more barcode sequences included in the adapters. A target nucleic acid library insert (e.g., depicted by nucleic acid molecule 705 in FIG. 7) length may be selected such that nucleic acid sequencing from both ends provides sequence reads having no or very minimal overlap. Inserts may be end-repaired and A-tailed. A synthetic double-stranded nucleic acid molecule may be designed such that it may loop and ligate with the insert, such that the synthetic double strand may contain T overhangs preferably without terminal phosphates. The sequence of the synthetic double-stranded nucleic acid molecule may be as follows: Barcode 2', PB' cleavable element, PA, Barcode 1. Barcode 1 and Barcode 2' may be commercially available, and Barcode 1 and Barcode 2' may or may not be different sequences. The barcode sequences used in the herein described methods may be well defined in order to be assigned to each other. The cleavable element may allow separation of the strands of the synthetic double-stranded nucleic acid molecule by chemical, light, heat, or other mechanisms. Following ligation and circularization, the synthetic double-stranded nucleic acid molecule may be cleaved and gap filled through polymerase-based extension. Two types of beads (see e.g., part 806 of FIG. 8) may be available for clonal amplification, one with immobilized PA (1-2) oligonucleotides or minimally a sub-portion of PA, and another with PB (4-2) oligonucleotides or minimally a sub-portion of PB immobilized.

Upon completion of an amplification process, the plurality of beads (e.g., the plurality of bead-nucleic acid molecule complexes) distributed amongst a plurality of partitions may be recovered from the plurality of partitions (e.g., droplets or wells), and the beads (e.g., the plurality of bead-nucleic acid molecule complexes) may be separated (e.g., magnetically separated) from the emulsion or mixture. Subsequently, the nucleic acid molecules or any derivatives thereof that may have formed during any of the previous amplification and/or processing steps may be assayed or analyzed (e.g., by determining the nucleotide sequence in a sequencer). In some cases, only nucleic acid molecules (e.g., amplification products or derivatives thereof) coupled to beads are sequenced. In other cases, only nucleic acid molecules (e.g., amplification products or derivatives thereof) that are not coupled to beads are sequenced. In some cases, both nucleic acid molecules coupled to beads and nucleic acid molecules (e.g., amplification products or derivatives thereof) not coupled to beads are sequenced (e.g., simultaneously or separately).

Hence, the advantages of the methods disclosed herein may be of particular importance when the biological sample contains low amounts and/or low concentrations of nucleic acid molecules (e.g., cfDNA). Similarly, the accuracy and sensitivity of the methods of the present disclosure may be of particular importance when analyzing samples to detect rare alleles (e.g., in cancer diagnosis and detection).

Methods and Systems for Clonal Amplification

Figure 10A:
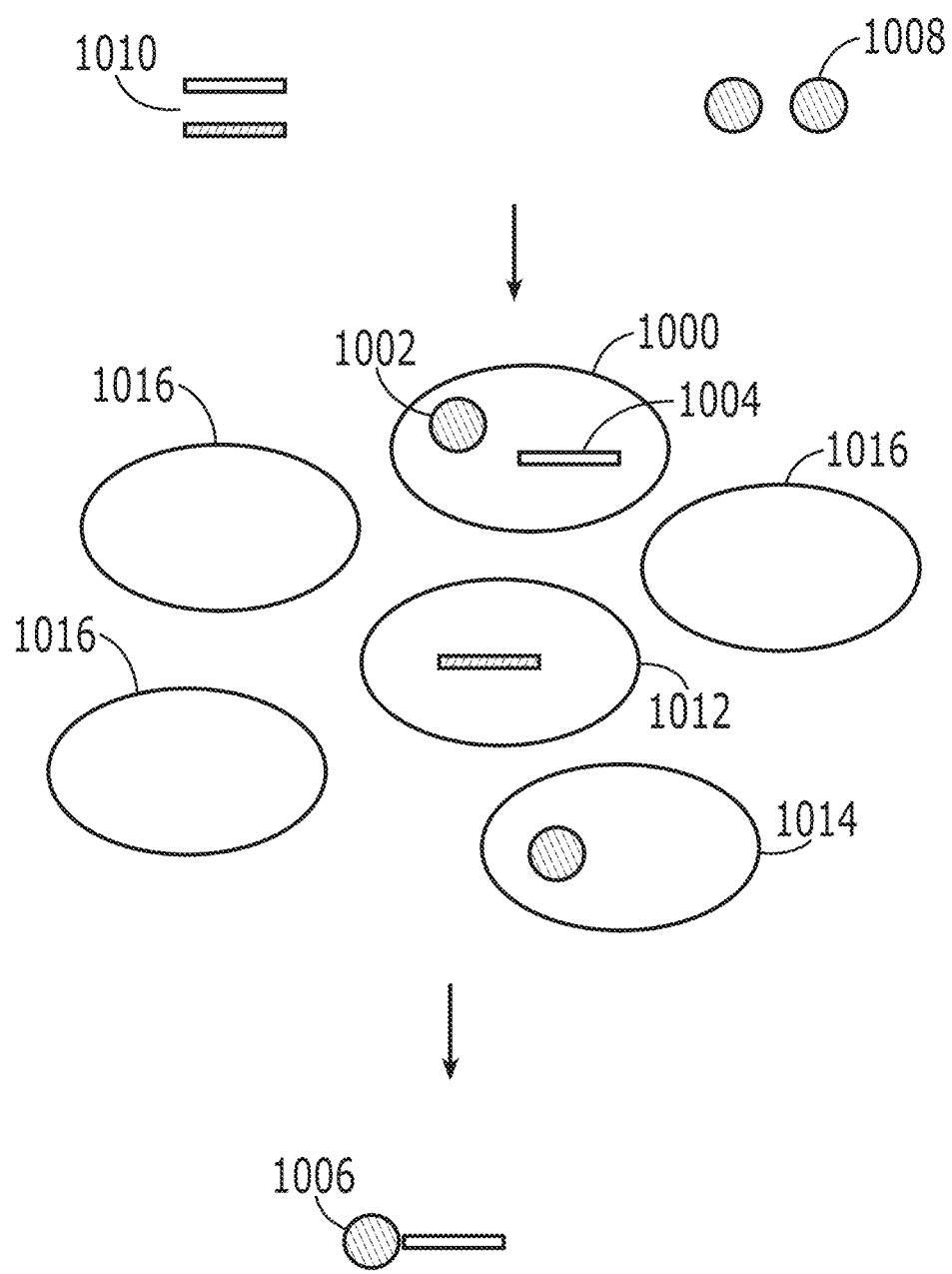
FIG. 10A illustrates an ePCR method that is limited by Poisson loading for both the beads and the templates.

Previous methods of emulsion PCR for clonal amplification of primer beads, in which a droplet is loaded with a single bead and a single template to ensure a monoclonal bead after amplification, can suffer from a large amount of reagents being ineffectively utilized due to the double Poisson distribution. FIG. 10A depicts an example schematic for achieving a droplet comprising a single bead and a single template. Droplets may be loaded with reagents (e.g., templates 1010 and beads 1008) according to the Poisson distribution, such as to ensure that a droplet has at most a single bead and/or at most a single template. However, as shown in FIG. 10A, this can result in only a few of the droplets (e.g., droplet 1000) having a bead 1002 and a template 1004. This can result in only a few amplified beads 1006 relative to the initial quantity of beads 1008 and templates 1010 that are input for partitioning. Such procedures can also use amplification reagents inefficiently because many of the emulsion droplets will lack a bead (e.g., droplet 1012), lack a template (e.g., droplet 1014), or even lack both beads and templates (e.g., droplet 1016). Some protocols can suggest loading only approximately 20-30% of all droplets with templates. The templates can distribute according to a Poisson distribution. At 30% loading, less than 15% of all amplified beads are likely to be polyclonal beads (2 or more templates in a partition). However, all the droplets without templates (e.g., remaining 70%) are not functional for downstream processing, and reagents such as polymerase, dNTPs, primer beads, and primers are wasted in those droplets. In some instances, the beads are also loaded according to a Poisson distribution, which additionally dilutes the number of 'functional' droplets (e.g., having a single bead and at least a bead). A second drawback is that if one is only interested in amplified primer beads, an additional enrichment step is necessary to sort amplified beads from unamplified beads (e.g., beads deriving from partitions without templates).

Figure 10B:
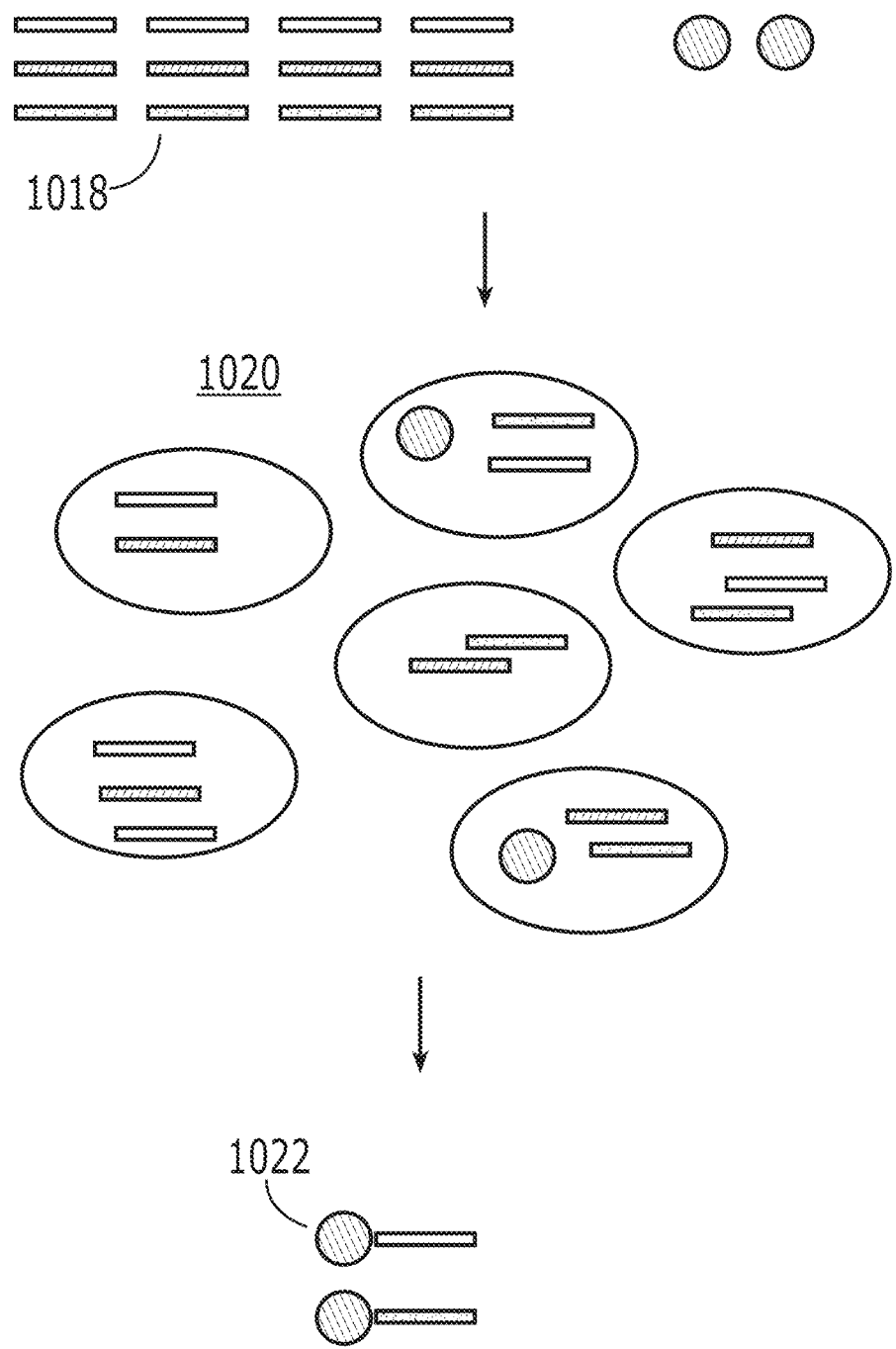
FIG. 10B illustrates an ePCR method that is limited by Poisson loading for the beads but achieves a density of templates that is greater than a Poisson distribution.

In contrast, with reference to FIG. 10B, the methods, systems, and compositions disclosed here can load substantially more templates 1018 into the emulsion such that many of the droplets 1020 contain more than one template, and still produce monoclonal beads 1022 that are viable for downstream processing. Without the features described herein, such over-loading (e.g., more than single loading) of templates is expected to result in a large percentage of polyclonal beads (e.g., a bead comprising copies deriving from multiple templates) after amplification. However, using the methods, systems, and compositions described herein, the resulting beads (e.g., amplified beads) remain substantially monoclonal (e.g., monoclonal beads 1022). Thus, provided herein are methods, systems, and compositions comprising a partition comprising multiple templates and a bead (or other support, e.g., surface), and methods, systems, and compositions for achieving a monoclonal bead (or other support, e.g., surface) from such partition comprising multiple templates.

Beneficially, the beads are also used more efficiently and, in some cases, may not require a separate enrichment procedure for amplified beads before being used in subsequent methods (e.g., for DNA sequencing). In some instances, the methods described herein result in about 50%, about 60%, about 70%, about 80%, about 90%, about 95%, or about 97% of the beads that are input for partitioning being amplified. In some instances, the methods described herein result in at least about 50%, at least about 60%, at least about 70%, at least about 80%, at least about 90%, at least about 95%, at least or about 97% of the beads that are input for partitioning being amplified.

Beneficially, the template is also used more efficiently which is especially important for rare or precious samples. In some instances, the methods described herein result in at least about 50%, about 60%, about 70%, about 80%, about 90%, about 95%, or about 97% of the template molecules that are input for partitioning being amplified. In some instances, the methods described herein result in at least about 50%, at least about 60%, at least about 70%, at least about 80%, at least about 90%, at least about 95%, at least or about 97% of the template molecules that are input for partitioning being amplified.

Figure 10C:
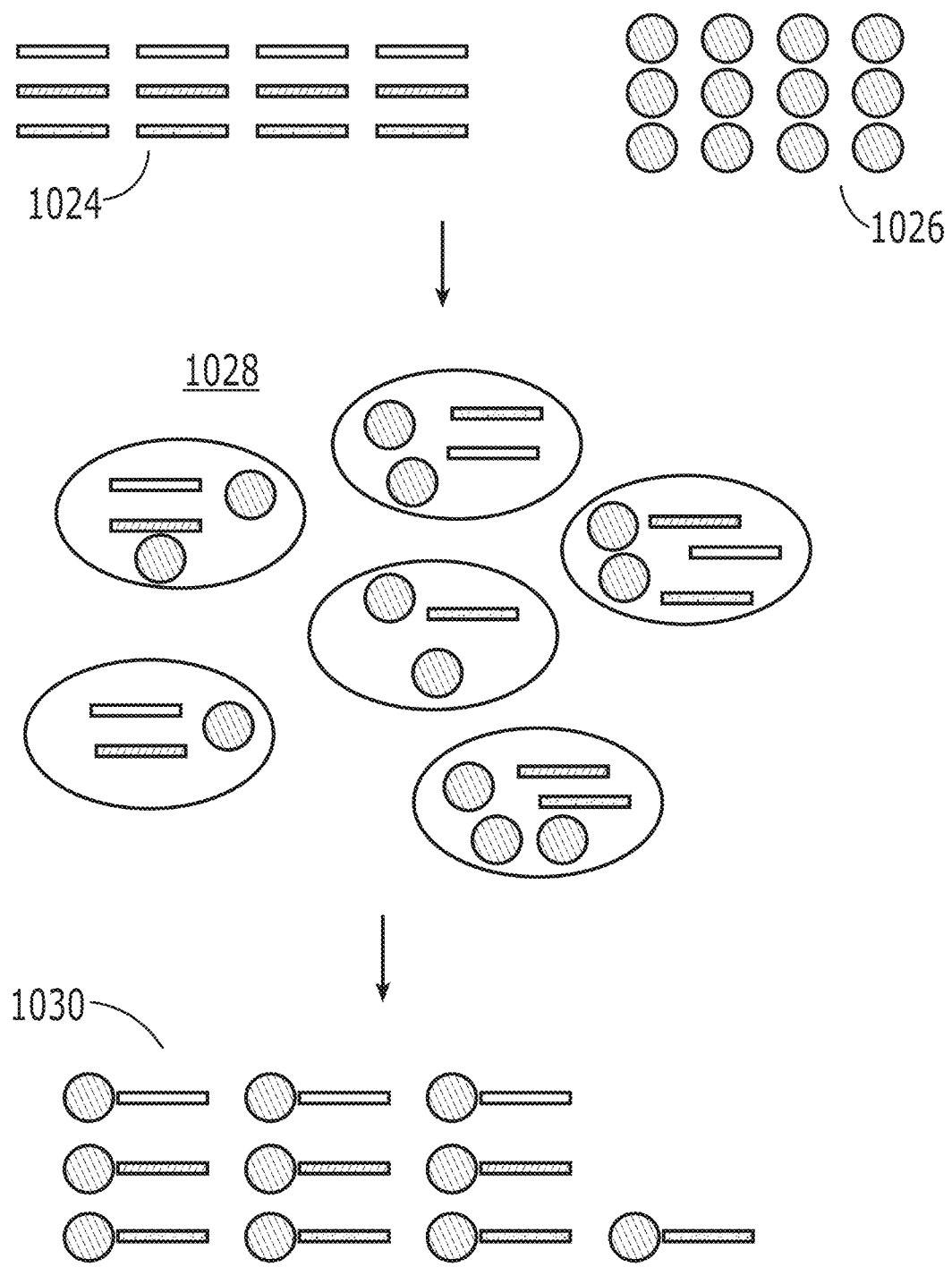
FIG. 10C illustrates an ePCR method that achieves a density of templates and a density of beads that are greater than a Poisson distribution.

The embodiment described in FIG. 10B can be more efficient than the embodiment of FIG. 10A because, while in the embodiment of FIG. 10A a monoclonal bead can result from droplets having a single bead and a single template, in FIG. 10B, most of the droplets that contain a bead and at least one template, regardless of number of templates, can result in a monoclonal bead. However, in such embodiments, droplets that lack a bead still waste amplification reagents. Therefore, the present disclosure provides embodiments such as shown in FIG. 10C where a relatively large number of templates 1024 and a relatively large number of beads 1026 are loaded relative to the number of droplets such that most of the droplets 1028 contain at least one bead and at least one template. Such embodiments can result in efficient use of the reagents, efficient use of the beads, and/or efficient use of the nucleic acid templates as monoclonal beads can result from droplets having at least one template and at least one bead. Thus, provided herein are methods, systems, and compositions comprising a partition comprising at least one template and at least one bead (or other support, e.g., surface), and methods, systems, and compositions for achieving a monoclonal bead (or other support, e.g., surface) from such partition comprising at least one template and at least one bead (or other support, e.g., surface).

The methods described herein can result in a large number of monoclonal amplified beads 1030 relative to the initial amount of beads 1026 and/or the initial number of nucleic acid templates 1024 that are input for partitioning. In some embodiments, the methods described herein result in about 50%, about 60%, about 70%, about 80%, about 90%, about 95%, or about 97% of the template nucleic acid molecules that are input for partitioning being amplified and attached to a bead. In some embodiments, the methods described herein result in at least about 50%, at least about 60%, at least about 70%, at least about 80%, at least about 90%, at least about 95%, at least or about 97% of the template nucleic acid molecules that are input for partitioning being amplified and attached to a bead.

In some cases, subsequent to partitioning, about 50%, about 60%, about 70%, about 80%, about 90%, about 95%, or about 97% of the droplets contain at least one bead and at least one nucleic acid template. In some cases, subsequent to partitioning, the methods described herein result in at least about 50%, at least about 60%, at least about 70%, at least about 80%, at least about 90%, at least about 95%, at least or about 97% of the droplets contain at least one bead and at least one nucleic acid template.

Any suitable proportion of the beads that are amplified can be monoclonal. For example, the methods described herein result in about 60%, about 70%, about 80%, about 90%, about 95%, or about 97% of the amplified beads being monoclonal. In some instances, at least about 60%, at least about 70%, at least about 80%, at least about 90%, at least about 95%, or at least about 97% of the amplified beads are monoclonal.

Figure 11:
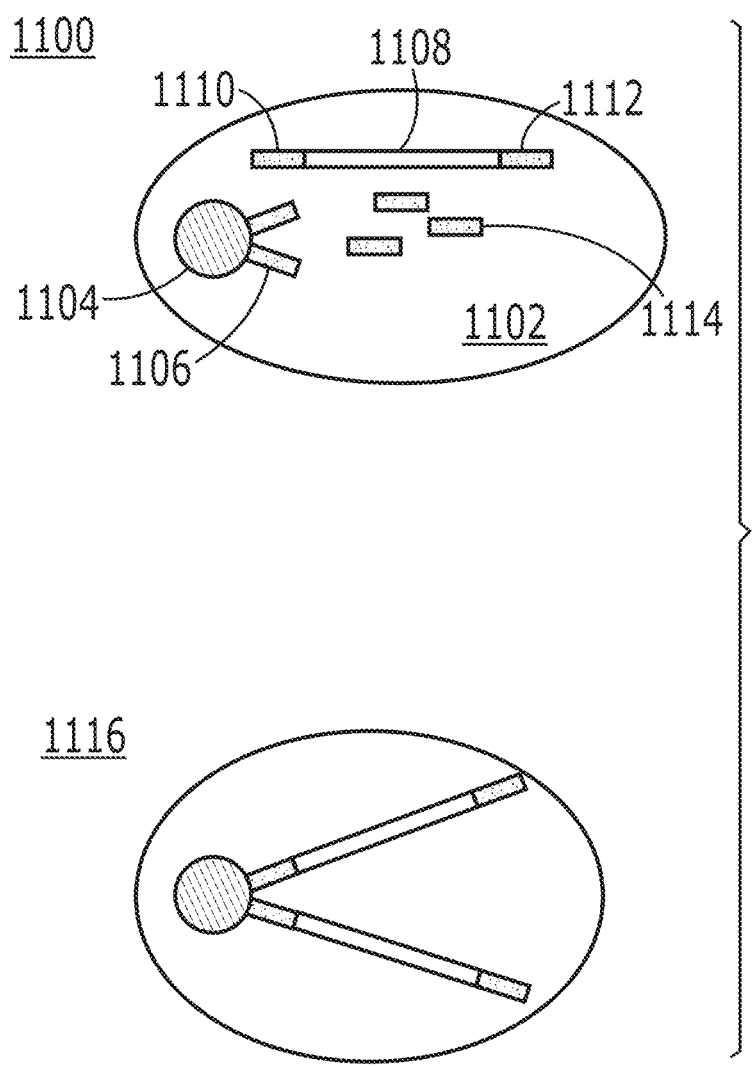
FIG. 11 illustrates an example ePCR method.

Nucleic acid templates can be attached to surfaces and amplified. For example, referring to FIG. 11, amplification can be performed in an emulsion, within droplets. The continuous phase 1100 of the emulsion (e.g., an oil) surrounds the dispersed phase 1102 (e.g., aqueous solution). The continuous phase can divide the dispersed phase into a plurality of partitions. A portion of the plurality of partitions can include one or more beads 1104 having multiple copies of a surface primer 1106 (first primer) attached to the surface of the bead. The plurality of first primers may have sequence homology to a first sequence. A nucleic acid template 1108 can also be in the partition of the dispersed phase. One end 1110 of the template can anneal to and/or be amplified by the surface primer 1106. The other end 1112 can anneal to and/or be amplified by a second primer 1114. In some cases, the second primer 1114 can be in the dispersed phase in the partition. Subsequent to amplification 1116, such a system can result in a bead having multiple (clonal) copies of the template nucleic acid (or reverse complement thereof) attached to the bead. Such a bead having clonal copies of the template can be used in a DNA sequencing method, for example, to amplify the sequencing signal compared to a signal that may be generated from a single copy of the template.

Figure 12:
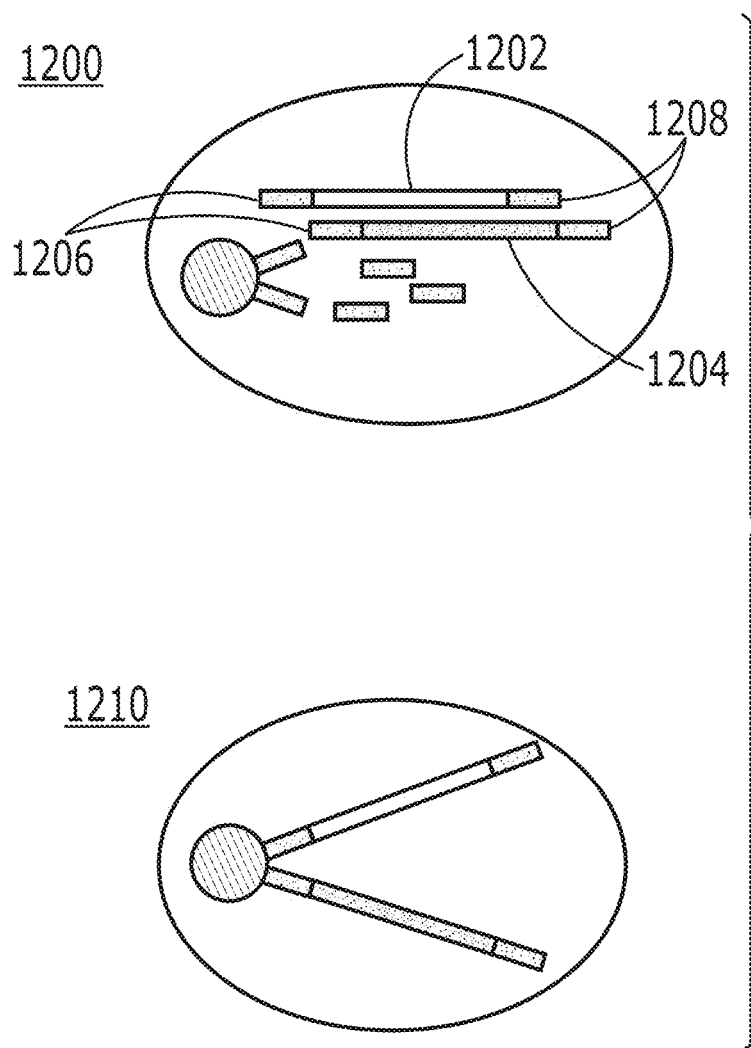
FIG. 12 illustrates an example ePCR method resulting in a polyclonal bead.

In prior methods, complications can arise when the dispersed phase includes two or more different template nucleic acids. The different templates can be non-clonal members of a nucleic acid library. For example, referring to FIG. 12, a partition 1200 of a plurality of partitions includes a first nucleic acid template 1202 and a second nucleic acid template 1204 that is different than the first nucleic acid template 1202. In the course of making the template library, a common first end 1206 and a common second end 1208 can be added to each of the respective templates (e.g., to facilitate attaching the library members to beads and amplifying using a single protocol). Subsequent to amplification 1210, such a system can result in a bead that is non-clonal (i.e., having at least a copy of the first template and at least a copy of the second template attached to the bead). If a non-clonal bead is used in a DNA sequencing method, for example, the sequencing data may be poor compared to a clonal bead. The signal from a non-clonal bead that comes from both templates can be difficult or impossible to resolve at the resolution of a single bead.

Recognized herein is a need for methods in which more than one nucleic acid template is loaded into a partition (e.g., droplet) but only one of the templates attaches to the bead (or other support) and is amplified. Provided herein are methods, systems, and compositions that address at least the abovementioned need(s). The systems, methods, and compositions of the present disclosure can waste less reagents than prior methods that are limited to single-templatepartitions (i.e., because using the presented methods allow more droplets which contain at least one nucleic acid template molecule, which are capable of amplification) without sacrificing the percentage of beads that are monoclonal.

The methods of the present disclosure involve controlling the overall process from partitioning to clonal amplification at two critical sages, first at first attachment of the template nucleic acid, or derivative thereof, to the surface, and subsequently at amplification of such attached template on the surface. The methods described herein can comprise decreasing the rate of the former (i.e., attachment) and/or increasing the rate of the latter (i.e., amplification). The result is that, even in the presence of multiple different templates, most of the beads have only clonal copies of a single template. For example, if attachment is slow and/or a rare event compared to amplification, the first template to attach to the surface will quickly be amplified and consume substantially all of the surface primer before a second template can attach to the surface.

Figure 13:
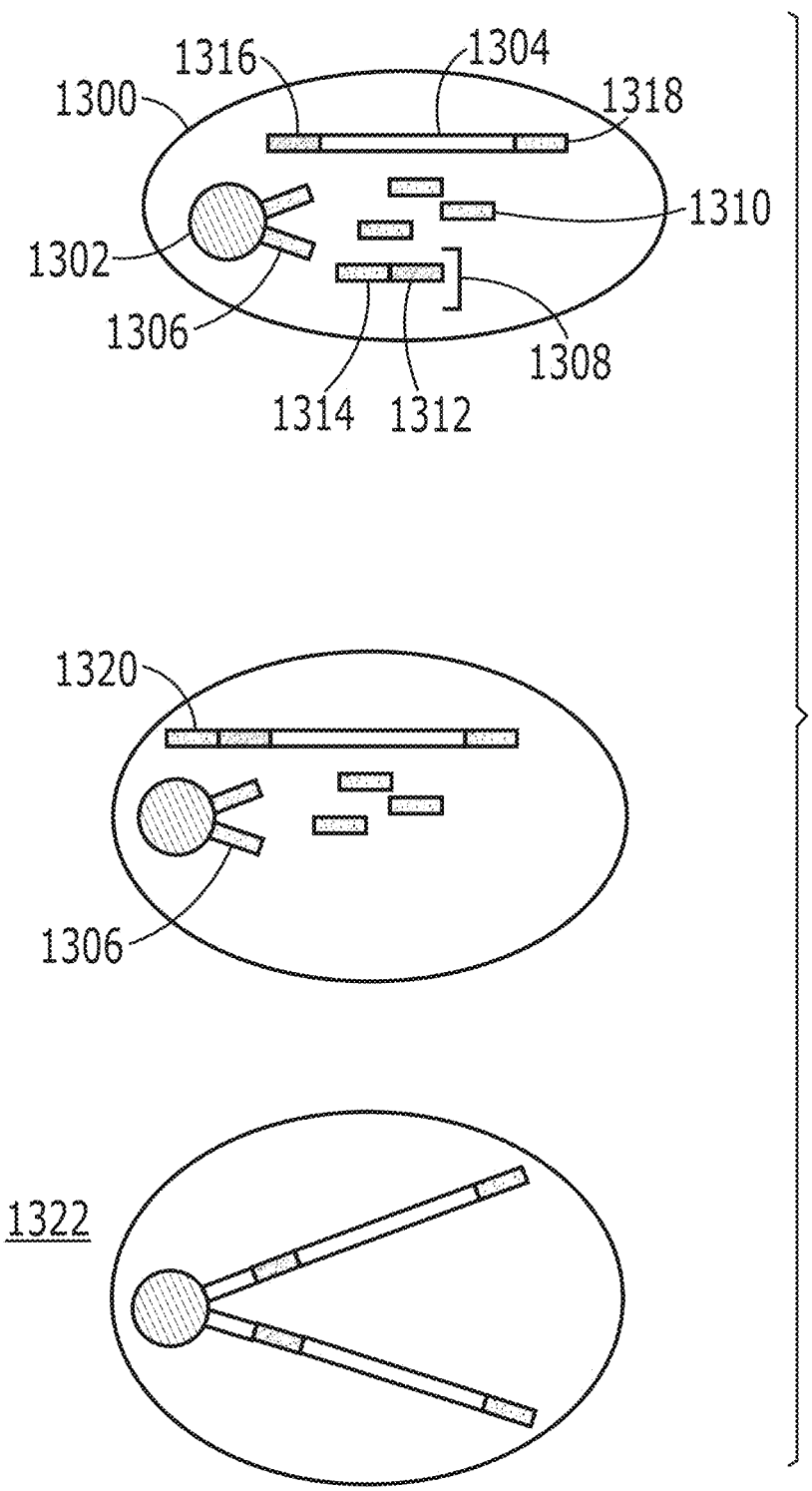
FIG. 13 illustrates an example ePCR method of the present disclosure.

With reference to FIG. 13, the emulsion droplet 1300 can comprise a bead 1302, a template nucleic acid molecule 1304, a first primer attached to the bead 1306, and a second primer 1308. The bead may comprise a plurality of first primers having sequence homology to a first sequence. The droplet can also comprise a third primer 1310 in solution. The template may comprise a first end 1316 and a second end 1318. Neither end of the template may be capable of annealing to the first primer 1306 on the bead prior to being extended by the second primer 1308 in some cases. For example, the end sequences of the template may not be complementary to the first sequence. The second primer 1308 has a first portion 1312 and a second portion 1314. The second portion may comprise an extension sequence. The first portion 1312 may anneal to the first end 1316 of the template, and the complex can be subject to a nucleic acid extension reaction to generate extension product 1320 that comprises the extension sequence or complement thereof. The extension product 1320 can anneal to the first primer 1306 on the bead using the extension sequence or complement thereof. The third primer 1310 can anneal to a second end 1318 of the nucleic acid template, or complement thereof, to initiate an extension reaction. There can be many copies of the first primer 1306 on the bead 1302 that can be used to amplify the extension product 1320 to create a clonally amplified template attached to the bead 1322.

Figure 14:
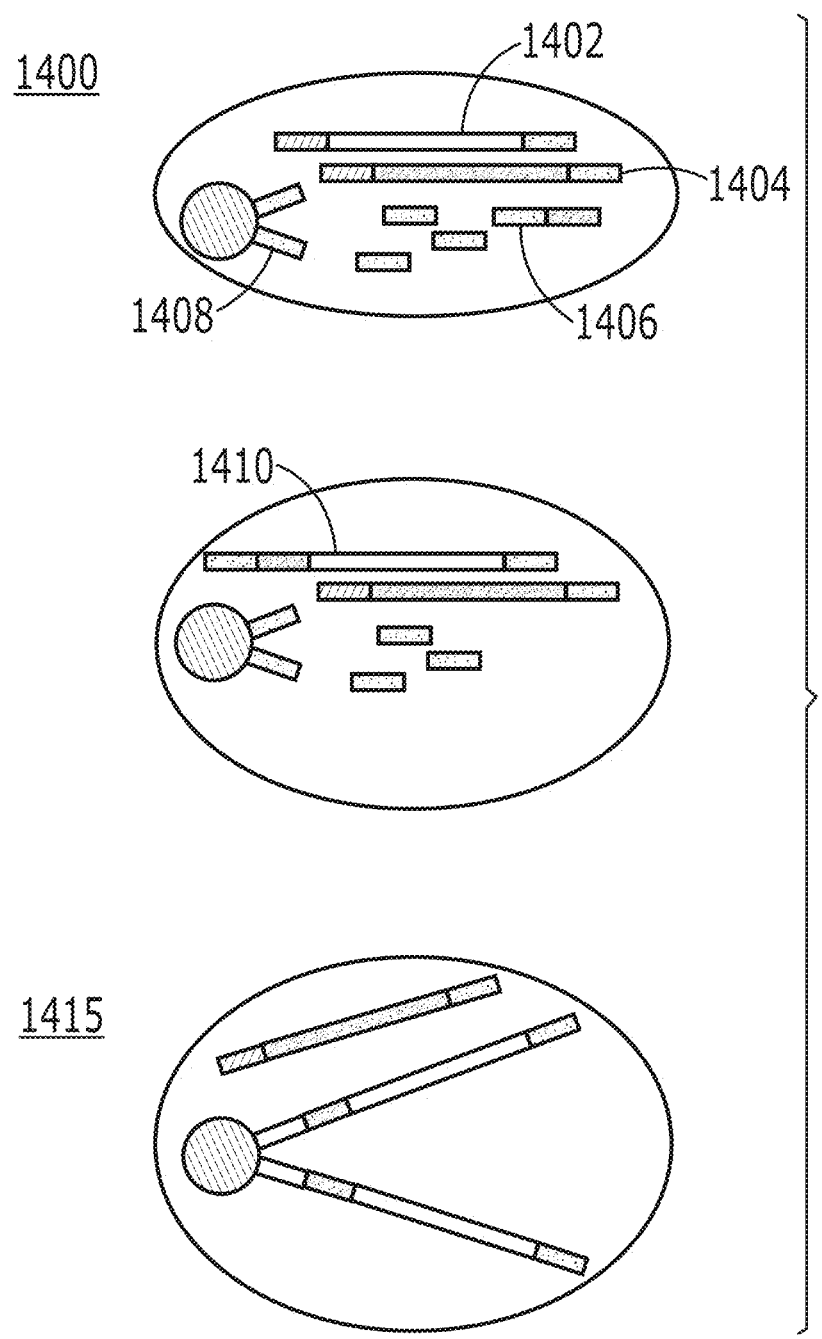
FIG. 14 illustrates an example ePCR method of the present disclosure having a plurality of templates.

The methods and systems described herein can be used to produce clonally amplified beads (i.e., beads that are not polyclonal). Referring to FIG. 14, an emulsion droplet 1400 can have more than one nucleic acid template molecule. The figure shows a first template 1402 and a second template 1404, although there can be more than two templates. Both of the templates can be capable of being extended by the second primer 1406. However, this process is engineered to be slower (e.g., occurs more rarely) relative to annealing of the extension product to the first primer attached to the bead 1408 and/or exponential amplification on the bead using the first primer. Therefore, it is highly likely that an extension product is created from the first nucleic acid template 1410 but not the second template, at least prior to subsequent amplification of the first nucleic acid template from the extension product of the first nucleic acid template. Since amplification is faster than extension and/or attachment, a bead can be created having a monoclonal amplification product corresponding to the first nucleic acid template 1415 even though a plurality of templates were originally loaded into the droplet. The bead can be recovered and/or the non-amplified templates can be washed away from the beads.

Figure 15A:
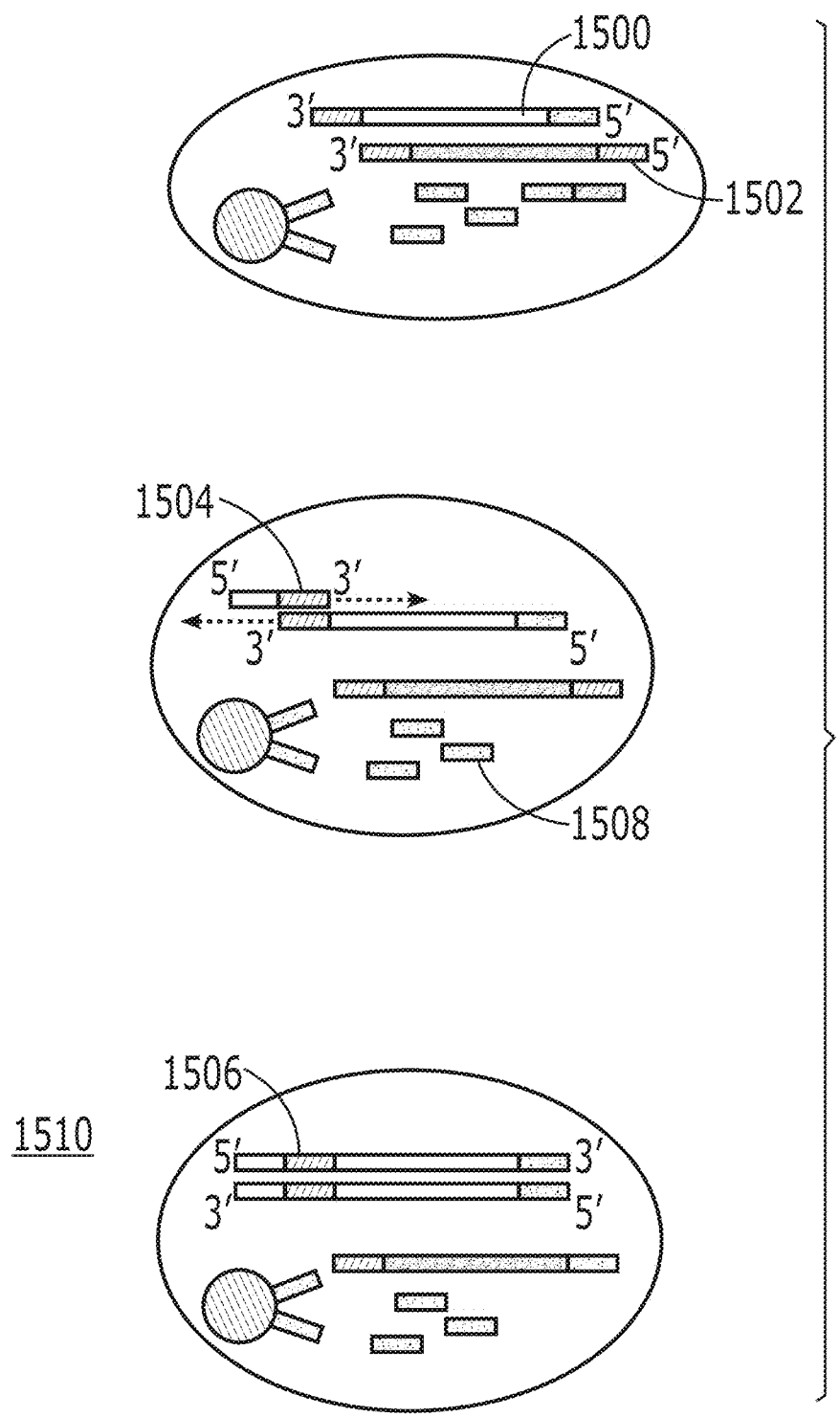
FIG. 15A, FIG. 15B, and FIG. 15C illustrate additional details of an ePCR method of the present disclosure.

The nucleic acid templates can be single stranded or double stranded. FIGS. 10-14 do not distinguish between single or double strandedness of the template, even if these figures show a single line to represent the nucleic acid templates. FIG. 15A specifically shows an embodiment where the first template 1500 and second template 1502 are initially single stranded. For clarity, the 5' and 3' ends of the single stranded templates are depicted. The first portion 1504 of the second primer can hybridize with the 3' end of the template nucleic acid molecules. The second primer and the first nucleic acid template can then be extended from their respective 3' ends to result in a double stranded extension product 1506. One advantage of the template being single stranded is that the third primer (third primer) 1508 does not amplify the template (even linearly) until the extension product is created.

In some cases, the second primer (i.e., extension primer) has a limiting concentration. In some cases, the emulsion droplet has only one copy 1510 of the extension primer. In such cases, the extension primer gets consumed and is not available to extend a second nucleic acid template. If a second template is not extended, it is not able to hybridize with the primer attached to the bead and the amplified bead is more likely to be monoclonal (even when the droplet contained many different templates initially). Limiting (lowering) the concentration of the extension primer can be beneficial even if there are several copies of the extension primer in a droplet. A low concentration of the extension primer can make the extension reaction less likely to happen (i.e., slower) relative to the rate of amplification on the bead subsequent to extension. This difference in rates of these processes can result in a high proportion of monoclonal beads. In some cases, a ratio of the concentration of the extension primer to the concentration of the first primer is on the order of about $10^{-1}$, $10^{-2}$, $10^{-3}$, $10^{-4}$, $10^{-5}$, $10^{-6}$, $10^{-7}$, $10^{-8}$, $10^{-9}$ or less. In some cases, a ratio of the concentration of the extension primer to the concentration of the third primer is on the order of about $10^{-1}$, $10^{-2}$, $10^{-3}$, $10^{-4}$, $10^{-5}$, $10^{-6}$, $10^{-7}$, $10^{-8}$, $10^{-9}$ or less.

Figure 15B:
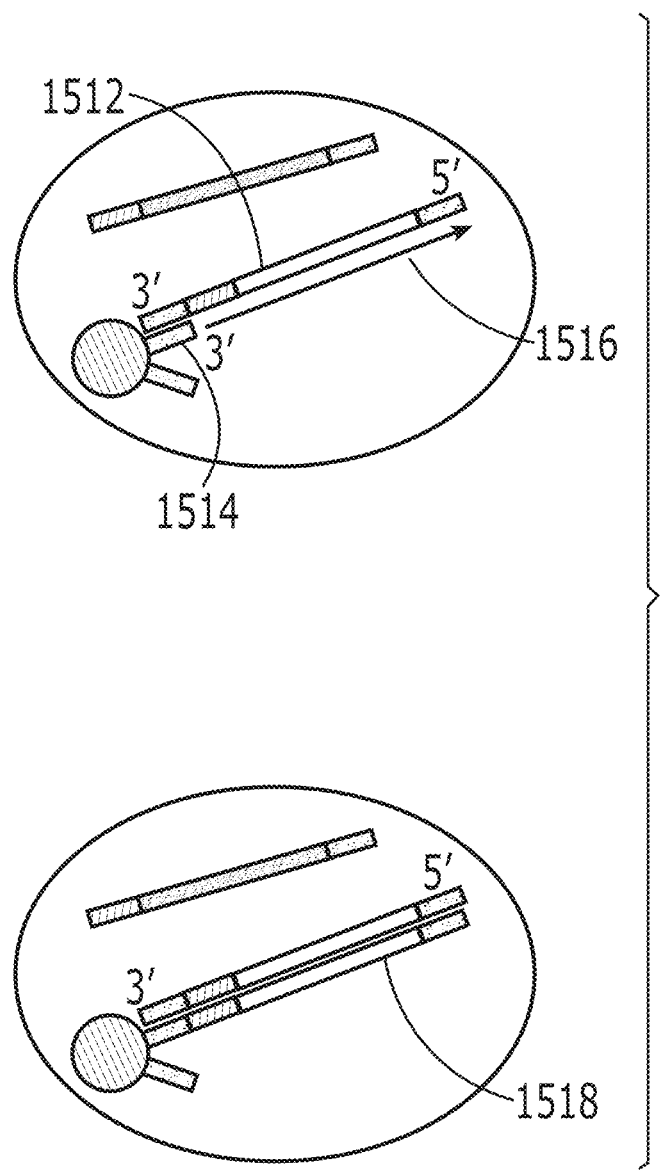
Figure 15C:
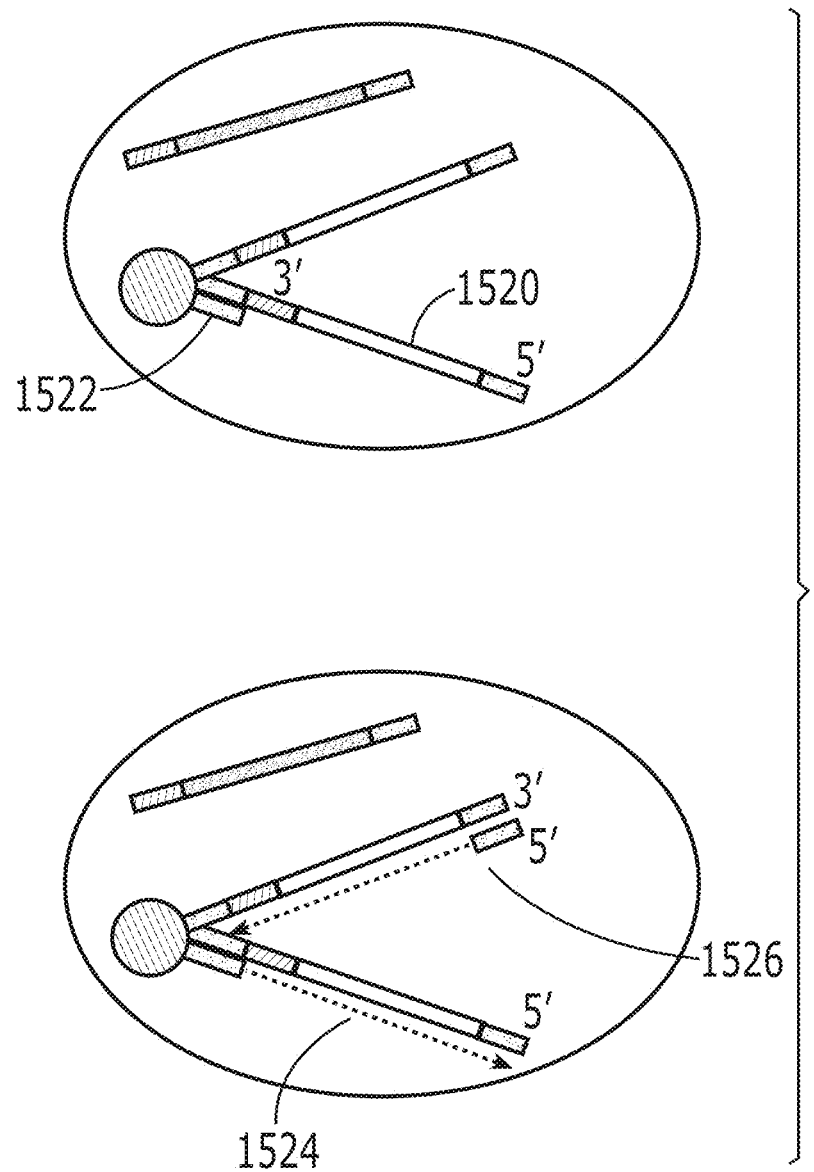

Continuing with FIG. 15B, the two strands in the double stranded extension product 1506 can disassociate (e.g., by denaturation) and one of the strands of the extension product 1512 can anneal (e.g., at its 3' end) with the first primer attached to the bead (surface primer) 1514. The surface primer can be extended 1516, resulting in a double stranded construct 1518 with one strand attached to the bead. Continuing with FIG. 15C, the strand of the double stranded construct that is not attached to the bead 1520 can dissociate and hybridize with a second copy of the surface primer 1522. This amplification process of the method (i.e., FIG. 15C) can be faster than extension and annealing (i.e., FIGS. 15A-15B). In some cases, the amplification is exponential. The second copy of the surface primer can be extended 1524. The extended copy of the first surface primer can also be used in conjunction with the solution primer (third primer) 1526 to create another template that is capable of extending yet more surface primers.

Figure 16A:
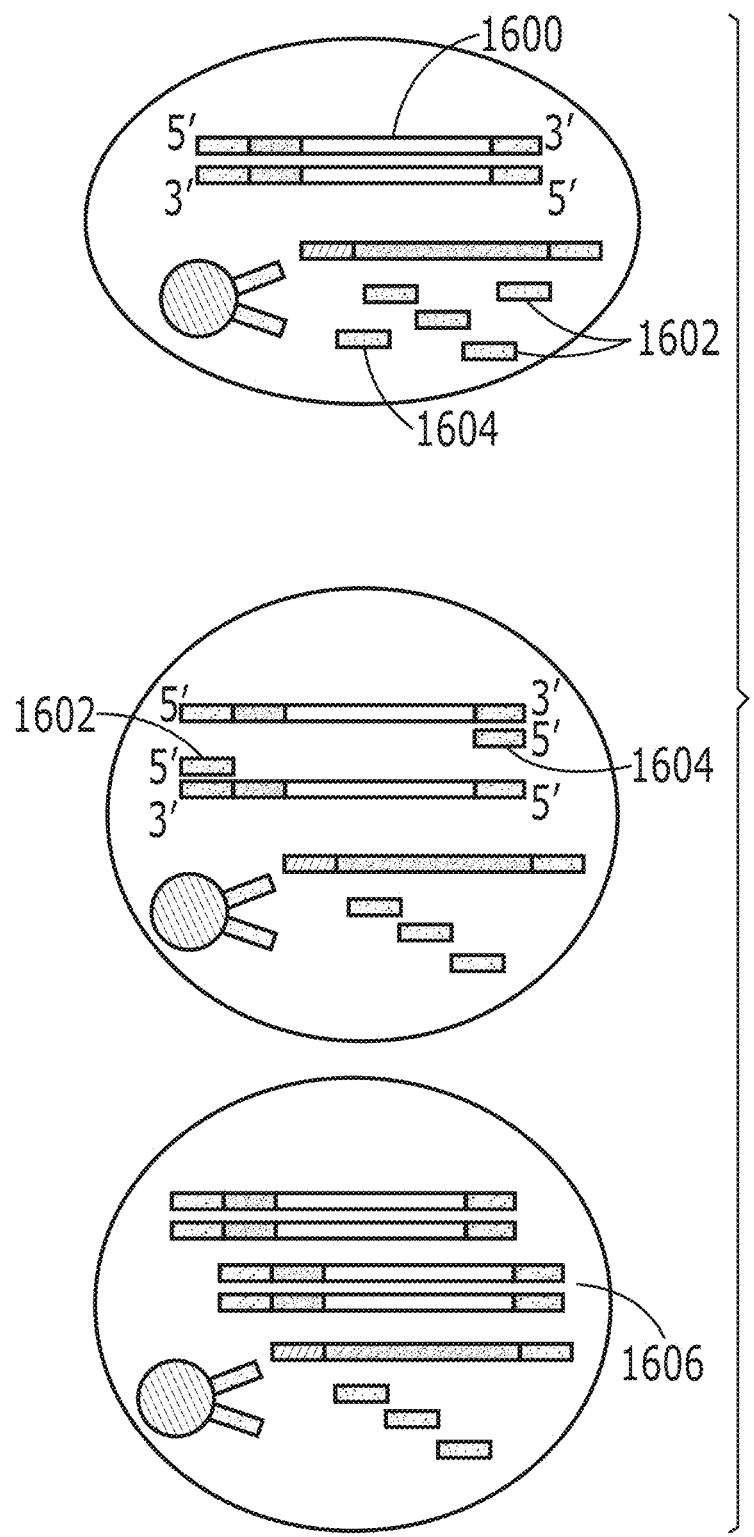
FIG. 16A and FIG. 16B illustrate additional details of an ePCR method of the present disclosure.

In some instances, the emulsion droplet can further comprise additional copies of the first primer that are not attached to the surface to facilitate the rate of amplification. With reference to FIG. 16A, following the initial extension of the template nucleic acid molecule (using the second primer) to create a double stranded extension product 1600, some additional first primers in solution 1602 can be used in conjunction with the solution (third) primer 1604 to exponentially amplify the extension product in solution. An advantage of this solution-based amplification can be that with additional solution copies of the extension product 1606, the extension product(s) can anneal faster to the bead for further exponential amplification. Following the slow extension step, the rest of the method can proceed quickly before a second template molecule can be extended.

Figure 16B:
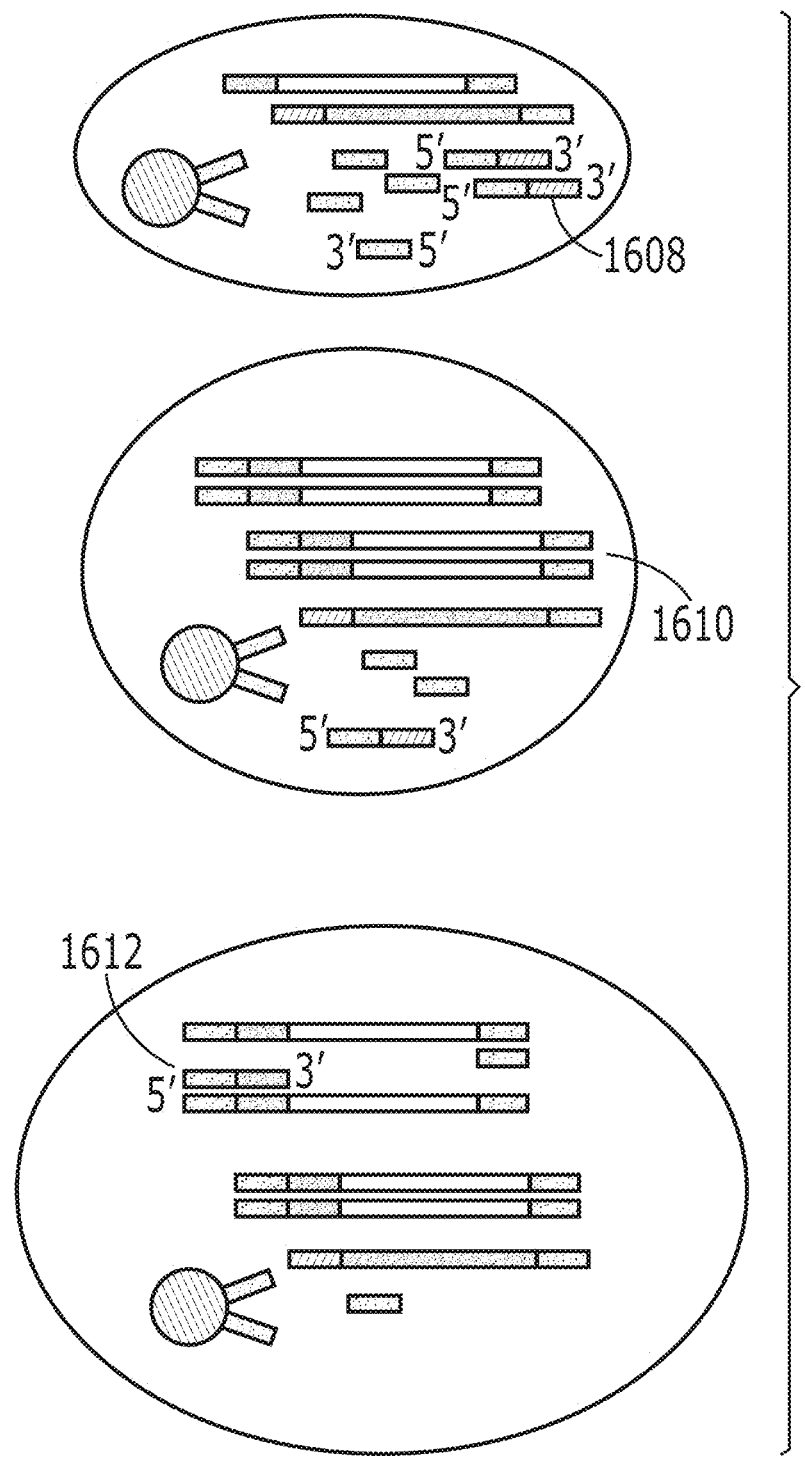

There can be additional advantages of having the first primer also in solution. With reference to FIG. 16B, extra copies of the second (extension) primer 1608 can be rapidly consumed subsequent to extension of the first template so that they are not available to extend a second template. The solution copies of the first primer can quickly create additional copies of the extension product 1610 without relying on the slower surface-based amplification (relative to solution-based amplification). The additional copies of the extension product can be substrates for hybridizing and consuming additional copies of the second primer 1612. All copies of the second primer may be quickly extended using the first nucleic acid template (or derivative copies thereof) before they can be used to extend a second nucleic acid template.

Figure 17A:
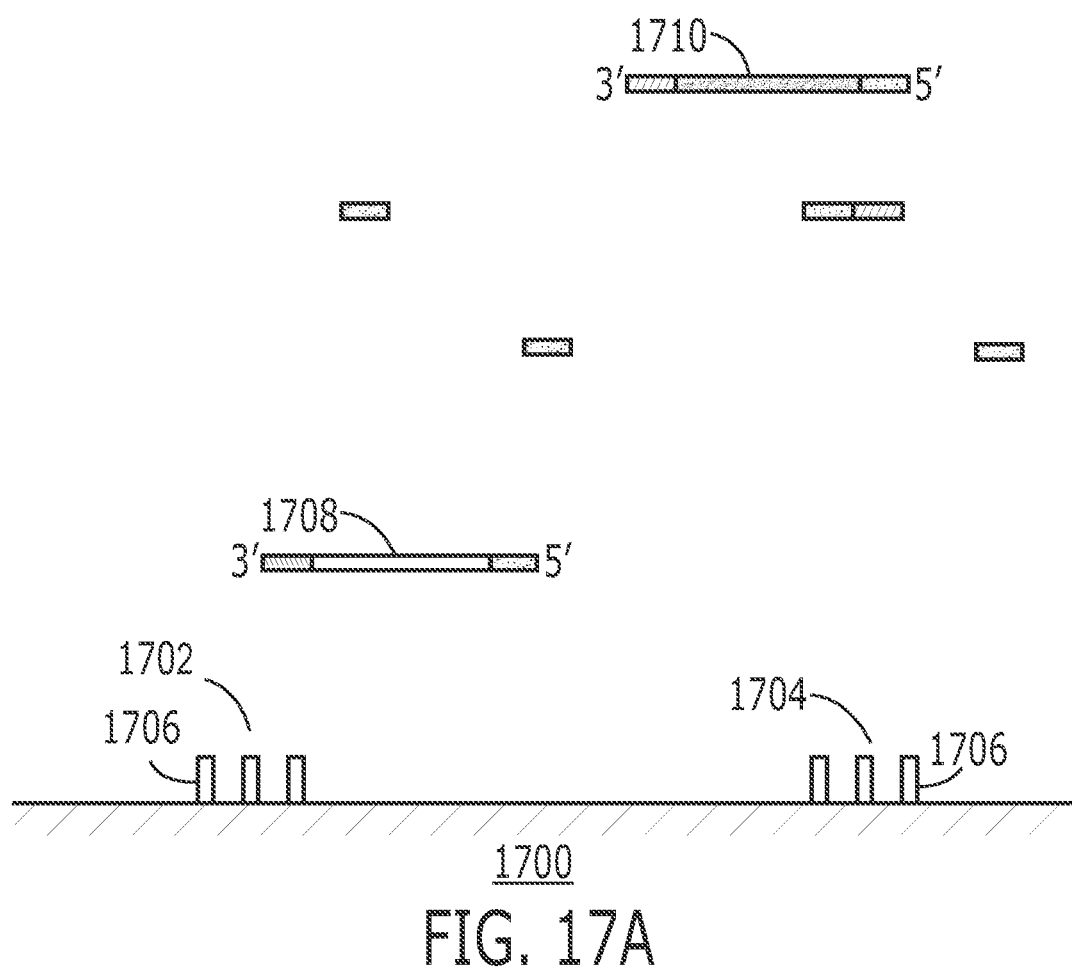
FIG. 17A, FIG. 17B, FIG. 17C, and FIG. 17D illustrate the methods of the present disclosure performed on an open surface.

It will be appreciated that the systems and methods described herein are not limited to clonal amplification of templates on beads and/or amplification in emulsions. With reference to FIG. 17A, the method can be performed on a surface 1700 such as a glass, plastic, silicon wafer, or any other suitable surface. The surface can have separated regions 1702, 1704, each region having a plurality of the first primer 1706 attached in the region of the surface. For example, each region may be separated by a sufficient gap region (having a lack of the first primer). In some instances, a minimum distance between any first primer in a first region and any first primer in a second region may be on the order of $10^{-1}$, $10^{-2}$, $10^{-3}$, $10^{-4}$, $10^{-5}$, $10^{-6}$, $10^{-7}$, $10^{-8}$, $10^{-9}$ m or less. A library of template nucleic acid molecules 1708, 1710 can be in fluidic contact with a plurality of the separated regions. That is, the methods described herein do not need to be performed in a plurality of emulsion droplets, though they may be.

Figure 17B:
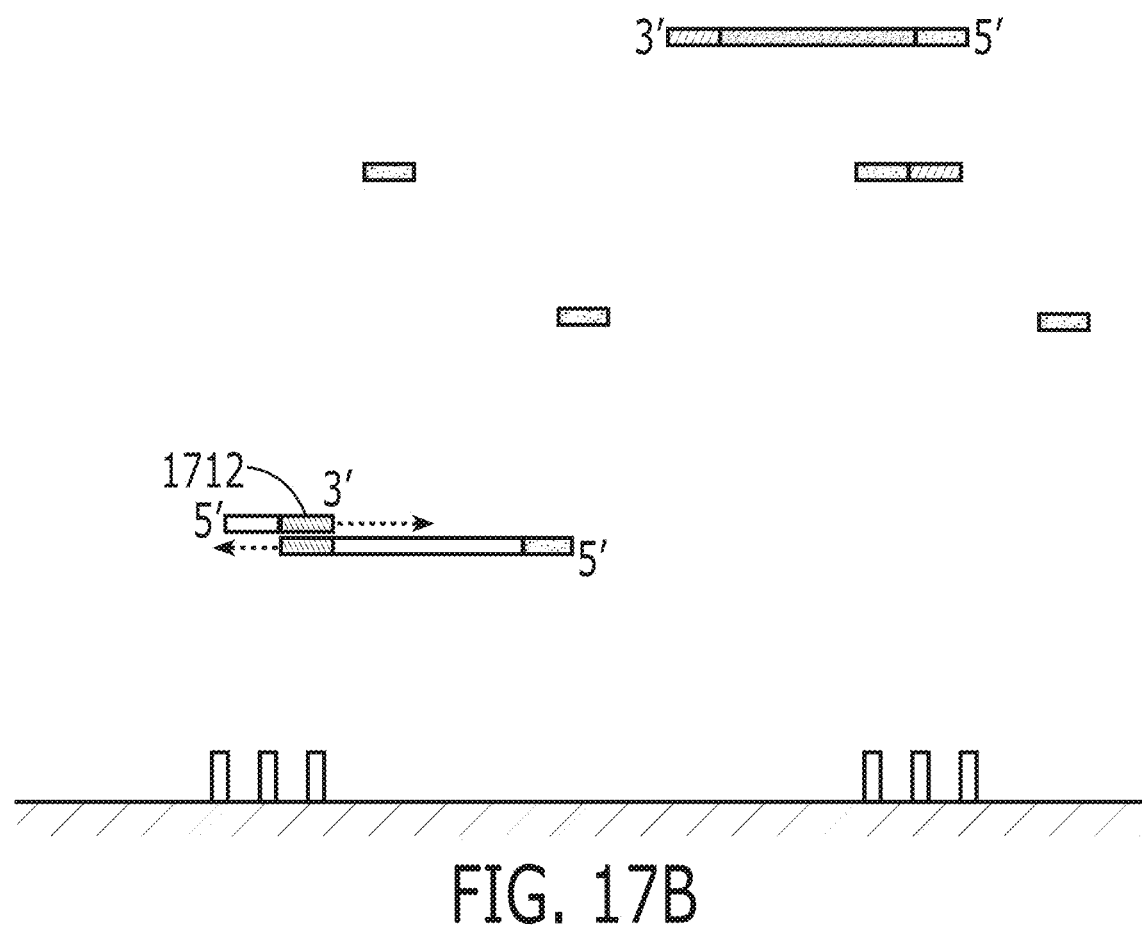
Figure 17C:
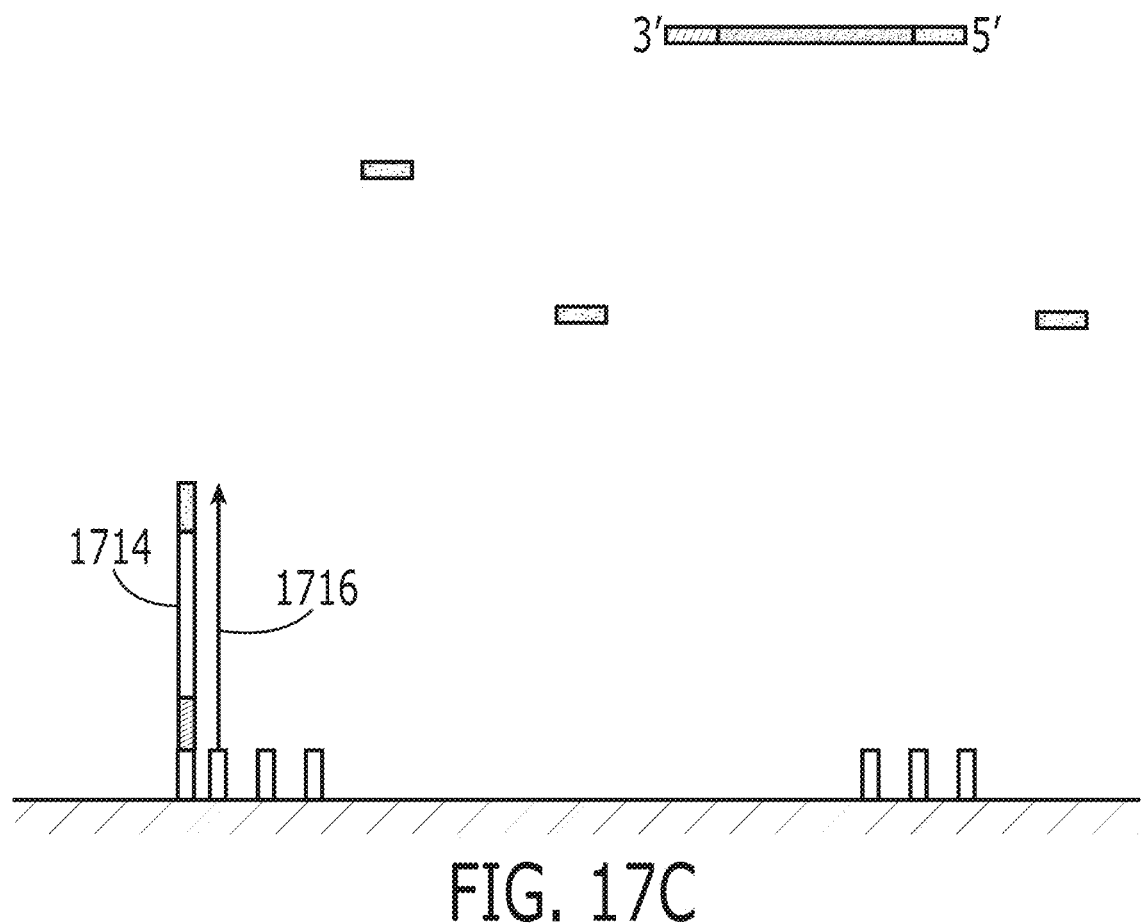
Figure 17D:
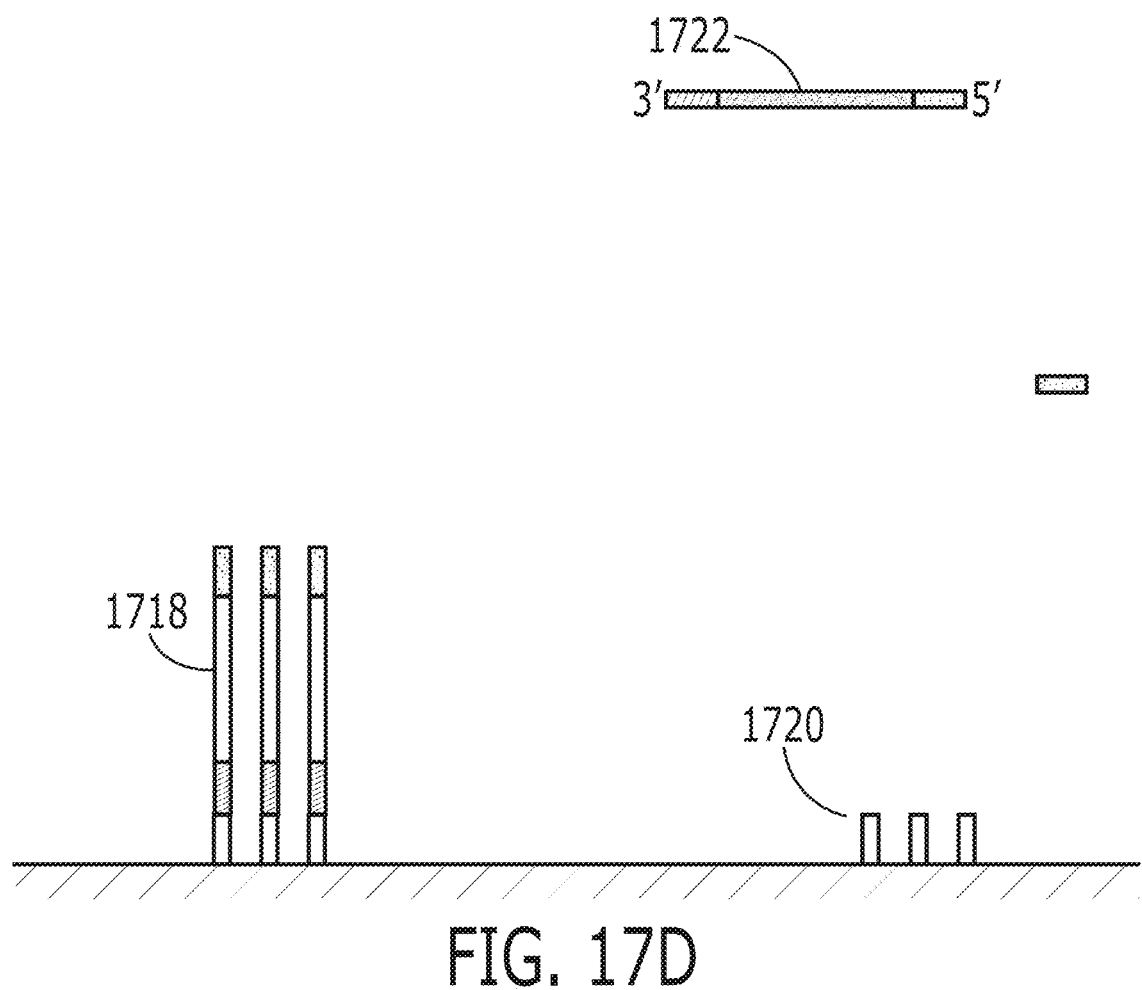

The principal mechanisms on an open surface with all of the components having fluidic access to a plurality of clusters of the first primer can be similar to when performed in an emulsion. With reference to FIG. 17B, the second primer 1712 can extend the first nucleic acid template. In FIG. 17C, the extension product 1714 can hybridize to one of the copies of the first primer on a first cluster on the open surface, which can be extended 1716. Subsequent to the slow process of creating the extension product, amplification on the surface can be faster such that substantially all of the copies of the first primer at a cluster location can be consumed (and be clonal) before an extension product derived from a second template can anneal at the same cluster location. With reference to FIG. 17D, a clonal cluster corresponding to a first nucleic acid template 1718 can be created. Other cluster locations 1720 can be available for clonal amplification of another nucleic acid template(s) 1722.

Figure 18A:
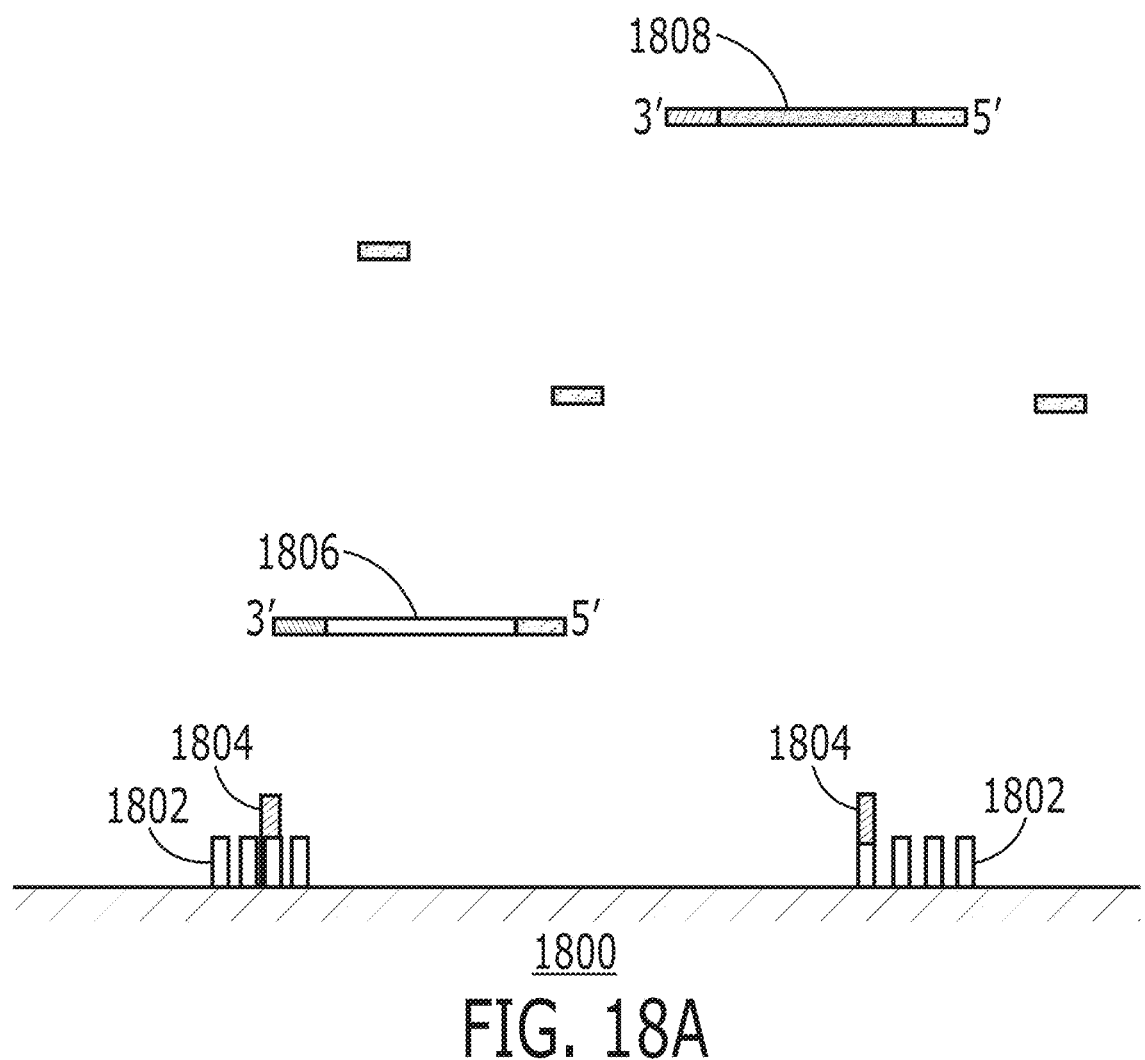
FIG. 18A and FIG. 18B illustrate an embodiment of the present disclosure where the second primer is attached to the surface.
Figure 18B:
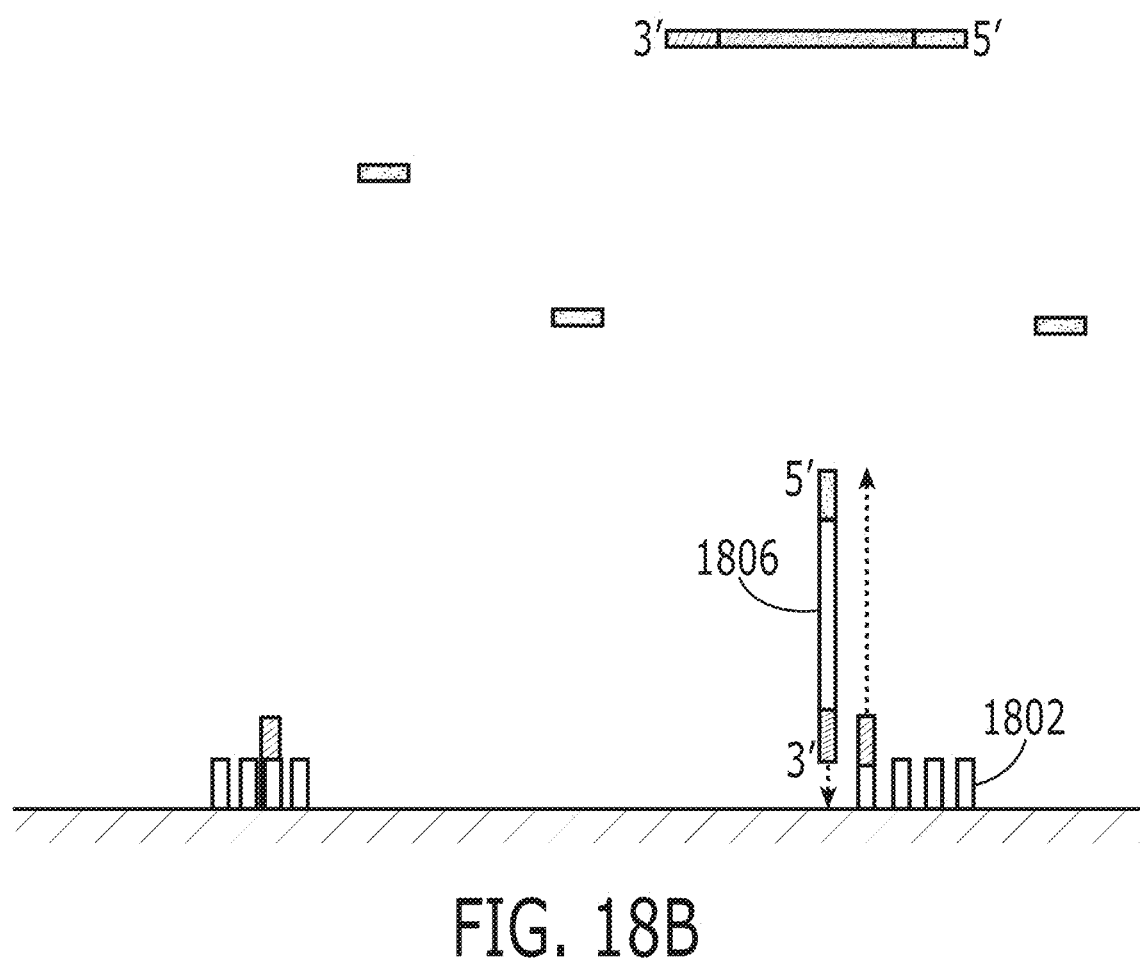

In some cases, the second primer is also attached to the surface (alternatively to or in addition to being present in solution). The concentration of the second primer can be limiting, e.g., low, relative to the number of the first primer attached in a cluster (or on a bead). An advantage of these embodiments can be that the initial processes of the method can be further slowed down in comparison with the later amplification processes that rapidly consume the local copies of the first primer. With reference to FIG. 18A, the surface 1800 can have a plurality of clusters. The clusters can form an array (e.g., for DNA sequencing by imaging of distinct clusters). The clusters can have several copies of the first primer 1802 and fewer copies of the second primer 1804. In some cases, a ratio of the concentration of the second primer to the concentration of the first primer is on the order of about $10^{-1}$, $10^{-2}$, $10^{-3}$, $10^{-4}$, $10^{-5}$, $10^{-6}$, $10^{-7}$, $10^{-8}$, $10^{-9}$ or less. The clusters can be in fluidic contact with a nucleic acid library comprising a first template 1806 and a second template 1808. Continuing to FIG. 18B, the first nucleic acid template 1806 can be extended with the second primer to create an extension product which can subsequently be amplified with the first primer 1802 to create a clonal cluster.

Figure 18C:
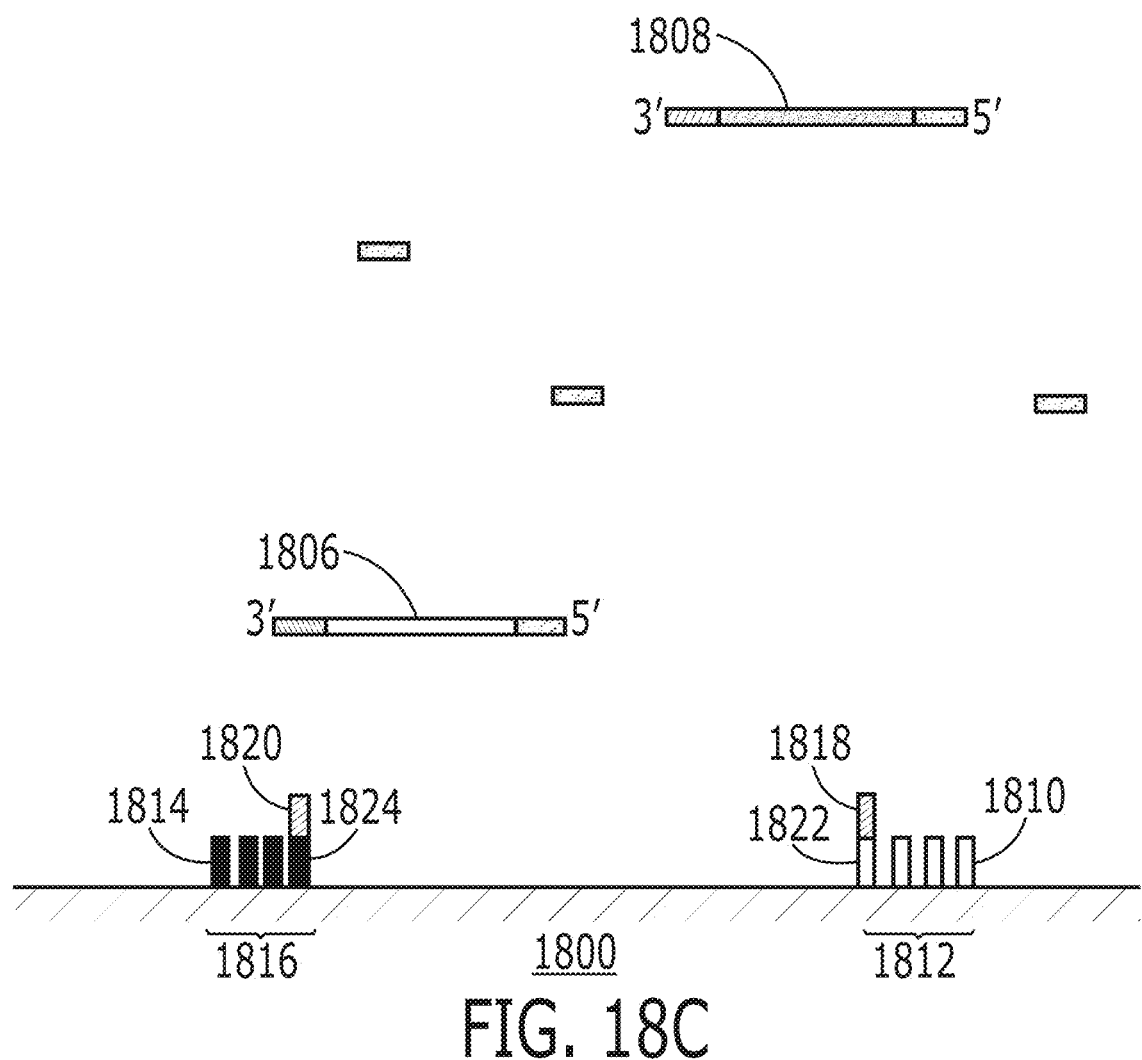
FIG. 18C, FIG. 18D and FIG. 18E illustrate an embodiment of the present disclosure where each of the colony locations on a surface have a different first primer.

In some embodiments, the respective sequences of the first primer are different at different cluster locations of the surface (or on different beads). With reference to FIG. 18C, the plurality of first primers 1810 at a first cluster location 1812 (or on a first bead) have a different sequence than a plurality of first primers 1814 at a second cluster location 1816 (or on a second bead). The second primers can also be different at different cluster or bead locations. In some cases, the second primers have a common first portion and different second portions. As shown in FIG. 18C, the first portion 1818 of a first second primer located at a first cluster location 1812 (or on a first bead) is the same as the first portion 1820 of a second second primer located at a second cluster location 1816 (or on a second bead). However, the second portions of the respective second primers can be different. In some instances, the second portion 1822 of the first second primer can be the same as the first first primer 1810. In some instances, the second portion 1824 of the second second primer can be the same as the second first primer 1814.

Having the first primers be different at different cluster locations (or on different beads) can result in a template that is initially extended at a cluster location developing an additional affinity for that cluster location (with no additional affinity for other cluster locations). The extension region from a given cluster location provides additional base pairs of homology and increased affinity to the given cluster location compared with the affinity of the hybridization between the non-extended template and the second primer. The annealing reaction, the extension reaction, and/or the incubation of the emulsion can be performed at conditions (e.g., temperature) that are of sufficient stringency such that, without extension, the annealing and/or extension are rare and/or slow events.

Figure 18D:
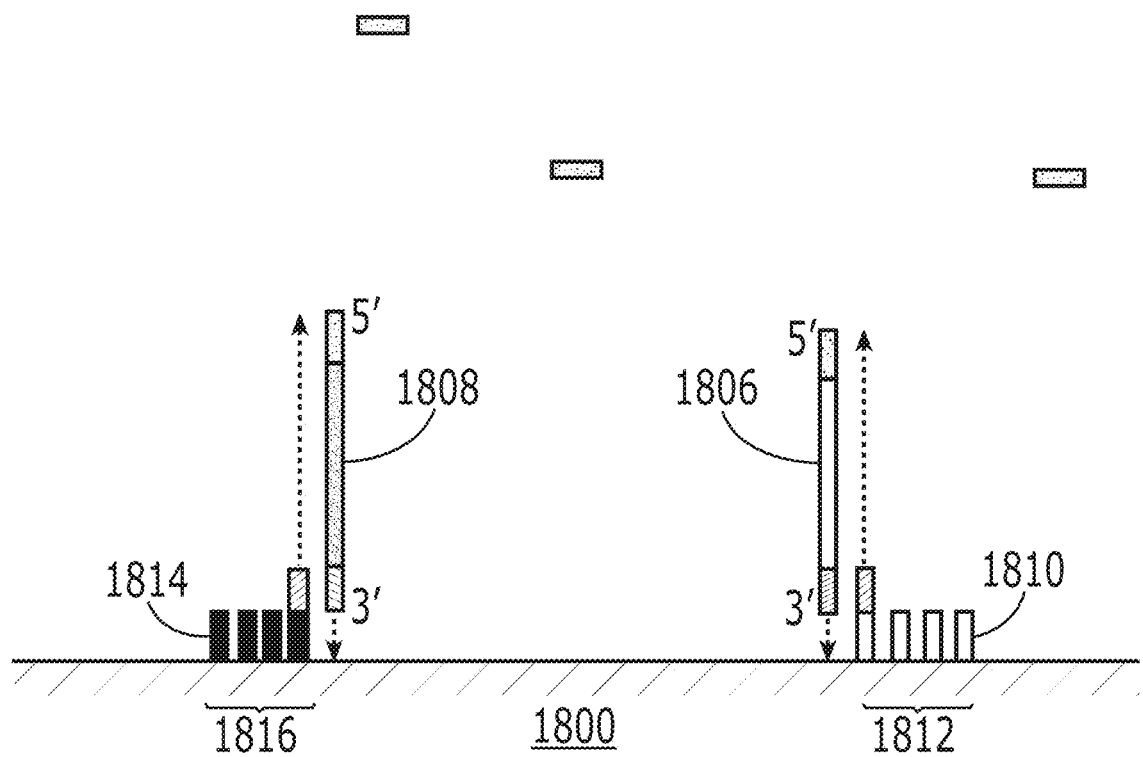
Figure 18E:
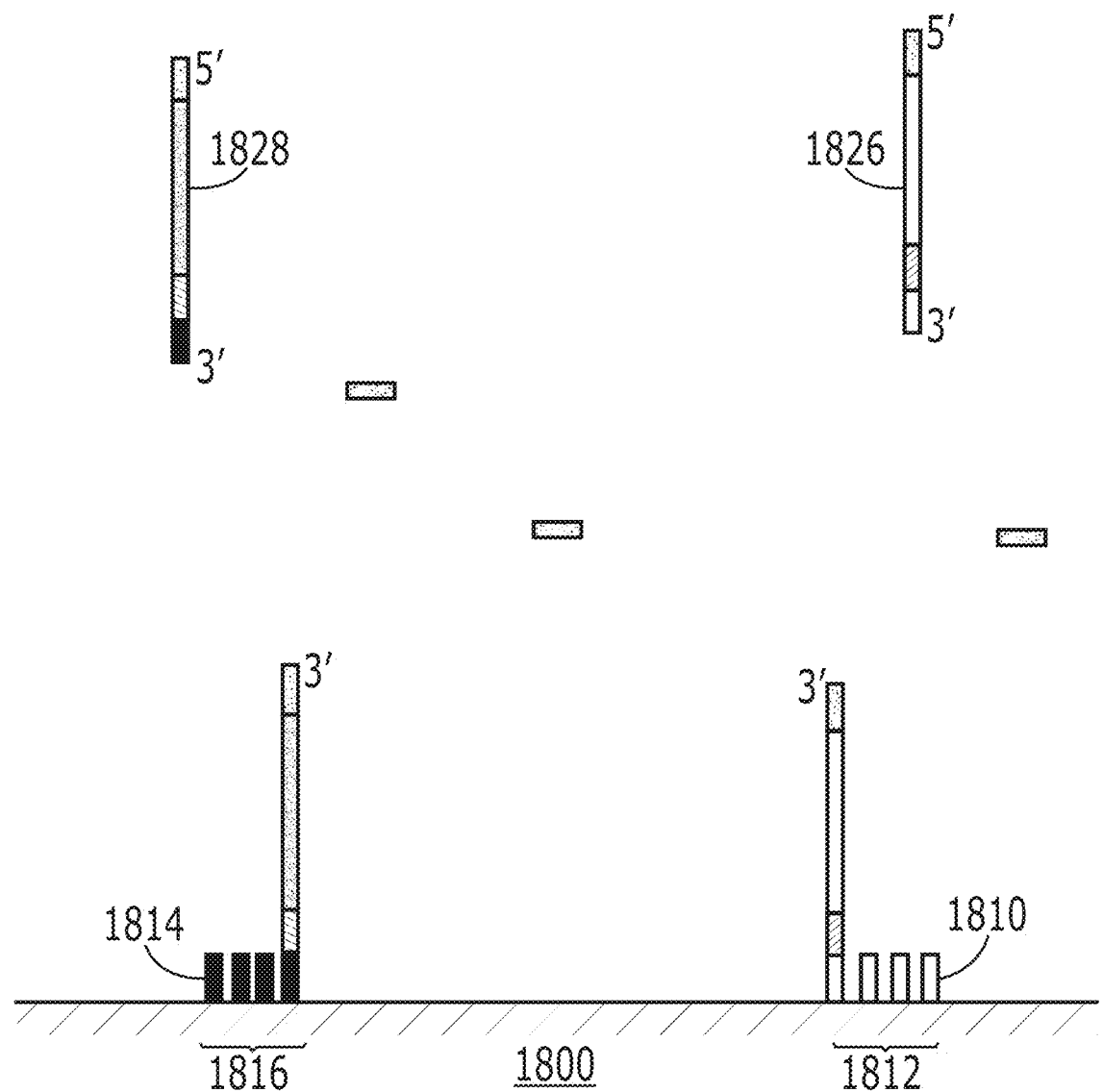

Referring to FIG. 18D, a first template 1806 can be extended at a first cluster location (or bead) 1812 to yield a first extension product that comprises a region complementary to the first first primer 1810. A second template 1808 can be extended at a second cluster location (or bead) 1816 to yield a second extension product that comprises a region complementary to the second first primer 1814. With reference to FIG. 18E, the first extension product 1826 has a region of homology with, and can anneal to, and can provide a template for extension of, a first primer at the first cluster location 1812 but not the second cluster location 1816, i.e., because the first template was originally extended at the first cluster location. Similarly, the second extension product 1828 has a region of homology with, and can anneal to, and can provide a template for extension of, a first primer at the second cluster location 1816 but not the second cluster location 1812, i.e., because the first template was originally extended at the second cluster location. Migration of extension products between cluster locations is not favored, especially if a temperature is used that is greater to or similar to an annealing temperature between the second primer and the nucleic acid template. Any solution described herein may refer to a bulk solution or an environment within a droplet (e.g., comprising a surface, e.g., a surface of a bead or other support).

The present disclosure can involve an initial slow or rare attachment of a template to a surface followed by a rapid amplification of the surface-attached template (or derivative thereof) to use up the surface primers, providing a clonally amplified template (or derivative thereof). As described above, this can be accomplished by using an extension of the template to allow for attachment. Furthermore, another slow or rare step prior to amplification can be added to the methods described herein. The further slow step can also involve extension of the template, this time at an end distal from the end of the template that attaches to the surface.

Figure 19A:
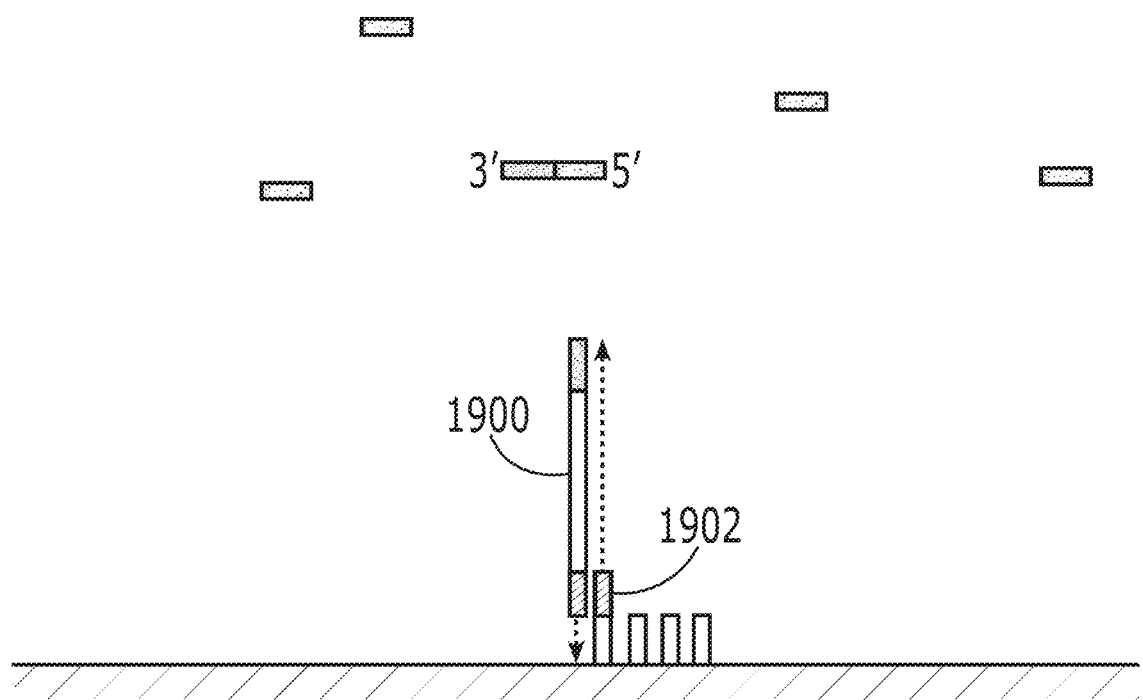
FIG. 19A, FIG. 19B, FIG. 19C, and FIG. 19D illustrate an embodiment of the present disclosure that includes a second slow extension step.
Figure 19B:
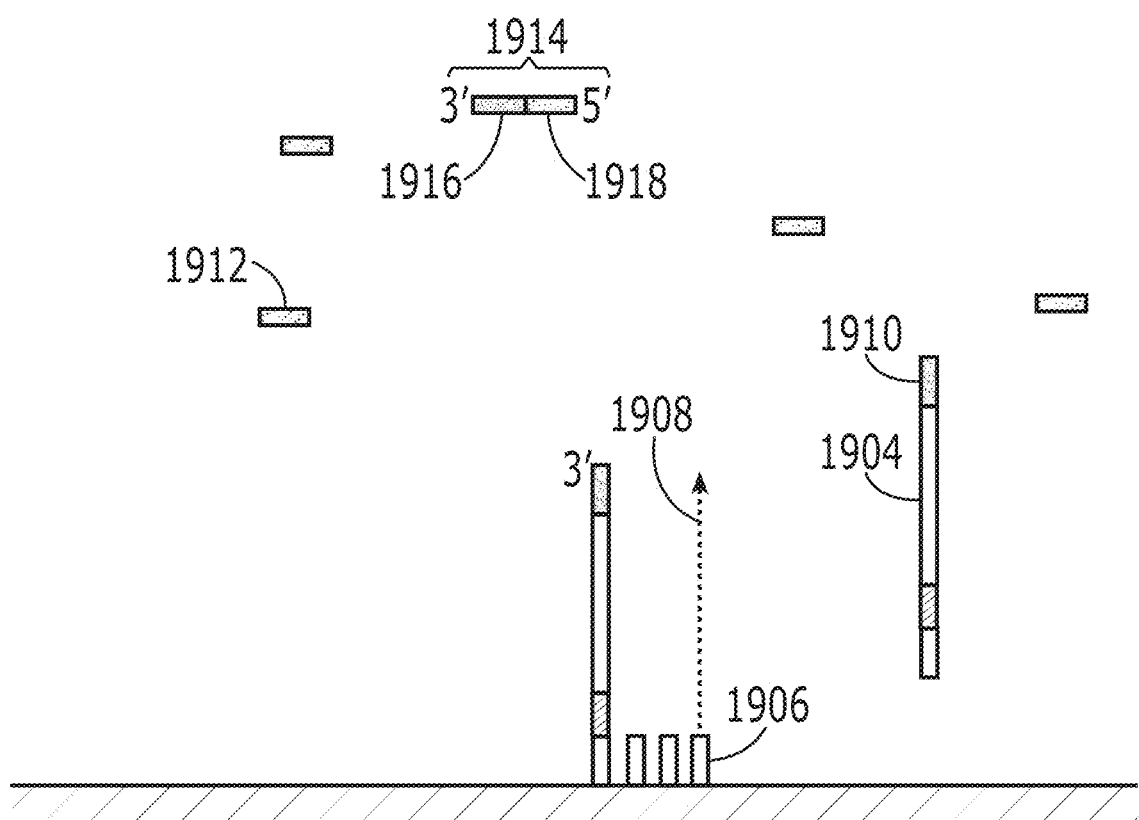

Referring to FIG. 19A, the systems, methods, and compositions can include a template 1900 that anneals to a second primer 1902 (immobilized on a surface) and extends to create an extension product. The second primer can be extended using the nucleic acid template molecule as a template, thereby creating the first copy of the eventual colony of nucleic acid molecules to be sequenced. Continuing with FIG. 19B, the extension product 1904 can diffuse away from the second primer, hybridize with a copy of the first primer 1906 attached to the surface, and serve as a template for extension of the first primer 1908. However, this extension is linear rather than exponential, i.e., only one copy of the first (surface) primers are extended in each cycle. This is because the distal end 1910 (an opposite end from the end that couples to a surface-immobilized primer) of the template and/or extension product 1904 is not initially complementary with the third primer 1912. The system can further include a fourth primer 1914 having a first portion 1916 and a second portion 1918. The first portion can anneal to the nucleic acid template and the second portion can be capable of extending the nucleic acid template such that the extension product can hybridize with the third primer.

Figure 19C:
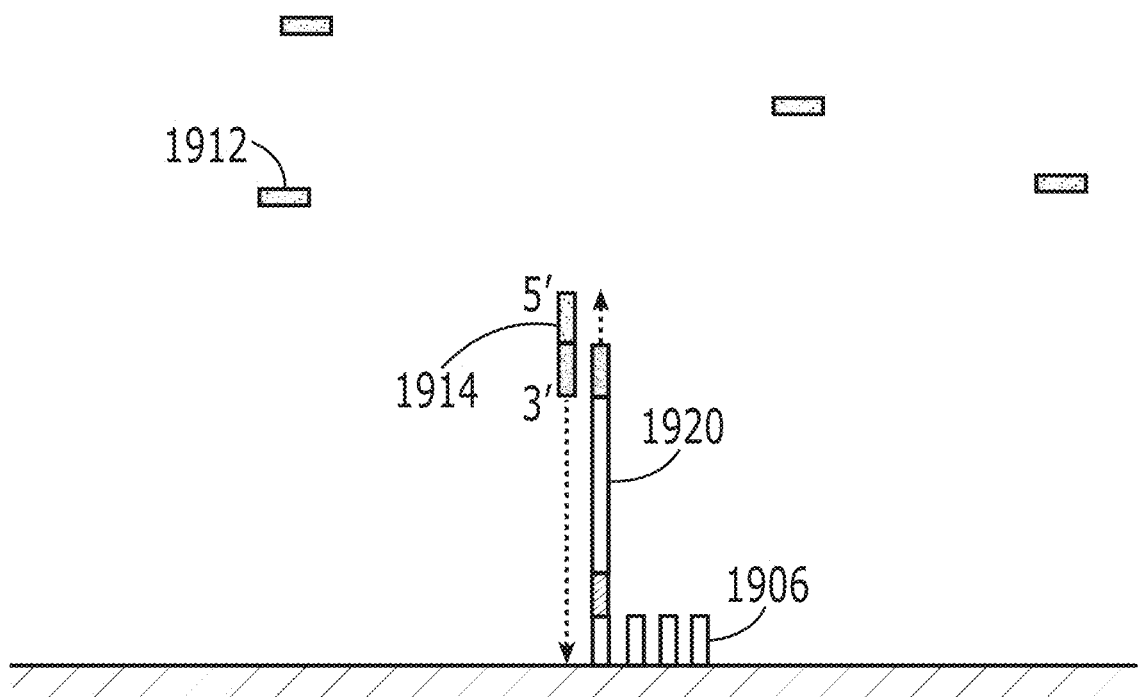

Continuing with FIG. 19C, the fourth primer 1914 can further extend the previously extended copy (from either a first or second primer) immobilized to the surface 1920. The fourth primer can also extend the template nucleic acid (or products thereof) in solution in some cases, e.g., when the library template is double stranded. In some cases, the library template is single stranded and the fourth primer does not hybridize with the library template until it has been first extended with the first or second primer.

Figure 19D:
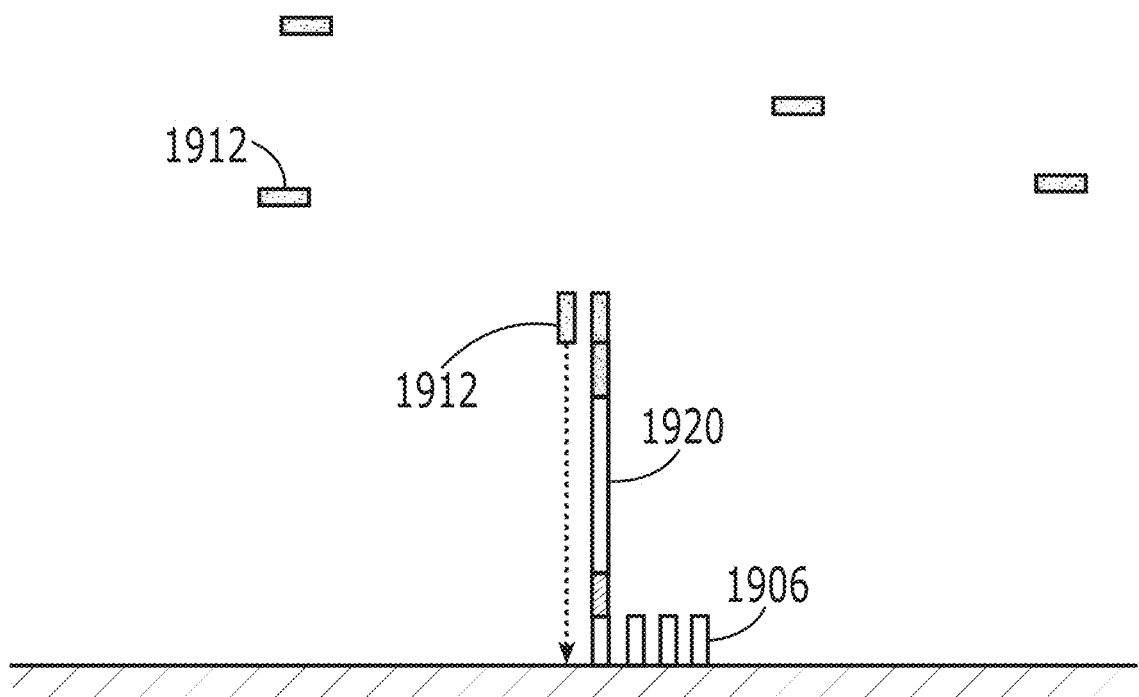

Following this extension, continuing with FIG. 19D, the third primer 1912 is now able to be extended to create additional polynucleotides capable of serving as templates for the extension of additional copies of the first primer 1906. The initial extensions of the original library template at each end (using the second and fourth primers) can be relatively slow and rare events compared to exponential amplification (using the first and third primers). In some cases, both extensions need to be completed before exponential amplification can fill up the colony location defined by a cluster of the first primer attached to the surface.

In another aspect, provided herein is a method for clonally amplifying a nucleic acid sample. The method can include forming an emulsion having a plurality of partitions. A partition of the plurality of partitions can comprise a template nucleic acid, a bead having multiple copies of a first primer attached to the bead, and a reagent mixture capable of performing an attachment reaction that allows the template nucleic acid or a derivative thereof to attach to the bead and an amplification reaction that uses the multiple copies of the first primer. The method can further include incubating the emulsion, thereby performing the attachment reaction to attach the template nucleic acid or a derivative thereof to the bead and performing the amplification reaction to amplify the template nucleic acid or a derivative thereof that was attached to the bead.

In some cases, a first period of time (which duration is described below) is greater than a second period of time (which duration is described below). The first period of time can begin when the emulsion begins incubation and conclude when the template nucleic acid or derivative thereof attaches to the bead. In some cases, the second period of time can begin when the template nucleic acid or derivative thereof attaches to the bead and concludes when amplification reaction concludes. In some cases, for the purpose of defining the second period of time, an amplification reaction can be deemed concluded when the first primers on a bead or a cluster of the first primers of a cluster location on a surface is completely extended. In some cases, for the purpose of defining the second period of time, an amplification reaction can be deemed concluded when at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more first primers on a bead or cluster of the first primers of a cluster location on a surface has been extended.

The first period of time can be greater than the second period of time by any suitable factor. In some embodiments, the first period of time is about 5, about 10, about 20, about 50, or about 100 times greater than the second period of time. In some embodiments, the first period of time is at least about 5, at least about 10, at least about 20, at least about 50, or at least about 100 times greater than the second period of time.

Methods for Providing Supports

Provided herein are methods for generating and/or providing a support comprising an extended primer (e.g., second primer), as described elsewhere herein. Any of the supports described herein may be subsequently partitioned, such as during an ePCR operation. A support comprising at least one extended primer molecule (e.g., second primer) and/or at least one template nucleic acid molecule may generally be referred to herein as an extended support. For example, an extended support comprises the surface 1800 with reference to FIG. 18A, which surface comprises a cluster of primers or a plurality of such clusters, and the cluster comprises a first number of first primers (e.g., 1802) and a second number of second primers (e.g., 1804). In some cases, the second number can be lower than the first number. For example, a ratio of the concentration of the second primer to the concentration of the first primer on the surface is on the order of about $10^{-1}$, $10^{-2}$, $10^{-3}$, $10^{4}$, $10^{-5}$, $10^{-6}$, $10^{-7}$, $10^{-8}$, $10^{-9}$ or less. In an example operation, as described herein, a nucleic acid template couples (e.g., anneals) to the second primer attached to the surface and is subjected to a nucleic acid extension reaction to create an extension product, which extension product, or derivative thereof, can subsequently be amplified with the first primer attached to the surface. In some cases, the nucleic acid template may not be able to capable of annealing to the first primer. In another example, an extended support comprises a surface, the surface comprising a cluster of primers or a plurality of primers, and a template nucleic acid molecule is coupled to a primer of the cluster.

Provided herein are methods for isolating an extended support from a mixture of un-extended support(s) and extended support(s). In some instances, the support can be a mobile support (e.g., beads, particles, etc.) that are capable of being transported from a first location to a second location, individually or collectively with other supports. The support may be any support described elsewhere herein. A composition, mixture, or solution of isolated extended supports may be particularly beneficial for downstream operations, such as subsequent partitioning into droplets, as described elsewhere herein, where occupancy of such droplets generally follow the Poisson distribution which leads to the generation of a majority of droplets that are either unoccupied or singularly occupied in order to ensure generation of effective concentrations of singularly occupied droplets. Advantageously, if only extended supports are partitioned, the population of droplets occupied by supports will not be diluted by droplets containing unextended supports which are more inefficient, if not unusable, for downstream operations (e.g., clonal amplification of libraries) than extended supports. Where an extended support comprises a template nucleic acid molecule coupled thereto, a double Poisson distribution (for each of the support occupancy and template occupancy in droplets) may be reduced to a single Poisson distribution (for a single template-support assembly occupancy in droplets). Extended supports may also beneficially allow for overloading of droplets (e.g., more than one in a droplet), as described elsewhere herein. Partitions other than droplets, such as wells or other containers, may be used. Extended supports may also benefit for use in bulk solution, as described elsewhere herein.

Figure 21:
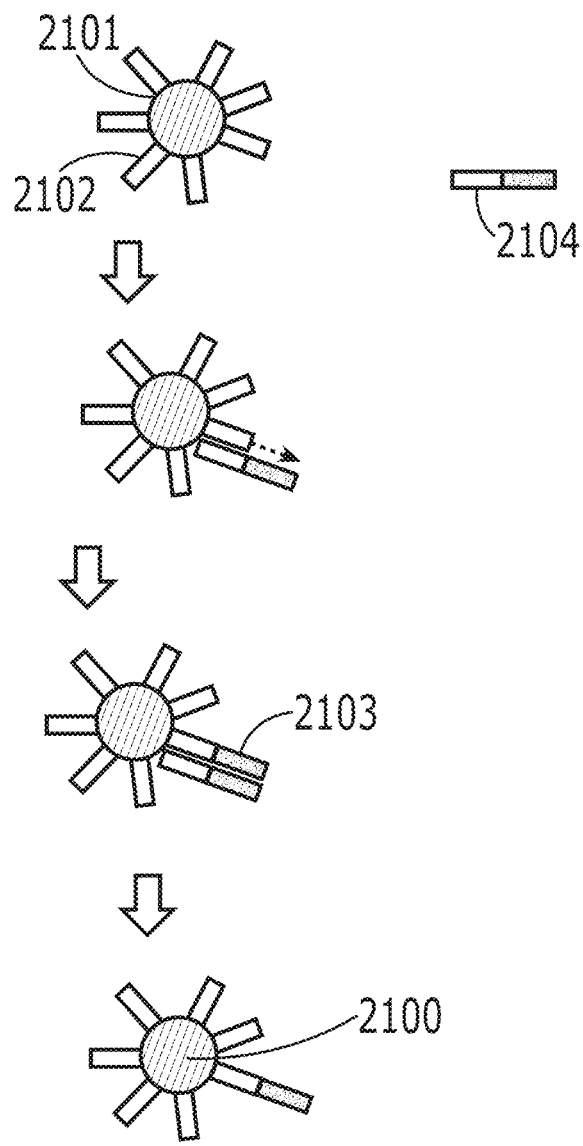
FIG. 21 illustrates an example of generating an extended support.

FIG. 21 illustrates an example method for generating and/or providing an extended support 2100, wherein the extended support 2100 comprises a plurality of primers attached thereto a surface of the support (e.g., a bead). The plurality of primers may comprise one or more of the first primer 2102 and one or more of the second primer 2103. In some instances, it may be of particular interest to generate an extended support 2100 comprising a cluster which comprises a relatively fewer number of the second primer 2103 compared to that of the first primer 2102. In some cases, the extended support has one copy of the second primer 2103 attached thereto. In other cases, the extended support has more than one copy of the second primer 2103, such as a few copies or several copies of the second primer 2103 (not illustrated). Alternatively or in addition, there may be a higher number or concentration of the first primer 2102 than that of the second primer 2103 attached to the surface of the support. In an example, when the extended support is used for sample preparation (e.g., for amplification of nucleic acid templates), as described herein, a nucleic acid template may be extended with the second primer, on rare occasions and therefore in a rate-limiting operation, to create an extension product which can subsequently be amplified with the first primer, which amplification can occur at significantly faster rates than the initial extension product generation reaction as there are more copies of the first primer than the second primer provided on the support. In some cases, the amplification reaction may exhaust (e.g., by coupling thereto) the copies of the first primer on the extended support before another nucleic acid template can be extended with another second primer (if any) in the reaction mixture, thereby facilitating a monoclonal population on the support (or within a cluster on the support).

A starting support 2101 (or un-extended support) may comprise a first primer 2102. The starting support may comprise a plurality of the first primer, such as a cluster of the first primer. The first primer can be attached to an extension primer 2104 for example via hybridization of complementary sequences, and subsequently extended to generate an extended primer, the second primer 2103, that is immobilized to the support. The attachment reaction (e.g., hybridization) may be performed in a solution, such as in bulk solution comprising a plurality of un-extended supports and/or in emulsion comprising a partition comprising an un-extended support. The attachment process (such as hybridization) may comprise a single cycle extension process. After the second primer is generated, a washing and/or melting operation may be performed to disassociate the extension primer to generate the extended support 2100.

In some instances, the respective concentrations of the un-extended support (e.g., 2101) and the extension primer (e.g., 2104) in a reaction mixture may be modulated to facilitate generation of an extended support comprising a minimal number (e.g., one, a few, several, etc.) of the second primer. For example, the extended support may comprise at least about 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, 99.9999% or more of the first primer (out of a total of the first primer and the second primer population).

For example, the reaction mixture may contain a fewer number or less concentration of the extension primer relative to the number or concentration of the first primer present (e.g., via attachment to the un-extended support). In some instances, the ratio of a concentration of extension primers to a concentration of un-extended supports in a solution is at most about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:100, 1:500, 1:1000, 1:5000, 1:10000, or less. Alternatively or in addition, the ratio of a concentration of extension primers to a concentration of un-extended supports in a solution is at least about 1:50, 1:40, 1:30, 1:20, 1:29, 1:18, 1:17, 1:16, 1:14, 1:13, 1:12, 1:11, 1:10, or greater. In some instances, the percentage of a concentration of extension primers to a concentration of un-extended supports in a solution is at most about 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or less. Alternatively or in addition, the percentage of a concentration of extension primers to a concentration of un-extended supports is at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or greater. A resulting mixture may comprise a mixture of extended support(s) and un-extended support(s) that remain un-extended.

Provided herein are methods of isolating an extended support from a mixture of un-extended support(s) and extended support(s).

Figure 22A:
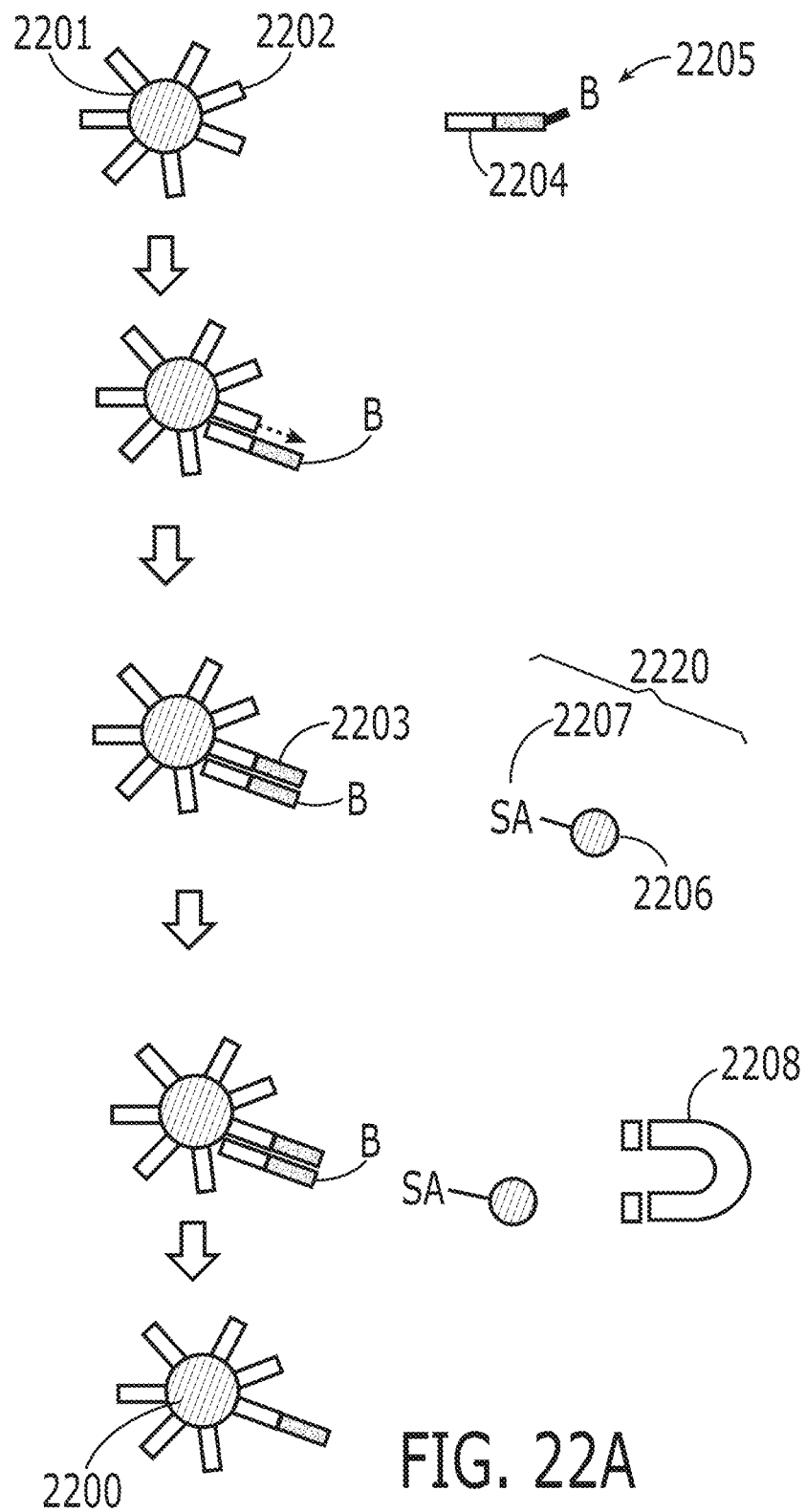
FIGS. 22A-22B illustrate examples of separating an extended support from a solution by applying a magnetic force.

FIG. 22A illustrates an example method for isolating an extended support. A starting support 2201 (or un-extended support) may comprise a first primer 2202. The starting support may comprise a plurality of the first primer, such as a cluster of the first primer. The starting support may be brought in contact with an extension group 2204. The first primer can be attached to the extension group. The extension group may comprise a primer molecule comprising a capture entity 2205. In some instances, the capture entity may comprise biotin (B), such that the primer molecule is biotinylated. In some instances, the capture entity may comprise a capture sequence (e.g., nucleic acid sequence). In some instances, a sequence of the primer molecule may function as a capture sequence. In other instances, the capture entity may comprise another nucleic acid molecule comprising a capture sequence. In some instances, the capture entity may comprise a magnetic particle capable of capture by application of a magnetic field. In some instances, the capture entity may comprise a charged particle capable of capture by application of an electric field. In some instances, the capture entity may comprise one or more other mechanisms configured for, or capable of, capture by a capturing entity.

The first primer 2202 may attach to the extension group 2204, for example via hybridization of complementary sequences (e.g., between a sequence of the first primer 2202 and a sequence of the primer molecule), and subsequently extended to generate an extended primer, the second primer 2203, that is immobilized to the support. The attachment reaction (e.g., hybridization) may be performed in a solution, such as in bulk solution comprising a plurality of un-extended supports and/or in emulsion comprising a partition comprising an un-extended support. The attachment process (such as hybridization) may comprise a single cycle extension process. After the second primer is generated, the extension group 2204 may remain associated with the first primer 2202 and immobilized to the support.

Figure 22B:
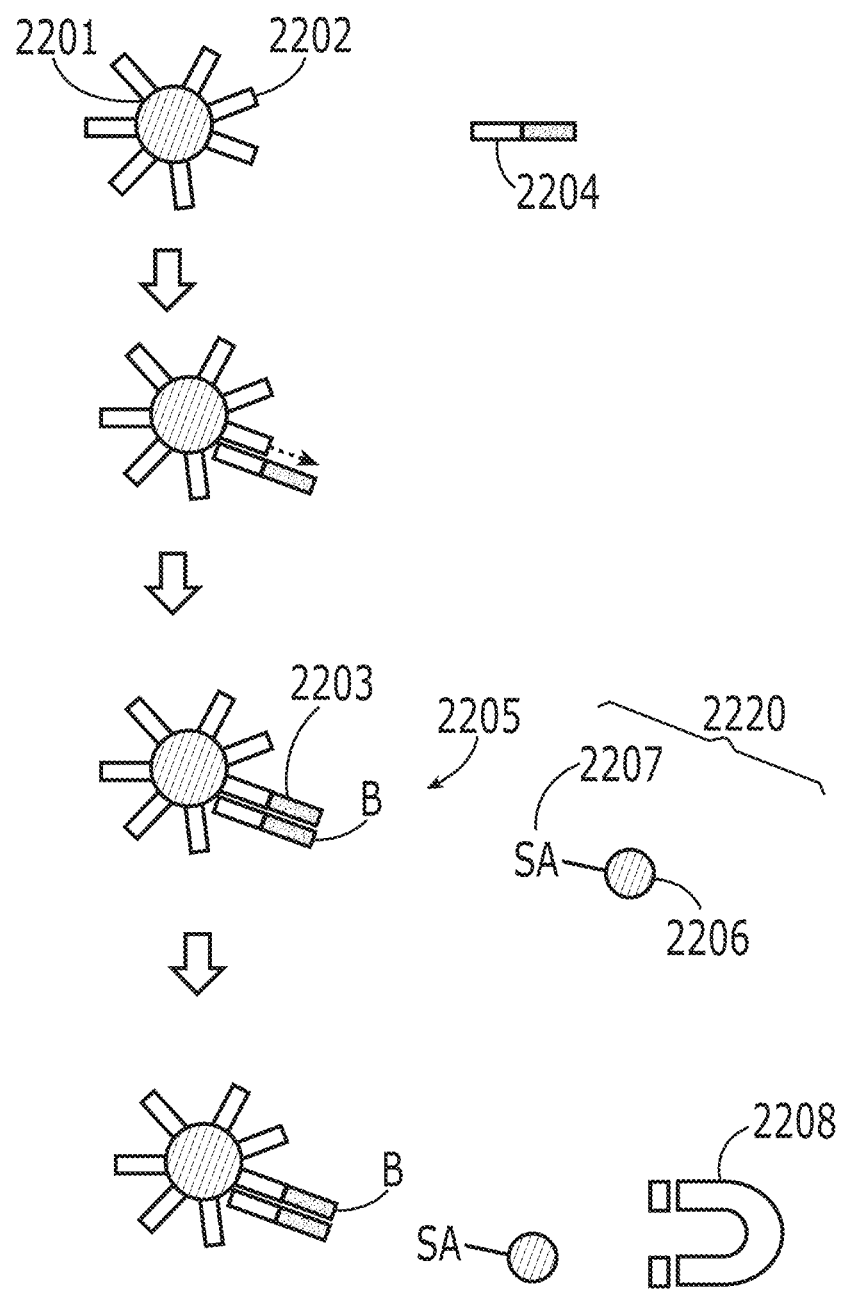

Alternatively, referring to FIG. 22B, a starting support 2201 (or un-extended support) may comprise a first primer 2202. The starting support may comprise a plurality of the first primer, such as a cluster of the first primer. The starting support may be brought in contact with an extension group 2204. The first primer can be attached to the extension group. The extension group in this example lacks a capture entity 2205. The first primer 2202 may attach to the extension group 2204, for example via hybridization of complementary sequences (e.g., between a sequence of the first primer 2202 and a sequence of the primer molecule), and subsequently extended to generate an extended primer, the second primer 2203, that is immobilized to the support. For the extension reaction, reagents comprising the capture entity (e.g., a nucleotide comprising the capture entity, such as a biotin) may be used resulting in the second primer 2203 comprising the capture entity 2205. In some instances, the capture entity may be biotin (B), such that biotin labeled nucleotides are used for the extension reaction. A single labeled base may be employed, such as labeled adenine, labeled thymine, labeled guanine, or labeled cytosine, or analogs thereof. The labeled nucleotide may be selected based on the sequence of the extension group 2204. In an example, only a single labeled nucleotide is added. This can be achieved by selecting a sequence for the extension group 2204 that comprises only one residue of a particular base. Alternatively, the extension can be performed in two operations. In the first operation, only the first nucleotide is added and this nucleotide is labeled with the capture entity 2205. A second extension reaction is performed with all the bases, wherein no labeled bases are used. This results in a second primer 2203 comprising only one capture entity 2205. Alternatively, the stepwise single labeled nucleotide addition can be performed at any other position of the extension (e.g., second position, third position, fourth position, etc.). In some instances, the capture entity may comprise a capture sequence (e.g., nucleic acid sequence). In some instances, the complement of the extension group 2204 is the capture sequence, such that the second primer 2203 comprises the capture sequence.

Referring back to FIG. 22A, the support comprising the extension group 2204 attached thereto may be brought in contact with, or otherwise subjected to capture by, a capturing group 2220. In some instances, the capturing group may comprise a capturing entity 2207 configured to capture the capture entity 2205. For example, the capturing entity may be configured to target the capture entity. In some instances, the capturing entity may comprise streptavidin (SA) when the capture moiety comprises biotin. In some instances, the capturing entity may comprise a complementary capture sequence when the capture entity comprises a capture sequence (e.g., that is complementary to the complementary capture sequence). In some instances, the capturing entity may comprise an apparatus, system, or device configured to apply a magnetic field when the capture entity comprises a magnetic particle. In some instances, the capturing entity may comprise an apparatus, system, or device configured to apply an electrical field when the capture entity comprises a charged particle. In some instances, the capturing entity may comprise one or more other mechanisms configured to capture the capture entity. In some instances, the capturing group may comprise a secondary capture entity 2206, for example, for subsequent capture by a secondary capturing entity 2208. The secondary capture entity and secondary capturing entity may comprise any one or more of the capturing mechanisms described elsewhere herein (e.g., biotin and streptavidin, complementary capture sequences, etc.). In some instances, the secondary capture entity can comprise a magnetic particle (e.g., magnetic bead) and the secondary capturing entity can comprise a magnetic system (e.g., magnet, apparatus, system, or device configured to apply a magnetic field, etc.). In some instances, the secondary capture entity can comprise a charged particle (e.g., charged bead carrying an electrical charge) and the secondary capturing entity can comprise an electrical system (e.g., magnet, apparatus, system, or device configured to apply an electric field, etc.).

When the support comprising the extension group 2204 attached thereto is brought in contact with, or otherwise subject to capture by, the capturing group 2220, the capturing entity 2207 of the capturing group may bind, couple, hybridize, or otherwise associate with the capture entity 2205 immobilized to the support. The association between the capture entity and the capturing entity may comprise formation of a non-covalent bond. The association may comprise formation of a covalent bond. The association may comprise formation of a releasable bond, for example, upon application of a stimulus. In some instances, the association may not form any bond. For example, the association may increase a physical proximity (or decrease a physical distance) between the capturing entity and capture entity. In some instances, a single capture entity may be capable of associating with a single capturing entity. Alternatively, a single capture entity may be capable of associating with multiple capturing entities. Alternatively or in addition, a single capturing entity may be capable of associating with multiple capture entities. The capture entity/capturing entity pair may be any combination. The pair may include, but is not limited to, biotin/streptavidin, azide/cyclooctyne, and thiol/maleimide. It will be appreciated by a skilled artisan that either molecule of the pair may be used as either the capture entity or the capturing entity, the capture entity capable of linking to a nucleotide. Chemically modified bases comprising biotin, an azide, cyclooctyne, tetrazole, and a thiol, and many others are suitable as capture entities.

A plurality of un-extended supports and a plurality of extension groups may be subject to the operations described herein in a bulk solution. In some instances, the respective concentrations of the un-extended support and the extension group in a reaction mixture may be modulated to facilitate generation of an extended support comprising a minimal number (e.g., one, a few, several, etc.) of the second primer.

For example, the reaction mixture may contain a fewer number or less concentration of the extension primer (e.g., primer molecule) relative to the number or concentration of the first primer present (e.g., via attachment to the un-extended support). In some instances, the ratio of a concentration of extension groups to a concentration of un-extended supports in a solution is at most about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:100, 1:500, 1:1000, 1:5000, 1:10000 or less. Alternatively or in addition, the ratio of a concentration of extension groups to a concentration of un-extended supports in a solution is at least about 1:50, 1:40, 1:30, 1:20, 1:29, 1:18, 1:17, 1:16, 1:14, 1:13, 1:12, 1:11, 1:10, or greater. In some instances, the percentage of a concentration of extension groups to a concentration of un-extended supports in a solution is at most about 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or less. Alternatively or in addition, the percentage of a concentration of extension groups to a concentration of un-extended supports is at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or greater. A resulting mixture may comprise a mixture of extended support(s) and un-extended support(s) that remain un-extended.

In some instances, the capturing group may isolate the extended support from a mixture of extended support(s) (each comprising the extension group attached thereto) and un-extended support(s) (not attached to an extension group) by targeting the extension group attached thereto. In some instances, the capturing group may isolate multiple extended supports from a mixture of extended support(s) (each comprising the extension group attached thereto) and un-extended support(s) (not attached to an extension group) by targeting the respective extension groups attached thereto. In some instances, a plurality of capturing groups may be used to isolate the extended support from a mixture of extended support(s) (each comprising the extension group attached thereto) and un-extended support(s) (not attached to an extension group) by targeting the extension group attached thereto.

Once isolated, a washing and/or melting operation may be performed to disassociate the extension group from the support to provide the extended support 2200.

In some instances, the capturing group 2220 may associate with the extended support without isolation of the extended support from the mixture. In some instances, where the capturing group further comprises a secondary capture entity 2206, the support may remain associated with the secondary capture entity in the mixture. The support may be brought into contact with, or otherwise subject to capture by, a secondary capturing entity 2208. The secondary capturing entity may bind, couple, hybridize, or otherwise associate with the secondary capture entity of the capturing group. The association between the secondary capture entity and the secondary capturing entity may comprise formation of a non-covalent bond. The association may comprise formation of a covalent bond. The association may comprise formation of a releasable bond, for example, upon application of a stimulus. In some instances, the association may not form any bond. For example, the association may increase a physical proximity (e.g., decrease physical distance) of the secondary capturing entity and secondary capture entity. In some instances, a single secondary capture entity may be capable of associating with a single secondary capturing entity. Alternatively, a single secondary capture entity may be capable of associating with multiple secondary capturing entities. Alternatively or in addition, a single secondary capturing entity may be capable of associating with multiple secondary capture entities. In some instances, the secondary capturing group may isolate the extended support from a mixture of extended support(s) (each comprising the capture group attached thereto) and un-extended support(s) (not attached to a capture group) by targeting the capture group attached thereto. In some instances, the secondary capturing group may isolate multiple extended supports from a mixture of extended support(s) (each comprising the capture group attached thereto) and un-extended support(s) (not attached to a capture group) by targeting the respective capture groups attached thereto. In some instances, a plurality of secondary capturing groups may be used to isolate the extended support from a mixture of extended support(s) (each comprising the capture group attached thereto) and un-extended support(s) (not attached to a capture group) by targeting the capture group attached thereto.

Once isolated, a washing and/or melting operation may be performed to disassociate the extension group and the capture group (and in some cases also the secondary capturing entity) from the support to provide the extended support 2200.

In some instances, the secondary capturing entity 2208 may associate with the extended support without isolation of the extended support from the mixture. In some cases, the secondary capturing entity may comprise a third capture entity configured for subsequent capture by a third capturing entity (not illustrated). It will be appreciated that any degree of capturing entity may comprise another capture group that may be captured by a next degree of capturing entity, for isolation from the mixture and/or association by the next degree of capturing entity. Once isolated, a washing and/or melting operation may be performed to disassociate the extension group (and any number of capture entities and/or capturing entities) from the support to provide the extended support 2200.

In an example operation, a plurality of supports each comprising a plurality of first primers is brought in contact with a plurality of extension groups each comprising a biotinylated primer molecule. In some instances, the primer molecule attaches to the first primer and subject to nucleic acid extension to generate the second primer immobilized to the support. The support remains associated with the biotinylated primer molecule and is brought in contact with a capture group comprising a streptavidin coupled to a magnetic bead. The streptavidin binds to the biotin, thereby associating the magnetic bead with the support. In some instances, a support does not come into contact with an extension group and is not associated with the magnetic bead. For example, a mixture may comprise extended support(s) associated with magnetic bead(s) and un-extended support(s) unassociated with a magnetic bead. A magnet is used, or other magnetic field is applied, to target the magnetic bead(s) and isolate the extended support(s) associated with the magnetic bead(s) from the mixture. A resulting isolated composition comprises only extended support(s) or a majority of extended support(s). It will be appreciated that there may be some contamination in the isolated composition. A washing operation is performed to disassociate the extension group(s) and/or the capture group(s) from the extended support(s).

Figure 23:
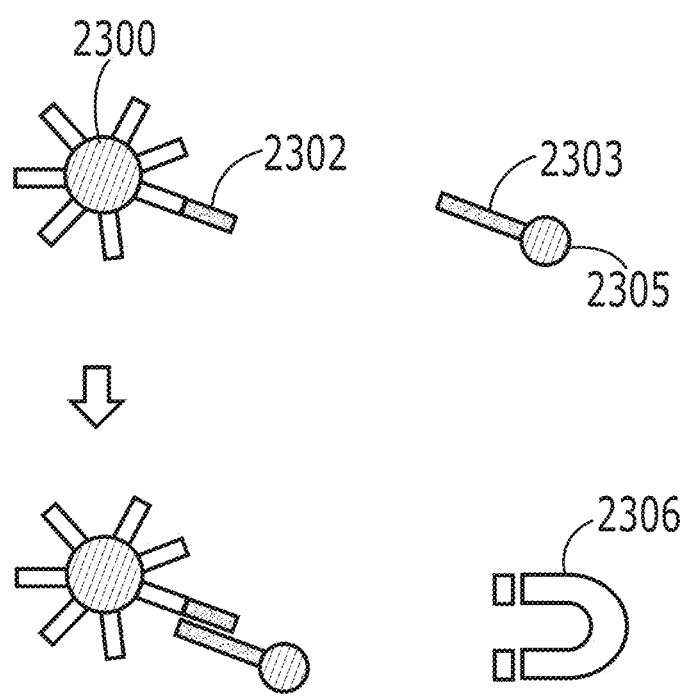
FIG. 23 illustrates another example of separating an extended support from a solution by applying a magnetic force.

FIG. 23 illustrate another example method for isolating an extended support. An extended support 2300 comprising a second primer 2302 may be provided, such as according to methods described with respect to FIG. 21. A capture group may be provided, comprising a capture entity 2305 (e.g., magnetic bead) and a nucleic acid sequence 2303 attached thereto. The nucleic acid sequence attached to the capture entity may comprise sequence homology with a sequence of the second primer attached to the extended support. The capture group may be associated with the extended support such as via hybridization of the nucleic acid sequence and the sequence of the second primer, thereby associating the capture entity with the extended support. The capture group-associated support can be brought into contact with, or otherwise subject to capture by, a capturing entity 2306 (e.g., magnet). The capture group, and/or the capture entity, may be capable of disassociating from the extended support after association. In some instances, the capture group may be reused. In some instances, the capture entity may be reused. In some instances, a nucleic acid molecule comprising the nucleic acid sequence 2303 may be reused. Reusing the different reagents may be a cost-effective approach for isolation of the extended supports. The capture entity and capturing entity may comprise any one or more of the capturing mechanisms described elsewhere herein (e.g., biotin and streptavidin, complementary capture sequences, magnetic particle and magnetic field, charged particle and electric field, etc.). For example, the capture entity may comprise a particle having magnetic properties and the capturing entity may be configured to apply a magnetic field. For example, the capture entity may comprise a charged particle carrying an electrical charge and the capturing entity may be configured to apply an electric field. For example, the capture entity may comprise a nucleic acid capture sequence and the capturing entity may comprise a complementary nucleic acid capture sequence. It will be understood by a skilled artisan that the nucleic acid sequence 2303 may be used to attach a capture entity 2305 directly to the second primer 2302. As was described in FIG. 22B, an extension reaction may be used to add a capture sequence or a modified nucleotide comprising the capture entity 2305 directly to a primer on the support. In FIG. 22B the primer was a first primer, but it will be understood that the primer can be a second primer 2302 as well.

Other methods may be used to separate the extended supports from a mixture solution. Such separation methods may comprise using one or more other sequences or moieties capable of binding the extended supports (e.g., 2300), thereby separating the extended supports from the rest of the support population. In some examples, such sequences or moieties may comprise a higher or significantly higher binding affinity for the extended supports compared to the rest of the reagents, materials, and/or moieties present in the solution. Therefore, such sequences or moieties (referred to herein as separation moieties) may be capable of binding to, associating with, and/or capturing the extended supports. Separating the extended supports from the rest of the solution may contribute to providing a more purified composition of the extended supports, which in some examples may be used as a reagent in an experiment, assay, or procedure, such as the methods and systems described elsewhere herein.

The extended supports may be generated, separated, manufactured, and/or prepared as a reagent. The extended supports may be included in a kit, such as an experimental kit or test. The extended supports may be used in experiments or other procedures. For example, a kit may comprise a composition comprising an extended support reagent solution having at least about 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or greater purity (concentration of extended supports to combined concentration of extended supports and un-extended supports).

The present disclosure provides methods of using the extended supports in experiments. For example, the extended supports may be provided with a library of sequences, such as a library of nucleic acid sequences to be analyzed in an experiment (such as a sequencing experiment, for example next generation sequencing, or any other type of sequencing). The library of sequences may comprise nucleic acid sequences, which may comprise one or more adapter sequences attached thereto. The library of sequences may comprise template nucleic acid sequences. The template nucleic acid sequences may comprise one or more adapter sequences attached thereto. For example, a template nucleic acid sequence may comprise an adapter sequence flanking a first end. In another example, a template nucleic acid sequence may comprise the same or different adapter sequences flanking the two ends. Alternatively, the template molecules may not comprise adapter sequences.

In some examples, the extended supports may be mixed with the library of nucleic acid sequences and the mixture may be subject to conditions sufficient to initiate a nucleic acid extension reaction that can immobilize a template nucleic acid sequence (or complement thereof) to the support. In some instances, such reaction may be performed in partitions (e.g., droplets in an emulsion), as described elsewhere herein, wherein a partition comprises one or more extended supports and one or more template nucleic acid sequences. In other instances, such reaction may be performed in bulk solution. In some examples, immobilization (e.g., hybridization) may be performed in solution (e.g., off-chip), and after immobilization in solution, the immobilized assemblies (combination of the extended support and the template molecule) may be encapsulated in partitions (such as partitions described herein) for subsequent operation. In some examples, partitions are droplets. In some examples, partitions are wells.

Pre-Enrichment

Provided herein are methods for generating a pre-assembled support, generally referred to herein as an assembly, wherein the assembly comprises a single template nucleic acid molecule immobilized to a single support. In subsequent operations, such assemblies, in collection, may be partitioned, as described herein, together with amplification reagents (e.g., solution primer) to facilitate amplification reactions of the template nucleic acid molecules within individual reaction chambers of an emulsion. Beneficially, a partition comprising a single assembly may immobilize a monoclonal population of amplification products to the same support within the partition. Compartmentalization or encapsulation of such assemblies in partitions may follow a Poisson distribution to include, for example, in addition to partitions comprising a single assembly, partitions not comprising any assemblies, and/or partitions comprising a plurality of assemblies (e.g., with different template sequences). By providing pre-assembled supports prior to partitioning, beneficially, a double Poisson problem for distribution amongst partitions of an emulsion may be reduced to a single Poisson distribution problem. If a plurality of supports and a plurality of templates (not immobilized to the supports) are partitioned, each following its own Poisson distribution model, significantly fewer partitions having a single support and a single template are generated compared to a first order Poisson distribution model. This results in inefficient use of valuable resources and loss of precious templates when compared to the methods described herein.

In some instances, a method may comprise providing a mixture comprising a plurality of extended supports and a plurality of template nucleic acid molecules (e.g., in a library) each having a different nucleic acid sequence. The plurality of extended supports may comprise a purified composition of the extended supports (from a mixture of extended supports and un-extended supports) as described elsewhere herein. Each of the template nucleic acid molecules may be configured to, and/or be capable to, anneal with a second primer. An extended support of the plurality of extended supports may comprise a plurality of first primers and a single copy, a few copies, several copies, and/or a significantly lower number of the second primers relative to a number of the plurality of first primers available for annealing to the template nucleic acid molecules. The mixture may be subject to conditions sufficient to anneal or otherwise associate the plurality of template nucleic acid molecules to a plurality of second primers distributed across the plurality of extended supports. The mixture may be subject to conditions sufficient to wash template nucleic acid molecules that have not coupled to a support. In some instances, this may be achieved by immobilizing the support to an immobilization platform (e.g., another surface or structure configured to immobilize the support, such as via some affinity (e.g., magnetic, electric, hydrophobic, hydrophilic, etc.) to the support, etc.) such that during washing the support remains stabilized. Because each extended support has only one copy, a few copies, several copies, and/or a significantly lower number of the second primers relative to a number of the plurality of first primers, the resulting reaction products may comprise a plurality of assemblies, wherein a majority of, or substantially all of, the assemblies each comprise a single template nucleic acid molecule immobilized to a support. Such assemblies may be partitioned, as described elsewhere herein, such as together with amplification reagents (e.g., including a solution primer) to facilitate amplification reactions of the template nucleic acid molecule within individual reaction chambers. Beneficially, a partition comprising a single assembly may immobilize a monoclonal population of amplification products to the same support within the partition.

In some examples, during the mixing process of extended supports and the template nucleic acid molecules, the concentration of extended supports may be lower than the concentration of the template nucleic acid molecules, where suitable (e.g., when there is an abundance of available sample). For example, sample(s) may be provided in excess. Providing the sample in excess may reduce the number of blank extended supports (lacking templates) resulting from mixing and hybridization.

Using some methods, a technician may have to make very precise measurements to prepare a sample, such as prior to mixing the sample with the supports to generate a useful population of assemblies. The extended supports provided in this disclosure may advantageously be compatible with processes that do not require as precise measurements of the concentration of the library in a reaction mixture. In some examples, merely providing the sample in excess may contribute to a successful hybridization (e.g., to extended supports) process, even when the concentration of the library is not measured with high precision. For example, in some cases, providing the sample in excess may allow decrease of the incubation time for hybridization reaction. Providing the sample (library) in excess may increase the rate of hybridization and yield. Alternatively, in some cases the sample may not be provided in excess (for example in cases where the sample is precious.

Figure 24A:
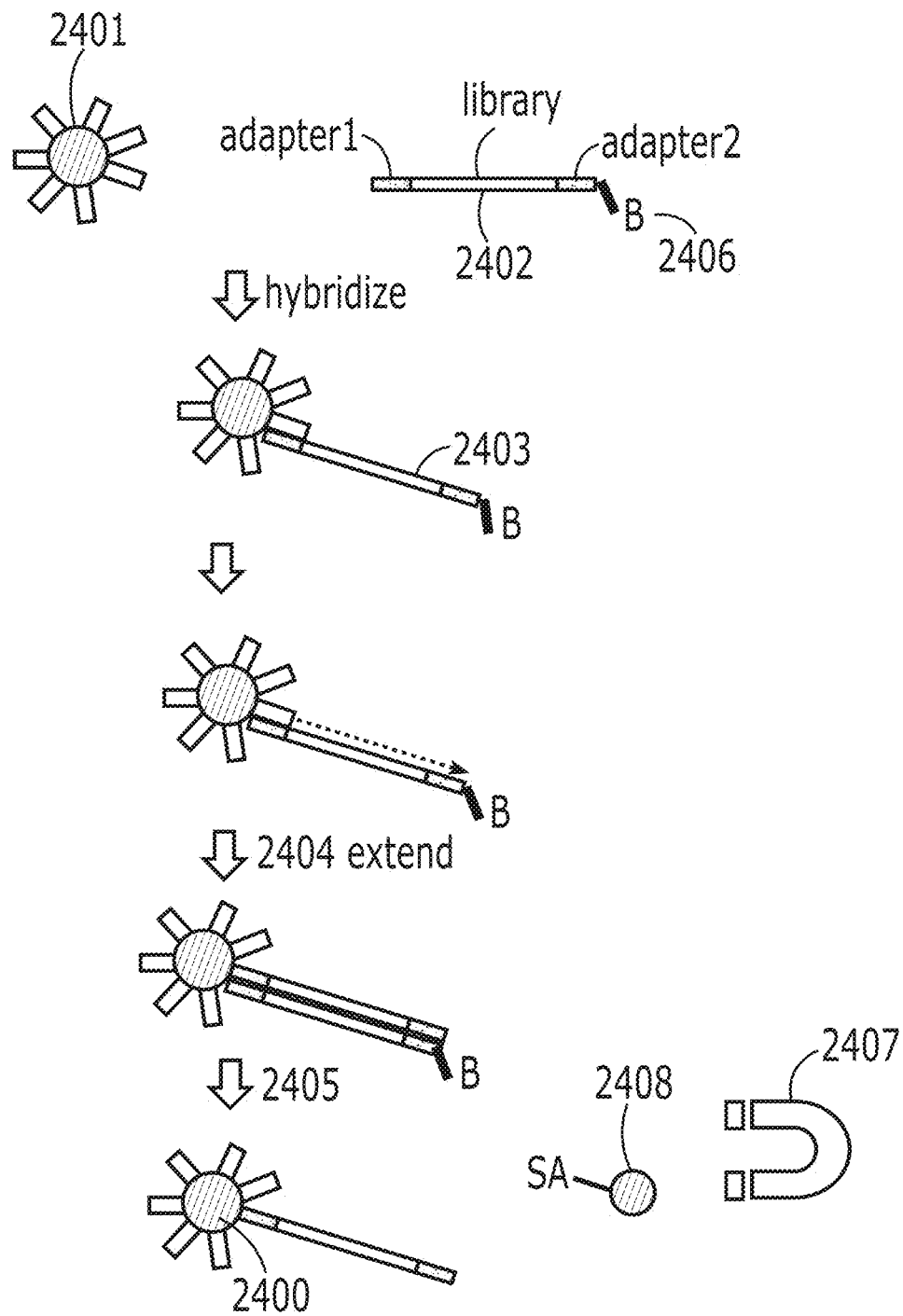
FIGS. 24A-24B illustrates an example pre-enrichment method for generating a plurality of pre-enriched supports.

In some instances, referring to FIG. 24A, a method may comprise providing a mixture comprising a plurality of supports (e.g., support 2401, un-extended support) and a plurality of template nucleic acid molecules (e.g., template nucleic acid molecule 2402) each having a different nucleic acid sequence. The template nucleic acid molecule may be configured to, and/or be capable to, anneal with a primer attached to the support. The template nucleic acid molecule may comprise a capture entity 2406 configured for subsequent capture by a capturing entity of a capturing group 2408. The support may comprise a plurality of primers available for annealing to the template nucleic acid molecules.

Figure 24B:
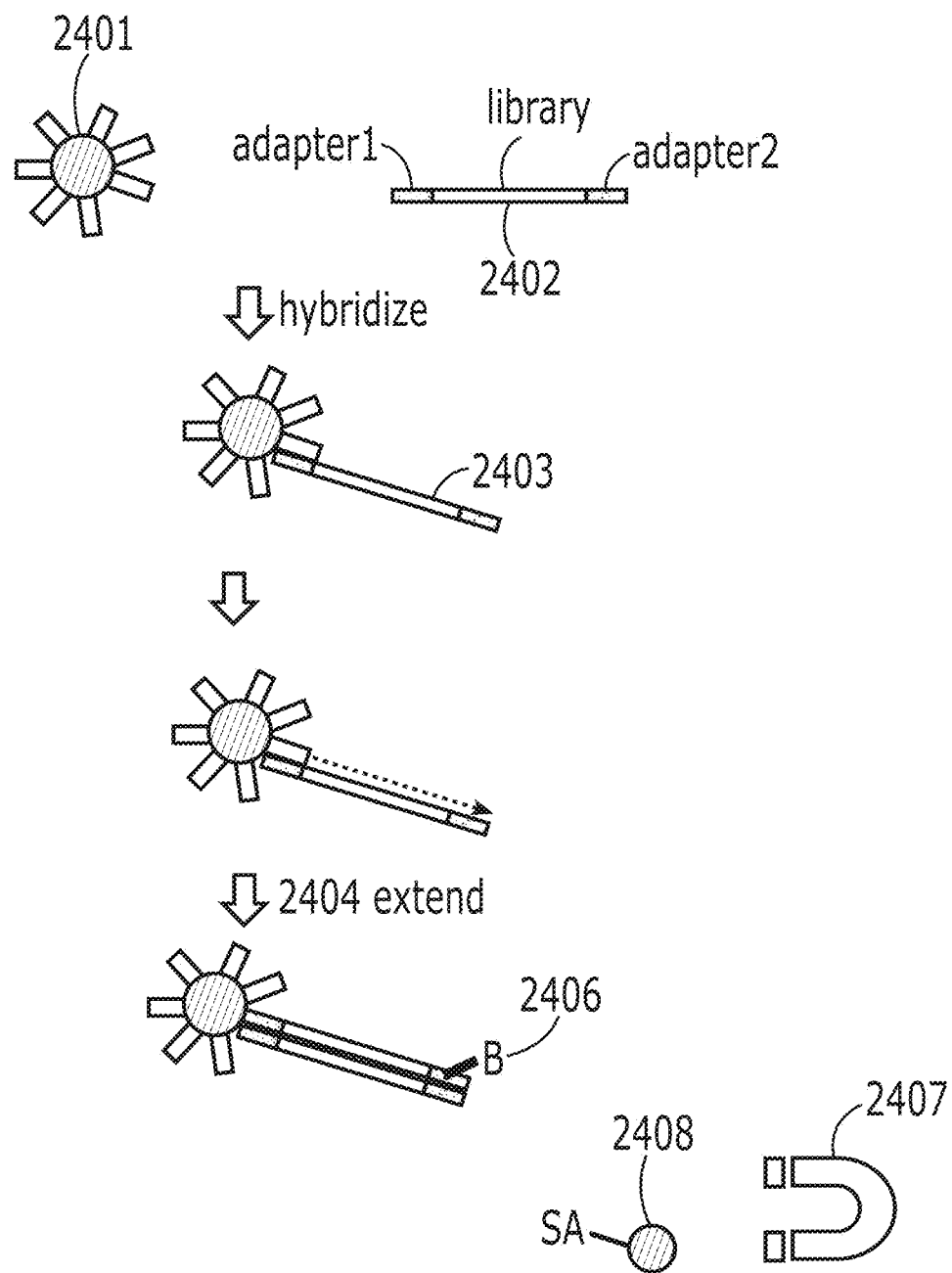

Alternatively, FIG. 24B illustrates an example method wherein the template nucleic acid molecule lacks a capture entity 2406, and the capture entity 2406 is added to the extension product. As described with respect to FIG. 24A, a mixture comprising a plurality of supports (e.g., support 2401, un-extended support) and a plurality of template nucleic acid molecules (e.g., template nucleic acid molecule 2402) each having a different nucleic acid sequence are provided. The template nucleic acid molecule lacking a capture entity may be configured to, and/or be capable to, anneal with a primer attached to the support. Similar to the description of FIG. 22B, a primer may attach to the template nucleic acid molecule, for example via hybridization of complementary sequences (e.g., between a sequence of the first primer and a sequence of adapter 1), and subsequently extended to generate an extension product that is immobilized to the support. For the extension reaction, reagents comprising the capture entity (e.g., nucleotides comprising the capture entity) may be used resulting in the extension product comprising the capture entity 2406. In some instances, the capture entity may be biotin (B), such that biotin labeled nucleotides are used for the extension reaction. A single labeled base may be employed, such as labeled adenine, labeled thymine, labeled guanine, or labeled cytosine, or analogs thereof. The labeled nucleotide may be selected based on the sequence of adapter 1 of the template 2402. In an example, only a single labeled nucleotide is added. This can be achieved by performing the extension in two operations. In the first operation, only the first nucleotide is added and this nucleotide is labeled with the capture entity 2406. This can be the first base present in a sequence of adapter 1 that is not complementary to a sequence of the first primer. A second extension reaction is performed with all the bases, wherein no labeled bases are used. This results in an extension product immobilized to the support comprising only one capture entity 2406. Alternatively, the stepwise single labeled nucleotide addition can be performed at any other position of the extension (e.g., second position, third position, fourth position, etc.).

In some instances, the respective concentrations of the supports and the template nucleic acid molecules in a reaction mixture may be modulated to facilitate generation of a majority of assemblies comprising a single support and a single template nucleic acid molecule (or complement thereof) immobilized to the support. For example, the resulting support may comprise at least about 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, 99.9999% or more of the primer not associated with a template nucleic acid molecule (out of the total primer population).

For example, the reaction mixture may contain a fewer number or less concentration of the template nucleic acid molecules relative to the number or concentration of the supports present. In some instances, the ratio of a concentration of template nucleic acid molecules to a concentration of supports in a solution is at most about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50 or less. Alternatively or in addition, the ratio of a concentration of template nucleic acid molecules to a concentration of supports in a solution is at least about 1:50, 1:40, 1:30, 1:20, 1:29, 1:18, 1:17, 1:16, 1:14, 1:13, 1:12, 1:11, 1:10, or greater. In some instances, the percentage of a concentration of template nucleic acid molecules to a concentration of supports in a solution is at most about 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or less. Alternatively or in addition, the percentage of a concentration of template nucleic acid molecules to a concentration of supports in a solution is at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or greater.

Referring back to FIG. 24A, the mixture may be subject to conditions sufficient to anneal (2403) the plurality of template nucleic acid molecules to a plurality of primers distributed across the plurality of supports, and subject to extension (2404) to generate complements of the respective template nucleic acid molecules immobilized thereto the respective supports. The supports may remain associated with the respective capture entities (e.g., 2406) of the respective template nucleic acid molecules (e.g., 2402). A resulting mixture may comprise a mixture of supports comprising one or more template nucleic acid molecules (and capture entities) associated thereto and supports not comprising any template nucleic acid molecules (and capture entities) associated thereto.

In some instances, the capture entity 2406 may comprise biotin (B). In some instances, the capture entity may comprise a capture sequence (e.g., nucleic acid sequence). In some instances, a sequence of the template nucleic acid molecule may function as a capture sequence. In other instances, the capture entity may comprise another nucleic acid molecule comprising a capture sequence. In some instances, the capture entity may comprise a magnetic particle capable of capture by application of a magnetic field. In some instances, the capture entity may comprise a charged particle capable of capture by application of an electric field. In some instances, the capture entity may comprise one or more other mechanisms configured for, or capable of, capture by a capturing entity, as described elsewhere herein.

The support 2401 comprising the template nucleic acid molecule 2402 associated thereto may be brought in contact with, or otherwise subjected to capture by, a capturing group 2408. The capturing group may comprise a capturing entity configured to capture the capture entity 2406. For example, the capturing entity may be configured to target the capture entity. In some instances, the capturing entity may comprise streptavidin (SA) when the capture moiety comprises biotin. In some instances, the capturing entity may comprise a complementary capture sequence when the capture entity comprises a capture sequence (e.g., that is complementary to the complementary capture sequence). In some instances, the capturing entity may comprise an apparatus, system, or device configured to apply a magnetic field when the capture entity comprises a magnetic particle. In some instances, the capturing entity may comprise an apparatus, system, or device configured to apply an electrical field when the capture entity comprises a charged particle. In some instances, the capturing entity may comprise one or more other mechanisms configured to capture the capture entity. In some instances, the capturing group may comprise a secondary capture entity, for example, for subsequent capture by a secondary capturing entity 2407. The secondary capture entity and secondary capturing entity may comprise any one or more of the capturing mechanisms described elsewhere herein (e.g., biotin and streptavidin, complementary capture sequences, etc.). In some instances, the secondary capture entity can comprise a magnetic particle (e.g., magnetic bead) and the secondary capturing entity can comprise a magnetic system (e.g., magnet, apparatus, system, or device configured to apply a magnetic field, etc.). In some instances, the secondary capture entity can comprise a charged particle (e.g., charged bead carrying an electrical charge) and the secondary capturing entity can comprise an electrical system (e.g., magnet, apparatus, system, or device configured to apply an electric field, etc.).

When the support comprising the capture entity 2406 associated thereto is brought in contact with, or otherwise subject to capture by, the capturing group 2408, the capturing entity of the capturing group may bind, couple, hybridize, or otherwise associate with the capture entity. The association between the capture entity and the capturing entity may comprise formation of a non-covalent bond. The association may comprise formation of a covalent bond. The association may comprise formation of a releasable bond, for example, upon application of a stimulus. In some instances, the association may not form any bond. For example, the association may increase a physical proximity (or decrease a physical distance) between the capturing entity and capture entity. In some instances, a single capture entity may be capable of associating with a single capturing entity. Alternatively, a single capture entity may be capable of associating with multiple capturing entities. Alternatively or in addition, a single capturing entity may be capable of associating with multiple capture entities.

In some instances, the capturing group 2408 may isolate the support 2401 comprising the template nucleic acid molecule 2402 (and capture entity 2406) from a mixture by targeting the capture entity. In some instances, the capturing group may isolate multiple supports each comprising one or more template nucleic acid molecules from a mixture. In some instances, a plurality of capturing groups may be used to isolate the support comprising the template nucleic acid molecule from a mixture. Once isolated, a washing and/or melting operation (2405) may be performed to disassociate the template nucleic acid molecule from the support to provide the assembly 2400.

In some instances, the capturing group 2408 may associate with the support without isolation of the support from the mixture. In some instances, where the capturing group further comprises a secondary capture entity, the support may remain associated with the secondary capture entity in the mixture. The support may be brought into contact with, or otherwise subject to capture by, a secondary capturing entity 2407. The secondary capturing entity may bind, couple, hybridize, or otherwise associate with the secondary capture entity of the capturing group. The association between the secondary capture entity and the secondary capturing entity may comprise formation of a non-covalent bond. The association may comprise formation of a covalent bond. The association may comprise formation of a releasable bond, for example, upon application of a stimulus. In some instances, the association may not form any bond. For example, the association may increase a physical proximity (e.g., decrease physical distance) of the secondary capturing entity and secondary capture entity. In some instances, a single secondary capture entity may be capable of associating with a single secondary capturing entity. Alternatively, a single secondary capture entity may be capable of associating with multiple secondary capturing entities. Alternatively or in addition, a single secondary capturing entity may be capable of associating with multiple secondary capture entities. In some instances, the secondary capturing group may isolate the support comprising the template nucleic acid molecule from a mixture. In some instances, the secondary capturing group may isolate multiple supports from a mixture. In some instances, a plurality of secondary capturing groups may be used to isolate the support from a mixture.

Once isolated, a washing and/or melting operation may be performed to disassociate the template nucleic acid molecule 2402 and the capture group 2408 (and in some cases also the secondary capturing entity 2407) from the support to provide the assembly 2400.

In some instances, the secondary capturing entity 2407 may associate with the support without isolation of the support from the mixture. In some cases, the secondary capturing entity may comprise a third capture entity configured for subsequent capture by a third capturing entity (not illustrated). It will be appreciated that any degree of capturing entity may comprise another capture group that may be captured by a next degree of capturing entity, for isolation from the mixture and/or association by the next degree of capturing entity. Once isolated, a washing and/or melting operation may be performed to disassociate the template nucleic acid molecule (and any number of capture entities and/or capturing entities) from the support to provide the assembly 2400.

Such assemblies may be partitioned, as described elsewhere herein, such as together with amplification reagents (e.g., including a solution primer) to facilitate amplification reactions of the template nucleic acid molecule within individual reaction chambers. Beneficially, a partition comprising a single assembly may immobilize a monoclonal population of amplification products to the same support within the partition.

Methods for pre-enrichment of the supports (with template nucleic acid molecules or complements thereof) may be performed in solution. In some examples, the pre-enrichment methods may be performed in a solution not comprising any emulsion or partitions. In other examples, the pre-enrichment method may be performed in partitions. Procedures may be integrated. Alternatively, processes may not be integrated.

Computer Control Systems

Figure 6:
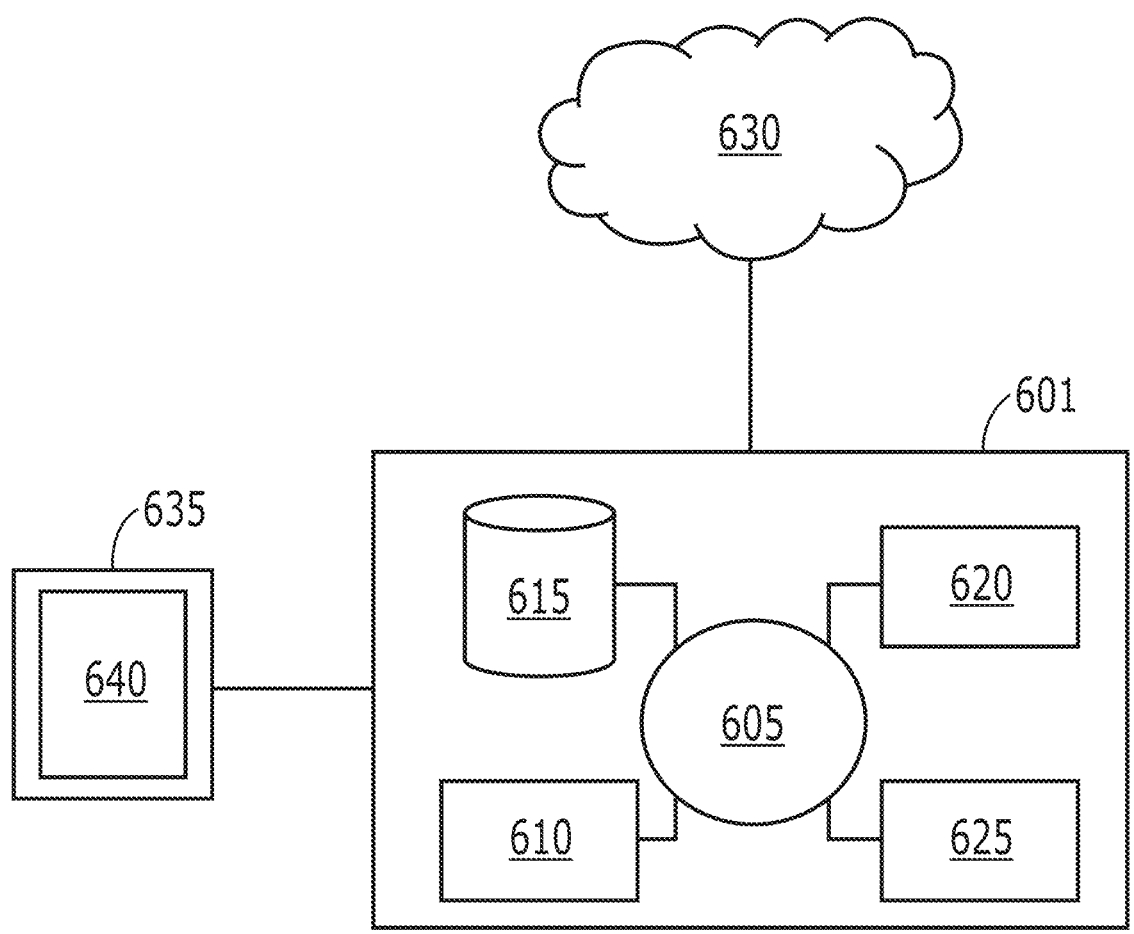
FIG. 6 shows a computer control system that is programmed or otherwise configured to implement methods provided herein.

The present disclosure provides computer control systems that are programmed to implement methods of the disclosure. FIG. 6 shows a computer system 601 that is programmed or otherwise configured to implement methods and systems of the present disclosure, such as performing nucleic acid sequence and sequence analysis.

The computer system 601 includes a central processing unit (CPU, also "processor" and "computer processor" herein) 605, which may be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 may be a data storage unit (or data repository) for storing data. The computer system 601 may be operatively coupled to a computer network ("network") 630 with the aid of the communication interface 620. The network 630 may be the Internet, an internet and/or extranet, or an intranet and/or extranet that is in communication with the Internet. The network 630 may be a telecommunication and/or data network. The network 630 may include one or more computer servers, which may enable distributed computing, such as cloud computing. The network 630, with the aid of the computer system 601, may implement a peer-to-peer network, which may enable devices coupled to the computer system 601 to behave as a client or a server.

The CPU 605 may execute a sequence of machine-readable instructions, which may be embodied in a program or software. The instructions may be stored in a memory location, such as the memory 610. The instructions may be directed to the CPU 605, which may subsequently program or otherwise configure the CPU 605 to implement methods of the present disclosure. Examples of operations performed by the CPU 605 may include fetch, decode, execute, and writeback.

The CPU 605 may be part of a circuit, such as an integrated circuit. One or more other components of the system 601 may be included in the circuit. The circuit may be an application specific integrated circuit (ASIC).

The storage unit 615 may store files, such as drivers, libraries and saved programs. The storage unit 615 may store user data, e.g., user preferences and user programs. The computer system 601 may include one or more additional data storage units that are external to the computer system 601, such as located on a remote server that is in communication with the computer system 601 through an intranet or the Internet.

The computer system 601 may communicate with one or more remote computer systems through the network 630. For instance, the computer system 601 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 601 via the network 630.

Methods as described herein may be implemented by way of machine (e.g., computer processor) executable code stored on an electronic storage location of the computer system 601, such as, for example, on the memory 610 or electronic storage unit 615. The machine executable or machine readable code may be provided in the form of software. During use, the code may be executed by the processor 605. The code may be retrieved from the storage unit 615 and stored on the memory 610 for ready access by the processor 605. In some situations, the electronic storage unit 615 may be precluded, and machine-executable instructions are stored on memory 610.

The code may be pre-compiled and configured for use with a machine having a processor adapted to execute the code, or may be compiled during runtime. The code may be supplied in a programming language that may be selected to enable the code to execute in a pre-compiled or as-compiled fashion.

Aspects of the systems and methods provided herein, such as the computer system 1101, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 may include or be in communication with an electronic display 635 that comprises a user interface (UI) 640 for providing, for example, results of nucleic acid sequence (e.g., sequence reads, consensus sequences, etc.). Examples of UI's include, without limitation, a graphical user interface (GUI) and web-based user interface.

Methods and systems of the present disclosure may be implemented by way of one or more algorithms. An algorithm may be implemented by way of software upon execution by the central processing unit 605. The algorithm can, for example, implement methods of the present disclosure.

EXAMPLES

The following examples are included to further describe certain aspects of the present disclosure, and do not be used to limit the scope of the disclosure.

Example 1

This example demonstrates that the approach described herein for analyzing nucleic acid samples is superior to other techniques.

Figure 3:
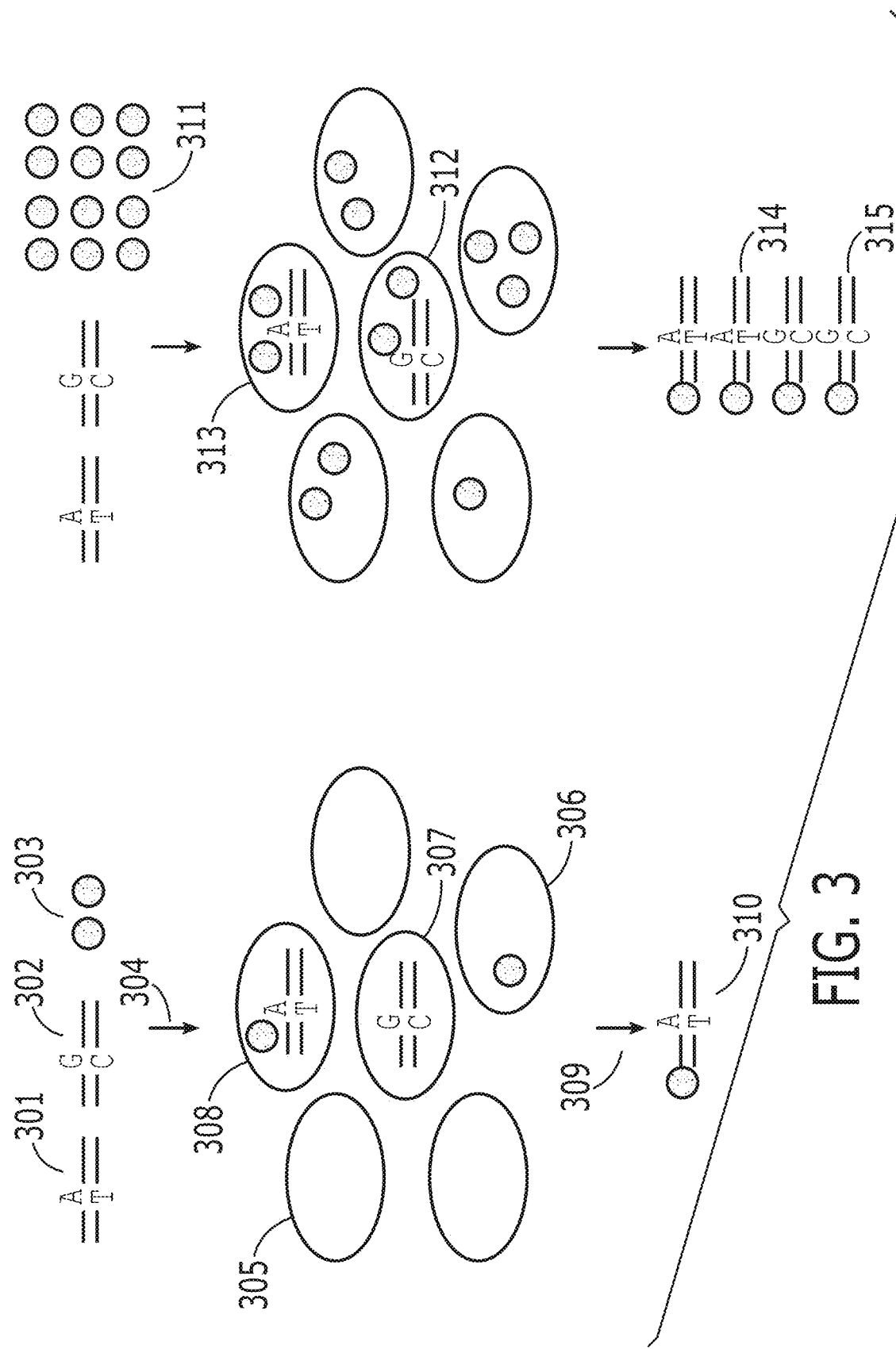
FIG. 3 shows a comparison of single-bead (left diagram) and multi-bead (right diagram) loading of partitions. As shown in the figure, multi-bead loading of droplets (or other partitions such as wells) during emulsion polymerase chain reaction (emPCR or ePCR) may significantly decrease loss of sample material (e.g., genomic material) in ePCR workflows, resulting in an improved accuracy and utilization of reagents while reducing noise during sequence analysis compared to methods involving single-bead loading (left diagram).

An ePCR workflow was performed and is shown in the left panel of FIG. 3. Variants 1 (301) and 2 (302) of a DNA template molecule together with beads (303) were emulsified (304). Both templates and beads were in low abundance compared to the total number of droplets in the emulsion resulting in minimal polyclonal beads and clonal copies. The majority of droplets were empty (305), some droplets contained only a single bead (306), and some droplets contained only a template nucleic acid molecule (307). Both (306) and (307) did not deliver amplified template positive beads, and the DNA template in (307) escaped the analysis workflow and thus was not analyzed. Only droplets comprising both a template nucleic acid molecule and a bead (e.g., 308) were functional amplification reactors capable of generating amplification products for subsequent analysis. Following emulsion breaking and enrichment (309), template positive beads delivered beads (310) useful for sequencing.

A nucleic acid analysis approach as described herein was carried out and is shown on the right panel of FIG. 3. As described herein, a significantly higher numbers of beads (311) were loaded into the emulsion droplets. Thus, a plurality of beads (e.g., 0-10 beads) was loaded into each droplet in a majority of the droplets in the emulsion as opposed to 0-1 beads per droplet in a majority of the droplets in the emulsion. All droplets comprising template nucleic acid molecules also included beads and hence generated multiple clonal copies of every bead (312), (313). Using one or more procedures as described herein, no template nucleic acid molecules were lost following breaking and enrichment, and both variants (314/315) were sequenced multiple times, resulting in increased accuracy.

In order to further enhance resolution (e.g., signal-to-noise ratio), unique molecular identifiers (UMI) were used for labeling of templates to assign a certain variant to an individual starting template.

This data demonstrates that the methods and compositions of the present disclosure may result in significantly enhanced accuracy for analyzing nucleic acid samples. This may be of particular importance when only very limited sample material is present and/or when detection rare variants is of importance.

Example 2

Figure 5A:
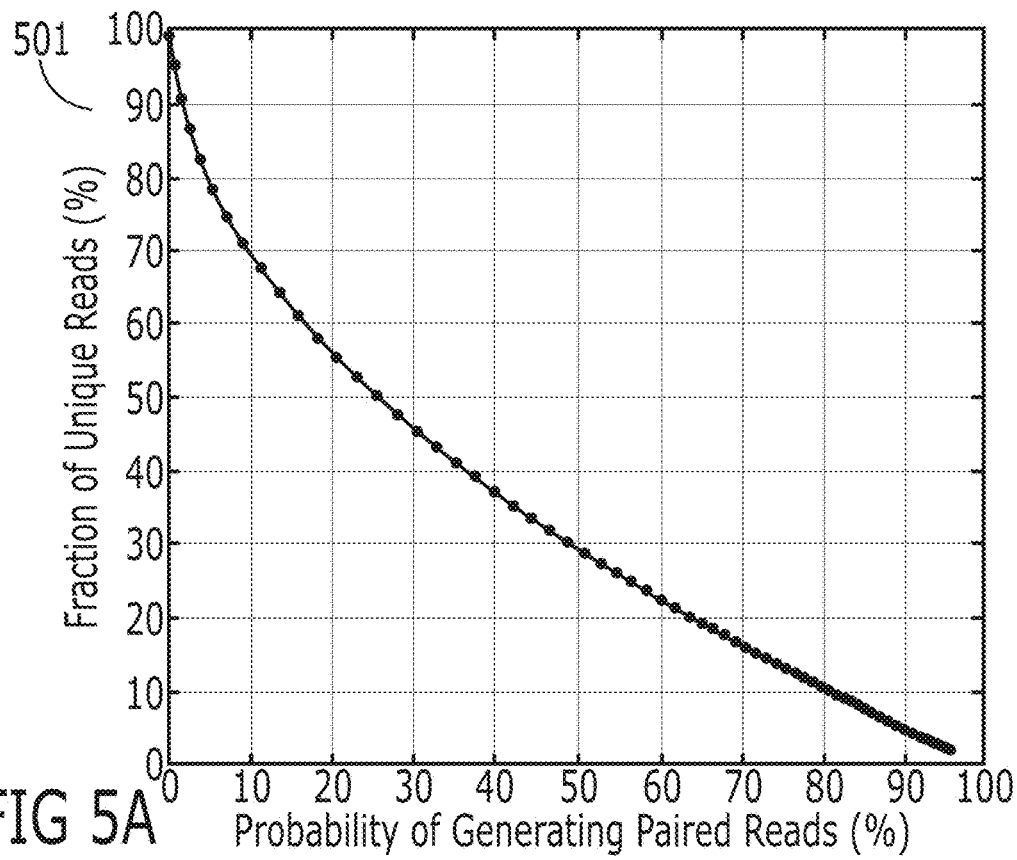
FIGS. 5A and 5B show read pairing outcomes for droplet loading, $L_{droplet}$, and sweep ($F_{split}$=50%, $F_{seq}$=100%).
Figure 5B:
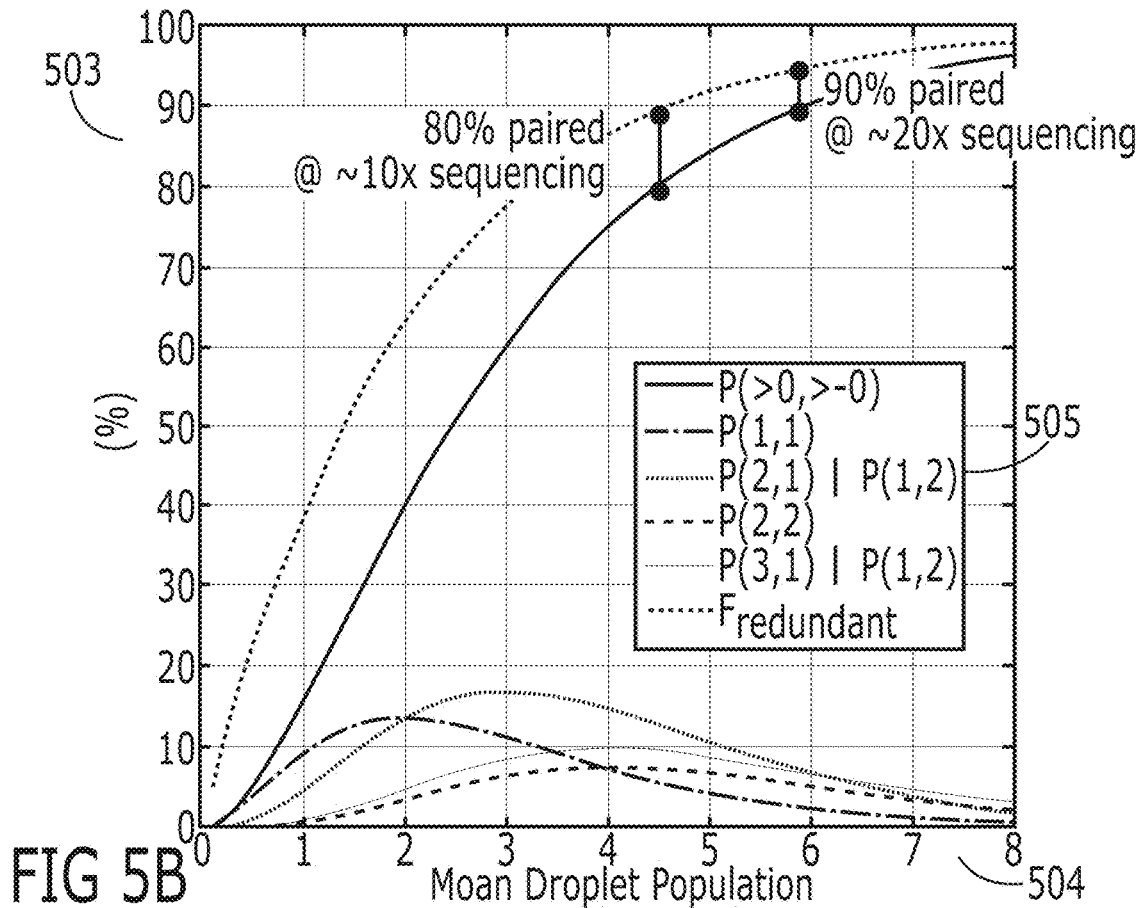

This example demonstrates a mathematical model that was used to generate the graphs depicted in FIG. 5A and FIG. 5B. FIG. 5A depicts a graph having a horizontal axis 502 for Probability of Generating Paired Reads (%), with 10% increment indices, and a vertical axis 501 for Fraction of Unique Reads (%), with 10% increment indices. FIG. 5B depicts a graph having a horizontal axis 504 for Mean Droplet Population, with 1 increment indices, and a vertical axis 503 for (%), with 10% increment indices.

The following mathematical relationship is used:

$$P_{Paired}(M_A, M_B | L_{droplet}, F_{split}, F_{seq}) =$$
$$\sum_{N_{droplet}} P_{Poisson}(N_{droplet} | L_{droplet}) \sum_{M'_A} P_{Binomial}(M'_A | N_{droplet}, F_{split})$$
$$P_{Binomial}(M_A | M'_A, F_{seq}) P_{Binomial}(M_B | N_{droplet} - M'_A, F_{seq})$$

where P(X|Y) indicates probability distribution of X given Y, MA and MB are the numbers of beads of population A and B, respectively, $L_{droplet}$ is the mean number of beads per droplet, $N_{droplet}$ is variable for the number of beads in droplet, $F_{split}$ is the fraction of beads that are type A, and $F_{seq}$ is the probability that a bead will be sequenced.

Example 3

This example shows an analytical relationship of the efficiency of random drop loading of bead types A and B (FIG. 5A).

Parametrically sweeping the mean bead loading, a relationship is established between the expected fraction of unique reads and the probability of generating paired reads, i.e., achieving at least one copy each of A and B. For example, for a 50% probability of generating paired reads, 30% of reads are unique. FIG. 5B shows the relationship between various read scenarios for a given mean droplet bead loading. The scenarios are labeled $P(N_A, N_B)$ where $N_A$ and $N_B$ are the numbers of beads of type A and B read, respectively. Index 505 labels the different graph lines, in order from top down, (i) P(>0,>0), (ii) P(1,1), (iii) P(2,1)|P(1,2), (iv) P(2,2), (v) P(3,1)|P(1,3), and (vi) $F_{redundant}$. The case $N_A$>0 and $N_B$>0, i.e., P(>0,>0), accounts for all scenarios in which an A & B read pair is obtained and is the highest solid curve. P(1,1) is the special instance in which one and only one copy of each read is obtained. The dotted curve is the fraction of reads that are redundant copies of A or B. $F_{split}$ is 50% and indicates both beads are equally likely. $F_{seq}$ is 100% and is the likelihood that a bead is sequenced. The annotation shows that attaining 100% efficiency to generate paired reads produces 90% redundancy in sequencing (additional copies of A and/or B).

Example 4

This example demonstrates a method for analyzing a biological sample (see e.g., FIG. 7).

This method to analyze a biological sample comprises two types of beads, each comprising primer sequences corresponding to a specific adapter of a plurality of adapters, wherein the plurality of adapters comprise a plurality of barcode sequences. The adapters may be coupled to ends of nucleic acid molecules (e.g., target nucleic acid molecules) of a plurality of nucleic acid molecules of the biological sample. The target nucleic acid library insert length (e.g., depicted by nucleic acid molecule 705 in FIG. 7) is selected such that nucleic acid sequencing from both ends provides sequence reads having no or very minimal overlap. Inserts are end-repaired and A-tailed prior to functionalization with adapters of the plurality of adapters. A synthetic double-stranded nucleic acid molecule is designed such that it may loop and ligate with the insert. For that reason, the synthetic double strand contains T overhangs preferably without terminal phosphates. The sequence of the synthetic double-stranded nucleic acid molecule is as follows: Barcode 2', PB' cleavable element, PA, Barcode 1. Barcode 1 and Barcode 2' may be any commercially available barcode sequences and may be different sequences. Alternatively, in some examples, Barcode 1 and Barcode 2'. may not be different sequences. However, the barcode sequences are well defined so they may be assigned to each other. The cleavable element allows separation of the strands of the synthetic double-stranded nucleic acid molecule by chemical, light, heat, or other mechanisms. Following ligation and circularization, the synthetic double-stranded nucleic acid molecule is cleaved and gap filled through polymerase-based extension. Two types of beads (e.g., those depicted by part 806 in FIG. 8) are available for clonal amplification, one with immobilized PA (1-8, FIG. 8) oligonucleotides or minimally a subportion of PA, and another with PB (4-8, FIG. 8) oligonucleotides or minimally a subportion of PB immobilized.

Thus, heat denaturation of the linearized gap-filled template allows annealing to the two bead types before distribution of the beads to well-separated compartment (e.g., partition) for clonal amplification such as in ePCR. Combination of this example with any of the herein described methods may allow elimination of the annealing process of a nucleic acid amplification reaction.

Example 5

Figure 20:
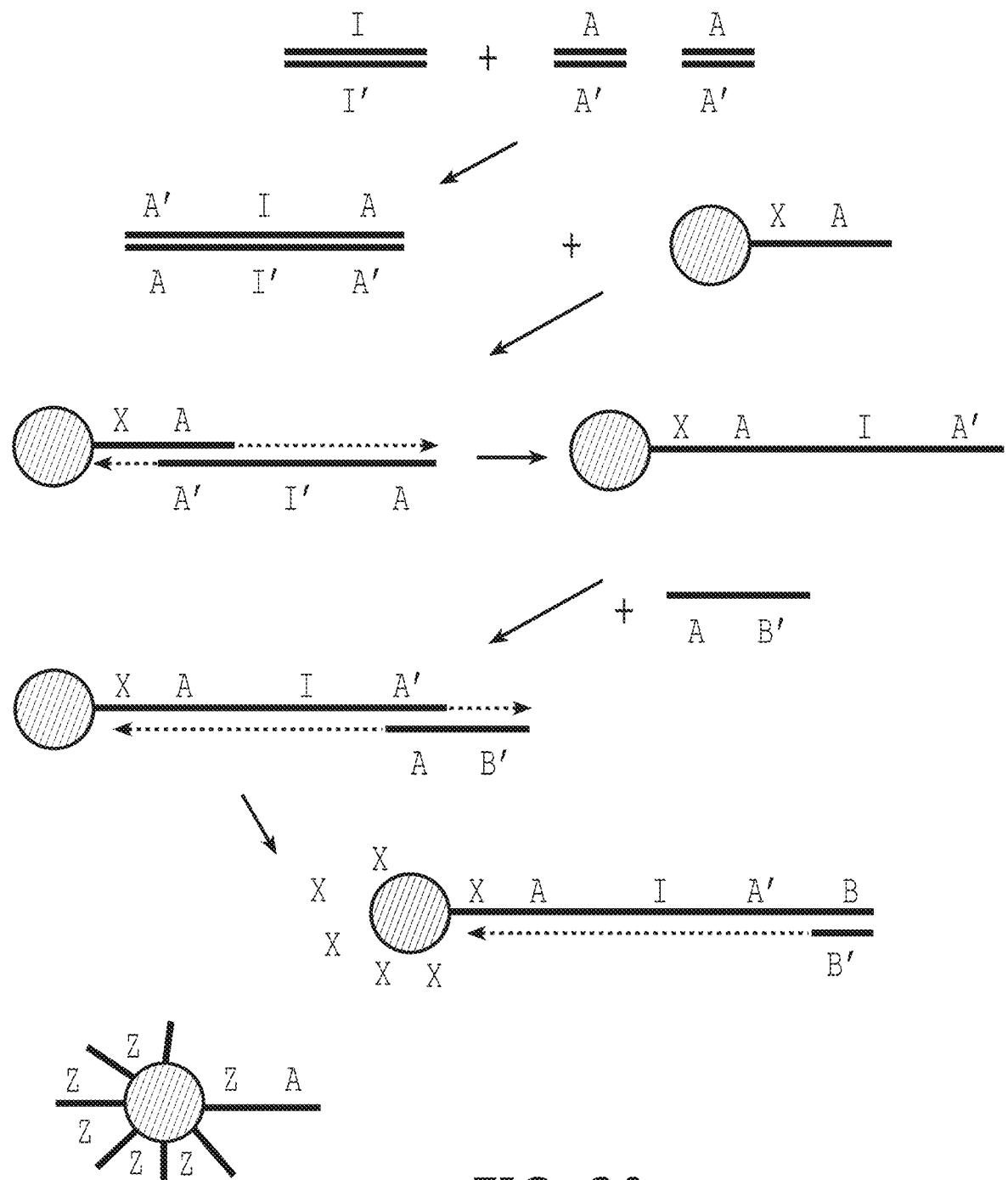
FIG. 20 illustrates an example where an adapter is attached to each end of the template nucleic acid molecule.

This example demonstrates a method for creating a clonally amplified bead using an insert library (I) having the same adapter pair (A/A') attached on each end (see e.g., FIG. 20). As used herein, a prime (') designates a reverse complement (e.g., A' is the reverse complement of A). The bead has a few copies of the second primer (X A) attached to it and many copies of the first primer (X). The adapted insert (A' I A) hybridizes with the second primer and is extended. The extension product is capable of extending further copies of the first primer (X) but not exponentially. Exponential amplification is permitted when the other end of the extended second (or first) primer is also extended using the fourth primer (A B'). Exponential surface amplification can now take place with the many copies of the surface primer (X) and many copies of the solution primer (third primer, B'). Other beads have a different first primer (Z) so extension products created off of the first bead (X) have no added affinity for the second bead (Z). Temperatures, concentrations and other amplification conditions are selected such that the first and second extensions are slow and/or rare events compared to exponential amplification. Temperatures, concentrations and other amplification conditions are selected such that first extension products (X) do not serve as templates for other beads (Z).

It is intended that the following claims define the scope of the invention and that methods and structures within the scope of these claims and their equivalents be covered thereby.

Example 6

Extended supports comprising a template nucleic acid molecule coupled thereto, as described herein, were prepared using the following procedure.

Annealing and extending the library: A reaction mixture containing a final volume of 100 microliters was prepared with the following components/concentrations: 1 10×TAQ polymerase reaction buffer, 8.2 millimolar (mM) of $MgCl_2$, 12 mM of dNTP, 10 picomolar (pM) of the library, 1 micromol/min (U) Taq DNA polymerase, and $6.00 \times 10^7$ beads/microliter. The mixture was incubated in a thermocycler using the conditions in Table 2:

TABLE 2

| Thermocycling conditions | | |
| --- | --- | --- |
| Step | Temperature | Time |
| 1 | 95° C. | 5 min |
| 2 | 50° C. | 1 hr |
| 3 | 70° C. | 1 hr |
| 4 | 12° C. | soak |

The beads were washed by adding 400 microliters (4) of TET Buffer (TE pH 8.0, 0.05% Triton X-100). The mixture was vortexed for 30 seconds, and spun down at 21,000 revolutions per minute (RPM) for 8 minutes in a centrifuge. The supernatant was removed to leave 100 µL. The beads were washed with 500 µL of 1× SA Bind Buffer (20 mM Tris pH 3.0, 50 mM NaCl, 0.05% Triton X-100). The mixture was vortexed for 30 seconds, and spun down at 21,000 RPM for 8 minutes in a centrifuge. The supernatant was removed to leave 100 µL.

Enriching the extended beads: 100 µL of magnetic Streptavidin beads were added to the extended beads. This mixture was mixed and incubated for 1 hour at room temperature. The beads were magnetized on an appropriate magnet until the solution was clear, and the supernatant was removed. The beads were washed with 500 µL of SA Bind Buffer by gentle resuspension. In a second magnetization operation, the beads were magnetized on an appropriate magnet until the solution was clear, and the supernatant was removed. The beads were washed with 500 µL of SA Bind Buffer by gentle resuspension. In a third magnetization operation, the beads were magnetized on an appropriate magnet until the solution was clear, and the supernatant was removed.

Eluting the extended beads: The beads were resuspended in 300 µL of 50° C. Meltoff Buffer (0.1 mol/liter (M) NaOH, 0.05% Triton X-100), and incubated for 5 minutes at 50° C. The mixture was vortexed briefly and the beads were magnetized on an appropriate magnet until the solution was clear. The supernatant containing the beads were removed and retained. In a second melt-off operation, the beads were resuspended in 300 µL of 50° C. Meltoff Buffer (0.1 mol/liter (M) NaOH, 0.05% Triton X-100), and incubated for 5 minutes at 50° C. The mixture was vortexed briefly and the beads were magnetized on an appropriate magnet until the solution was clear. The supernatant containing the beads were removed and retained, and combined with the earlier supernatant containing the beads. The eluted beads were spun down at 21,000 RPM for 8 minutes in a centrifuge, and the supernatant was removed to leave 100 µL. The beads were washed with 500 µL of 1× SA Bind Buffer, and vortexed for 30 seconds. The beads were spun down at 21,000 RPM for 8 minutes in a centrifuge, and the supernatant was removed to leave 100 µL. The beads were washed with 500 µL of TET Buffer, and vortexed for 30 seconds. The beads were spun down at 21,000 RPM for 8 minutes in a centrifuge, and the supernatant was removed to leave 100 µL.

The enriched beads were subsequently used in ePCR procedures.

Example 7

Table 3 below and FIG. 25 show the results of amplification using pre-enrichment (e.g., enriching a mixture of supports (e.g., beads), prior to clonal amplification, to use isolated and/or concentrated extended support mixtures for amplification) procedures against control procedures in absence of performing pre-enrichment procedures. Amplification was performed on E. coli Library templates and artificial templates.

TABLE 3

| Pre-enrichment vs Control Results | | | | |
| --- | --- | --- | --- | --- |
| Process | Template | % Enrichment | % Amplification | % Polyclonal |
| Pre-enrichment | E. coli Library | 5 | 95 | N/A |
| Pre-enrichment | Artificial templates | 1.6 | 90 | 13.25 |
| Control | Artificial templates | N/A | 17 | 11 |

Figure 25A:
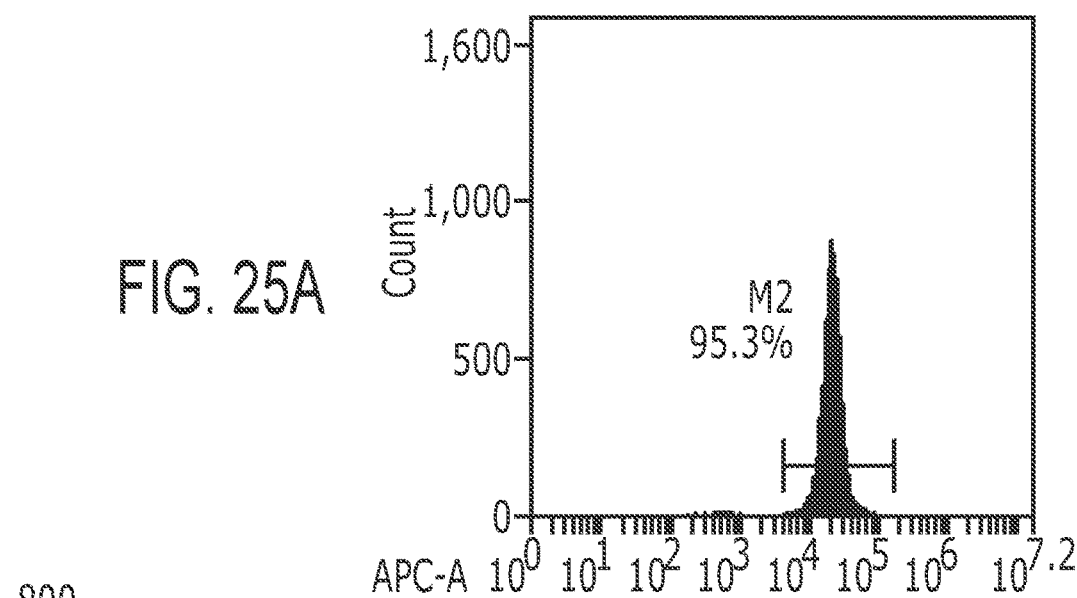
FIGS. 25A-25C show the results of amplification using pre-enrichment procedures.
Figure 25B:
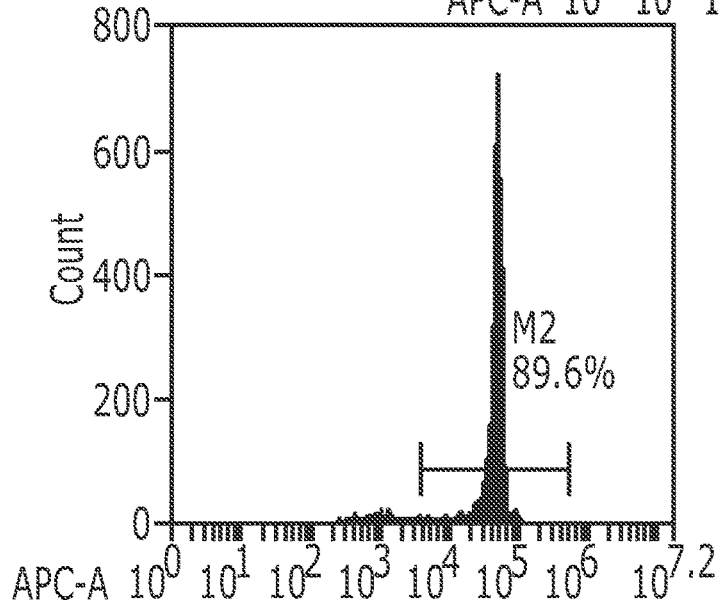
Figure 25C:
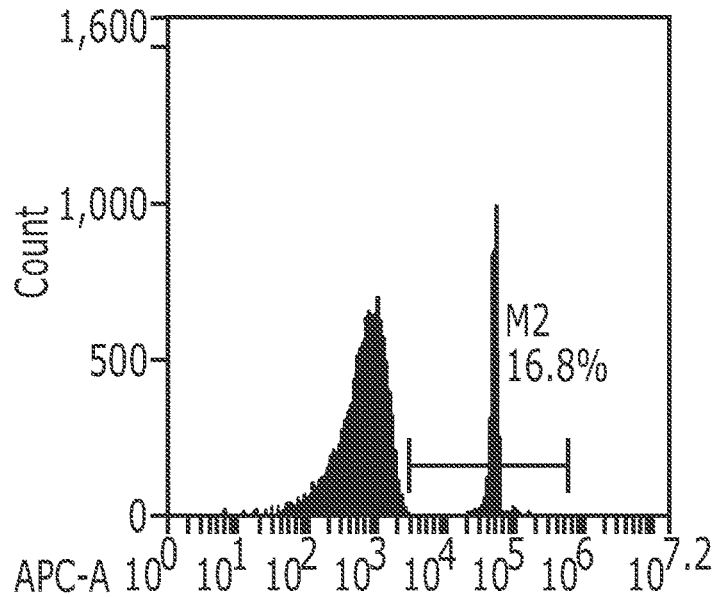

FIG. 25A shows an E. coli library that was subjected to pre-enrichment procedures, FIG. 25B shows an artificial template library that was subjected to pre-enrichment procedures, and FIG. 25C shows an artificial template library that was subjected to control procedures (in absence of pre-enrichment). Each graph shows a distribution of count vs. allophycocyanin (APC) fluorescence. For FIG. 25A and FIG. 25C, the vertical axis indices read in increasing order 0, 500, 1,000, and 1,600, respectively, and the horizontal axis indices read in increasing order, 100, 101, 102, 103, 104, 105, 106, and 107.2, respectively. For FIG. 25B, the vertical axis indices read in increasing order 0, 200, 400, 600, and 800, respectively, and the horizontal axis indices read in increasing order, 100, 101, 102, 103, 104, 105, 106, and 107.2, respectively. As shown in FIG. 25A, the E. coli library (pre-enrichment) resulted in 5% enrichment (against a theoretical 10%), and 95.3% amplification. As shown in FIG. 25B, the artificial template library (pre-enrichment) resulted in 1.6% enrichment (against a theoretical 10%), and 89.6% amplification. As shown in FIG. 25C, the artificial template library (control) resulted in 16.8% amplification. Approximately 13.25% of the pre-enrichment artificial template library population resulted in polyclonal amplification. Approximately 11% of the post-enrichment artificial template library population resulted in polyclonal amplification.

Example 8

Extended supports comprising an extension primer sequence configured to attach to a template nucleic acid molecule (e.g., adapter attached thereto), as described herein, were prepared using the following procedure.

A serial dilution of biotinylated extension primer molecules was prepared from 10 micromolar stock to each of 10 nanomolar (nM), 1 nM, 0.1 nM, and 0.01 nM stocks in 10 millimolar (mM) Tris pH 8.0, and these were further diluted to achieve a final concentration of 1000, 100, 10, and 1 picomolar (pM) in 60 million beads/µL. A biotinylated extension primer molecule comprises a complement of an extension primer sequence. Pre-annealing between primer molecules on the bead and the biotinylated extension primer molecules occurred at 95° C. for 2 minutes. The mixture was slowly cooled to 50° C., and held for a total of 45 minutes in 1× EpiMark® buffer. The primer was extended for 20 minutes at a 70° C. heat block, and washed twice with 1× BW buffer. Magnetic Streptavidin beads were hybridized with the biotin-templated beads for 1.5 hours on rotor at room temperature. The beads were magnetically captured. After magnetic capture, the beads (with single extension primer sequence) were eluted using 0.1% NaOH and 0.05% and Triton X-100 in water at 50° C. for 5 minutes. The enriched beads were washed three times using 1× EpiMark® buffer and subsequently used in ePCR procedures.

Example 9

Table 4 below and FIGS. 26A-27B show the results of enriched beads captured after primer extension at different extension primer: bead input ratios.

TABLE 4

Capture of Enriched Beads

| Extension Primer (PM) | Extension Primer: Bead (ratio) | Predicted % of beads with N ext. primers | | | Predicted % Beads of captured | Observed % of Beads captured |
|---|---|---|---|---|---|---|
| | | N = 0 | N = 1 | N = 2+ | | |
| 1000 | 10:1 | 0% | 0% | 100% | 100% | 51% |
| 100 | 1:1 | 37% | 37% | 26% | 63% | 35% |

For 1000 pM concentration of extension primers, and extension primer:bead ratio of 10:1, the predicted % for beads with 0, 1, and 2+ templates are 0%, 0%, and 100%, respectively. Accordingly, the predicted % of beads captured (having at least N=1 extension primer) is 100%. The observed % of beads captured was 51%.

For 100 pM concentration of extension primers, and extension primer:bead ratio of 1:1, the predicted % for beads with 0, 1, and 2+ templates are 37%, 37%, and 26% respectively. Accordingly, the predicted % of beads captured (having at least N=1 extension primer) is 63%. The observed % of beads captured was 35%.

Figure 26A:
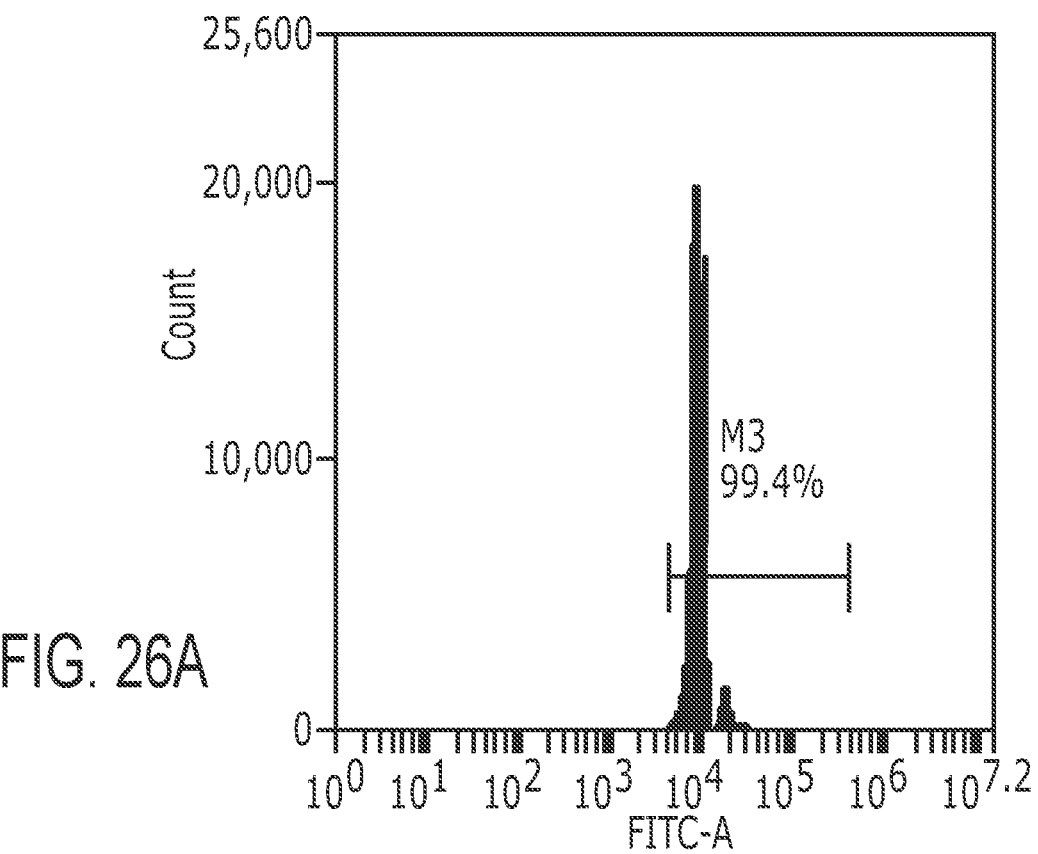
FIGS. 26A-26B show the presence of enriched beads captured, at different extension primer input concentrations.
Figure 26B:
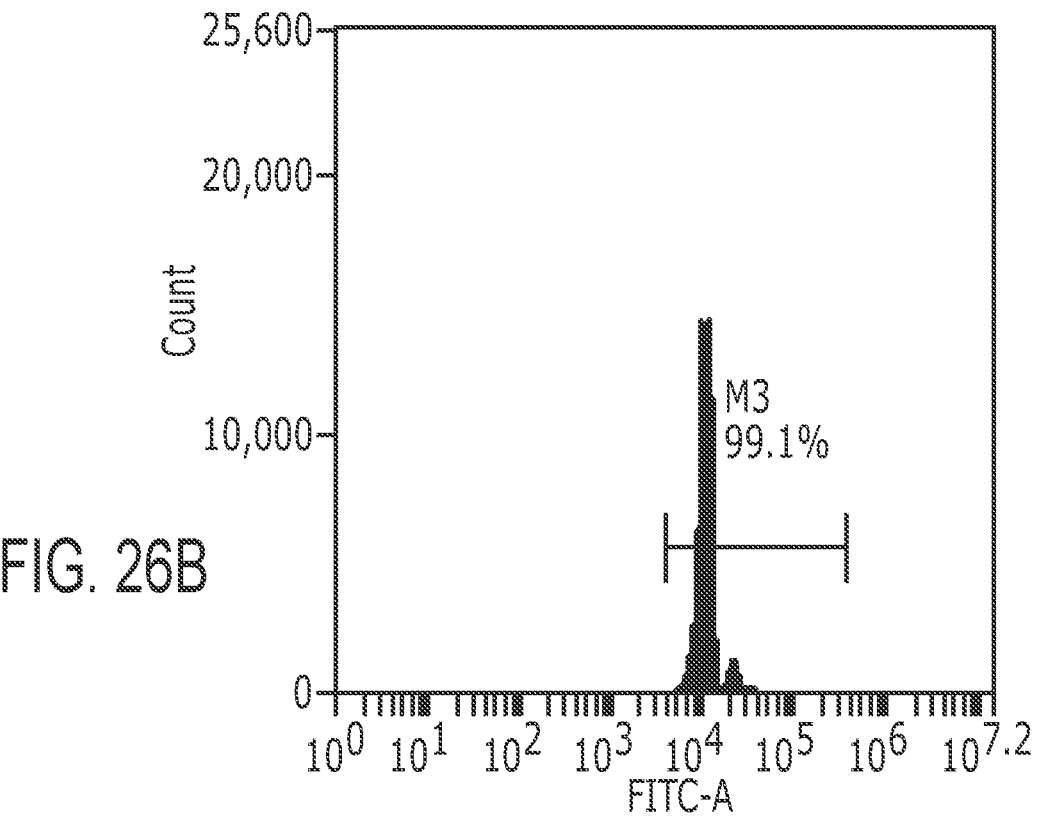

FIG. 26A shows the presence of enriched beads captured at 1000 pM extension primer input concentration, and FIG. 26B shows the presence of enriched beads captured at 100 pM extension primer input concentration. Each graph shows a distribution of count vs. fluorescein isothiocyanate (FITC) fluorescence, with 800 FITC threshold. For each graph, the vertical axis indices read in increasing order 0, 10,000, and 25,600, respectively, and the horizontal axis indices read in increasing order, $10^0$, $10^1$, $10^2$, $10^3$, $10^4$, $10^5$, $10^6$, and $10^{7.2}$, respectively.

Figure 27A:
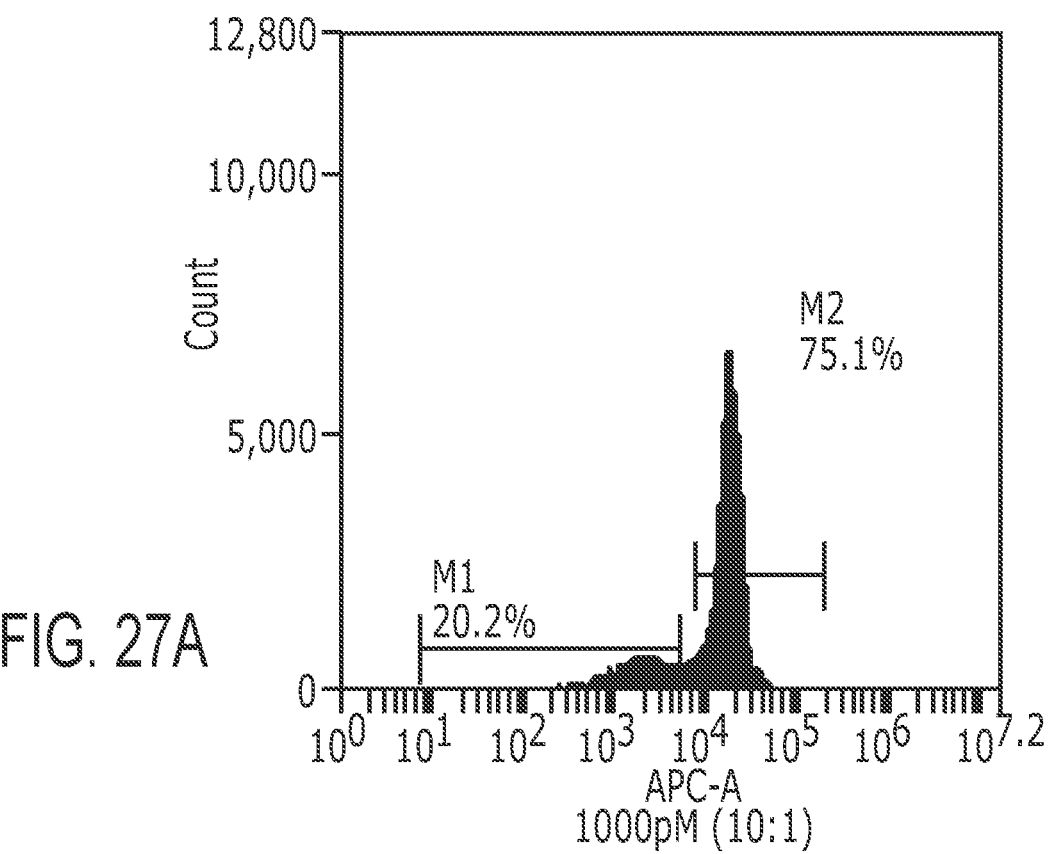
FIGS. 27A-27B show the presence of extension primer sequences in enriched beads, at different extension primer input concentrations.
Figure 27B:
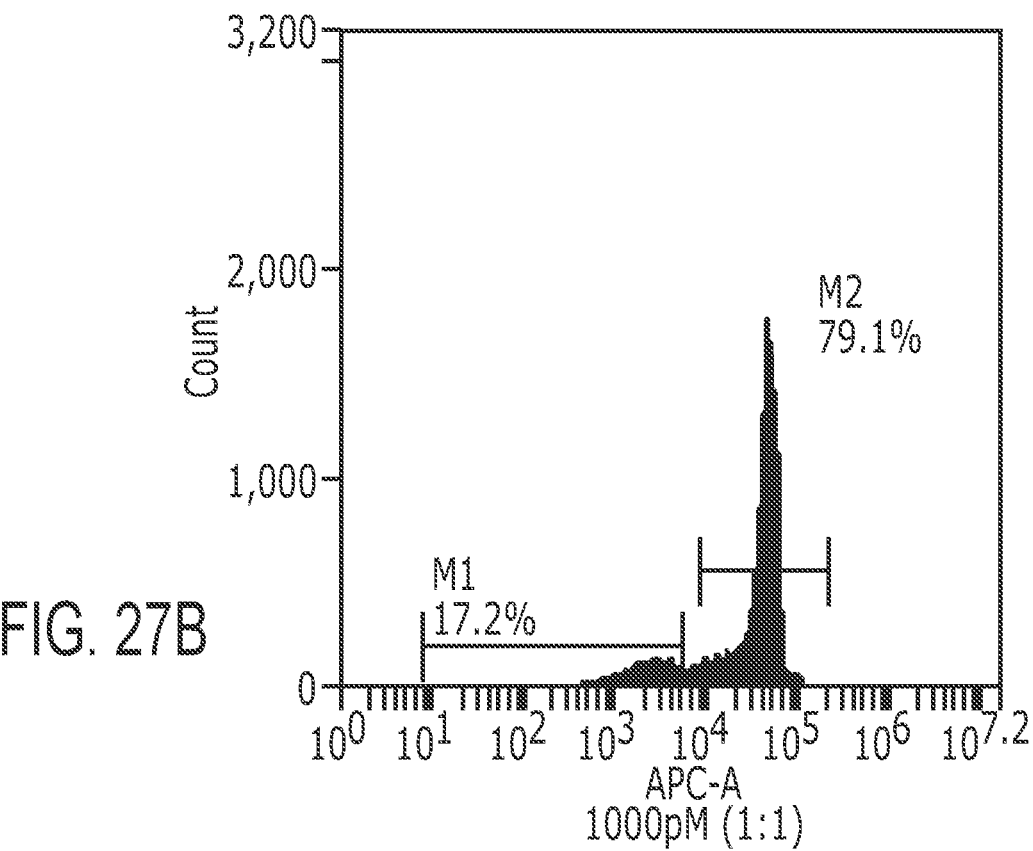

FIG. 27A shows the presence of the extension primer sequence in enriched beads, at 1000 pM extension primer input concentration and 10:1 extension primer:bead ratio, and FIG. 27B shows the presence of the extension primer sequence in enriched beads, at 100 pM extension primer input concentration and 1:1 extension primer:bead ratio. Each graph shows a distribution of count vs. allophycocyanin (APC) fluorescence. For FIG. 27A, the vertical axis indices read in increasing order 0, 5,000, 10,000, and 12,800, respectively, and the horizontal axis indices read in increasing order, $10^0$, $10^1$, $10^2$, $10^3$, $10^4$, $10^5$, $10^6$, and $10^{7.2}$, respectively. For FIG. 27B, the vertical axis indices read in increasing order 0, 1,000, 2,000, and 3,200, respectively, and the horizontal axis indices read in increasing order, $10^0$, $10^1$, $10^2$, $10^3$, $10^4$, $10^5$, $10^6$, and $10^{7.2}$, respectively. As shown in FIGS. 27A-27B, 75.1% and 79.1% of the enriched beads, respectively, were observed to contain at least one extension primer sequence.

Example 10

Extended supports comprising an extended primer sequence were attached to a template nucleic acid molecule (e.g., adapter attached thereto), as described herein, using the following procedure.

Pre-annealing library template to an extended support: A mixture of two species of single stranded templates and extended beads (a bead comprising the extended primer sequence) was provided at 20-fold excess of template: enriched bead, and left to anneal at 95° C. for 2 minutes, slowly cooled to 50° C., and held for a total of 45 minutes in 1× EpiMark® buffer. The mixture was incubated additional times at 50° C. while rotating for 2-20 hours. The beads were washed once with 1× EpiMark® buffer. The resulting beads have a template molecule (e.g., single template molecule) coupled thereto.

Partitioning templated extended support for ePCR: The templated beads were partitioned into droplets for ePCR. It will be appreciated that prior to partitioning for ePCR, the templated bead (e.g., bead coupled to a template molecule via an extension primer sequence) may be coupled to the template via annealing of the template to the extension primer sequence and/or via extension from the extension primer sequence to generate a complement of the template coupled to the bead.

Example 11

Table 5 below and FIGS. 28A-29B show the results of ePCR amplification using templated beads at different extension primer: bead input ratios. Atto probes for two species of templates were annealed to the amplified beads and total amplification measured.

Figure 28A:
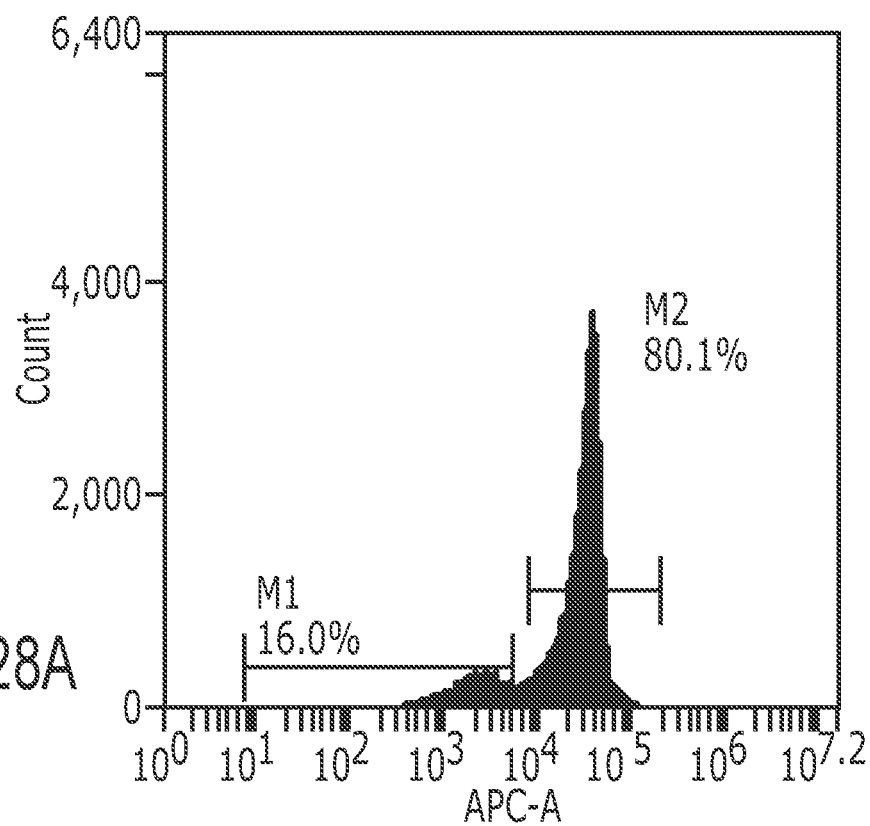
FIGS. 28A-28B show the presence of amplified beads, at different extension primer input concentrations.
Figure 28B:
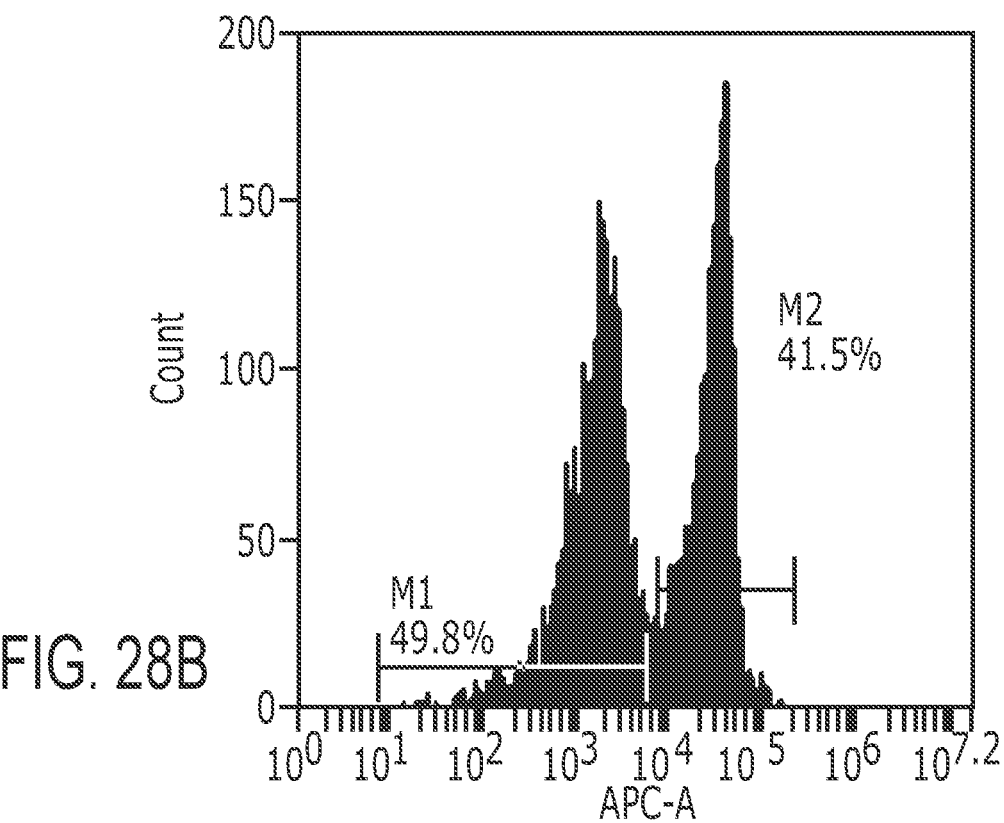

FIG. 28A shows the presence of amplified beads (or library-positive beads) at 1000 pM extension primer input concentration, 10:1 extension primer:bead input ratio, 200 pM template input concentration, and 1:20 enriched bead: template input ratio, and FIG. 28B shows the presence of amplified beads (or positive beads) at 100 pM extension primer input concentration, 1:1 extension primer:bead input ratio, 200 pM template input concentration, and 1:20 enriched bead:template input ratio. Each graph shows a distribution of count vs. allophycocyanin (APC) fluorescence. For FIG. 28A, the vertical axis indices read in increasing order 0, 2000, 4000, and 6400, respectively, and the horizontal axis indices read in increasing order, $10^0$, $10^1$, $10^2$, $10^3$, $10^4$, $10^5$, $10^6$, and $10^{7.2}$, respectively. For FIG. 28B Panel (B), the vertical axis indices read in increasing order 0, 100, 150, and 200, respectively, and the horizontal axis indices read in increasing order, $10^0$, $10^1$, $10^2$, $10^3$, $10^4$, $10^5$, $10^6$, and $10^{7.2}$, respectively. As shown in FIGS. 28A-28B, 80.1% and 41.5% of the enriched beads, respectively for 1000 pM and 100 pM extension primer input concentrations, were amplified.

Figure 29A:
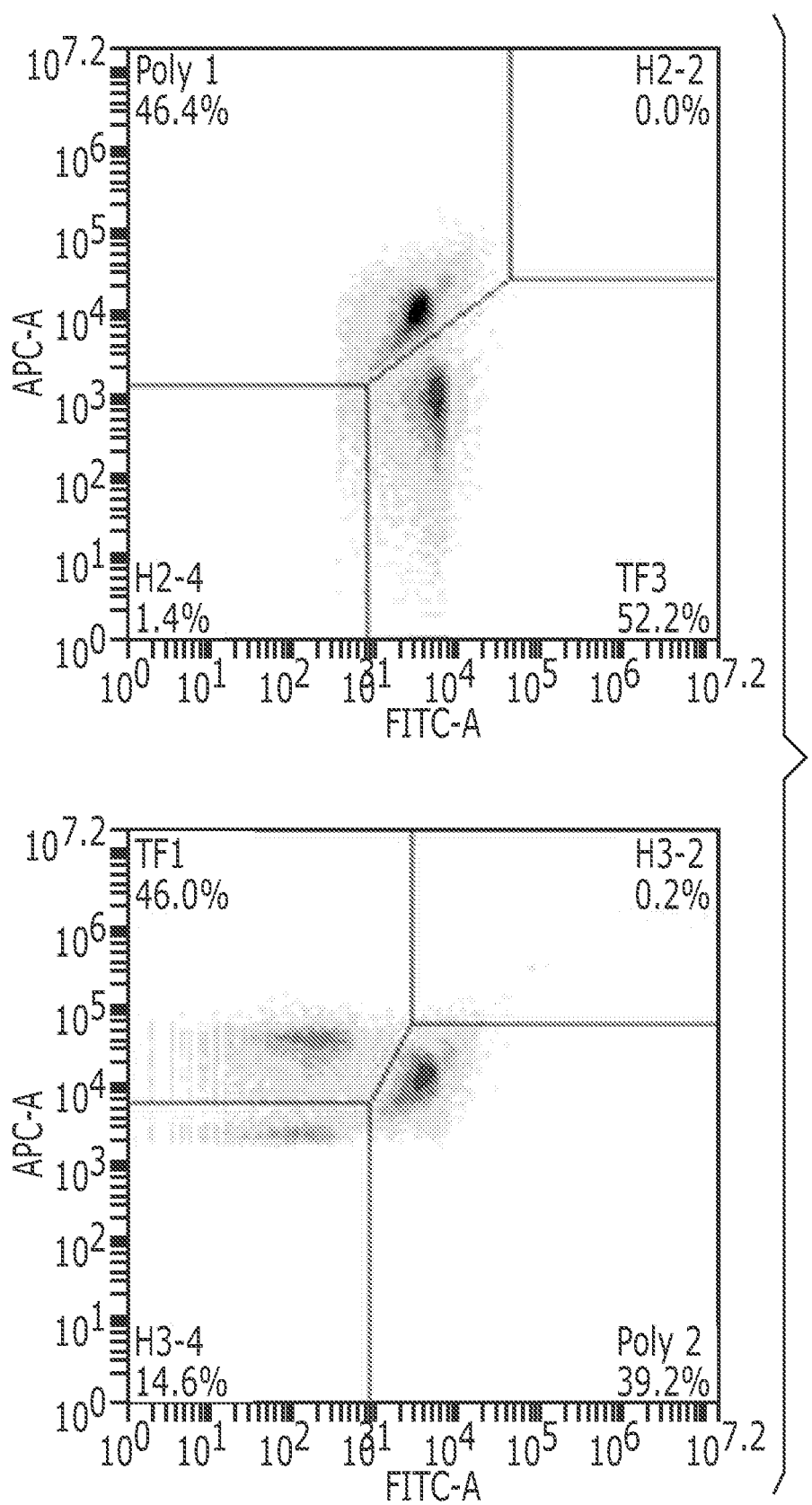
FIGS. 29A-B show polyclonality in amplified beads, at different extension primer input concentrations.
Figure 29B:
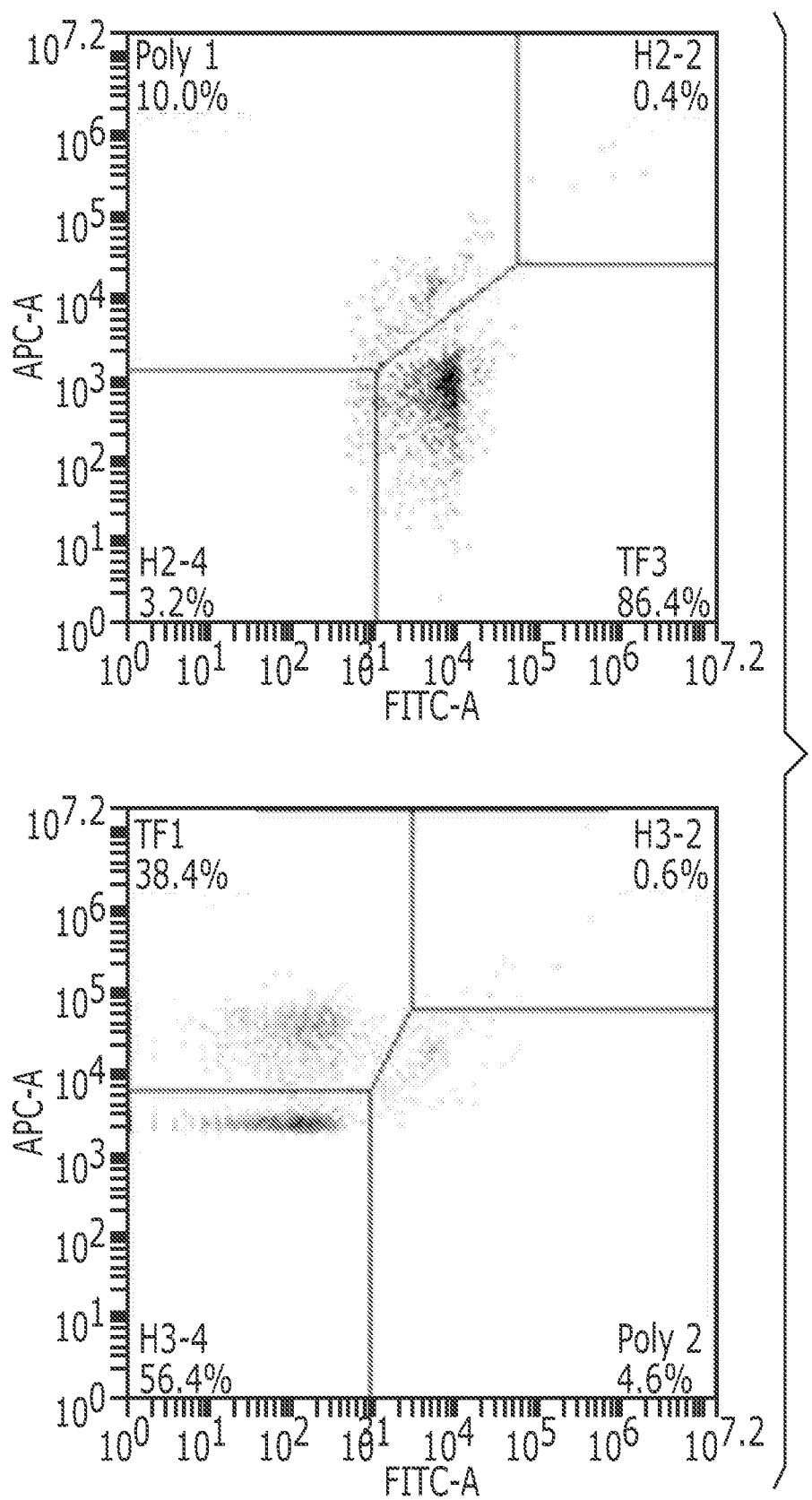

FIG. 29A shows two graphs indicative of polyclonality of amplified beads at 1000 pM extension primer input concentration, 10:1 extension primer:bead input ratio, 200 pM template input ratio, and 1:20 enriched bead:template input ratio, and FIG. 29B shows two graphs indicative of polyclonality of amplified beads at 100 pM extension primer input concentration, 1:1 extension primer:bead input ratio, 200 pM template input concentration, and 1:20 enriched bead:template input ratio. Each graph shows a distribution of APC fluorescence vs FITC fluorescence. For each of the vertical and horizontal axis of each graph, the axis indices read in increasing order $10^0$, $10^1$, $10^2$, $10^3$, $10^4$, $10^5$, $10^6$, and $10^{7.2}$, respectively. The two top graphs have a threshold on the FITC, and the two bottom graphs have a threshold on the APC fluorescence.

TABLE 5

Polyclonal %

| Extension Primer Concentration (pM) (Bead:Extension Primer) | Template Concentration (pM) (Enriched Bead:Template) | Predicted % Polyclonal | Observed % Polyclonal |
|---|---|---|---|
| 1000 (1:10) | 200 (1:20) | 67% | 30% |
| 100 (1:1) | 200 (1:20) | 23% | 6% |

As shown in Table 5, the observed polyclonal percentage for pre-enriched beads was much lower at 30% and 6% (for 1000 pM and 100 pM extension primer input concentrations, respectively) than theory predicts at 67% and 23% polyclonality, respectively. Furthermore, the predicted polyclonal percentage for performing ePCR without pre-enrichment is 44% and 22% for 80.1% and 41.5% library-positive rates (see, e.g., library-positive bead results with respect to FIGS. 28A-B), respectively. Accordingly, results showed that performing the pre-enrichment procedures described herein generates lower levels of polyclonality at a given rate of library-positive beads than with standard Poisson loading (without pre-enrichment).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for nucleic acid processing, comprising
    (a) generating a plurality of droplets with a plurality of beads and a plurality of nucleic acid molecules, wherein a droplet of said plurality of droplets comprises (i) a bead of said plurality of beads, wherein said bead comprises a first primer comprising a first primer sequence, wherein said droplet does not comprise any other beads, (ii) at least two nucleic acid molecules of said plurality of nucleic acid molecules, comprising a first nucleic acid molecule and a second nucleic acid molecule, wherein said first nucleic acid molecule and said second nucleic acid molecule have different nucleic acid sequences and each of said first nucleic acid molecule and said second nucleic acid molecule comprises a first adaptor sequence, wherein said first primer sequence does not have sequence complementarity with said first adaptor sequence, and (iii) one or more reagents comprising a second primer within said droplet, said second primer not attached to any beads and comprising a first portion and a second portion, wherein said first portion is configured to hybridize to said first adaptor sequence, and wherein said second portion comprises a second primer sequence that corresponds to said first primer sequence, wherein a ratio of a concentration of said second primer within said droplet to a concentration of said first primer in said droplet is on an order of 10-1 or less;
    (b) in said droplet, with said second primer hybridized to said first adaptor sequence of said first nucleic acid molecule, (i) using said one or more reagents to generate one or more extension products of said first nucleic acid molecule comprising said second primer sequence or reverse complement thereof, (ii) attaching an extension product of said one or more extension products to said bead by annealing said second primer sequence or reverse complement thereof to said first primer sequence and extending said first primer, and (iii) generating amplification products of said first nucleic acid molecule attached to said bead, thereby monoclonally amplifying said first nucleic acid molecule on said bead;
    (c) recovering said bead from said droplet; and
    (d) assaying an amplification product of said amplification products attached to said bead, to identify a sequence of said first nucleic acid molecule.

2. The method of claim 1, wherein (a) comprises bringing (i) a first solution comprising said plurality of nucleic acid molecules and (ii) a second solution comprising said plurality of beads in contact with a fluid that is immiscible with said first solution and said second solution, to generate said plurality of droplets.

3. The method of claim 1, wherein said bead has attached thereto a plurality of first primers comprising said first primer for performing one or more amplification reactions to generate said amplification products of said first nucleic acid molecule attached to said bead.

4. The method of claim 1, wherein each of at least 50% of said plurality of droplets comprises two or more beads of said plurality of beads.

5. The method of claim 1, wherein each of at least 50% of said plurality of droplets comprises one or more nucleic acid molecules of said plurality of nucleic acid molecules.

6. The method of claim 1, wherein said one or more reagents comprise nucleic acid molecules comprising priming sequences.

7. The method of claim 6, wherein said nucleic acid molecules comprising said priming sequences further comprise unique molecular identifier sequences.

8. The method of claim 6, wherein said nucleic acid molecules comprising said priming sequences further comprise barcode sequences.

9. The method of claim 1, wherein said one or more reagents comprise one or more polymerizing enzymes.

10. The method of claim 1, wherein (d) comprises sequencing said amplification product while said amplification product is attached to said bead.

11. The method of claim 1, further comprising generating said plurality of droplets, wherein each of at least 50% of said plurality of droplets comprises at least one bead and at least one nucleic acid template.

12. The method of claim 1, further comprising generating said plurality of droplets, wherein each of at least 80% of said plurality of droplets comprise at least one bead and at least one nucleic acid template.

13. The method of claim 1, wherein said plurality of nucleic acid molecules comprises isolated nucleic acid molecules.

14. The method of claim 10, wherein said bead is placed on a planar substrate for said sequencing.

15. The method of claim 1, wherein at most 50% of said plurality of droplets are unoccupied by said plurality of beads or said plurality of nucleic acid molecules.

16. The method of claim 1, wherein said one or more reagents comprises first solution primers not attached to said bead, wherein each of said first solution primers comprises said first primer sequence.

17. The method of claim 1, wherein said one or more reagents comprises third solution primers not attached to said bead, wherein said at least two nucleic acid molecules each comprises a second adaptor sequence different from said first adaptor sequence, and wherein each of said third solution primers comprises a third primer sequence that is identical or a reverse complement to said second adaptor sequence.

18. The method of claim 1, wherein said ratio of said concentration of said second primer within said droplet to said concentration of said first primer in said droplet is on an order of $10^{-2}$ or less.

19. The method of claim 1, wherein said ratio of said concentration of said second primer within said droplet to said concentration of said first primer in said droplet is on an order of $10^{-3}$ or less.

20. The method of claim 1, wherein said bead of said plurality of beads comprises a plurality of first primers comprising said first primer, and wherein a ratio of a concentration of said second primer within said droplet to a concentration of said plurality of first primers in said droplet is on an order of $10^{-1}$ or less.

21. The method of claim 1, wherein said droplet has a diameter of about 1 nanometer (nm) to about 1 millimeter (mm).

22. The method of claim 1, wherein said first adapter sequence of said first nucleic acid molecule and said second nucleic acid molecule comprises a same sequence.

* * * * *